(12) United States Patent
Donohue et al.

(10) Patent No.: US 11,447,754 B2
(45) Date of Patent: Sep. 20, 2022

(54) IN VITRO METHODS OF CHEMICAL CONVERSION USING NON-STEREOSPECIFIC GLUTATHIONE LYASES

(71) Applicant: WISCONSIN ALUMNI RESEARCH FOUNDATION, Madison, WI (US)

(72) Inventors: Timothy James Donohue, Middleton, WI (US); Daniel Leo Gall, Madison, WI (US); Wayne S. Kontur, Madison, WI (US); Hoon Kim, Madison, WI (US); John Ralph, Madison, WI (US); Daniel R. Noguera, Madison, WI (US); Brian Fox, Madison, WI (US); Craig Bingman, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 65 days.

(21) Appl. No.: 17/038,971

(22) Filed: Sep. 30, 2020

(65) Prior Publication Data

US 2021/0095265 A1 Apr. 1, 2021

Related U.S. Application Data

(63) Continuation of application No. 16/103,275, filed on Aug. 14, 2018, now Pat. No. 10,829,745.

(60) Provisional application No. 62/545,214, filed on Aug. 14, 2017.

(51) Int. Cl.
*C12N 9/10* (2006.01)
*C12P 7/22* (2006.01)
*C12P 7/26* (2006.01)
*C12N 9/88* (2006.01)

(52) U.S. Cl.
CPC .............. *C12N 9/1088* (2013.01); *C12P 7/22* (2013.01); *C12P 7/26* (2013.01); *C12N 9/88* (2013.01); *C12Y 114/16005* (2013.01); *C12Y 205/01018* (2013.01)

(58) Field of Classification Search
None
See application file for complete search history.

(56) References Cited

U.S. PATENT DOCUMENTS

| | | | |
|---|---|---|---|
| 8,569,465 B2 | 10/2013 | Ralph et al. | |
| 8,685,672 B2 | 4/2014 | Grabber et al. | |
| 9,441,235 B2 | 9/2016 | Wilkerson et al. | |
| 9,487,794 B2 | 11/2016 | Wilkerson et al. | |
| 9,493,783 B2 | 11/2016 | Wilkerson et al. | |
| 10,829,745 B2 * | 11/2020 | Donohue | C12N 9/1088 |

OTHER PUBLICATIONS

Adams, P.D., Afonine, P.V., Bunkóczi, G., Chen, V.B., Davis, I.W., Echols, N., Headd, J.J., Hung, L.-W., Kapral, G.J., Grosse-Kunstleve, R.W., et al. (2010). PHENIX: a comprehensive Python-based system for macromolecular structure solution. *Acta Crystallogr. D Biol. Crystallogr.* 66, 213-221.

Adler E, Eriksoo E: Guaiacylglycerol and its β-guaiacyl ether. *Acta chemica Scandinavia*: 1955, 9:341-342.

Adler E: Structural elements of lignin. *Industrial & Engineering Chemistry* 1957, 49:1377-1383.

Adler E. (1977) Lignin Chemistry—past, present and future. *Wood Sci Technol* 11(3):169-218.

Afonine, P.V., Grosse-Kunstleve, R.W., Echols, N., Headd, J.J., Moriarty, N.W., Mustyakimov, M., Terwilliger, T.C., Urzhumtsev, A., Zwart, P.H., and Adams, PD. (2012). Towards automated crystallographic structure refinement with phenix.refine. *Acta Crystallogr. D Biol. Crystallogr.* 68, 352-367.

Akiyama T, Sugimoto T, Matsumoto Y, Meshitsuka G: Erythro/threo ratio of β-O-4 structures as an important structural Characteristic of lignin. I: Improvement of ozonation method for the quantitative analysis of lignin side-chain structure. *Journal of Wood Science* 2002, 48:210-215.

Bubeck P, Winkler M, Bautsch W. (1993) Rapid Cloning by homologous recombination in vivo. *Nucleic Acids Res* 21(15):3601-3602.

Bunkóczi, G., and Read, RJ. (2011). Improvement of molecular-replacement models with Sculptor. *Acta Crystallogr. D Biol. Crystallogr.* 67, 303-312.

Bryksin AV, Matsumura I: Overlap extension PCR Cloning: a simple and reliable way to create recombinant plasmids. *Biotechniques* 2010, 48:463-465.

Casanas, A., Warshamanage, R., Finke, A.D., Panepucci, E., Olieric, V., Nöll, A., Tampé, R., Brandstetter, S., Förster, A., Mueller, M., et al. (2016). EIGER detector: application in macromolecular crystallography. *Acta Crystallogr D Struct Biol* 72, 1036-1048.

Cohen-Bazire G, Sistrom WR, Stanier RY (1957) Kinetic studies of pigment synthesis by non-sulfur purple bacteria. *J Cell Comp Physiol* 49(1):25-68.

(Continued)

*Primary Examiner* — Christian L Fronda
(74) *Attorney, Agent, or Firm* — Daniel A. Blasiole; DeWitt LLP

(57) ABSTRACT

Enzymes for depolymerizing lignin. The enzymes include dehydrogenases, β-etherases, and glutathione lyases. The dehydrogenases can comprise one or more or LigD, LigO, LigN, and LigL. The β-etherases can comprise one or more of LigE, LigF, LigP, and BaeA. The glutathione lyases can comprise any one or more of LigG and a number of non-stereospecific, optionally recombinant glutathione lyases derived from *Sphingobium* sp. SYK-6, *Novosphingobium aromaticivorans*, *Escherichia coli*, *Streptococcus sanguinis*, *Phanerochaete chrysosporium*, and other microorganisms. The enzymes can be combined in compositions and/or used in methods of processing lignin or other aromatic compounds in vitro.

21 Claims, 33 Drawing Sheets
(27 of 33 Drawing Sheet(s) Filed in Color)
Specification includes a Sequence Listing.

(56) References Cited

OTHER PUBLICATIONS

Crawford RL, Kirk TK, Harkin JM, McCoy E (1973) Bacterial cleavage of an arylglycerol-β-aryl ether bond. *Appl Microbiol* 25(2):322-324.

Del Rio JC, Rencoret J, Prinsen P, Martinez AT, Ralph J, Gutierrez A: Structural characterization of wheat straw lignin as revealed by analytical pyrolysis, 2D-NMR, and reductive cleavage method. *Journal of Agricultural and Food Chemistry* 2012, 60:5922-5935.

Doherty AJ, Ashford SR, Brannigan JA, Wigley DB (1995) a superior host strain for the over-expression of cloned genes using the T7 promoter based vectors. *Nucleic Acids Res* 23(11): 2074-2075.

Emsley, P., and Cowtan, K. (2004). Coot: model-building tools for molecular graphics. *Acta Crystallogr. D Biol. Crystallogr.* 60, 2126-2132.

Fredrickson JK, Brockman FJ, Workman DJ, Li SW, Stevens TO (1991) Isolation and characterization of a subsurface bacterium capable of growth on toluene, naphthalene, and other aromatic compounds. *Appl Environ Microbiol* 57(3):796-803.

Fredrickson JK, et al. (1995) Aromatic-degrading Sphingomonas isolates from the deep subsurface. *Appl Environ Microbiol* 61(5):1917-1922.

Gall DL, Kim H, Lu F, Donohue TJ, Noguera DR, Ralph J: Stereochemical features of glutathione-dependent enzymes in the *Sphingobium* sp. strain SYK-6 β-aryl etherase pathway. *J Biol Chem* 2014, 289:8656-8667.

Gall DL, Ralph J, Donohue TJ, Noguera DR: a group of sequence-related sphingomonad enzymes catalyzes cleavage of β-aryl ether linkages in lignin β-guaiacyl and β-syringyl ether dimers. *Environmental Science & Technology* 2014, 48:12454-12463.

Gall DL, β-Etherase and benzoyl-CoA pathway enzymes mediate biodegradation of lignin-derived Aromatic Compounds, Thesis 2015 (Broken into Parts 1 thru 4).

Gall DL, Ralph J, Donohue TJ, Noguera DR: Biochemical transformation of lignin for deriving valued commodities from lignocellulose. (*In Review*). *Current Opinion in Biotechnology* 2017.

Gall et al., In Vitro Enzymatic Depolymerization of Lignin with Release of Syringyl, Guaiacyl, and Tricin Units, *Applied and Environ. Micro.* 2018, vol. 84, Issue 3, 1-17.

Gay P, Le Coq D, Steinmetz M, Berkelman T, Kado CI: Positive selection procedure for entrapment of insertion sequence elements in gram-negative bacteria. *J Bacteriol* 1985, 164(2):918-921.

Goren MA, Nozawa A, Makino S, Wrobel R, Fox BG: Cell-free translation of integral membrane proteins into unilamelar liposomes. *Meth. Enzymol.* 2009, 463:647-673.

Grabber JH, Ralph J, Hatfield RD, Quideau S, Kuster T, Pell AN. Dehydrogenation polymer—cell wall complexes as a model for lignified grass walls. *J. Agric. Food Chem.*, 1996, 44(6):1453-1459.

Helmich KE, Pereira JH, Gall DL, Heins RA, McAndrew RP, Bingman C, Deng K, Holland KC, Noguera DR, Simmons BA, et al.: Structural basis of stereospecificity in the bacterial enzymatic cleavage of β-aryl ether bonds in lignin. *Journal of Biological Chemistry* 2016, 291:5234-5246.

Higuchi T: Lignin structure and morphological distribution in plant cell walls. In *Lignin biodegradation: microbiology, chemistry and potential applications*. Edited by Kirk TK, Higuchi T, Chang H: CRC Press; 1980:1-20. vol. I.

Hishiyama S, Otsuka Y, Nakamura M, Ohara S, Kajita S, Masai E, Katayama Y: Convenient synthesis of chiral lignin model compounds via optical resolution: four stereoisomers of guaiacylglycerol-β-guaiacyl ether and both enantiomers of 3-hydroxy-1-(4-hydroxy-3-methoxyphenyl)-2-(2-methoxy-phenoxy)-prop an-1-one (erone). *Tetrahedron Letters* 2012, 53:842-845.

Horton RM: In vitro recombination and mutagenesis of DNA : SOEing together tailor-made genes. *Methods in molecular biology* (Clifton, N.J.) 1993, 15:251-261.

Horton RM, Cai Z, Ho SN, Pease LR: Gene splicing by overlap extension: tailor-made genes using the polymerase chain reaction. *Biotechniques* 2013, 54:129-133.

Kabsch, W. (2010). XDS. *Acta Crystallogr. D Biol. Crystallogr.* 66, 125-132.

Katoh K, Misawa K, Kuma K, Miyata T. Mafft: a novel method for rapid multiple sequence alignment based on fast Fourier transform. *Nucleic Acids Res.* 2002, 9(14):3059-3066.

Kontur WS, Bingman CA, Olmsted CN, Wassarman DR, Ulbrich A, Gall DL, Smith RW, Yusko LM, Fox BG, Noguera DR, Coon JJ, Donohue TJ: *Novosphingobium aromaticivorans* uses a Nu-class glutathione S-transferase as a glutathione lyase in breaking the β-aryl ether bond of lignin. *J. Biol. Chem.* 2018, 293: 4955-4968.

Lan W, Lu FC, Morreel K, Rencoret J, Del Rio JC, Zakai U, Jones D, Zhu YM, Boerjan W, Ralph J: Tricin: a novel monomer in grass lignins. *Abstracts of Papers of the American Chemical Society* 2014, 247.

Lan W, Lu FC, Regner M, Zhu YM, Rencoret J, Ralph SA, Zakai UI, Morreel K, Boerjan W, Ralph J: Tricin, a flavonoid monomer in monocot lignification. *Plant Physiology* 2015, 167:1284-U1265.

Lan W, Morreel K, Lu FC, Rencoret J, Del Rio JC, Voorend W, Vermerris W, Boerjan W, Ralph J: Maize tricin-oligolignol metabolites and their implications for monocot lignification. *Plant Physiology* 2016, 171:810-820.

Larkin MA, Blackshields G, Brown NP, Chenna R, McGettigan PA, McWilliam H, Valentin F, Wallace IM, Wilm A, Lopez R, Thompson JD, Gibson TJ, Higgins DG. (2007). Clustal W and Clustal X version 2.0. Bioinformatics, 23, 2947-2948.

Lewis NG, Yamamoto E: Lignin—occurrence, biogenesis and biodegradation. *Annual Review of Plant Physiology and Plant Molecular Biology* 1990, 41:455-496.

Makino S, Beebe ET. Markley JL, Fox BG: Cell-free protein synthesis for functional and structural studies. *Methods Mol. Biol.* 2014, 1091:161-178.

Masai E, Katayama Y, Nishikawa S, Yamasaki M, Morohoshi N, Haraguchi T: Detection and localization of a new enzyme catalyzing the β-aryl ether cleavage in the soil bacterium (*Pseudomonas paucimobilis* SYK-6). *Febs Letters* 1989, 249:348-352.

Masai E, Kubota S, Katayama Y, Kawai S, Yamasaki M, Morohoshi N: Characterization of the Cα-dehydrogenase gene involved in the Cleavage of β-aryl ether by *Pseudomonos poucimobilis*. *Bioscience Biotechnology and Biochemistry* 1993, 57:1655-1659.

Masai E, Katayama Y, Kubota S, Kawai S, Yamasaki M, Morohoshi N: A bacterial enzyme degrading the model lignin compound β-etherase is a member of the glutathione-S-transferase superfamily. *Febs Letters* 1993, 323:135-140.

Masai E, Ichimura A, Sato Y, Miyauchi K, Katayama Y, Fukuda M: Roles of the enantioselective glutathione S-transferases in cleavage of β-aryl ether. *Journal of Bacteriology* 2003, 185:1768-1775.

Masai E, Katayama Y, Fukuda M (2007) Genetic and biochemical investigations on bacterial catabolic pathways for lignin-derived aromatic compounds. *Biosci Biotechnol Biochem* 71(1):1-15.

Mashiyama, S.T., Malabanan, M.M., Akiva, E., Bhosle, R., Branch, M.C., Hillerich, B., Jagessar, K., Kim, J., Patskovsky, Y., Seidel, R.D., et al. (2014). Large-scale determination of sequence, structure, and function relationships in cytosolic glutathione transferases across the biosphere. PLoS Biol. 12, e1001843.

McCoy, A.J., Grosse-Kunstleve, R.W., Adams, P.D., Winn, M.D., Storoni, L.C., and Read, R.J. (2007). Phaser crystallographic software. *J Appl Crystallogr* 40, 658-674.

Moore DD: Current protocols in molecular biology. Edited by Ausubel FM, Brent R, Kingston RE, Moore DD, Seidman JG, Smith JA, Struhl K: John Wiley & Sons; 2003 (Book—Copy Not Provided).

Notomista E, et al. (2011) the marine isolate *Novosphingobium* sp. PP1Y shows specific adaptation to use the aromatic fraction of fuels as the sole carbon and energy source. *Microb Ecol* 61(3):582-594.

Ohta Y, Nishi S, Hasegawa R, Hatada Y. (2015) Combination of six enzymes of a marine Novosphingobium converts the stereoisomers of β-O-4 lignin model dimers into the respective monomers. *Sci Rep* 5:15105.

Palamuru S, et al. (2015) Phylogenetic and kinetic characterization of a suite of dehydrogenases from a newly isolated bacterium, strain SG61-1L, that catalyze the turnover of guaiacylglycerol-β-guaiacyl ether stereoisomers. *Appl Environ Microbiol* 81(23):8164-8176.

(56) References Cited

OTHER PUBLICATIONS

Pal, R., Bhasin, V.K., and Lal, R. (2006). Proposal to reclassify [*Sphingomonas*] *xenophaga* Stolz et al. 2000 and [*Sphingomonas*] *taejonensis* Lee et al. 2001 as *Sphingobium xenophagum* comb. nov. and *Sphingopyxis taejonensis* comb. nov., respectively. *Int. J. Syst. Evol. Microbiol.* 56, 667-670.
Patskovsky Y, et al. PDB ID: 4mzw Crystal structure of nu-class glutathione transferase Yghu from *Streptococcus sanguinis* SK36, complex with glutathione disulfide, target EFI-507286. doi:10.2210/pdb4mzw/pdb.
Pereira JH, Heins RA, Gall DL, McAndrew RP, Deng K, Holland KC, Donohue TJ, Noguera DR, Simmons BA, Sale KL, et al.: Structural and biochemical characterization of the early and late enzymes in the lignin β-aryl ether cleavage pathway from *Sphingobium* sp. SYK-6. *Journal of Biological Chemistry* 2016, 291:10228-10238.
Pettersen EF, et al. (2004) UCSF Chimera—a visualization system for exploratory research and analysis. *J Comput Chem* 25(13):1605-1612.
The PyMOL Molecular Graphics System, Version 1.8.2.1 Schrödinger, LLC Available at: https://www.pymol.org/.
Rahimi A, Azarpira A, Kim H, Ralph J, Stahl SS: Chemoselective metal-free aerobic alcohol oxidation in lignin. *Journal of the American Chemical Society* 2013, 135:6415-6418.
Rahimi A, Ulbrich A, Coon JJ, Stahl SS: Formic-acid-induced depolymerization of oxidized lignin to aromatics. *Nature* 2014, 515:249-252.
Ralph J, Peng JP, Lu FC, Hatfield RD, Helm RF: Are lignins optically active? *Journal of Agricultural and Food Chemistry* 1999, 47:2991-2996.
Reiter J, Pick A, Wiemann LO, Schieder D, Sieber V: a novel natural NADH and NADPH dependent glutathione reductase as tool in biotechnological applications. *JSM Biotechnol Bioeng* 2014, 2:1028-1035.
Santos RB, Hart P, Jameel H, Chang H. Wood based lignin reactions important to the biorefinery and pulp and paper industries. *BioResources* 2013, 8(1):1456-1477.
Sato Y, et al. (2009) Identification of three alcohol dehydrogenase genes involved in the stereospecific catabolism of arylglycerol-β-aryl ether by *Sphingobium* sp. strain SYK-6. *Appl Environ Microbiol* 75(16):5195-5201.
Schäfer, A., Tauch, A., Jäger, W., Kalinowski, J., Thierbach, G., and Pühler, A. (1994). Small mobilizable multi-purpose cloning vectors derived from the *Escherichia coli* plasmids pK18 and pK19: selection of defined deletions in the chromosome of *Corynebacterium glutamicum. Gene* 145, 69-73.
Shevchuk NA, Bryksin AV, Nusinovich YA, Cabello FC, Sutherland M, Ladisch S: Construction of long DNA molecules using long PCR-based fusion of several fragments simultaneously. *Nucleic Acids Research* 2004, 32.
Shuai L, Amiri MT, Questell-Santiago YM, Héroguel F, Li Y, Kim H, Meilan R, Chapple C, Ralph J, Luterbacher JS: Stabilization with formaldehyde facilitates the high-yield production of monomers from lignin during integrated biomass depolymerization. *Science* 2016, 354(6310):329-333.
Simon, R., Priefer, U., and Pühler, A. (1983). A Broad Host Range Mobilization System for in Vivo Genetic Engineering: Transposon Mutagenesis in Gram Negative Bacteria. *Nat Biotech* 1, 784-791.

Sinha AK, Sharma UK, Sharma N: A comprehensive review on vanilla flavor: Extraction, isolation and quantification of vanillin and others constituents. *International Journal of Food Sciences and Nutrition* 2008, 59:299-326.
Sistrom WR (1962) The kinetics of the synthesis of photopigments in *Rhodopseudomonas spheroides. J Gen Microbiol* 28:607-616.
Stanier RY, Palleroni NJ, Doudoroff M (1966) The aerobic pseudomonads: a taxonomic study. *J Gen Microbiol* 43(2):159-271.
Stewart JJ, Akiyama T, Chapple C, Ralph J, Mansfield SD: The effects on lignin structure of overexpression of ferulate 5-hydroxylase in hybrid poplar. *Plant Physiology* 2009, 150:621-635.
Stolz A, et al. (2000) Description of *Sphingomonas xenophaga* sp. nov. For strains BN6$^T$ and N,N which degrade xenobiotic aromatic compounds. *Int J Syst Evol Microbiol* 50 Pt 1:35-41.
Stourman NV, et al. (2011) Structure and function of YghU, a nu-class glutathione transferase related to YfcG from *Escherichia coli. Biochemistry* 50(7):1274-1281.
Studier FW (2005) Protein production by auto-induction in high density shaking cultures. *Protein Expr Purif* 41(1):207-234.
Sugimoto T, Akiyama T, Matsumoto Y, Meshitsuka G: the erythro/threo ratio of β-O-4 structures as an important structural characteristic of lignin—Part 2. Changes in erythro/threo (E/T) ratio of β-O-4 structures during delignification reactions. *Holzforschung* 2002, 56:416-421.
Tanamura K, Kasai D, Nakamura M, Katayama Y, Fukuda M, Masai E: Identification of the third glutathione S-transferase gene involved in the stereospecific cleavage of β-aryl ether in *Sphingobium* sp. strain SYK-6. Journal of Biotechnology 2010, 150:S235-S235.
Tavano CL, Podevels AM, Donohue TJ (2005) Identification of genes required for recycling reducing power during photosynthetic growth. *J Bacteriol* 187(15):5249-5258.
Taylor, R.G., Walker, D.C., and McInnes, R.R. (1993). *E. coli* host strains significantly affect the quality of small scale plasmid DNA preparations used for sequencing. *Nucleic Acids Res.* 21, 1677-1678.
Thuillier, A., Roret, T., Favier, F., Gelhaye, E., Jacquot, J.-P., Didierjean, C., and Morel-Rouhier, M. (2013). Atypical features of a Ure2p glutathione transferase from Phanerochaete chrysosporium. *FEBS Lett.* 587, 2125-2130.
Tsien RY. (1998) The green fluorescent protein. *Annu Rev Biochem.* 67:509-44.
U.S. DOE (2015) Lignocellulose Biomass for Advanced Biofuels and Bioproducts: Workshop Report, DOE/SC-0170. U.S. Department of Energy Office of Science. Available at: http://genomicscience.energy.gov/biofuels/lignocellulose/ [Accessed May 17, 2017].
Vicuña R, González B, Mozuch MD, Kirk TK (1987) Metabolism of lignin model compounds of the arylglycerol-β-aryl ether type by *Pseudomonas acidovorans* D(3). *Appl Environ Microbiol* 53(11):2605-2609.
Wadington MC, Ladner JE, Stourman NV, Harp JM, Armstrong RN (2009) Analysis of the structure and function of YfcG from *Escherichia coli* reveals an efficient and unique disulfide bond reductase. *Biochemistry* 48(28):6559-6561.
Wadington MC, Ladner JE, Stourman NV, Harp JM, Armstrong RN (2010) Correction to Analysis of the structure and function of YfcG from *Escherichia coli* reveals an efficient and unique disulfide bond reductase. *Biochemistry* 49(50):10765.
Wood WB (1966) Host specificity of DNA produced by *Escherichia coli*: bacterial mutations affecting the restriction and modification of DNA. *J Mol Biol* 16(1):118-133.

\* cited by examiner

```
NaGSTNu     M---------SSEYVPPKVWKWDKANGGAFASVNRPVAGPTSERELPVGKHPFQVYSLGT  51
SYK6GSTNu   MADSDPSMNQPTGYVPPKVWTWDKENGGQFSNINAPTAGARQDVTLPVGEHPIQLYSLGT  60
ecYghU      MT--------DNTYQPAKVWTWDKSAGGAFANINRPVSGPTHEKTLPVGKHPLQLYSLGT  52
ssYghU      M-----------TYQLPKVWSAADSDQGKFSGINQPTAGVRFEQKLPVGKEPFQLYSLGT  49
ecYfcG      M----------------------------------------------------IDLYFAPT   9
GST3        M----------------------------------------------------LELWTSET   9
PcUre2pB1   MA--------TNT-----------------------------------DKPVVHYTAPT  16

*                                    *         **
NaGSTNu     PNGQKATIMLEELLQLGFSEAEYDAWLIKIFEGD------QFTSG-FVDINPNSKIPAMV 104
SYK6GSTNu   PNGQKVTIMLEELLAAGF-DAEYDAWLIKIYTGE------QFGSD-FVAINPNSKIPAMM 112
ecYghU      PNGQKVTIMLEELLALGVTGAEYDAWLIRIGDGD------QFSSG-FVEVNPNSKIPALR 105
ssYghU      PNGVKVTIMLEELLAAGVTEATYDLYKISIMDGD------QFGSD-FVKINPNSKIPALL 102
ecYfcG      PNGHKITLFLEEA------ELDYRLIKVDLGKGG------QFRPE-FLRISPNNKIPAIV  56
GST3        PNGWKTTIMLEEL------DANYTLRPISLTNRE------QKEDW-YLARNPNGRIPTLI  56
PcUre2pB1   PNGWVPAILLEELKAV-YGGPDYETVKMSIRDADIGKVHNQVKSDWFLKICPNGRIPAI-  74

**
NaGSTNu     DRS---GPEPFRVFESGAILMHLAEKFGVFLP------TSGPARAECLSWLFWQVGSAPF 155
SYK6GSTNu   DHG---LDPPLRLFESGSMLVYLAEKFGAFLP------TEIRKRTETFNWLMWQMGSAPF 163
ecYghU      DHT---HNPPIRVFESGSILLYLAEKFGYFLP------QDLAKRTETMNWLFWLQGAAPF 156
ssYghU      DQS---GHKPIPVFESANILLYLAEKFGKLIP------SDLAGRTEVLNWLFWQTGAAPF 153
ecYfcG      DHSPADGGEPLSLFESGAILLYLAEKTGLFLS------HETRERAATLQWLFWQVGGLGP 110
GST3        DHEVDAGNGGFAVFESGAILIYLAEKFGRFLP------ADTMGRSRAIQWVMWQMSGLGP 110
PcUre2pB1   ------THEGFPVFETSAILLYLAQHFDKENAFSRDPVKDPKGYSEELQWLFFAHGGIGP 129

#        *
NaGSTNu     IGGGFGHFYNYAPIKIEYAIDRYAMETKRLFDVANRRLAESRYLAGDEYTIADLATYTWF 215
SYK6GSTNu   VGGGFGHFYAYAPFKIEYAIDRYAMETKRQLDVLDKNLADREFMIGDEITIADFAIFPWY 223
ecYghU      LGGGFGHFYHYAPVKIEYAINRFTMEAKRLLDVLDKQLAQHKFVAGDEYTIADMAIWPWF 216
ssYghU      LGGGFGHFFNYAPEKLEYPINRFTMEAKRQLDLLDKELAKKAYIAGEDYSIADIAIWSWY 213
ecYfcG      MLGQNHHFNHAAPQTIPYAIERYQVETQRLYHVLNKRLENSPWLGGENYSIADIACWPWV 170
GST3        MMGQATVFNRYFEPRLPEVIDRYTRESRRLFEVMDTHLADNEFLAG-DYSIADIACFPWV 169
PcUre2pB1   MQGQANHFNLYAPEKIPYAINRYLNESKRLYRVLDDRLKGREYILG-TYGIADIKIFGWA 187

NaGSTNu     GNIYRGEAYGEAATFLSMHEYEHVGRWVGEIDARPGVLRGRLVNSSKG-----LAERHDA 270
SYK6GSTNu   GSIMRGG-Y-NAQEFLSTHEYRNVDRWVTQLSERTGVKRGLLVNSAGRP-GGGIAERHSA 280
ecYghU      GNVVLGGVY-DAAEFLDAGSYKHVQRWAKEVGERPAVKRGRIVNRTNGPLNEQLHERHDA 275
ssYghU      GQLVQDKLYPGAAEFLDAASYKHLSAWAEKIAARPAVQRGLA------------AEYQEI 261
ecYfcG      NA--------WTRQRIDLAMYPAVKNWHERIRSRPATGQALLKAQLG-------DERSDS 215
GST3        RG--------HDWACIDMEGLPHLQRWFETIGERPAVQRGLLLPEPPKA-----DEMAEK 216
PcUre2pB1   RI--------APRTGLDLDEFPNVKAWVERIEKRPAVQAGI--NSCN------------- 224

NaGSTNu     SDFDALPPESLQAIVKG-F      288   SEQ ID NO:18
SYK6GSTNu   ADLDASIKAAEQEAAKTEA      299   SEQ ID NO:22
ecYghU      SDFETNTEDKRQG------      288   SEQ ID NO:26
ssYghU      K------------------      262   SEQ ID NO:32
ecYfcG      -------------------      215   SEQ ID NO:30
GST3        T--------TRQGKNIL-A      226   SEQ ID NO:34
PcUre2pB1   -------------------      224   SEQ ID NO:36
```

FIG. 5

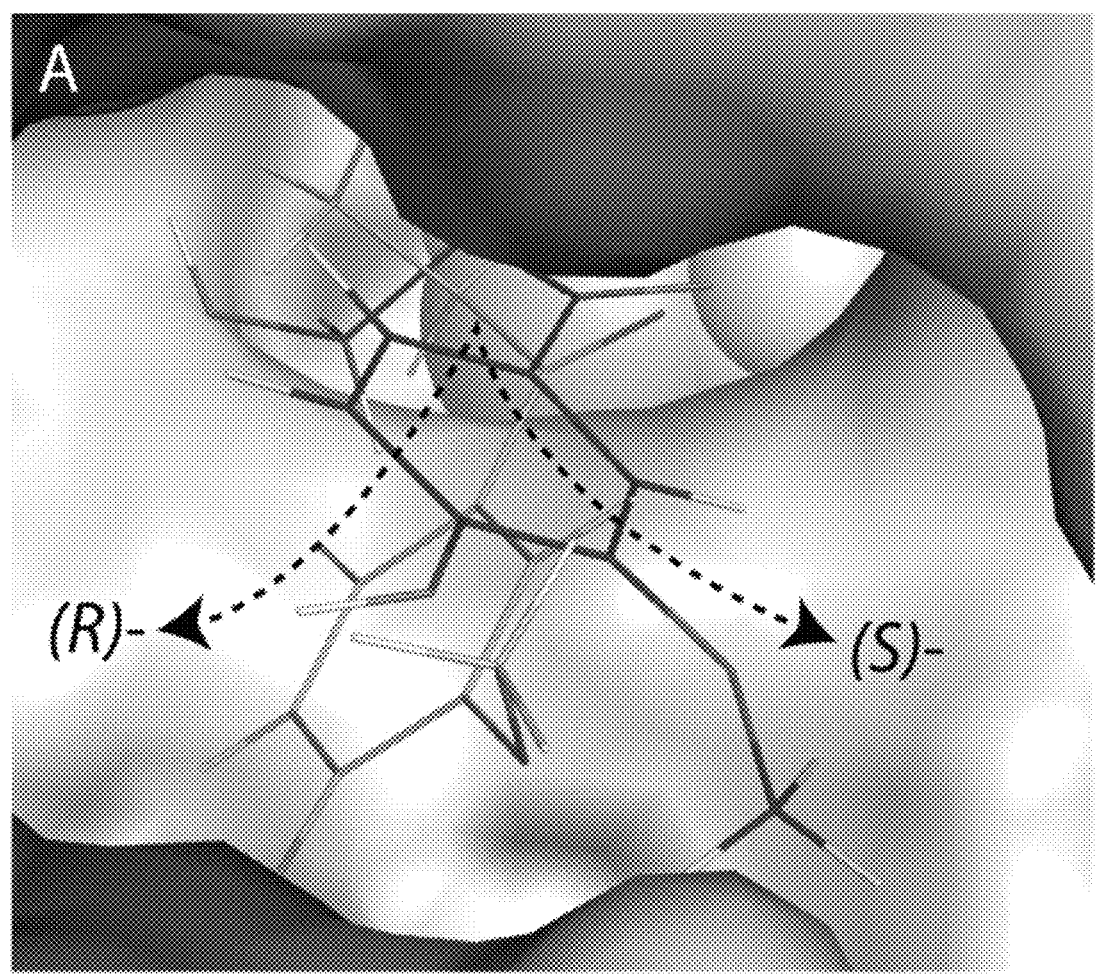
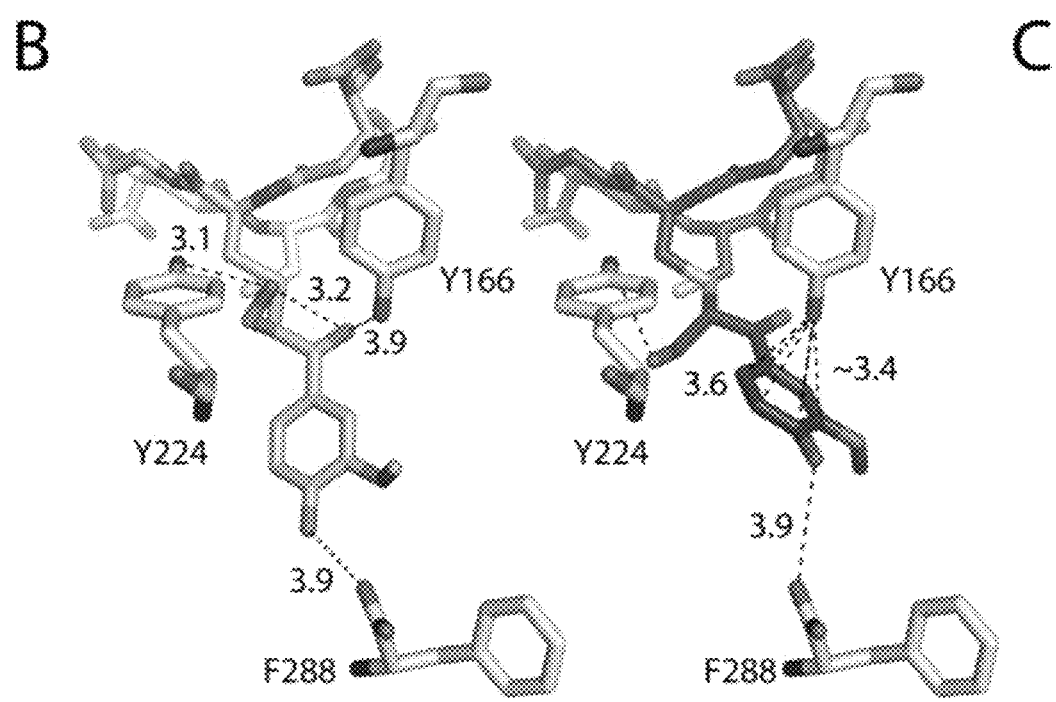
FIG. 10

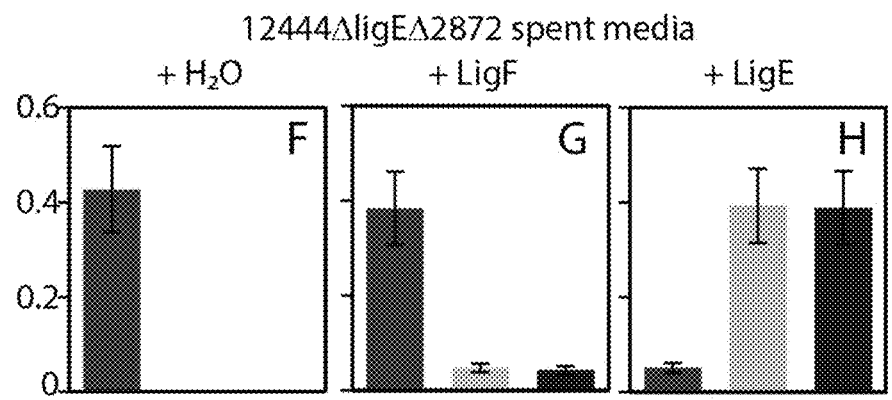
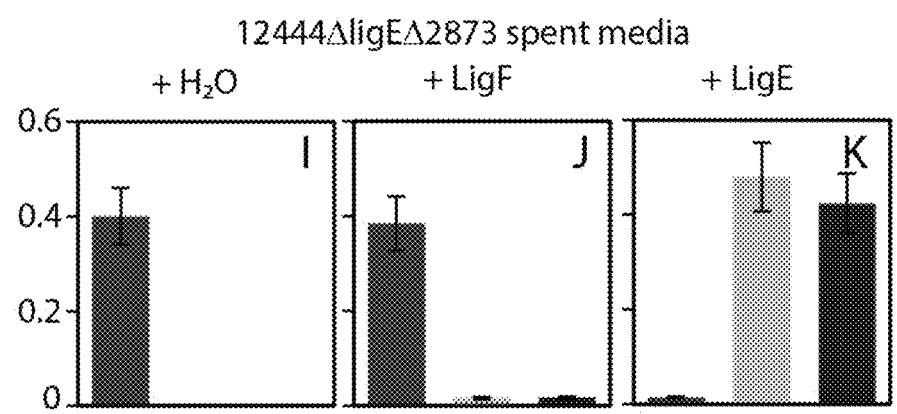
Concentrations of MPHPV, GS-HPV, and guaiacol following *in vitro* reactions (mM)
FIG. 25

Alignments of Saro_2872 and Saro_2873 with known LigF enzymes.

```
Saro_2872      ---------------MSALLYHGEPNGASLTVLAALAETGLDIECRRIDLLAGERHSLPGIVDPV  50
Saro_2873      --------------MDEVSLYHWEPNANSGKPMLALMEKGVPFSSHYIDMLQFDQHK-------PE  45
Saro_2865      ---------------MALKYYHAEPLANSLKSMVPLKEKGLAYESIYVDLHKFEQHQ-------PW  44
Saro_2091      MVIPLGEDNTIMLKLYSFGPAANSMKPLLTVFEKGLDVEKHRLDPAKFEHHT--------DW  54
SLG_08650      ---------------MTLKLYSFGPGANSLKPLATLYEKGLEFEQVFVDPSKFEQHS-------DW  44
PP1Y_AT11660   ---------------MTLYSFGPGANSLKPLLALYEKGLEFTPRFVDPTRFEHHE-------EW  43
GST4_MBES04    ---------------MLTLYSFGPGANSLKPLLALYEKGLEFTPRFVDPTKFEHHE-------EW  43
                              *  . *  .    :  : *.*:       :*      ::*

Saro_2872      ALDLSIEGEGPVLVIDGEAMTESVFLAQYLDEAAGGV------GLQPTDAYARWEMMMWCR  105
Saro_2873      YLAINPQGTIPAMTHNGQVLTESTAIMEYVNDRFDGP------DLMPADAQDRWRVRWWMK  100
Saro_2865      FTAINPEGQVPVLDHDGTIITHTTVINEYLEDAFPDAQPADAPLRPRDPVGAARMRYWNK  104
Saro_2091      FKAINPRGQVPALVDGDKVVTESTVICEYLEDEYPTE-V----ALRPADSFGKAQMRIWTK  110
SLG_08650      FKKINPRGQVPALWHDGKVVTESTVICEYLEDVFPESGN-----SLRPADPFKRAEMRVWTK  101
PP1Y_AT11660   FKKINPRGQVPALDHDGHIITESTVICEYLEDAFPEA-P----RLRPVDPVMIAEMRVWTK  99
GST4_MBES04    FKKINPRGQVPALDHDGNVITESTVICEYLEDAFPDA-P----RLRPTDPVQIAEMRVWTK  99
                :. .*  *.:  ..  :*.:.. : :*:::         * *    .: *  :

Saro_2872      QITERLSPAAALLGNLATSQSAIAAIPAEDFAILA-ARIVSDDLRERWQALNDDAVNAAQ  164
Saro_2873      FMDQWLGPSFSMIGWSVFVGPMVRQRDPAELAAAI-DRIPLPERRTAWRKAINGDFSESE  159
Saro_2865      FIDEHVMNYVSMHGWHRMVGVIARNIASGDFEKLL-ESIPLPDQRKKWATARSG-FSEAD  162
Saro_2091      WVDEYFCWCVSTIGWHRYVGNMVKSLSDAEFEEKV-KAIPVIEQQVKWRRAREG-FPQDM  168
SLG_08650      WVDEYFCWCVSTIGWAFGIKAIAQKMSDEEFEEHINKNVPIPEQQLKWRRARNG-FPQEM  160
PP1Y_AT11660   WVDEYFCWCVSTIGWERMIGPMARALSDEEFEAKV-ARIPVPEQRTKWRTARTG-FPKEV  157
GST4_MBES04    WVDEYFCWCVSTIGWERGIGPMARALSDEEFEEKV-KRIPIPEQQAKWRSARAG-FPKEV  157
                 : :.    :  *        ::         : ::* ..

Saro_2872      VADSETKVAAAVDRCEKQLGDGREWLMGTFSIADLVTYSWLAGMEP----LR--PAAFADA  219
Saro_2873      MAESRRRVGLGIAKLEEELGKRPYVGSNQYSLADINIFNSTYSLPI---SQPDLAGKDRT  216
Saro_2865      LANATAKIEYALDKVEKQLGETKWLAGDTYTLADINFYSHCGAMVE----RMFPEMEVARRA  220
Saro_2091      LDEEMRKIAYSVRKLDDHLADHEWLVPGQYTLADICNFAIANGMQF----GFAELVNKQDT  225
SLG_08650      LDEEFRKVGVSVARLEETLSKQDYLVDTGYSLADICNFAIANGLQRPGGFFGDYVNQEKT  220
PP1Y_AT11660   LDEEMRKIGVSVNRLETRLAESPWLAGENFSLADVCNFAIANGMQN----GFSDIVNREAT  214
GST4_MBES04    LDEEMRKIRVSIDRLEKRLSESTWLAGEDYTLADICNFAIANGMEK----GFDDIVNTAAT  214
                 :  :: .:: : : *..  :::**:  :     .:         :

Saro_2872      PLVKAWLARTAARPCVQAALARATISEPLRAWAPGPEINRWG            261
Saro_2873      PNIMRWLKRVYTREAVKKTWAMGKTDLAHRYGLIMAEIEG---            256
Saro_2865      PRLCEWRDRVAARPAVAEALKSEDRTAPGLRVWSGEVR-----            258
Saro_2091      PHLVRWIEQINERPAVKQMFAQVELEKLGPRE----------            257
SLG_08650      PGLCAWLDRINARPAIKEMFEKSKREDLLKRQNEKVA------            257
PP1Y_AT11660   PHLVAWIEKINDRPACKAMFANSKSEFADRGQKVTA------            250
GST4_MBES04    PNLVAWIERINARPACIEMFAKSKSEFAARKPFAKSEEQAQA            256
                *   :  *    :   *   .

Saro_2872      SEQ ID NO:40
Saro_2873      SEQ ID NO:42
Saro_2865      SEQ ID NO:43
Saro_2091      SEQ ID NO:44
SLG_08650      SEQ ID NO:45
PP1Y_AT11660   SEQ ID NO:46
GST4_MBES04    SEQ ID NO:47
```

FIG. 29

IN VITRO METHODS OF CHEMICAL CONVERSION USING NON-STEREOSPECIFIC GLUTATHIONE LYASES

This invention was made with government support under DE-FC02-07ER64494 and DE-SC0018409 awarded by the US Department of Energy. The government has certain rights in the invention.

FIELD OF THE INVENTION

The invention relates to the enzymatic depolymerization of lignin and the enzymatic processing of other aromatic compounds.

BACKGROUND

Lignin provides structural rigidity in terrestrial plants and is largely comprised of guaiacyl and syringyl monoaromatic phenylpropanoid units that are covalently linked together in a purely chemical radical coupling polymerization process. The most prevalent type of inter-unit linkage between units is the β-ether linkage in so-called β-ether units making up the lignin polymer.

Because lignin is rich in aromatics, lignin can potentially serve as a source for a number of valuable aromatic polymers, oligomers, and monomers. However, lignin is notoriously difficult to process or depolymerize into simpler compounds.

A number of chemical methods for depolymerizing lignin are known, but these methods tend to involve high temperatures or pressures, expensive catalysts, and organic solvents. Tools and methods of depolymerizing lignin that avoid at least some of these drawbacks are needed.

SUMMARY OF THE INVENTION

The invention at least in part is directed to an enzymatic system that catalyzes β-ether cleavage of actual lignin in vitro with the recycling of cosubstrates $NAD^+$ and GSH. In an exemplary version, the system uses the known LigD, LigN, LigE, and LigF enzymes from *Sphingobium* sp. strain SYK-6, plus a novel, non-stereospecific glutathione transferase from *Novosphingobium aromaticivorans* DSM12444 ($NaGST_{Nu}$). BaeA can be used in addition to or in place of LigE. A glutathione reductase from *Allochromatium vinosum* DSM180 (AvGR) is used to recycle the cosubstrates. The depolymerization of actual lignin with these enzymes is illustrated in FIGS. 1 and 16. The enzymatic depolymerization of lignin provided herein has several advantages over chemical routes as it (1) does not require high temperatures or pressures; (2) does not require expensive catalysts; (3) could be performed in an aqueous environment, eliminating the need for solvents (and subsequent separation/recycle); and (4) results in a well-defined set of aromatic monomers that have not undergone chemical transformations, and hence are more amenable for downstream processing (i.e., upgrading).

More generally, the invention encompasses methods of processing lignin. One method of the invention comprises contacting lignin comprising β-O-4 ether (β-ether) linkages in vitro with a dehydrogenase, a β-etherase, and a glutathione lyase. The dehydrogenase preferably comprises at least one of LigD, LigO, LigN, and LigL. The β-etherase preferably comprises at least one of LigE, LigF, LigP, and BaeA. The glutathione lyase preferably comprises at least one of LigG and a non-stereospecific glutathione lyase comprising an amino acid sequence at least about 80%, 85%, 90%, or 95% identical to any of: SEQ ID NO:18 ($NaGST_{Nu}$); residues 21-313 of SEQ ID NO:20 (recombinant $NaGST_{Nu}$); SEQ ID NO:22 ($SYK6GST_{Nu}$); residues 21-324 of SEQ ID NO:24 (recombinant $SYK6GST_{Nu}$); SEQ ID NO:26 (ecYghU); residues 21-313 of SEQ ID NO:28 (recombinant ecYghU); SEQ ID NO:30 (ecYfcG); SEQ ID NO:32 (ssYghU); SEQ ID NO:34 (GST3); and SEQ ID NO:36 (PcUre2pB1).

In some versions, the non-stereospecific glutathione lyase comprises at least one, at least two, at least three, at least four, at least five, at least six, at least seven, at least eight, at least nine, at least ten, or all of: asparagine or a conservative variant of asparagine at a position corresponding to position 25 of SEQ ID NO:18 ($NaGST_{Nu}$); threonine or a conservative variant of threonine at a position corresponding to position 51 of SEQ ID NO:18 ($NaGST_{Nu}$); asparagine or a conservative variant of asparagine at a position corresponding to position 53 of SEQ ID NO:18 ($NaGST_{Nu}$); glutamine or a conservative variant of glutamine at a position corresponding to position 86 of SEQ ID NO:18 ($NaGST_{Nu}$); lysine, a conservative variant of lysine, arginine, or a conservative variant of arginine at a position corresponding to position 99 of SEQ ID NO:18 ($NaGST_{Nu}$); isoleucine or a conservative variant of isoleucine at a position corresponding to position 100 of SEQ ID NO:18 ($NaGST_{Nu}$); glutamate or a conservative variant of glutamate at a position corresponding to position 116 of SEQ ID NO:18 ($NaGST_{Nu}$); serine, threonine, a conservative variant of serine, or a conservative variant of threonine at a position corresponding to position 117 of SEQ ID NO:18 ($NaGST_{Nu}$); tyrosine or a conservative variant of tyrosine at a position corresponding to position 166 of SEQ ID NO:18 ($NaGST_{Nu}$); arginine or a conservative variant of arginine at a position corresponding to position 177 of SEQ ID NO:18 ($NaGST_{Nu}$); and tyrosine or a conservative variant of tyrosine at a position corresponding to position 224 of SEQ ID NO:18 ($NaGST_{Nu}$).

In some versions, the contacting occurs in the presence of a glutathione (GSH) reductase that catalyzes reduction of glutathione disulfide (GSSG). The GSH reductase in some versions comprises an amino acid sequence at least 95% identical to SEQ ID NO:38 (AvGR).

Another method of the invention is a method of chemical conversion. The chemicals converted in the method preferably comprise aromatic chemicals. One method comprises contacting a first compound in vitro with a non-stereospecific glutathione lyase to yield a second compound. The non-stereospecific glutathione lyase may comprise any of those described above or elsewhere herein but preferably comprises a non-stereospecific glutathione lyase having an amino acid sequence at least about 80%, 85%, 90%, or 95% identical to any of: SEQ ID NO:18 ($NaGST_{Nu}$); residues 21-313 of SEQ ID NO:20 (recombinant $NaGST_{Nu}$); SEQ ID NO:22 ($SYK6GST_{Nu}$); residues 21-324 of SEQ ID NO:24 (recombinant $SYK6GST_{Nu}$); SEQ ID NO:26 (ecYghU); residues 21-313 of SEQ ID NO:28 (recombinant ecYghU); SEQ ID NO:30 (ecYfcG); SEQ ID NO:32 (ssYghU); SEQ ID NO:34 (GST3); and SEQ ID NO:36 (PcUre2pB1). The first compound preferably has a structure of Formula I or a salt thereof:

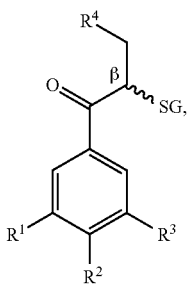

(I)

wherein R¹, R², and R³ are each independently —H, —OH, —O-alkyl, —O-lignin, or -lignin; R⁴ is —H, —OH, —SH, —COOH, —SO₃H, or —O-lignin; and SG is glutathione bound in an S or R configuration. The second compound has a structure of Formula II or a salt thereof:

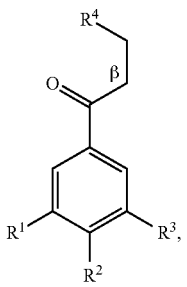

(II)

wherein R¹, R², R³, and R⁴ are as defined above.

The invention also encompasses compositions. The compositions may include any of the components employed in the methods described herein. One composition of the invention comprises lignin comprising β-O-4 ether linkages, a dehydrogenase, a β-etherase, and a glutathione lyase. The dehydrogenase, a β-etherase, and a glutathione lyase preferably include any of those described above or elsewhere herein. In some versions, the composition further comprises a glutathione (GSH) reductase that catalyzes reduction of glutathione disulfide (GSSG). The GSH reductase in some versions comprises a sequence at least about 95% identical to SEQ ID NO:38 (AvGR).

The invention also encompasses recombinant enzymes. The recombinant enzymes may include recombinant versions of any of the enzymes described above or elsewhere herein. The recombinant enzymes preferably include a recombinant non-stereospecific glutathione lyase. The non-stereospecific glutathione lyase may comprise any of those described above or elsewhere herein but preferably comprises a non-stereospecific glutathione lyase having an amino acid sequence at least about 80%, 85%, 90%, or 95% identical to any of: SEQ ID NO:18 (NaGST$_{Nu}$); residues 21-313 of SEQ ID NO:20 (recombinant NaGST$_{Nu}$); SEQ ID NO:22 (SYK6GST$_{Nu}$); residues 21-324 of SEQ ID NO:24 (recombinant SYK6GST$_{Nu}$); SEQ ID NO:26 (ecYghU); residues 21-313 of SEQ ID NO:28 (recombinant ecYghU); SEQ ID NO:30 (ecYfcG); SEQ ID NO:32 (ssYghU); SEQ ID NO:34 (GST3); and SEQ ID NO:36 (PcUre2pB1). The recombinant non-stereospecific glutathione lyase preferably comprises at least one non-native modification selected from the group consisting of an amino acid addition, an amino acid deletion, and an amino acid substitution.

The invention also encompasses processed lignin or compounds obtained through any of the methods described herein.

The objects and advantages of the invention will appear more fully from the following detailed description of the preferred embodiment of the invention made in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 4A:
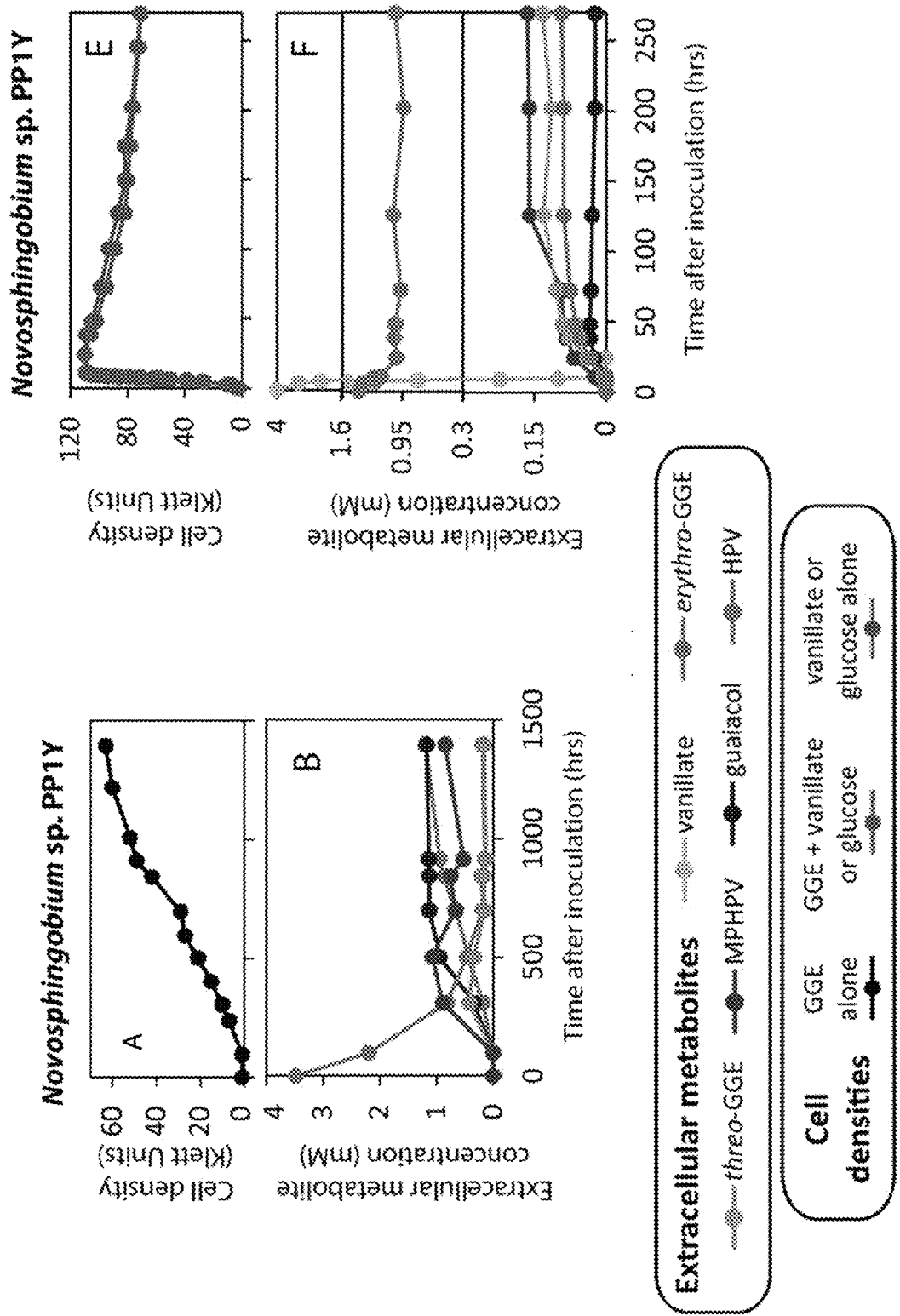
Figure 4B:
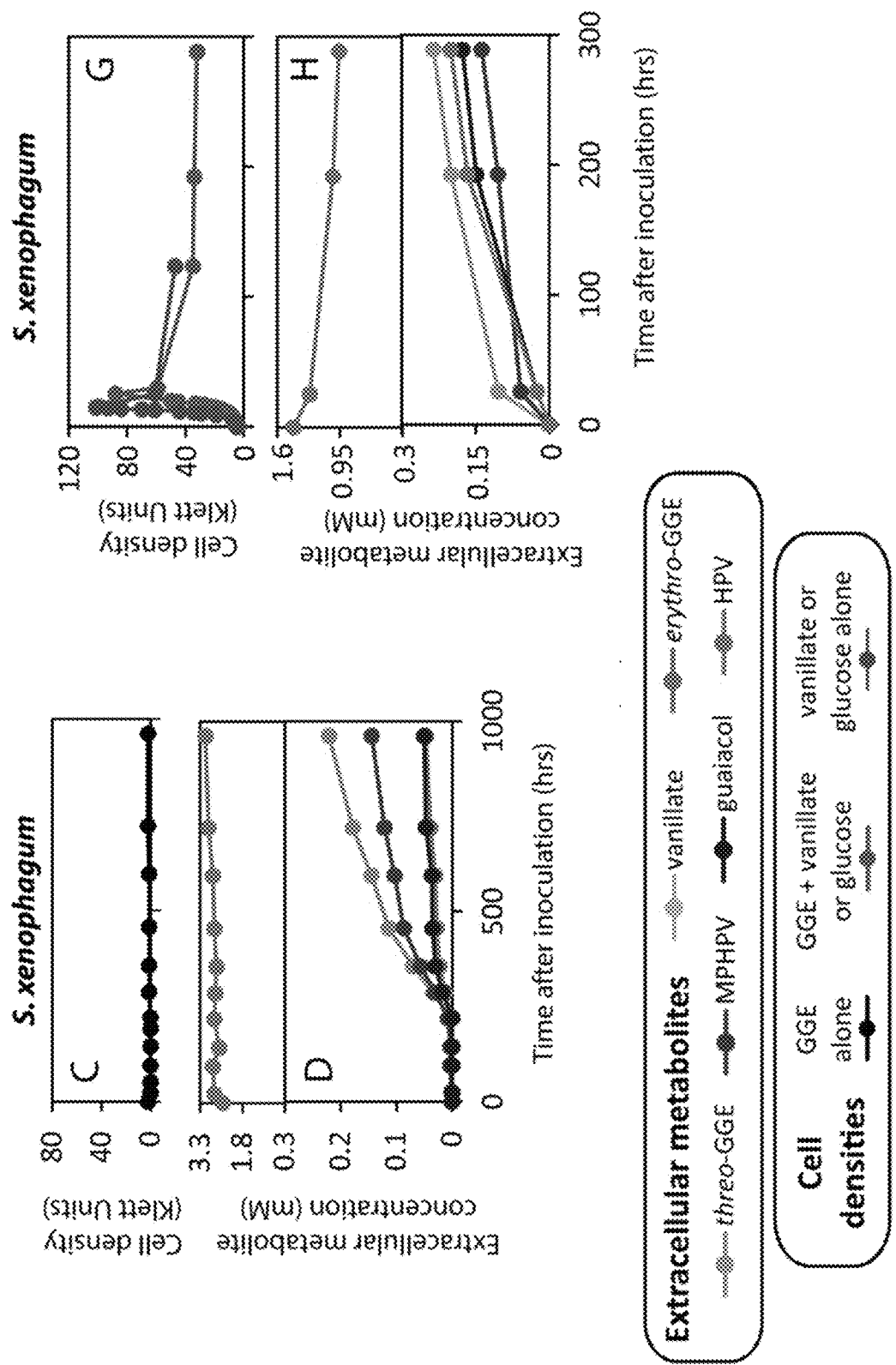

FIGS. 4A and 4B show cell densities and extracellular metabolite concentrations from cultures of *Novosphingo-* bium sp. PP1Y (FIG. 4A, panels A,B,E,F) and *Sphingobium xenophagum*(FIG. 4B, panels C,D,G,H) grown in SMB containing 3 mM GGE (FIGS. 4A and 4B, panels A,B,C,D); or 4 mM vanillate (FIG. 4A, panels E,F) or glucose (FIG. 4B, panels G,H) with 1.5 mM GGE. The y-axis segments of panels D,F,H of FIGS. 4A and 4B are at different concentration scales. For comparison, cell density data for cultures grown in SMB containing 4 mM vanillate only are included in panels.

FIG. 5 shows an amino acid sequence alignment of various exemplary non-stereospecific glutathione lyases of the invention. The aligned glutathione lyase sequences include those of NaGST$_{Nu}$ (SEQ ID NO:18), SYK6GST$_{Nu}$ (SEQ ID NO:22), ecYghU (SEQ ID NO:26), ecYfcG (SEQ ID NO:30), ssYghU (SEQ ID NO:32), GST3 (SEQ ID NO:34), and PcUre2pB1 (SEQ ID NO:36). The NaGST$_{Nu}$, ecYghU, ssYghU, ecYfcG, and PcUre2pB1 proteins have been structurally characterized. Residues from structurally solved proteins predicted to interact with GSH or GSSG molecules indicated with "*" and correspond to the following residues in SEQ ID NO:18 (NaGST$_{Nu}$): Asn25, Thr51, Asn53, Gln86, Lys99, Ile100, Glu116, Ser117, and Arg177. Residues predicted to be involved in the reaction mechanism are indicated with "#" and correspond to the following residues in SEQ ID NO:18 (NaGST$_{Nu}$): Tyr166, Tyr224, and Phe288. Alignment was made using MAFFT version 7 (mafft.cbrc.jp) (Katoh et al. 2002) in MegAlign Pro, which is part of the Lasergene 14.0 suite (DNASTAR, Madison, Wis.).

Figure 6:
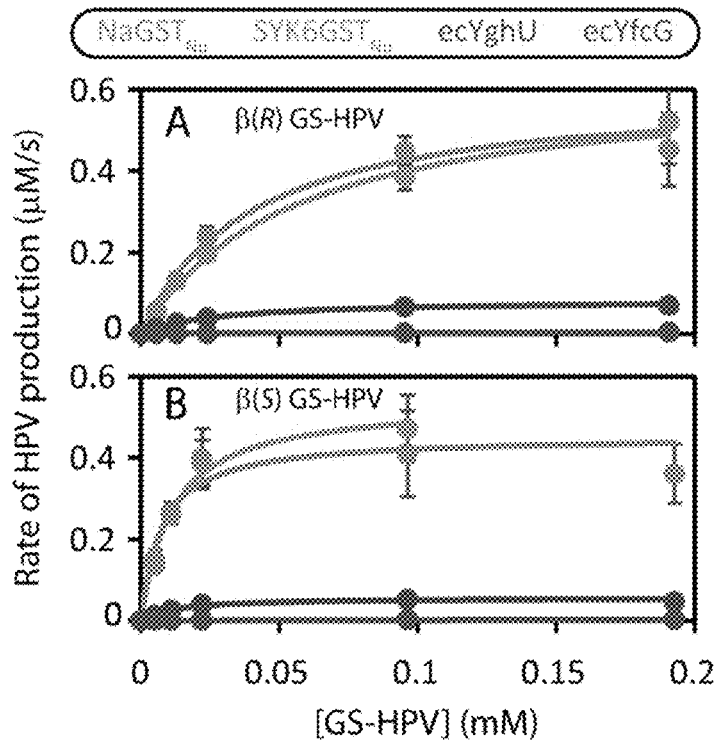

FIG. 6 shows kinetics of the conversion of the β(R)-(A) and β(S)-(B) stereoisomers of GS-HPV into HPV. Reactions used 8 nM NaGST$_{Nu}$, 195 nM ecYghU, 195 nM ecYfcG, or 47 (A) or 18 (B) nM SYK6-GST$_{Nu}$. The lines are non-linear least squares best fits to the experimental data using the Michaelis-Menten equation.

Figure 7:
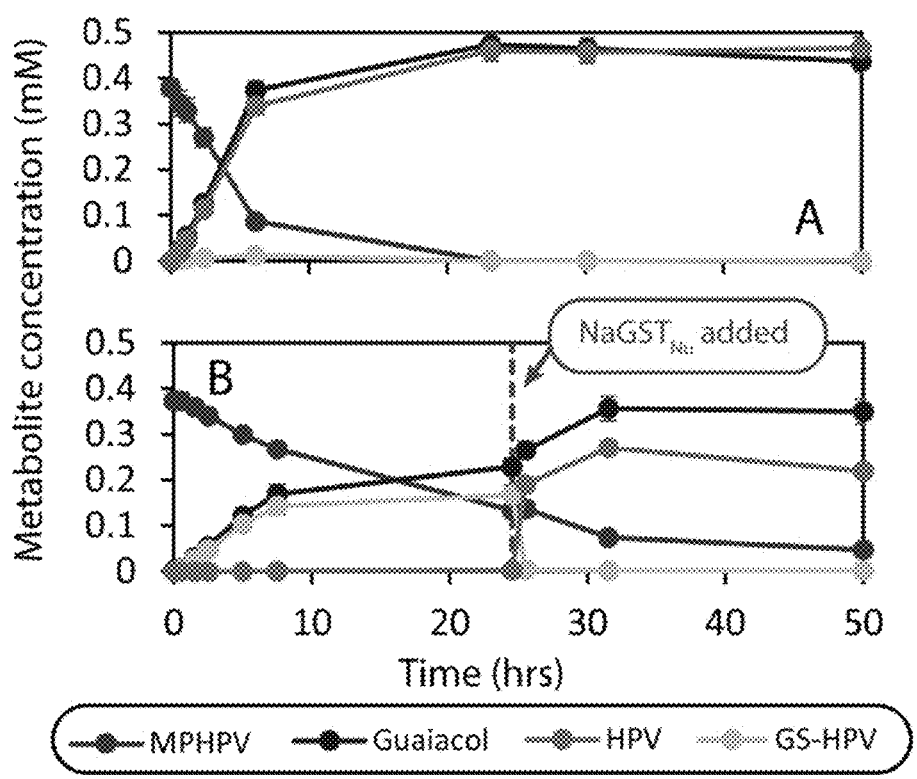

FIG. 7 shows time courses for the reaction of cell extracts from *N. aromaticivorans* strains 12444Δ1879 (A) and 12444Δ2595 (B) with a racemic sample of β(R)- and β(S)-MPHPV. The red dotted line in panel B indicates the time at which recombinant NaGST$_{Nu}$ and additional GSH were added to the reaction.

Figure 8:
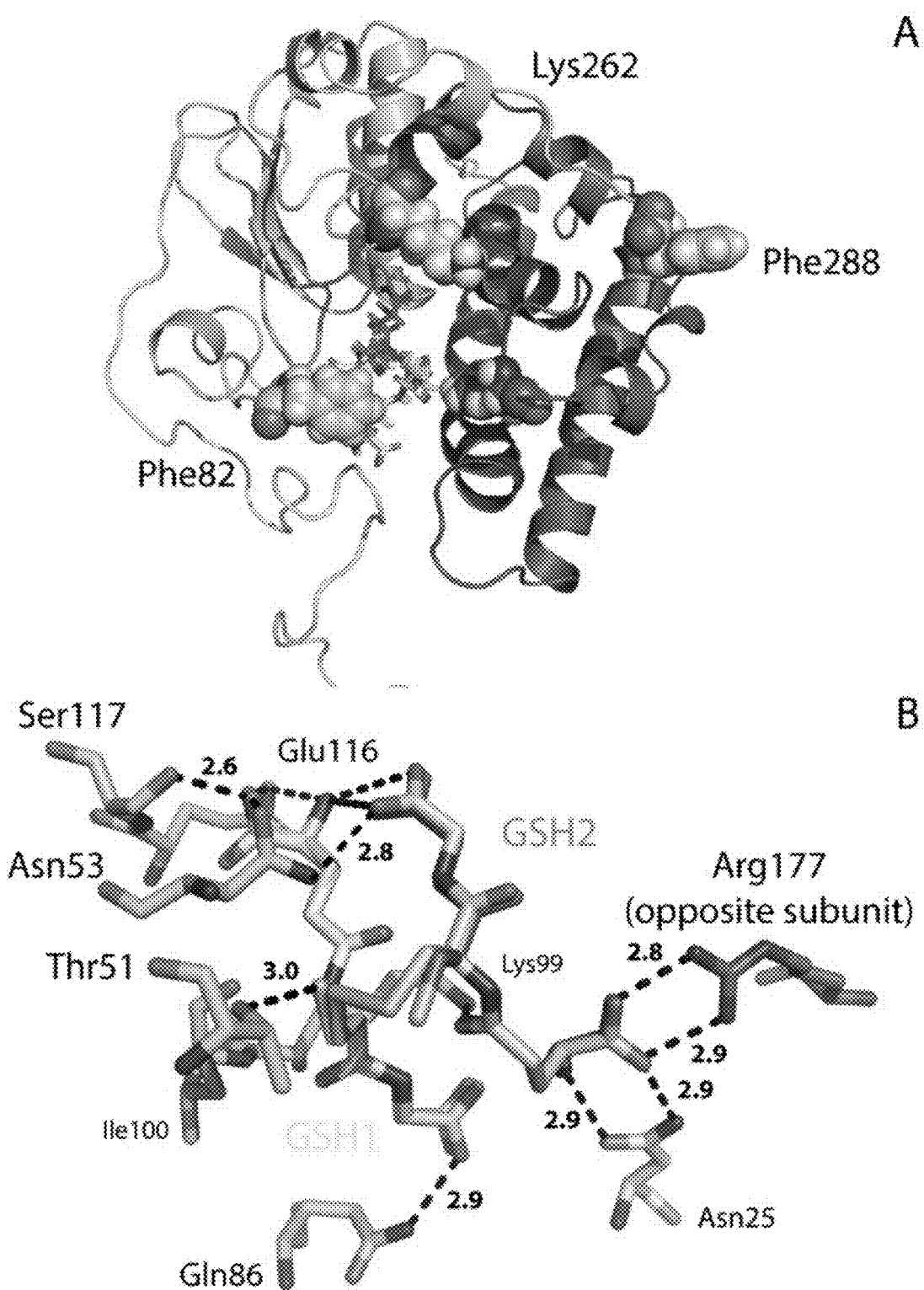

FIG. 8 shows the structure of NaGST$_{Nu}$ (pdb 5uuo). (A) Domain structure of one subunit of the homodimer. The GST1 N-terminal (thioredoxin) domain extends from Val39 to Gly129 (green), the GST2 C-terminal domain extends from Ser135 to Leu257 (maroon), and an extension of the C-terminal extends from Val258 to Phe288 (orange). (B) Residue contacts to the GSH dithiol (60% occupancy) and GS-SG (40%) in the NaGST$_{Nu}$ 5uuo structure. The carbon atoms of GSH1 are colored light cyan; those of GSH2 are dark cyan; those of GS-SG are light orange. NaGST$_{Nu}$ residues with 3.2 Å or shorter contacts to either GSH1 or GSH2 are labeled, and colored according to domain origin defined above. Selected distances between interacting atoms are shown.

Figure 9:
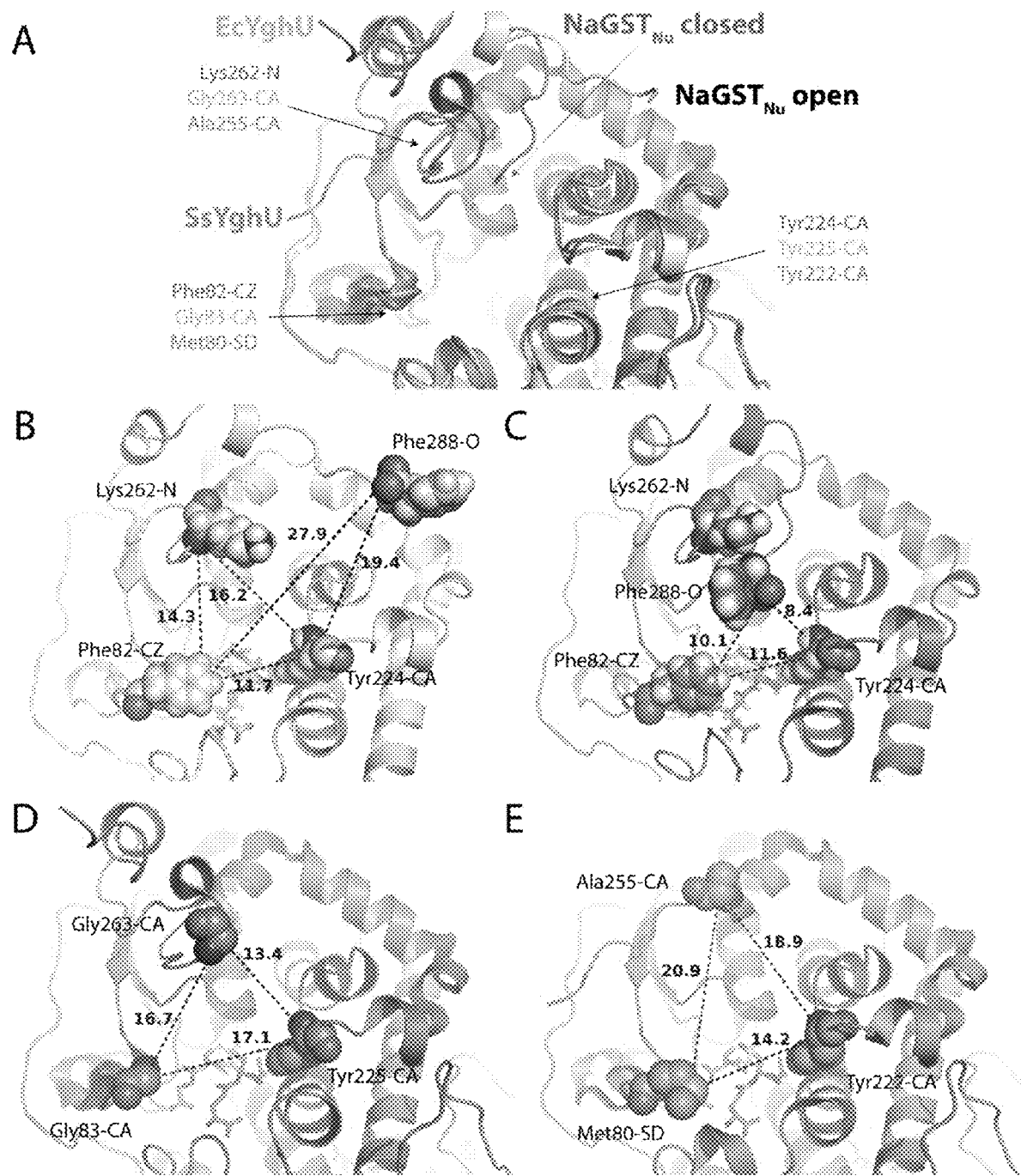

FIG. 9 shows a comparison of the active site in closely related Nu-class GSTs. (A) Alignment of subunits of NaGST$_{Nu}$ (pdb 5uuo; open form, white; closed form, blue), ecYghU (pdb 3ec8; orange), and ssYghU (pdb 4mzw; green). (B) Spatially conserved positions (Phe82, Tyr224 and Lys262) in the open form subunit of NaGST$_{Nu}$ that define a triangle over the entrance to the active site used to approximate the size of the channel opening. (C) Positions (Phe82, Tyr224 and Phe288) and triangle defined in the closed form of NaGST$_{Nu}$. (D) Positions (Gly83, Tyr225 and Gly263) and triangle defined in ecYghU. (E) Positions (Met80, Tyr222 and Ala255) and triangle defined in ssYghU.

FIG. 10 shows: (A) Molecular docking and energy-minimized positions of (R)- and (S)-GS-HPV (orange and purple lines, respectively) in the outwardly branching entrance to the active site of NaGST$_{Nu}$ (the sulfur atom of GSH1 in the active site is visible as a yellow sphere); (B) Predicted residue interactions with (R)-GS-HPV; and (C) Predicted residue interactions with (S)-GS-HPV.

Figure 11:
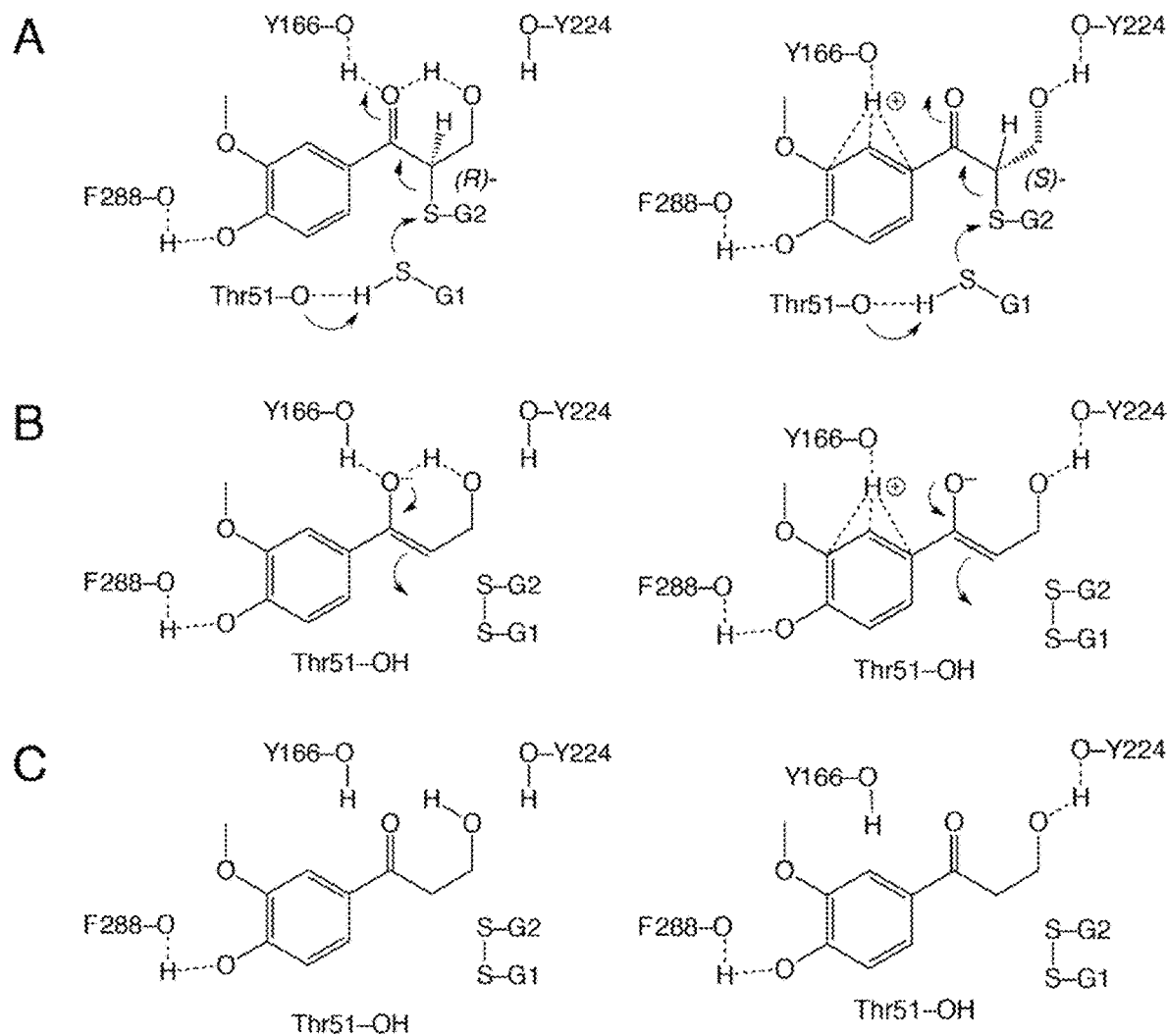

FIG. 11 shows a proposed mechanism for NaGST$_{Nu}$-catalyzed cleavage of either (R)- (left column) or (S)- (right column) thioether bonds in GS-HPV. (A) SG1 is close to the thiol of GHS2. Conserved Thr51, which lies within 3.0 Å of SG1, provides a hydrogen bond that promotes attack of SG1 on SG2 and formation of G1S-SG2. (B) Rupture of the thioether bond is facilitated by Y166, which stabilizes a transient enolate intermediate. (C) Collapse of the enolate to the observed products.

Figure 12:
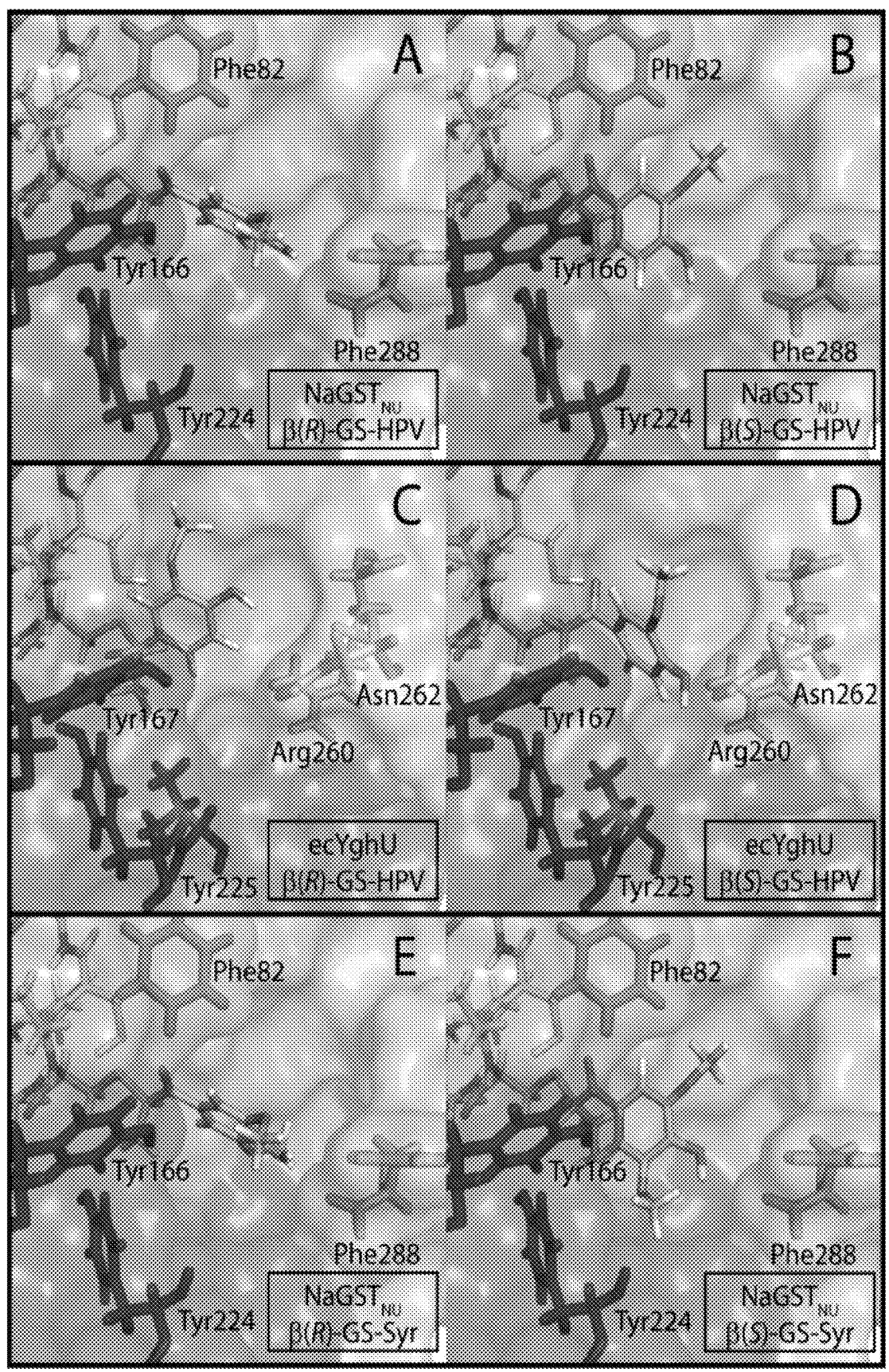

FIG. 12 shows modeling of substrates into the active sites of NaGST$_{Nu}$ and ecYghU. Panels (A) and (B) show modeling of β(R)- and β(S)-GS-HPV into NaGST$_{Nu}$. Panels (C) and (D) show modeling of β(R)- and β(S)-GS-HPV into ecYghU. Panels (E) and (F) show modeling of β(R)- and β(S)-GS-conjugated syringyl phenylpropanoids into NaGST$_{Nu}$. Coloring for NaGST$_{Nu}$ is the same as in FIG. 8 (with residues for ecYghU in parentheses): E4 (T5) to P38 (P39) in gray; V39 (V40) to G129 (G130) in green; V130 (Y131) to T134 (Q135) in gray; S135 (D136) to L257 (1257) in maroon; V258 (V258) to F288 (G288) in orange. Residues predicted to be involved in catalysis of the glutathione lyase reaction are Tyr66 and Tyr224 (Tyr167 and Tyr225 in ecYghU). Resides that contribute to differences in active site channel interiors between NaGST$_{Nu}$ and ecYghU are Phe82 and Phe288 in NaGST$_{Nu}$, and Arg260 and Asn262 in ecYghU. Carbon atoms of GSH1 are yellow, and those of the GS-conjugated substrates (GS-HPV or the syringyl analogue) are cyan.

Figure 13:
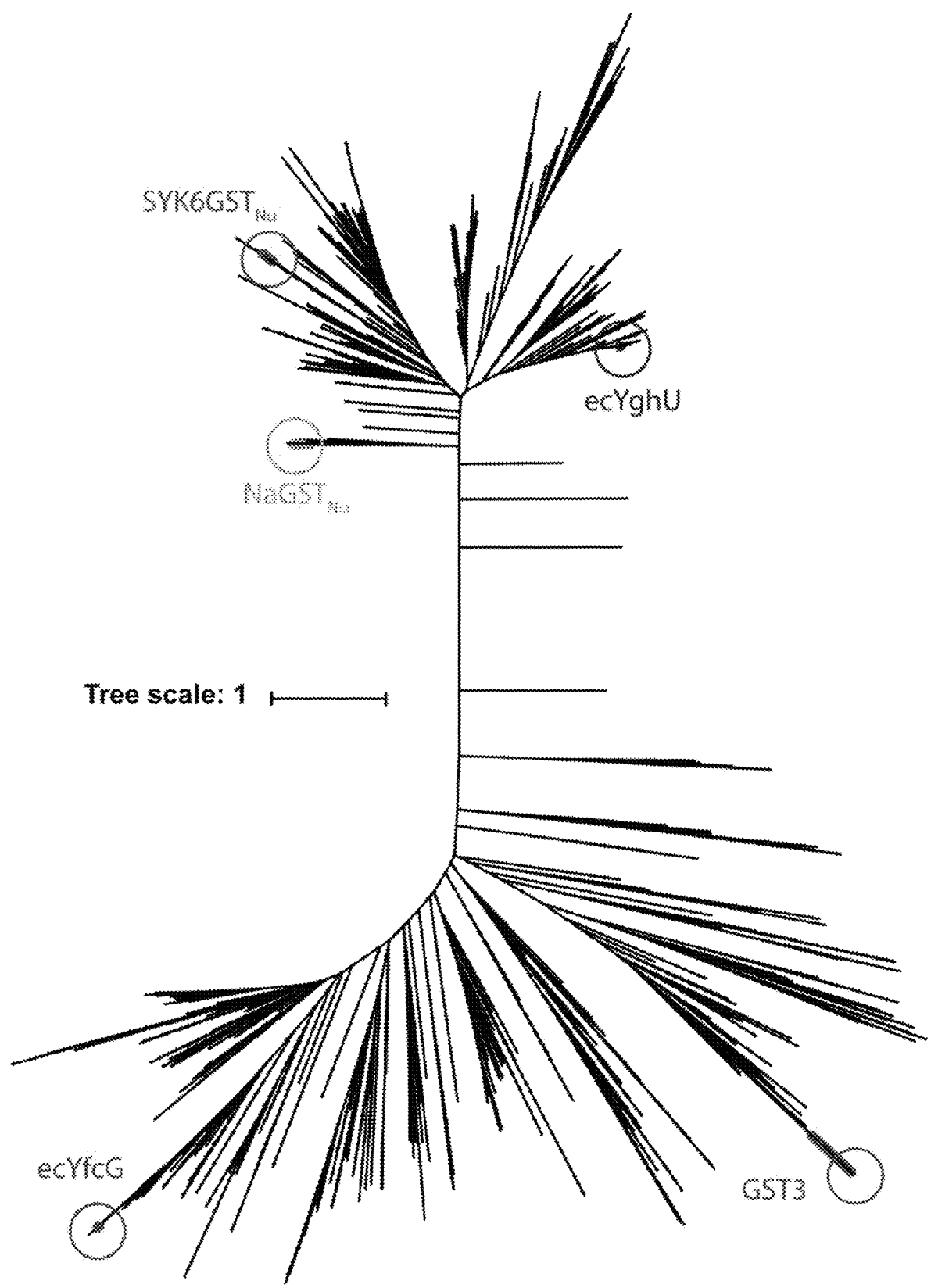

FIG. 13 shows a phylogenetic analysis of Nu-class glutathione-S-transferases. BLAST searches of the NCBI non-redundant protein database were performed using NaGST$_{Nu}$ and GST3 as queries. The top 5,000 hits from both of these searches were collected; every fifth member from each of these sets was transferred into a new combined set of 2,000 proteins. Sequences for SYK6GST$_{Nu}$ and ecYfcG were added to the combined set, to give a set of 2,002 proteins. Proteins in this set were aligned using MAFFT in MegAlign Pro, which is part of the Lasergene 14.0 suite (DNASTAR, Madison, Wis.). A phylogenetic tree was calculated via the maximum likelihood method in RAxML v8.2.3 (Stamatakis, 2014), using 100 rapid bootstrap inferences. The tree was visualized using Interactive Tree of Life v3 (http://itol.embl.de). Enzymes experimentally reported here (NaGST$_{Nu}$, SYK6GST$_{Nu}$, ecYghU, ecYfcG) or elsewhere (GST3 (Ohta et al., 2015)) to be able to convert GS-HPV into HPV are identified.

Figure 14:
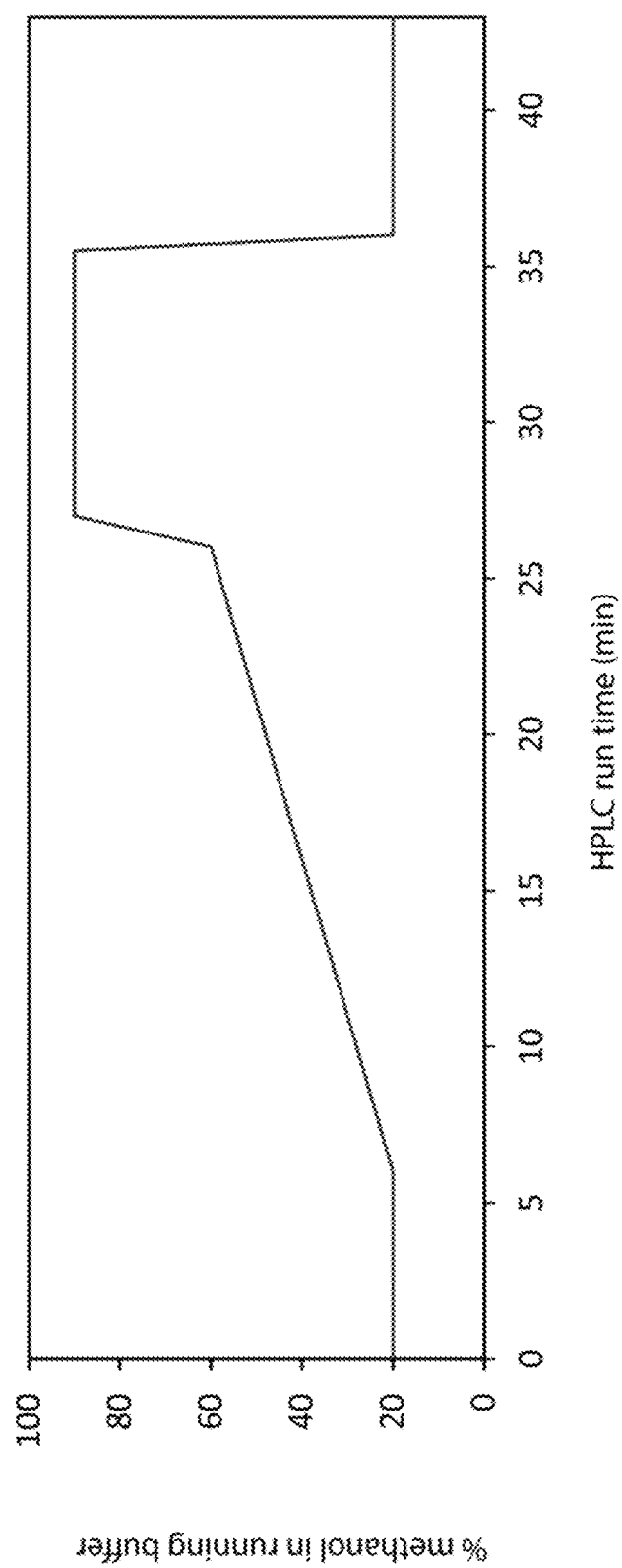

FIG. 14 shows percent methanol in the running buffer during HPLC analysis as used in the experiments in Example 1. The remainder of the running buffer was Buffer A (5 mM formic acid, 5% acetonitrile in H$_2$O), and the flow rate was 1 mL/minute.

Figure 15:
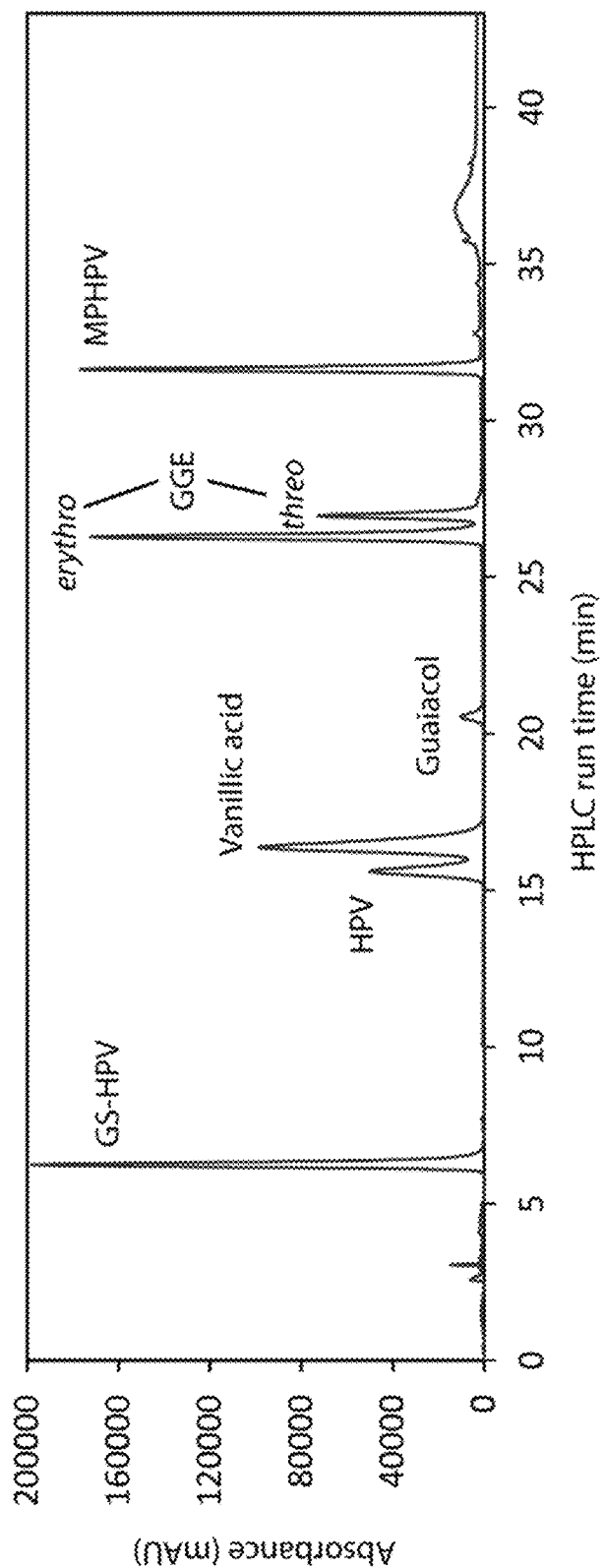

FIG. 15 shows absorbance (280 nm) and retention times of metabolites identified by HPLC as described in Example 1.

Figure 16:
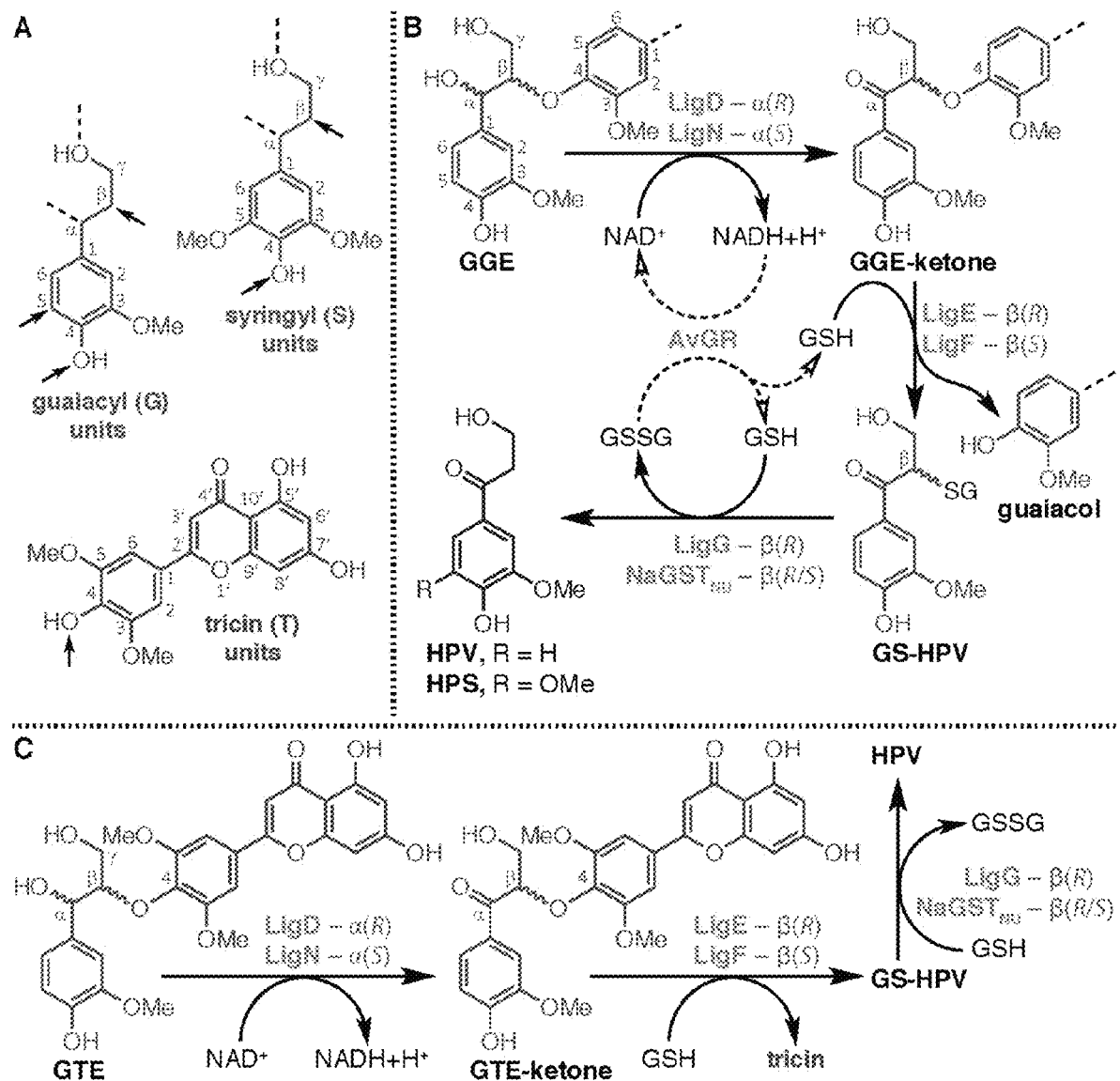

FIG. 16 shows aromatic monomers and the β-etherase pathway. Panel (A) shows the structures of predominant monomeric phenylpropanoids found in lignin, guaiacyl (G, in blue), syringyl (S, in red), as well as tricin (T, in green) units. Arrows indicate where inter-unit linkages are formed during radical coupling reactions. Dashed lines indicate positions that may form additional covalent bonds during post-coupling reaction mechanisms. Panel (B) shows β-etherase pathway-mediated degradation of the diaromatic β-ether-linked model compound GGE via NAD$^+$-dependent dehydrogenases LigD and LigN to form GGE-ketone (also referred to herein as "β-(2-methoxyphenoxy)-γ-hydroxypropiovanillone" or "MHPV") and NADH. GGE-ketone undergoes GSH-dependent β-ether cleavage by β-etherase enzymes LigE and LigF to yield guaiacol and GS-HPV as monoaromatic derivative products. GS-HPV undergoes GSH-dependent thioether cleavage by NaGST$_{Nu}$ or LigG, producing GSSG and monoaromatic product HPV. As indicated by the dashed arrows, AvGR recycles co-substrates GSH and NAD$^+$ via NADH-dependent reduction of GSSG. For reactions involving an R- or S-configured epimer as the substrate, the isomer towards which each enzyme exhibits activity is shown in grey text. Panel (C) shows how β-etherase pathway enzymes degrade GTE through intermediate GTE-ketone to yield tricin and HPV.

Figure 17A:
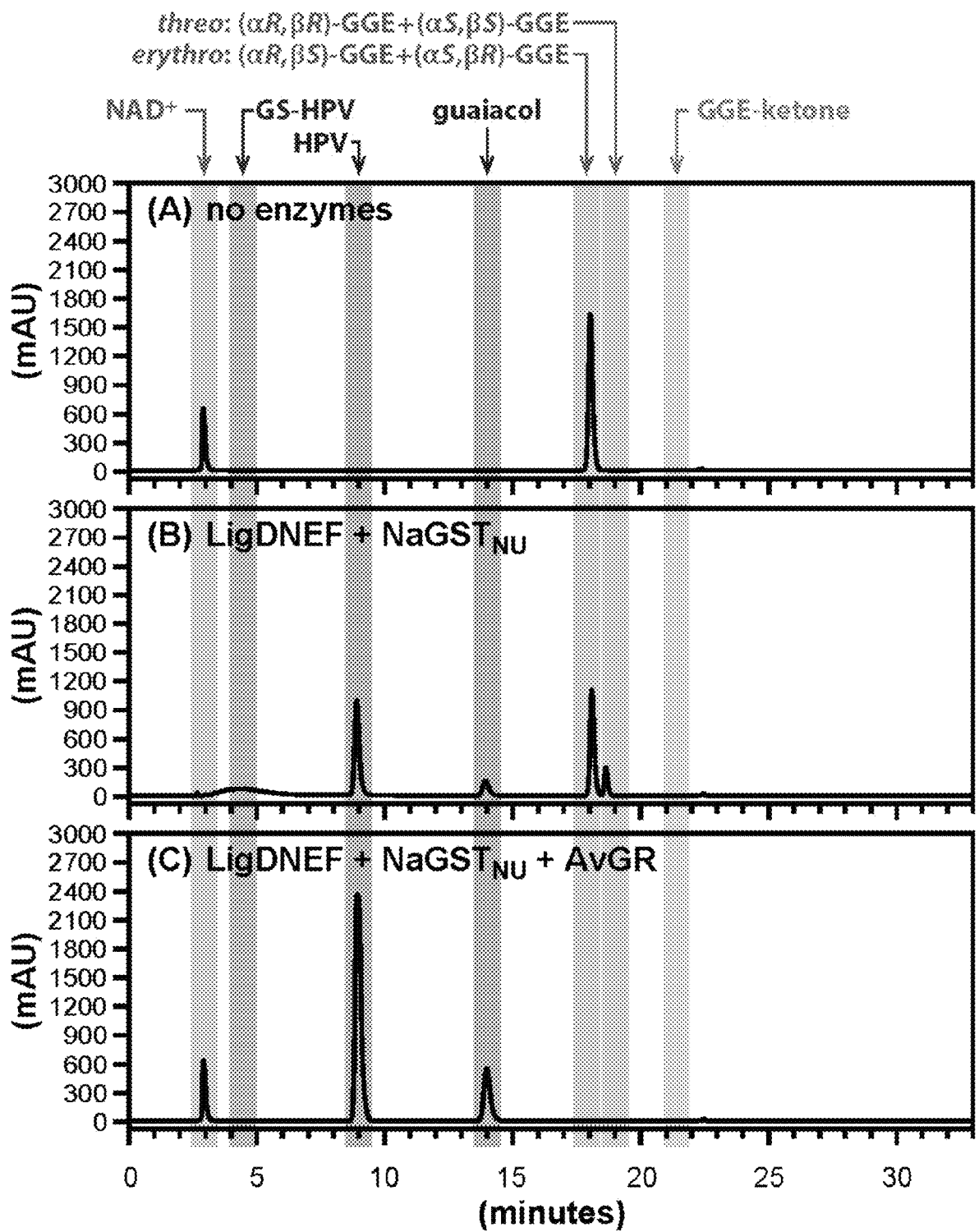
Figure 17B:
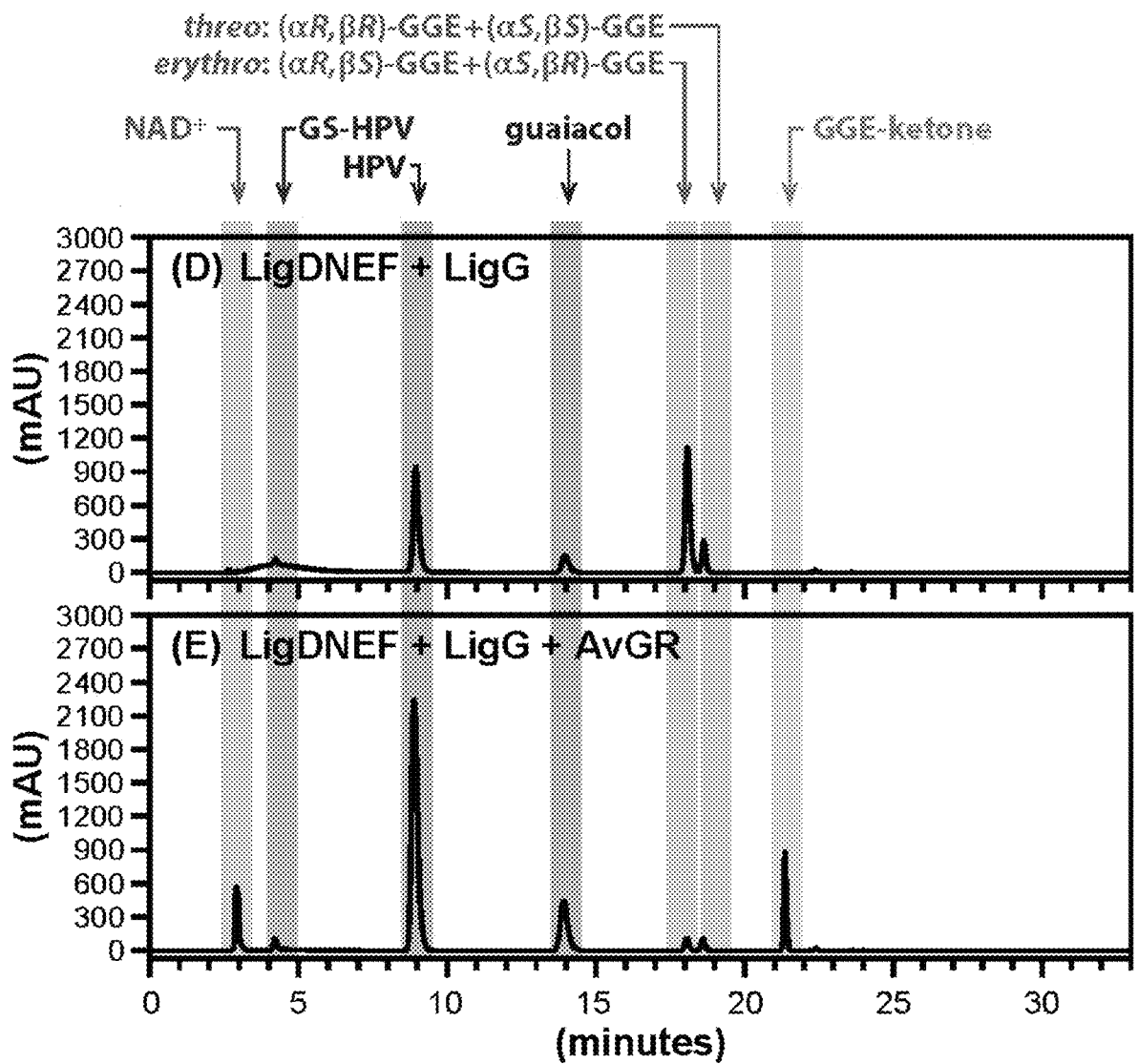

FIGS. 17A and 17B show HPLC chromatographic traces of substrates and products of β-etherase pathway assays using NAD$^+$ (2.0 mM), GSH (4.0 mM), and erythro-GGE (6.0 mM). Elution time of compounds (absorbance at 280 nm) are highlighted by shading: NAD$^+$ and NADH (~3.0 min), GS-HPV (~4.5 min), HPV (~9.0 min), guaiacol (~14.0 min), erythro-GGE (~18.0 min), threo-GGE (~19.0 min), and GGE-ketone (~21.5 min). Structures of GS-HPV, HPV, guaiacol, GGE, and GGE-ketone are shown in FIG. 16 (B). Panel (A) of FIG. 17A shows a control sample to which no enzymes were added. After 4 h incubation with one of the following combinations of enzymatic catalysts (50 μg/mL each): the remaining panels in FIGS. 17A and 17B show products in assays containing (FIG. 17A, panel B) LigDNEF and NaGST$_{Nu}$; (FIG. 17A, panel C) LigDNEF, NaGST$_{Nu}$, and AvGR; (FIG. 17B, panel D) LigDNEF and LigG; and (FIG. 17B, panel E) LigDNEF, LigG, and AvGR.

Figure 18:
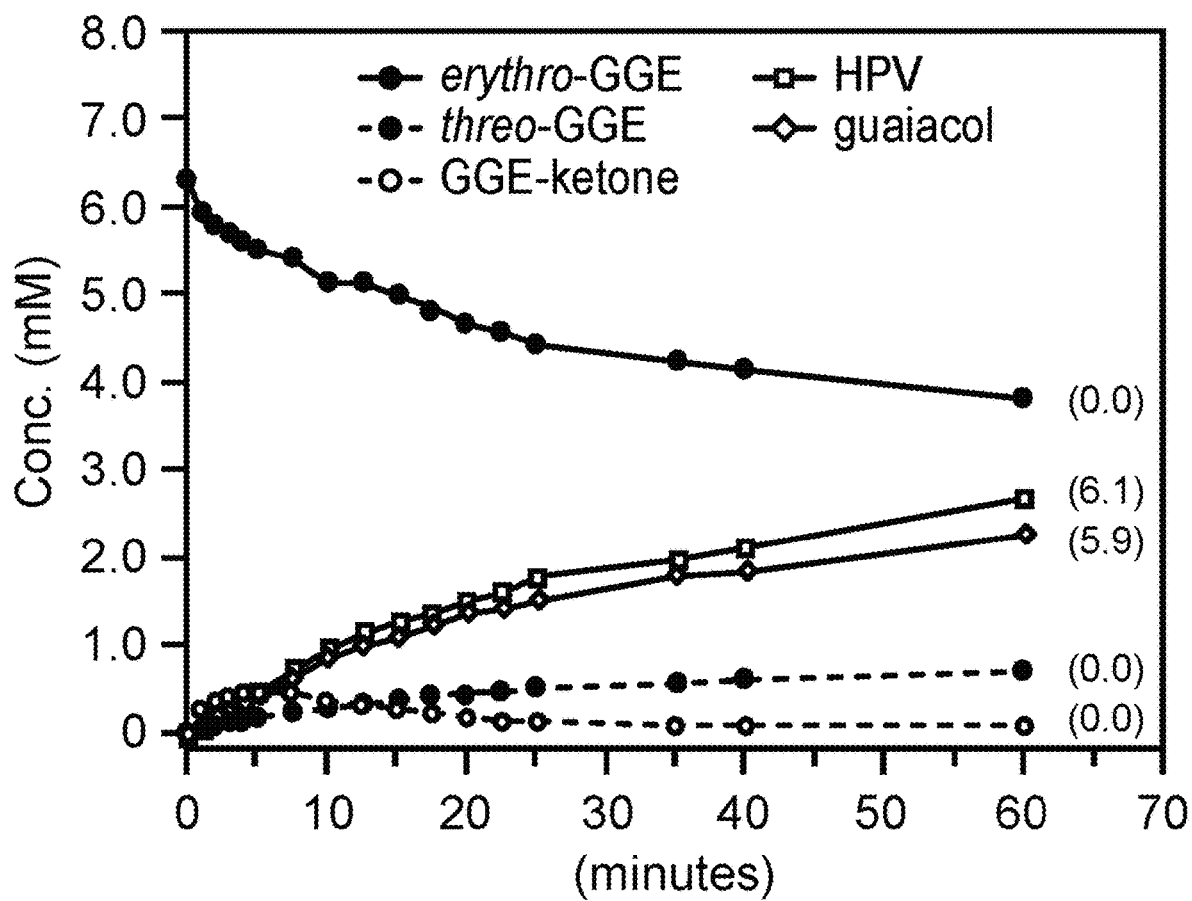

FIG. 18 shows time-dependent changes in concentrations of erythro-GGE (-◆-), threo-GGE (-●-), GGE-ketone (-○-), HPV (-□-), and guaiacol (-◇-) in an assay that, at 0 min, was supplemented with NAD$^+$ (2.0 mM), GSH (4.0 mM), and erythro-GGE (6.0 mM), as well as (50 μg/mL each) LigD, LigN, LigE, LigF, NaGST$_{Nu}$, and AvGR. Numbers in parentheses represent the measured concentration (mM) of each compound after 4 h of incubation. Structures of HPV, guaiacol, GGE, and GGE-ketone are shown in FIG. 16 (B). erythro-GGE is a mixture of enantiomers (αR,βS)-GGE and (αS,βR)-GGE. threo-GGE is a mixture of enantiomers (αS,βS)-GGE and (αR,βR)-GGE.

Figure 19A:
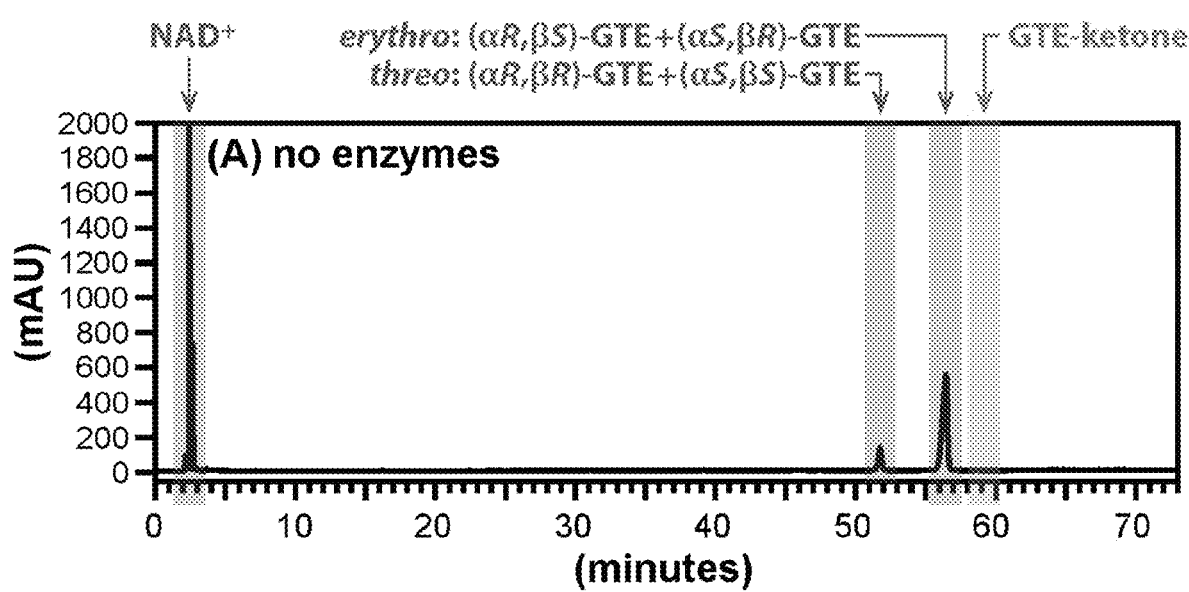
Figure 19B:
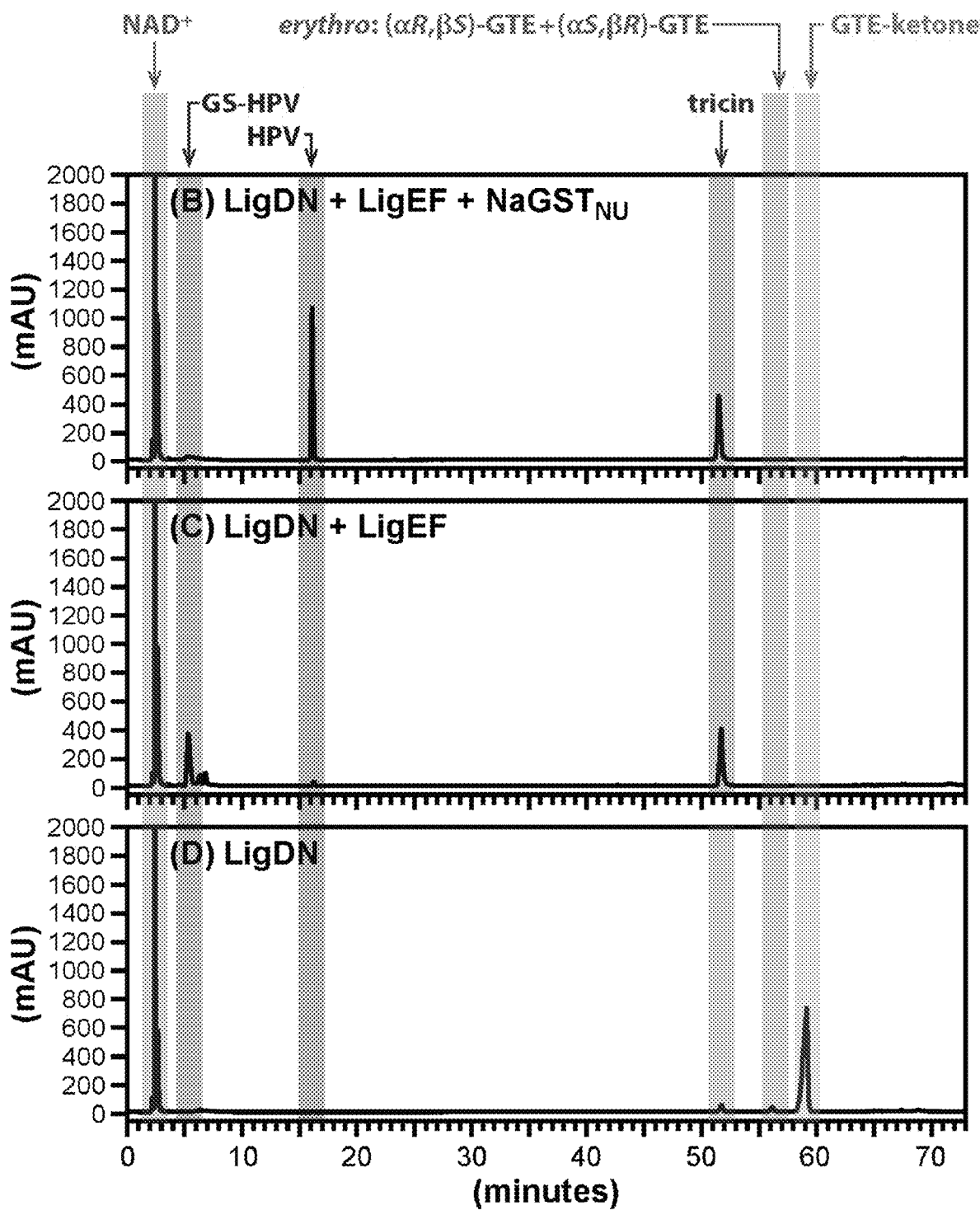

FIGS. 19A and 19B show HPLC chromatographic traces of β-etherase pathway products in reactions containing the indicated enzymes and NAD$^+$ (5.0 mM), GSH (5.0 mM), and GTE (1.0 mM, a 6:1 mixture of erythro-GTE to threo-GTE). Elution time of compounds (absorbance at 280 nm) are highlighted: NAD$^+$ and NADH (~3.0 min), GS-HPV (~5.5 min), HPV (~16.5 min), tricin (~51.5 min), threo-GTE (~52.0 min), erythro-GTE (~56.0 min), and GTE-ketone (~58.5 min). Panel (A) of FIG. 19A shows the control sample to which no enzymes were added. After 4 h incubation with one of the following combinations of enzymatic catalysts (50 μg/mL each): the panels in FIG. 19B show products in assays containing (panel B) LigD, LigN, LigE, LigF, and NaGST$_{Nu}$; (panel C) LigD, LigN, LigE and LigF; (panel D) LigD and LigN. Structures of GS-HPV, HPV, tricin, GTE, and GTE-ketone are shown in FIG. 16 (C).

Figure 20:
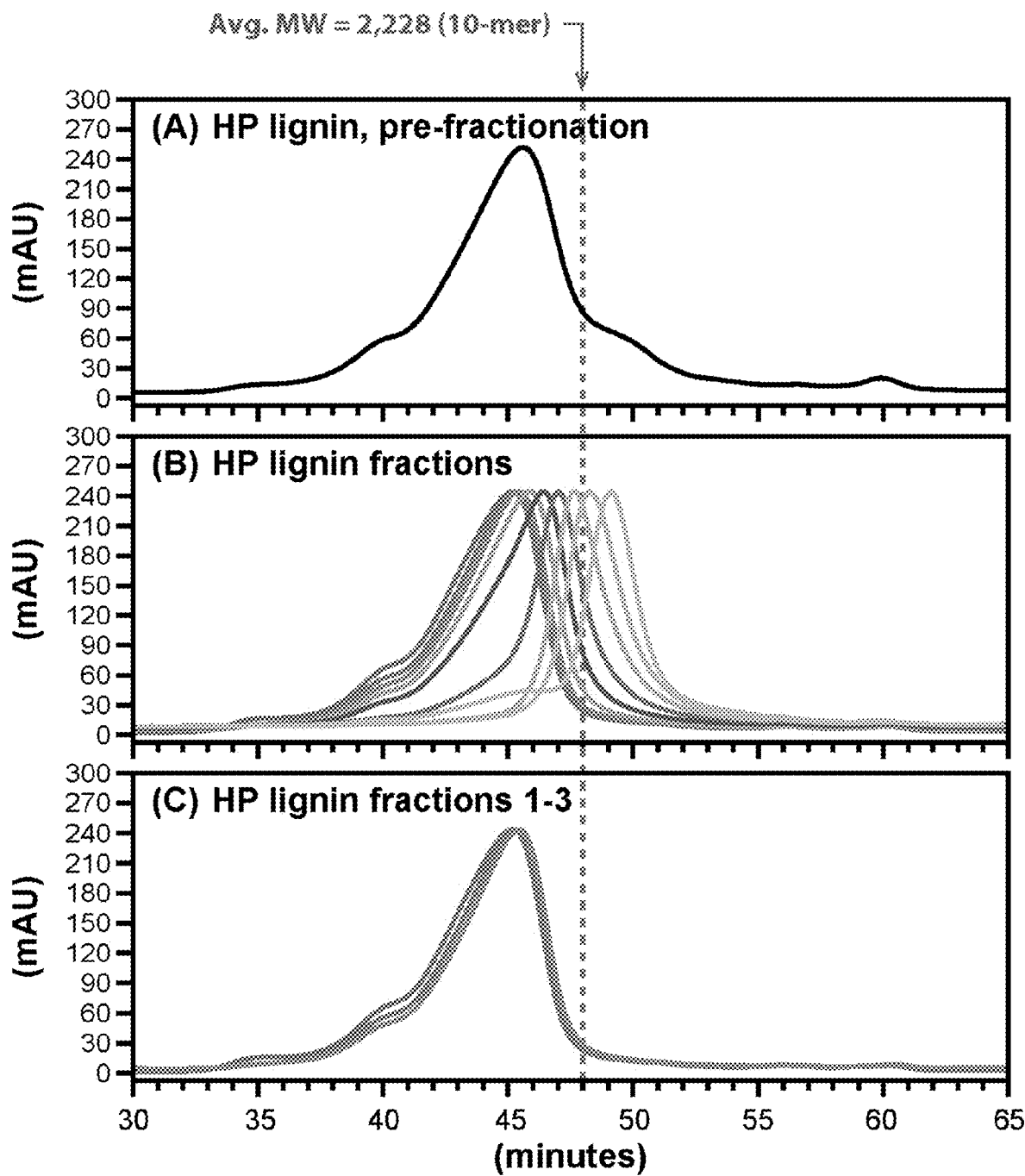

FIG. 20 shows analytical GPC traces (λ=200 nm) showing the size distribution of (A) unfractionated HP lignin (MW=8,665), (B) fractions of MCS lignin collected from preparative GPC, and (C) the fractions that were pooled and used as the substrate in enzyme assays: fraction 1 (MW=11,550), fraction 2 (MW=10,780), and fraction 3 (MW=9,340). For reference, the approximate MW of a 10-mer is indicated with a dashed line.

Figure 21:
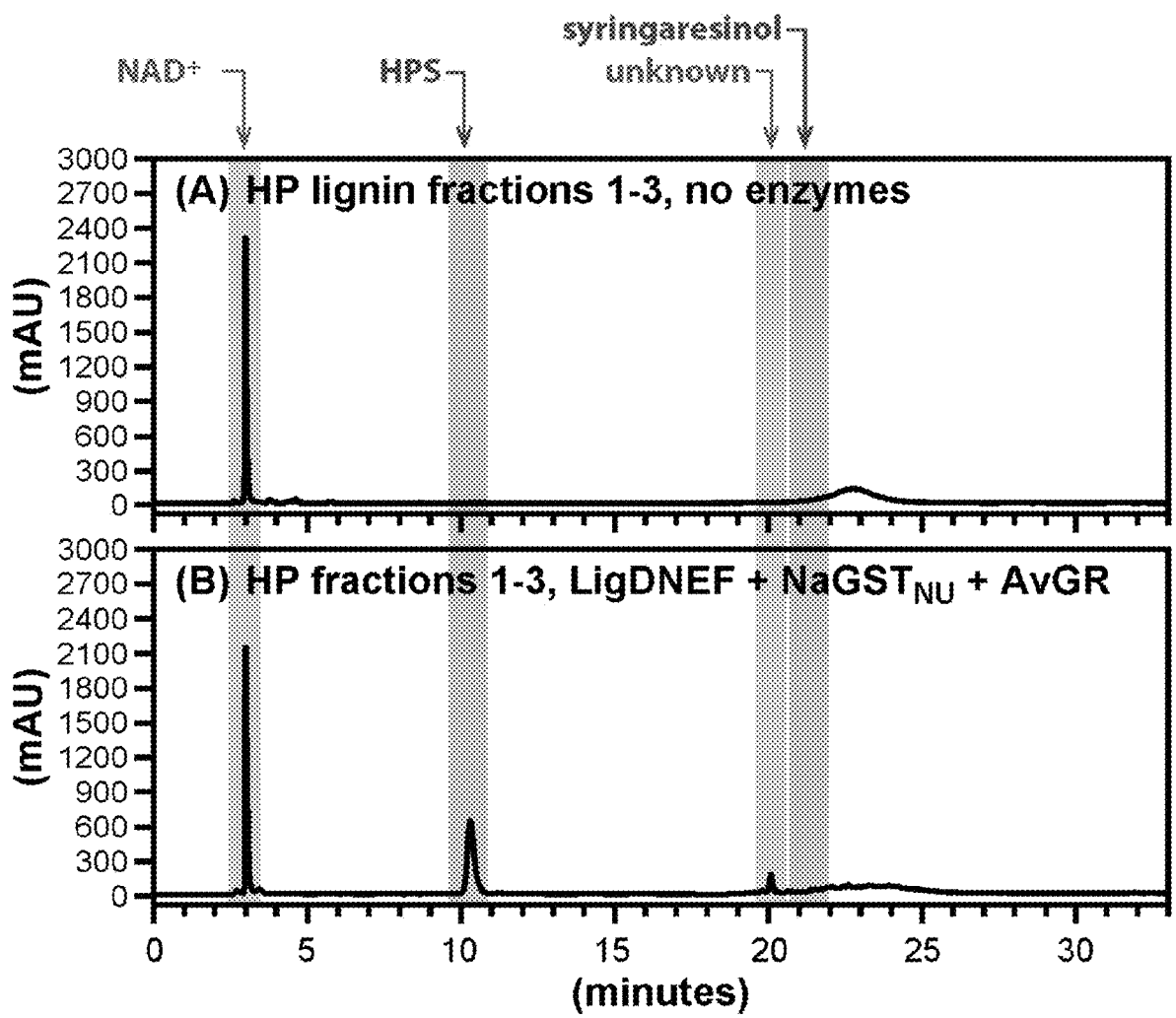

FIG. 21 shows HPLC chromatographic traces of coupled β-etherase pathway reactions supplemented with NAD$^+$ (2.0 mM), GSH (4.0 mM), and HP lignin fractions (2.2 mg mL$^{-1}$). Elution times of compounds (absorbance at 280 nm) are highlighted: NAD$^+$ and NADH (~3.0 min), HPS (~10.0 min), unknown (grey, ~20.0 min), and syringaresinol (~21.5 min). Panel (A) shows the pooled GPC fractions 1 (MW=11,550), 2 (MW=10,780), and 3 (MW=9,340) without enzyme addition. Panel (B) shows after 4 h incubation with LigD, LigN, LigE, LigF, NaGST$_{Nu}$ and AvGR (50 μg/mL each) and pooled HP lignin fractions 1-3 as the substrate.

Figure 22:
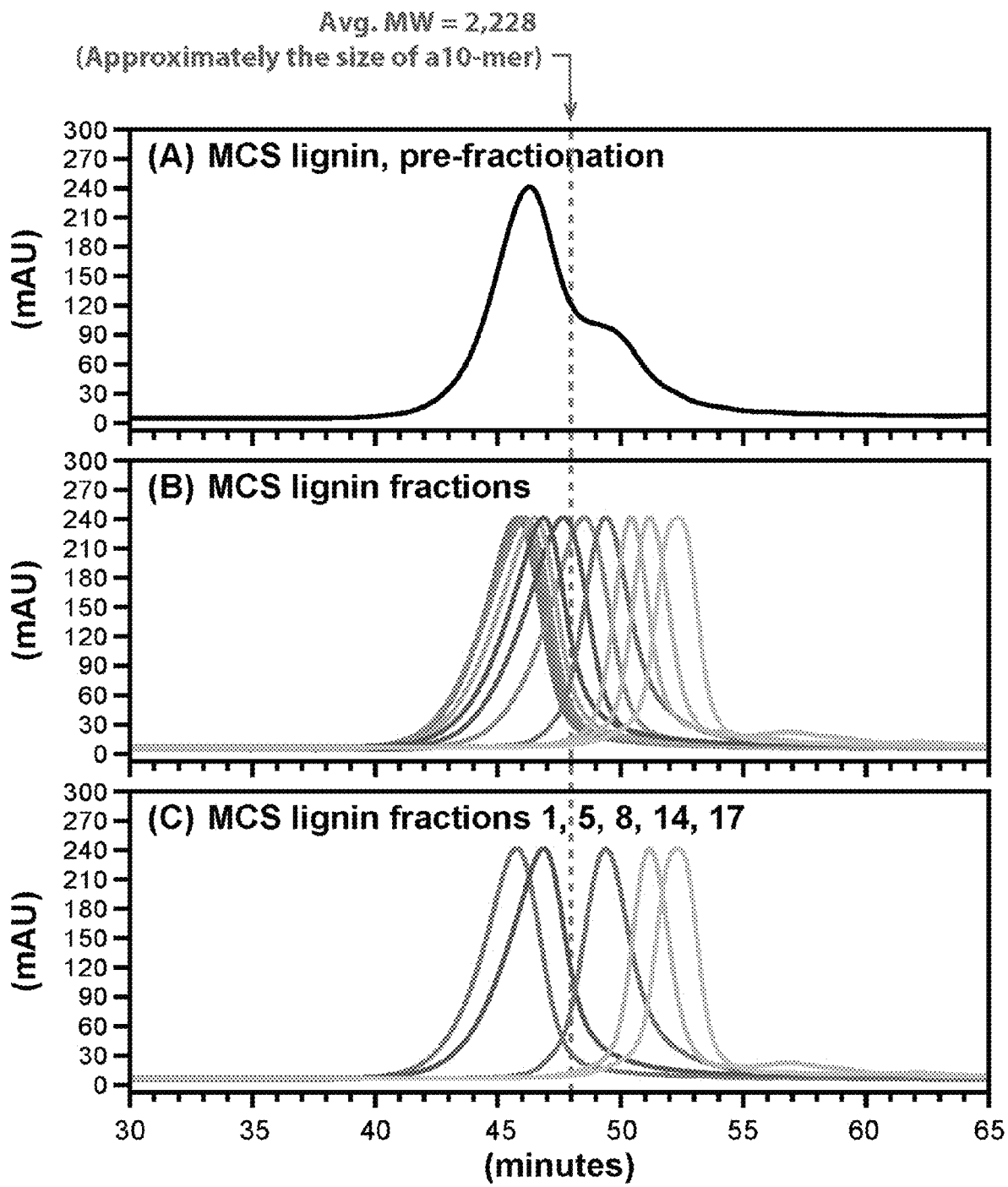

FIG. 22 shows analytical GPC traces (λ=200 nm) showing the distribution of (A) unfractionated MCS lignin (MW=5,980), (B) fractions of MCS lignin collected from preparative GPC, and (C) the fractions used as substrates in enzyme assays: fraction 1 (MW=10,710), fraction 5 (MW=5,370), fraction 8 (MW=1,390), fraction 14 (MW=660), and fraction 17 (MW=460). For reference, the approximate MW of a 10-mer is indicated with a dashed line.

Figure 23A:
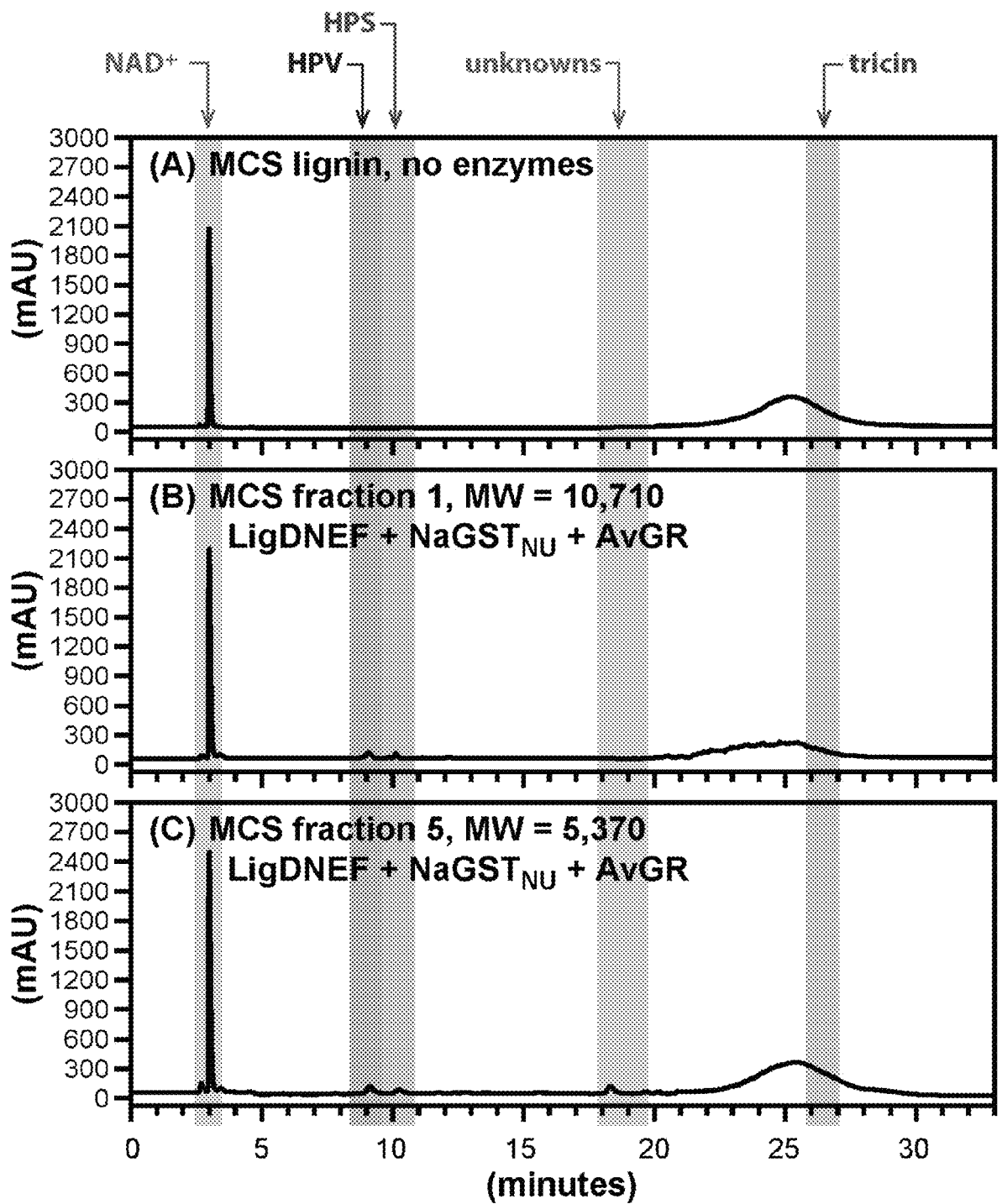
Figure 23B:
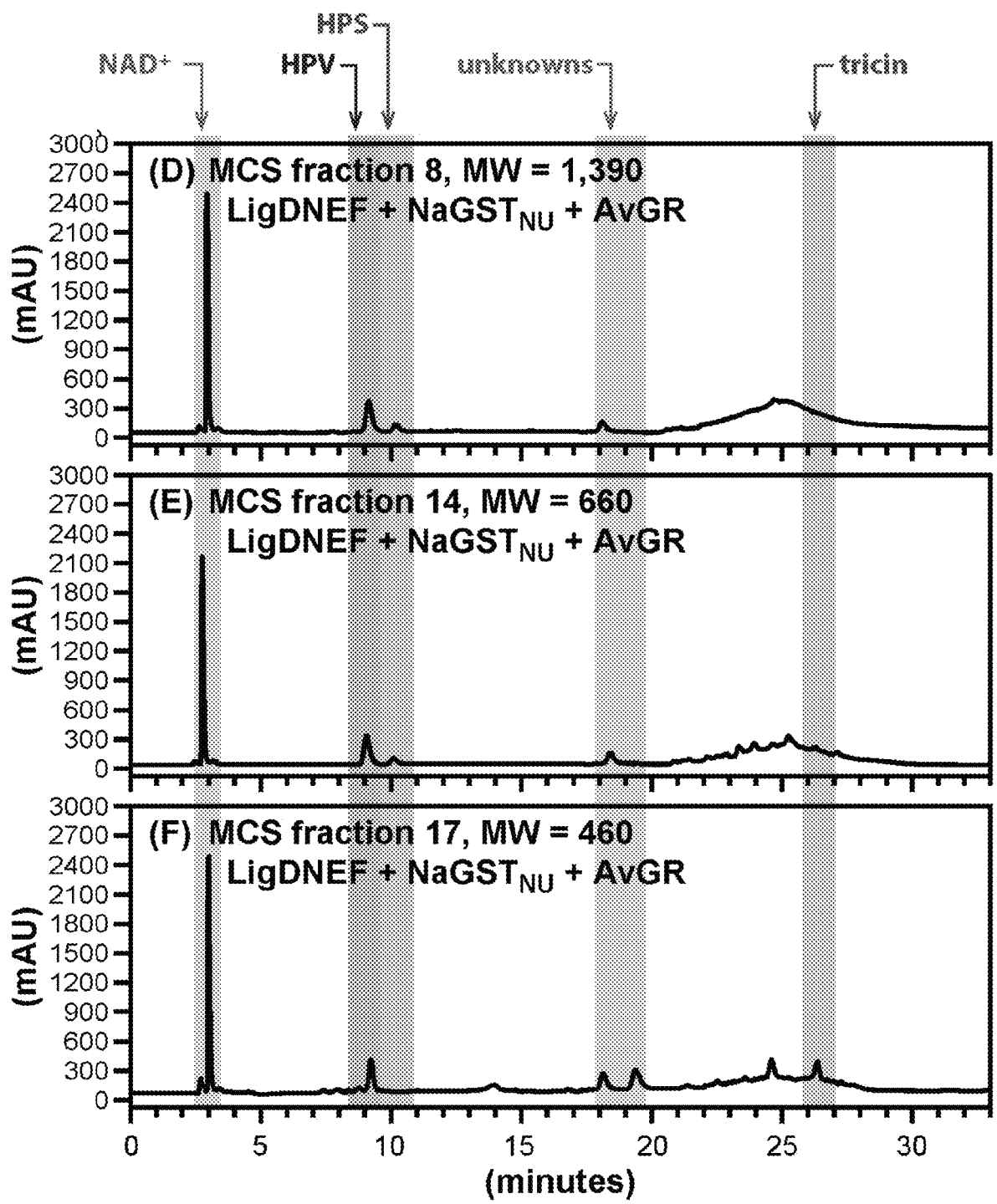

FIGS. 23A and 23B show HPLC chromatographic traces of β-etherase pathway enzyme activities in reactions containing NAD$^+$ (2.0 mM), GSH (4.0 mM), and MCS lignin or the indicated MCS lignin fractions (2.2 mg mL$^{-1}$). Elution times (absorbance at 280 nm) are highlighted by shading: NAD$^+$ (~3.0 min), HPV (~9.0 min), HPS (~10.0 min), unknowns (grey, ~18.0-19.0 min), and tricin (~26.5 min), and an unknown broad peak (orange, ~22.0-29.0 min). Panel A in FIG. 23A shows the control sample (unfractionated by GPC) to which no enzymes were added. The remaining panels in FIGS. 23A and 23B show products after 4 h incubation with 50 μg/mL each of LigD, LigN, LigE, LigF, NaGST$_{Nu}$ and AvGR, and one of the following MCS lignin fractions: (FIG. 23A, panel B) fraction 1 (MW=10,710), (FIG. 23A, panel C) fraction 5 (MW=5,3670), (FIG. 23B, panel D) fraction 8 (MW=1,390), (FIG. 23B, panel E) fraction 14 (MW=660), and (FIG. 23B, panel F) fraction 17 (MW=460). Structures of HPV, HPS, and tricin are shown in FIG. 16.

Figure 24:
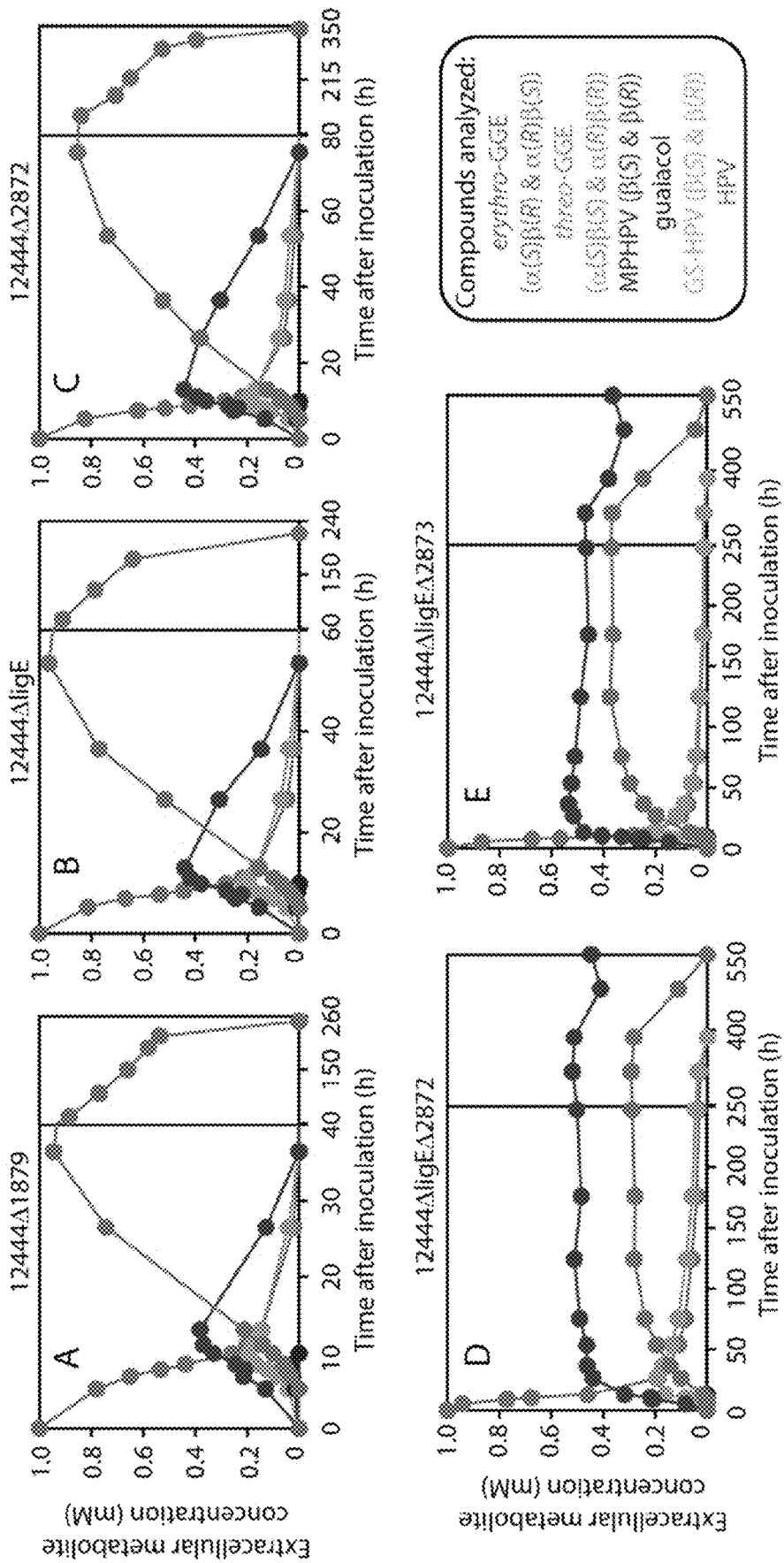

FIG. 24 shows the extracellular concentration of metabolites with growth of N. aromaticivorans strains 12444Δ1879 (effective wild-type; A), 12444ΔligE (B), 12444Δ2872 (C), 12444ΔligEΔ2872 (D), and 12444ΔligEΔ2873 (E) in Standard Mineral Base (SMB) containing 3 mM vanillate and 1 mM erythro-GGE. Extracellular concentrations of vanillate are not shown. The segments of panels A-E use different x-axis scales for clarity of presentation.

FIG. 25 shows stereoisomer(s) of MPHPV remaining in the media in samples from the final time point of the experiment shown for FIG. 24 for the 12444ΔligEΔ2872 and 12444ΔligEΔ2873 cultures (F-H and I-K, respectively). The final time point samples were combined with H$_2$O, recombinant LigF, or recombinant LigE to determine which stereoisomer(s) of MPHPV remained in the media. The two stereoisomers each of erythro-GGE, threo-GGE, MPHPV, and GS-HPV are not distinguishable in our method of analysis.

Figure 26:
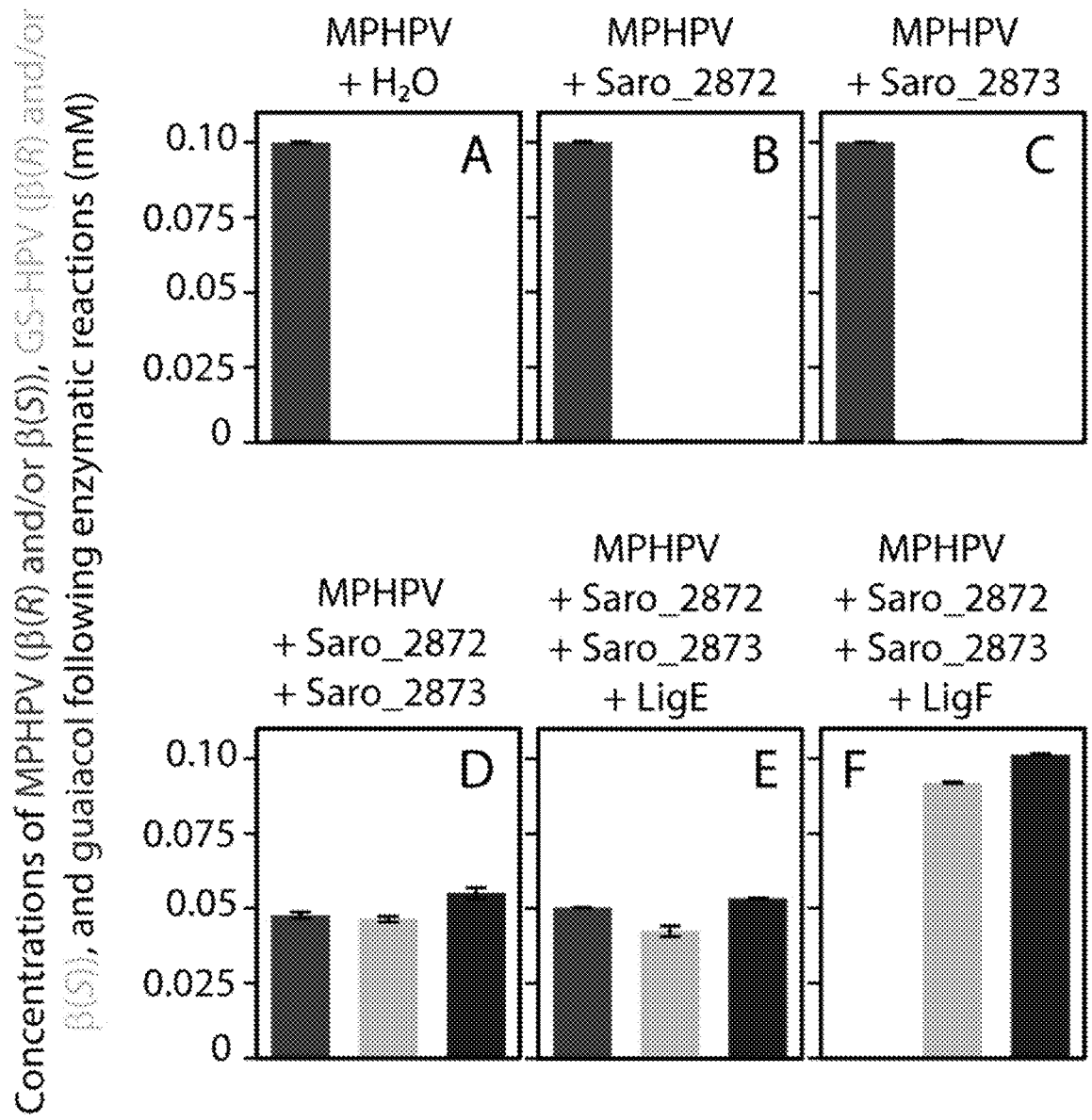

FIG. 26 shows reactions of racemic MPHPV with the Saro_2872 and Saro_2873 polypeptides individually and combined. Racemic (β(R) and β(S)) MPHPV was initially mixed with H$_2$O (A), or the Saro_2872 or Saro_2873 polypeptides individually (B,C), or combined (D). The samples containing both Saro_2872 and Saro_2873 was then split and combined with either LigE (Saro_2405) or LigF1 (Saro_2091). All reactions contain at least 5 mM GSH. The β(R) and β(S) stereoisomers of both MPHPV and GS-HPV are indistinguishable in our analysis.

Figure 27:
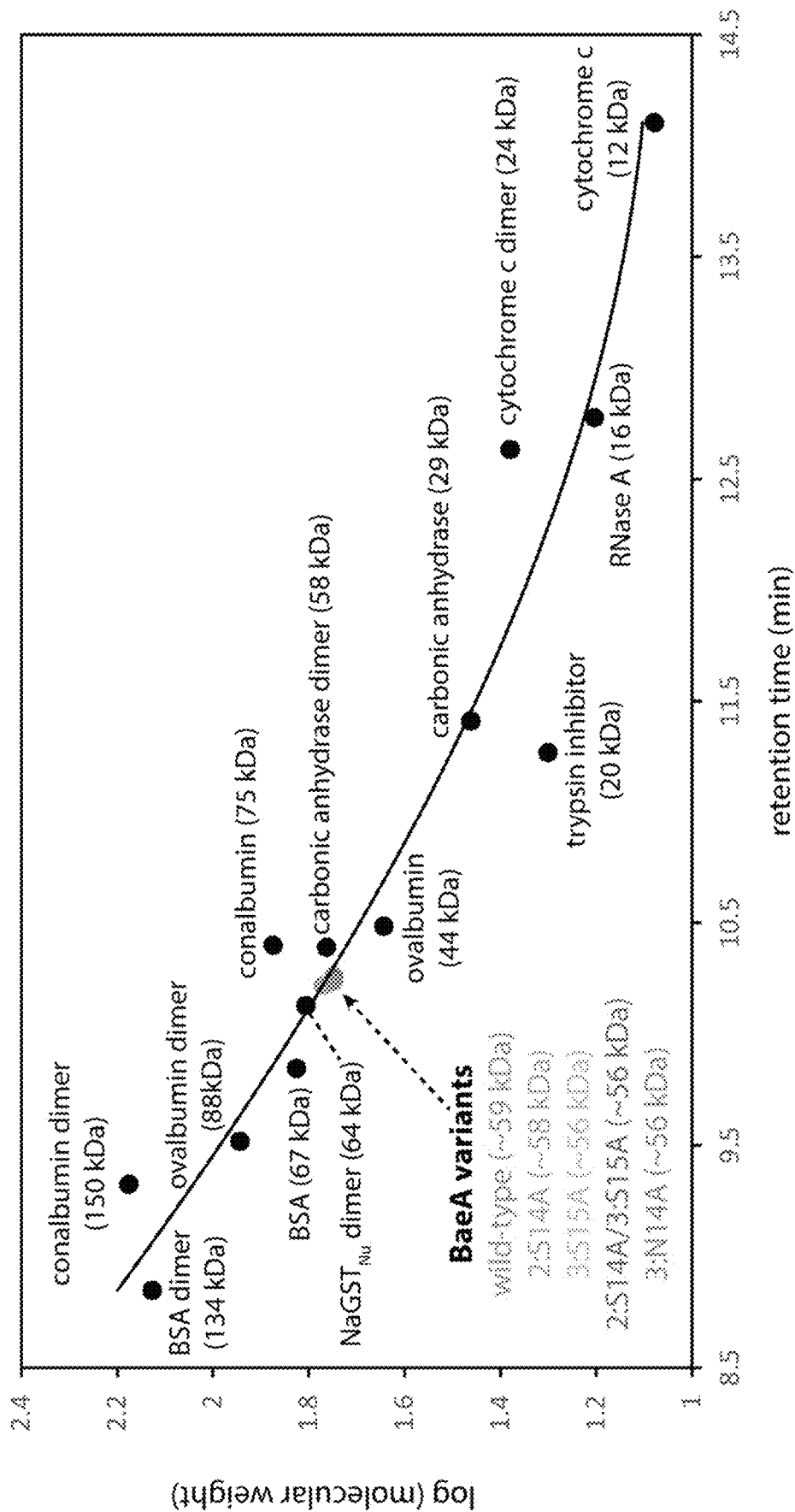

FIG. 27 shows gel permeation chromatography of various BaeA (Saro_2872 and Saro_2873 heterodimer) variants and other standard proteins of known molecular weights.

Figure 28:
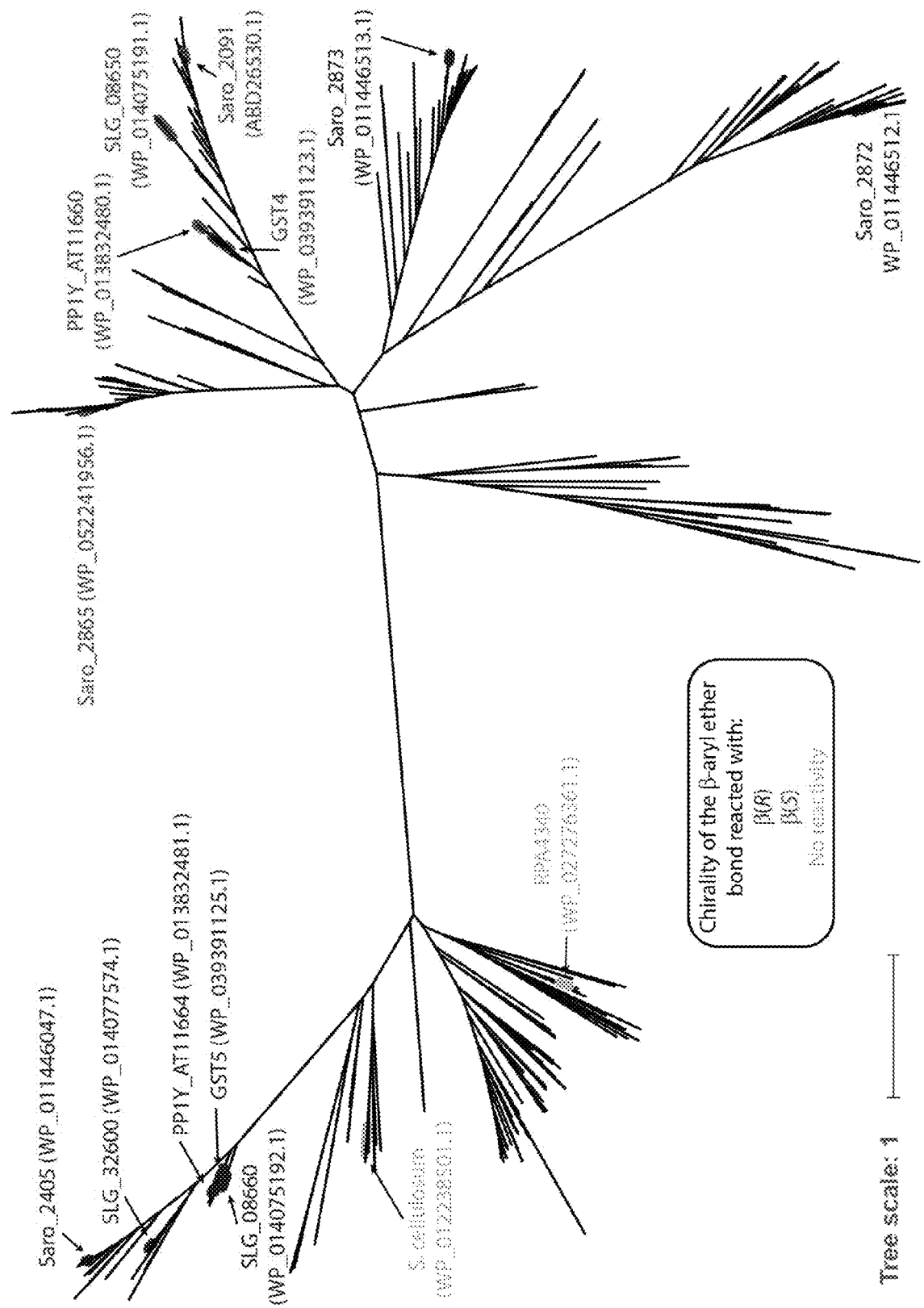

FIG. 28 shows a phylogentic tree of LigE and LigF homologues and the Saro_2872 and Saro_2873 polypeptides.

FIG. 29 shows a polypeptide sequence alignment of Saro_2872 and Saro_2873 with known LigF enzymes.

DETAILED DESCRIPTION OF THE INVENTION

One aspect of the invention includes methods of processing lignin. The term "lignin" used herein refers to any compound comprising covalently linked phenylpropanoid units. Phenylpropanoids include compounds commonly referred to as "phenylpropane units," "lignin monomer units," or variants thereof, and are well-known compounds in the art. Phenylpropanoids include a substituted or non-substituted six-carbon aromatic phenyl group and a substituted or non-substituted three-carbon tail. The phenyl group and tail may be substituted or unsubstituted. The tail may be saturated or unsaturated. The substitutions on the phenyl group may include hydroxy and alkoxy (e.g., methoxy) groups, among others. The substitutions on the tail may include hydroxy, alkoxy, carboxy, thiol, and sulfonate groups, among others. Exemplary phenylpropanoid units include the p-hydroxyphenyl (H), guaiacyl (G), and syringyl (S) units derived from p-coumaryl alcohol, coniferyl alcohol, and sinapyl alcohol, respectively. The phenylpropanoid units can be linked to other phenylpropanoid units, flavonoid units such as tricin, or other types of chemical units. The phenylpropanoid units are preferably linked through radical coupling. Exemplary linkages include β-O-4, 5-5, β-5, β-1, 4-O-5, and β-β linkages. See, e.g., Santos et al. 2013.

Two types of lignin include natural lignin and synthetic lignin. "Natural lignin" refers to lignin in which the phenylpropanoid units are covalently linked in nature (in vivo), regardless of whether or not the lignin is subsequently processed in vitro. Natural lignin encompasses lignin from non-genetically engineered plants as well as genetically engineered plants. The genetically engineered plants include plants that have been genetically engineered for altered lignin production, such as incorporation of ferulates moieties (U.S. Pat. Nos. 8,569,465 and 9,388,285), flavan-3-ols and/or gallic acid derivatives (U.S. Pat. No. 8,685,672), high syringyl content (see the examples), or other modifications (U.S. Pat. Nos. 9,487,794; 9,441,235; and 9,493,783). "Synthetic lignin" refers to lignin in which the phenylpropanoid units are covalently linked in vitro. Methods of covalently linking phenylpropanoid units in vitro through radical coupling reactions are well known in the art. See, e.g., Grabber et al. 1996.

"Processing" or grammatical variants thereof refers herein to modifying lignin in any manner to result in at least one structural change. Processing can occur through chemical, physical, or enzymatic methods. Examples of processing include depolymerization, oxidation, acid treatment, base treatment, enzyme treatment, heating, mechanical shearing, etc. The processing may depolymerize the lignin (at least to some degree), chemically modify the lignin, physically break apart the lignin, remove or add functional groups on the lignin, or result in other structural changes.

Certain methods of the invention are directed to enzymatically processing lignin comprising β-O-4 linkages (β-ether linkage) to break at least a portion of the β-O-4 linkages and/or release compounds from the lignin. The processing can advantageously be performed in vitro using one or more enzymes. The term "in vitro" in this context refers to processing with enzymes in which the enzymes are not actively produced by any intact, living organisms, and is contrasted with in vivo processing, in which the enzymes involved with the processing are actively produced by one or more intact, living organisms. Thus, in some versions, the enzymes involved in the processing are not actively produced during the duration of the processing. In some versions, the processing occurs in the absence of intact, living microorganisms. In some versions, the processing occurs in the absence of any intact, living *Sphingobium* species, *Erythrobacter* species, *Novosphingobium* species, *Escherichia* species, *Streptococcus* species, and/or *Phanerochaete* species.

In some versions, the enzymes involved in the processing are purified enzymes. The term "isolated" or "purified" means a material that is removed from its original environment, for example, the natural environment if it is naturally occurring, or a fermentation broth if it is produced in a recombinant host cell fermentation medium. A material is said to be "purified" when it is present in a particular composition in a higher or lower concentration than the concentration that exists prior to the purification step(s). For example, with respect to a composition normally found in a naturally-occurring or wild type organism, such a composition is "purified" when the final composition does not include some material from the original matrix. As another example, where a composition is found in combination with other components in a recombinant host cell fermentation medium, that composition is purified when the fermentation medium is treated in a way to remove some component of the fermentation, for example, cell debris or other fermentation products, through, for example, centrifugation or distillation. As another example, a naturally-occurring polynucleotide or polypeptide present in a living animal is not isolated, but the same polynucleotide or polypeptide, separated from some or all of the coexisting materials in the natural system, is isolated, whether such process is through genetic engineering or mechanical separation. In another example, a polynucleotide or protein is said to be purified if it gives rise to essentially one band in an electrophoretic gel or a blot.

A first step in the enzymatic processing involves contacting lignin comprising β-O-4 (β-ether) linkages with a dehydrogenase. The dehydrogenase is preferably capable of oxidizing α-hydroxyls on β-ether units to corresponding α-ketones. The term "β-ether unit" is used herein to refer to a phenylpropanoid moiety linked to a second phenylpropanoid moiety via a β-O-4 linkage. See, e.g., FIGS. 1 and 16. Exemplary enzymes used for this step include any one or more of LigD, LigO, LigN, and LigL. Exemplary LigD, LigO, LigN, and LigL enzymes include those from *Sphingobium* sp. SYK-6 having the sequences of SEQ ID NO:2, SEQ ID NO:4, SEQ ID NO:6, and SEQ ID NO:8, respectively, which are encoded by SEQ ID NO:1, SEQ ID NO:3, SEQ ID NO:5, and SEQ ID NO:7, respectively. LigD, LigO, LigN, and LigL enzymes are found in organisms other than *Sphingobium* sp. SYK-6 and can be used in place of or in addition to those from *Sphingobium* sp. SYK-6. Modified forms of the native LigD, LigO, LigN, and LigL enzymes can also suitably be used, provided the modified forms maintain the activity of the native enzymes. Such modified forms that maintain the activity of the native enzymes are also referred to herein as LigD, LigO, LigN, and LigL enzymes. The modified forms comprise sequences at least 95% identical to the amino acid sequences of the corresponding native enzymes.

The LigD and LigO enzymes from *Sphingobium* sp. SYK-6 have a specificity for α-hydroxyls in the α(R) stereochemical configuration. The LigN and LigL enzymes from *Sphingobium* sp. SYK-6 have a specificity for α-hydroxyls in the α(S) stereochemical configuration. To ensure efficient processing in a non-stereospecific manner, it is preferred that the lignin is contacted with at least one α(R) stereospecific enzyme and least one α(S) stereospecific enzyme. Accordingly, preferred combinations include one or more of LigD and LigO with one or more of LigN and LigL.

LigD, LigO, LigN, and LigL homologs from *Erythrobacter* sp. SG61-1L can react with all four possible stereoisomers of GGE (see Palamuru et al. 2015) and can be used in place of or in combination with the enzymes from *Sphingobium* sp. SYK-6.

A second step in the enzymatic processing involves contacting preprocessed (preliminarily processed) lignin, such as a product of the first step, with a β-etherase. The β-etherase is preferably capable of catalyzing glutathione-dependent β-ether cleavage to yield a β-glutathione-linked phenylpropanoid unit in place of the β-ether phenylpropanoid unit. See, e.g., FIGS. 1 and 16. The second step can be performed simultaneously with or subsequent to the first step. Exemplary enzymes used for this step include any one or more of LigE, LigF, LigP, and BaeA.

Exemplary LigE, LigF, and LigP enzymes include those from *Sphingobium* sp. SYK-6 having the sequences of SEQ ID NO:10, SEQ ID NO:12, and SEQ ID NO:14, respectively, which are encoded by SEQ ID NO:9, SEQ ID NO:11, and SEQ ID NO:13, respectively. LigE, LigF, and LigP enzymes are found in organisms other than *Sphingobium* sp. SYK-6 and can suitably be used in place of or in addition to those from *Sphingobium* sp. SYK-6. Modified forms of the native LigE, LigF, and LigP enzymes can also suitably be used, provided the modified forms maintain the activity of the native enzymes. Such modified forms that maintain the activity of the native enzymes are also referred to herein as LigE, LigF, and LigP enzymes. The modified forms comprise sequences at least 95% identical to the amino acid sequences of the corresponding native enzymes.

"BaeA" refers to a heterodimer of a first polypeptide having an amino acid sequence of SEQ ID NO:40 or an amino acid seqeuence at least 80%, 85%, 90%, 95%, 96%, 97%, 98%, 99%, or more identical thereto and a second polypeptide having an amino acid sequence of SEQ ID NO:42 or an amino acid seqeuence at least 80%, 85%, 90%, 95%, 96%, 97%, 98%, 99%, or more identical thereto. An exemplary BaeA is a heterodimer of Saro_2872 from *Novosphingobium aromaticivorans* (encoded by SEQ ID NO:39 and represented by SEQ ID NO:40) and Saro_2873 from *Novosphingobium aromaticivorans* (encoded by SEQ ID NO:41 and represented by SEQ ID NO:42). The second polypeptide preferably comprises an asparagine or a conservative variant of asparagine at a position corresponding to position 14 of SEQ ID NO:41 and/or a serine or a conservative variant of serine at a position corresponding to position 15 of SEQ ID NO:42.

The LigE and LigP enzymes from *Sphingobium* sp. SYK-6 and BaeA have a specificity for cleaving β-ether linkages in the β(R) stereochemical configuration. The LigF enzyme from *Sphingobium* sp. SYK-6 has a specificity for cleaving β-ether linkages in the β(S) stereochemical configuration. To ensure efficient processing in a non-stereospecific manner, it is preferred that the substrate is contacted with at least one β(R) stereospecific enzyme and least one β(S) stereospecific enzyme. Accordingly, preferred combinations include one or more of LigE, LigP, and BaeA with LigF.

LigE/P and LigF homologues from other organisms are also expected to be stereospecific. See for example Gall and Ralph et al. 2014. SLG_08660 (SYK-6 LigE), PP1Y_AT11664 (*Novosphingobium* sp. PP1Y), SLG_32600 (SYK-6 LigP), and Saro_2405 (*Novosphingobium aromaticivorans*) were all shown to be specific for β(R)-compounds. Likewise, SLG_08650 (SYK-6 LigF), Saro_2091 (*Novosphingobium aromaticivorans*), and Saro_2865 (*Novosphingobium aromaticivorans*) were all shown to be specific for β(S)-compounds.

A third step in the enzymatic processing involves contacting preprocessed lignin, such as a product of the second step, with a glutathione lyase. The glutathione lyase is preferably capable of cleaving glutathione from β-glutathione-linked phenylpropanoid units. The cleavage may use glutathione as a cosubstrate and produce glutathione disulfide in the process. See, e.g., FIGS. 1 and 16. The third step can be performed simultaneously with or subsequent to the second step and/or the first and second steps. Exemplary enzymes used for this step include any one or more of LigG from *Sphingobium* sp. SYK-6 having the amino acid sequence of SEQ ID NO:16 (encoded by SEQ ID NO:15), a Nu-class glutathione S-transferase (GST) from *Novosphingobium aromaticivorans* DSM 12444 having the amino acid sequence of SEQ ID NO:18 (NaGST$_{Nu}$) (encoded by SEQ ID NO:17), a recombinant NaGST$_{Nu}$ having the amino acid sequence of residues 21-313 of SEQ ID NO:20 (encoded by SEQ ID NO:19 prior to cleavage), a Nu-class GST from *Sphingobium* sp. SYK-6 having the amino acid sequence of SEQ ID NO:22 (SYK6GST$_{Nu}$) (encoded by SEQ ID NO:21), a recombinant SYK6GST$_{Nu}$ having the amino acid sequence of residues 21-324 of SEQ ID NO:24 (encoded by SEQ ID NO:23 prior to cleavage), a Nu-class GST from *Escherichia coli* DH5a having the amino acid sequence of SEQ ID NO:26 (ecYghU) (encoded by SEQ ID NO:25), a recombinant ecYghU having the amino acid sequence of residues 21-313 of SEQ ID NO:28 (encoded by SEQ ID NO:27 prior to cleavage), a Nu-class GST from *Escherichia coli* DH5a having the amino acid sequence of SEQ ID NO:30 (ecYfcG) (encoded by SEQ ID NO:29), a Nu-class GST from *Streptococcus sanguinis* SK36 having the amino acid sequence of SEQ ID NO:32 (ssYghU) (encoded by SEQ ID NO:31), a Nu-class GST from *Novosphingobium* sp. MBES04 having the amino acid sequence of SEQ ID NO:34 (GST3) (encoded by SEQ ID NO:33), and a Nu-class GST from *Phanerochaete chrysosporium* RP-78 having the amino acid sequence of SEQ ID NO:36 (PcUre2pB1) (encoded by SEQ ID NO:35).

The LigG from *Sphingobium* sp. SYK-6 has a specificity for β-glutathione-linked phenylpropanoid units with the glutathione moieties linked in the β(R) stereochemical configuration and is referred to herein as a "stereospecific glutathione lyase." By contrast, the Nu-class glutathione S-transferase (GST) from *Novosphingobium aromaticivorans* DSM 12444 having the amino acid sequence of SEQ ID NO:18 (NaGST$_{Nu}$) (encoded by SEQ ID NO:17), the recombinant NaGST$_{Nu}$ having the amino acid sequence of residues 21-313 of SEQ ID NO:20 (encoded by SEQ ID NO:19 prior to cleavage), the Nu-class GST from *Sphingobium* sp. SYK-6 having the amino acid sequence of SEQ ID NO:22 (SYK6GST$_{Nu}$) (encoded by SEQ ID NO:21), the recombinant SYK6GST$_{Nu}$ having the amino acid sequence of residues 21-324 of SEQ ID NO:24 (encoded by SEQ ID NO:23 prior to cleavage), the Nu-class GST from *Escherichia coli* DH5a having the amino acid sequence of SEQ ID NO:26 (ecYghU) (encoded by SEQ ID NO:25), the recombinant ecYghU having the amino acid sequence of residues 21-313 of SEQ ID NO:28 (encoded by SEQ ID NO:27 prior to cleavage), the Nu-class GST from *Escherichia coli* DH5a having the amino acid sequence of SEQ ID NO:30 (ecYfcG) (encoded by SEQ ID NO:29), the Nu-class GST from *Streptococcus sanguinis* SK36 having the amino acid sequence of SEQ ID NO:32 (ssYghU) (encoded by SEQ ID NO:31), the Nu-class GST from *Novosphingobium* sp. MBES04 having the amino acid sequence of SEQ ID NO:34 (GST3) (encoded by SEQ ID NO:33), and the Nu-class GST from *Phanerochaete chrysosporium* having the amino acid sequence of SEQ ID NO:36 (PcUre2pB1) (encoded by SEQ ID NO:35) are capable or predicted to be capable of cleaving β-glutathione-linked phenylpropanoid units with the glutathione moieties linked in either the β(R) or β(S) stereochemical configuration and are referred to herein as "non-stereospecific glutathione lyases." To ensure efficient processing in a non-stereospecific manner, it is preferred that the substrate is contacted with at least one non-stereospecific glutathione lyase. Accordingly, preferred combinations include one or more of any of the non-stereospecific glutathione lyases described herein with or without LigG.

Other non-stereospecific glutathione lyases that can be used in place of or in addition to the non-stereospecific glutathione lyases described above include enzymes at least about 35%, at least about 40%, at least about 45%, at least about 50%, at least about 60%, at least about 65%, at least about 70%, at least about 75%, at least about 80%, at least about 85%, at least about 90%, or at least about 95% identical to any one of SEQ ID NO:18 (NaGST$_{Nu}$), residues 21-313 of SEQ ID NO:20 (recombinant NaGST$_{Nu}$), SEQ ID NO:22 (SYK6GST$_{Nu}$), residues 21-324 of SEQ ID NO:24 (recombinant SYK6GST$_{Nu}$), SEQ ID NO:26 (ecYghU), residues 21-313 of SEQ ID NO:28 (recombinant ecYghU), SEQ ID NO:30 (ecYfcG), SEQ ID NO:34 (GST3); SEQ ID NO:32 (ssYghU), and SEQ ID NO:36 (PcUre2pB1). Such enzymes may be native enzymes or modified forms of native enzymes.

As discussed in the following examples, a number of residues of the non-stereospecific glutathione lyases described herein play at least some role in the enzymatic activity. See, e.g., FIG. 5. These include Asn25 of SEQ ID NO:18 (NaGST$_{Nu}$), Thr51 of SEQ ID NO:18 (NaGST$_{Nu}$), Asn53 of SEQ ID NO:18 (NaGST$_{Nu}$), Gln86 of SEQ ID NO:18 (NaGST$_{Nu}$), Lys99 of SEQ ID NO:18 (NaGST$_{Nu}$), Ile100 of SEQ ID NO:18 (NaGST$_{Nu}$), Glu 116 of SEQ ID NO:18 (NaGST$_{Nu}$), Ser117 of SEQ ID NO:18 (NaGST$_{Nu}$), Tyr166 of SEQ ID NO:18 (NaGST$_{Nu}$), Arg177 of SEQ ID NO:18 (NaGST$_{Nu}$), Tyr224 of SEQ ID NO:18 (NaGST$_{Nu}$), and corresponding residues in the other enzymes. A number of these residues are conserved across all the non-stereospecific glutathione lyases described herein. These include Thr51 of SEQ ID NO:18 (NaGST$_{Nu}$), Asn53 of SEQ ID NO:18 (NaGST$_{Nu}$), Gln86 of SEQ ID NO:18 (NaGST$_{Nu}$), Ile100 of SEQ ID NO:18 (NaGST$_{Nu}$), Glu 116 of SEQ ID NO:18 (NaGST$_{Nu}$), Arg177 of SEQ ID NO:18 (NaGST$_{Nu}$), and corresponding residues in the other enzymes.

Accordingly, suitable enzymes at least about 60%, at least about 65%, at least about 70%, at least about 75%, at least about 80%, at least about 85%, at least about 90%, or at least about 95% identical to the non-stereospecific glutathione lyases described herein preferably comprise at least one, at least two, at least three, at least four, at least five, at least six, at least seven, or all of threonine or a conservative variant of threonine at a position corresponding to position 51 of SEQ ID NO:18 (NaGST$_{Nu}$), asparagine or a conservative variant of asparagine at a position corresponding to position 53 of SEQ ID NO:18 NaGST$_{Nu}$), glutamine or a conservative variant of glutamine at a position corresponding to position 86 of SEQ ID NO:18 (NaGST$_{Nu}$), lysine, a conservative variant of lysine, arginine, or a conservative variant of arginine at a position corresponding to position 99 of SEQ ID NO:18 (NaGST$_{Nu}$), isoleucine or a conservative variant of isoleucine at a position corresponding to position 100 of SEQ ID NO:18 (NaGST$_{Nu}$), glutamate or a conservative variant of glutamate at a position corresponding to position 116 of SEQ ID NO:18 (NaGST$_{Nu}$), serine, threonine, a conservative variant of serine, or a conservative variant of threonine at a position corresponding to position 117 of SEQ ID NO:18 (NaGST$_{Nu}$), arginine or a conservative variant of arginine at a position corresponding to position 177 of SEQ ID NO:18 (NaGST$_{Nu}$).

Suitable enzymes at least about 60%, at least about 65%, at least about 70%, at least about 75%, at least about 80%, at least about 85%, at least about 90%, or at least about 95% identical to the non-stereospecific glutathione lyases described herein more preferably comprise at least one, at least two, at least three, at least four, at least five, at least six, at least seven, at least eight, at least nine, at least ten, or all of asparagine or a conservative variant of asparagine at a position corresponding to position 25 of SEQ ID NO:18 (NaGST$_{Nu}$), threonine or a conservative variant of threonine at a position corresponding to position 51 of SEQ ID NO:18 (NaGST$_{Nu}$), asparagine or a conservative variant of asparagine at a position corresponding to position 53 of SEQ ID NO:18 (NaGST$_{Nu}$), glutamine or a conservative variant of glutamine at a position corresponding to position 86 of SEQ ID NO:18 (NaGST$_{Nu}$), lysine, a conservative variant of lysine, arginine, or a conservative variant of arginine at a position corresponding to position 99 of SEQ ID NO:18 (NaGST$_{Nu}$), isoleucine or a conservative variant of isoleucine at a position corresponding to position 100 of SEQ ID NO:18 (NaGST$_{Nu}$), glutamate or a conservative variant of glutamate at a position corresponding to position 116 of SEQ ID NO:18 (NaGST$_{Nu}$), serine, threonine, a conservative variant of serine, or a conservative variant of threonine at a position corresponding to position 117 of SEQ ID NO:18 (NaGST$_{Nu}$), tyrosine or a conservative variant of tyrosine at a position corresponding to position 166 of SEQ ID NO:18 (NaGST$_{Nu}$), arginine or a conservative variant of arginine at a position corresponding to position 177 of SEQ ID NO:18 (NaGST$_{Nu}$), and tyrosine or a conservative variant of tyrosine at a position corresponding to position 224 of SEQ ID NO:18 (NaGST$_{Nu}$).

Positions in a given enzyme that correspond to positions in a given sequence such as SEQ ID NO:18 (NaGST$_{Nu}$), SEQ ID NO:40 (Saro_2872), and SEQ ID NO:42 (Saro_2873), or any other sequence provided herein, can be identified through alignment of the sequence of the enzyme with the given sequence. A number of sequence alignment algorithms are known in the art. Exemplary sequence alignment algorithms include MAFFT version 7 (mafft.cbrc.jp)

(Katoh et al. 2002) and Clustal W and other Clustal programs (Larkin et al. 2007). Other algorithms and programs are known in the art.

"Conservative variant" refers to residues that are functionally similar to a given residue such that one or more of the functionally similar residues may substitute for the given residue. Conservative variants of the standard amino acids are well known in the art. In some versions, aliphatic, non-polar amino acids (Gly, Ala, Ile, Leu, and Val) are conservative variants of one another. In some versions, aliphatic, polar amino acids (Cys, Ser, Thr, Met, Asn, Tyr and Gln) are conservative variants of one another. In some versions, aromatic amino acids (Phe, Tyr, Trp, and His) are conservative variants of one another. In some versions, basic amino acids (Lys, Arg, and His) are conservative variants of one another. In some versions, acidic amino acids (Asp and Glu) are conservative variants of one another. In some versions, an amino acid with an acidic side chain, Glu or Asp, is a conservative variant of its uncharged counterpart, Gln or Asn, respectively; or vice versa. In some versions, each of the following groups contains other exemplary amino acids that are conservative variants of one another: Ala and Gly; Asp and Glu; Asn and Gln; Arg and Lys; Ile, Leu, Met, and Val; Phe, Tyr, and Trp; Ser and Thr; and Cys and Met.

A fourth step in the enzymatic processing involves conducting the first three steps in the presence of a glutathione (GSH) reductase that catalyzes reduction of glutathione disulfide (GSSG). The GSH reductase regenerates the GSH cosubstrate of the second and third steps from the GSSG co-product of the third step and regenerates the $NAD^+$ cosubstrate of the first step from the NADH co-product of the first step. See, e.g., FIGS. 1 and 16. An exemplary GSH reductase is the GSH reductase from *Allochromatium vinosum* DSM180 (AvGR) having the sequence of SEQ ID NO:38 (encoded by SEQ ID NO:37). Other GSH reductases are known in the art and can be used in this step. Modified forms of the native AvGR and other suitable enzymes can also suitably be used, provided the modified forms maintain the activity of the native enzymes. The modified forms comprise sequences at least 95% identical to the amino acid sequences of the corresponding native enzymes.

The enzymatic processing outlined above is capable of depolymerizing lignin and/or releasing compounds therefrom. Compounds that are capable of being released from lignin include monomeric phenylpropanoid units and monomeric flavones. Examples of monomeric phenylpropanoid units capable of being released from lignin include monomeric guaiacyl phenylpropanoid units, monomeric syringyl phenylpropanoid units, and monomeric p-hydroxyphenyl phenylpropanoid units. Examples of flavones capable of being released from lignin include monomeric tricin units.

The lignin subjected to the enzymatic processing outlined above may have any of a number of average molecular weights (MW). The average molecular weight (MW) in some versions, for example, may be at least about 100, at least about 200, at least about 300, at least about 400, at least about 500, at least about 600, at least about 700, at least about 800, at least about 900, at least about 1000, at least about 1,250, at least about 1,500, at least about 1,750, at least about 2,000, at least about 2,500, at least about 3,000, at least about 3,500, at least about 4,000, at least about 4,500, at least about 5,000, at least about 6,000, at least about 7,000, at least about 8,000, at least about 9,000, at least about 10,000, at least about 11,000, at least about 13,000, at least about 15,000, or more. The average molecular weight (MW) in some versions may be up to about 150, up to about 200, up to about 300, up to about 400, up to about 500, up to about 600, up to about 700, up to about 800, up to about 900, up to about 1000, up to about 1,250, up to about 1,500, up to about 1,750, up to about 2,000, up to about 2,500, up to about 3,000, up to about 3,500, up to about 4,000, up to about 4,500, up to about 5,000, up to about 6,000, up to about 7,000, up to about 8,000, up to about 9,000, up to about 10,000, up to about 11,000, up to about 13,000, up to about 15,000, up to about 20,000 or more.

Certain methods of the invention are directed to methods of chemical conversion. Such methods may comprise contacting a first compound in vitro with a non-stereospecific glutathione lyase to yield a second compound.

The non-stereospecific glutathione lyase used in the methods of chemical conversion may comprise any of the non-stereospecific glutathione lyases described herein. Preferred non-stereospecific glutathione lyases include non-stereospecific glutathione lyases comprising an amino acid sequence at least about 60% identical, at least about 65% identical, at least about 70% identical, at least about 75% identical, at least about 80% identical, at least about 85% identical, at least about 90% identical, or at least about 95% identical to any of SEQ ID NO:18 ($NaGST_{Nu}$), residues 21-313 of SEQ ID NO:20 (recombinant $NaGST_{Nu}$), SEQ ID NO:22 ($SYK6GST_{Nu}$), residues 21-324 of SEQ ID NO:24 (recombinant $SYK6GST_{Nu}$), SEQ ID NO:26 (ecYghU), residues 21-313 of SEQ ID NO:28 (recombinant ecYghU), SEQ ID NO:30 (ecYfcG), SEQ ID NO:32 (ssYghU), SEQ ID NO:34 (GST3), and SEQ ID NO:36 (PcUre2pB1).

The first compound contacted with the non-stereospecific glutathione lyase in the methods of chemical conversion preferably has a structure of Formula I or a salt thereof:

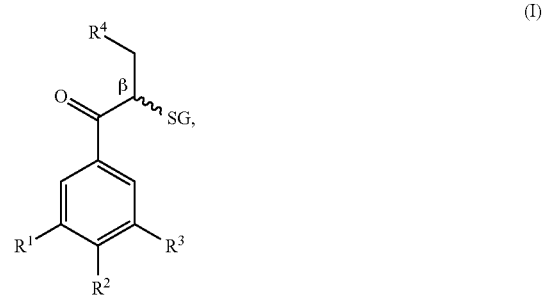

(I)

wherein: $R^1$, $R^2$, and $R^3$ are each independently —H, —OH, —O-alkyl, —O-lignin, or -lignin; $R^4$ is —H, —OH, —SH, —COOH, —$SO_3H$, or —O-lignin; and SG is glutathione bound in an S or R configuration.

The second compound yielded by contacting the first compound with the non-stereospecific glutathione lyase in the methods of chemical conversion preferably has a structure of Formula II or a salt thereof:

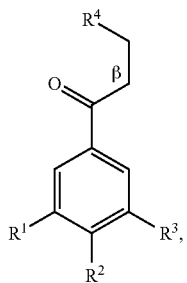
(II)

wherein R¹, R², R³, and R⁴ are as defined above.

Contacting the first compound with the non-stereospecific glutathione lyase in the methods of chemical conversion may occur in in the presence of NADH and a GSH reductase that catalyzes reduction of glutathione disulfide, such as a GSH reductase comprising an amino acid sequence at least 95% identical to SEQ ID NO:38 (AvGR).

The first compound may be generated by contacting lignin comprising β-O-4 ether linkages with any dehydrogenase described herein and/or any β-etherase described herein. The lignin may be contacted with these enzymes in vitro.

Another aspect of the invention includes recombinant enzymes. The recombinant enzymes may be used in any of the methods described herein. The recombinant enzymes may comprise recombinant versions of any enzyme described or encompassed herein, including non-stereospecific glutathione lyases or other enzymes. The term "recombinant" used with reference to an enzyme refers to non-naturally occurring enzymes containing two or more linked polypeptide sequences. Thus, the recombinant enzymes may contain one or more non-native modifications selected from the group consisting of an amino acid addition, an amino acid deletion, and an amino acid substitution. "Non-native modification" refers to a modification that is not found in any native protein. The recombinant enzymes can be produced by recombination methods, particularly genetic engineering techniques, or can be produced by chemical synthesis.

In some versions, the recombinant enzyme comprises a recombinant non-stereospecific glutathione lyase of the invention. The recombinant non-stereospecific glutathione lyase may be a recombinant version of any of the non-stereospecific glutathione lyases described or encompassed herein. Preferred recombinant non-stereospecific glutathione lyases include non-stereospecific glutathione lyases comprising an amino acid sequence at least about 60% identical, at least about 65% identical, at least about 70% identical, at least about 75% identical, at least about 80% identical, at least about 85% identical, at least about 90% identical, or at least about 95% identical to any of: SEQ ID NO:18 (NaGST$_{Nu}$); residues 21-313 of SEQ ID NO:20 (recombinant NaGST$_{Nu}$); SEQ ID NO:22 (SYK6GST$_{Nu}$); residues 21-324 of SEQ ID NO:24 (recombinant SYK6GST$_{Nu}$); SEQ ID NO:26 (ecYghU); residues 21-313 of SEQ ID NO:28 (recombinant ecYghU); SEQ ID NO:30 (ecYfcG); SEQ ID NO:32 (ssYghU); SEQ ID NO:34 (GST3); and SEQ ID NO:36 (PcUre2pB1). The design of amino acid deletions and substitutions in the recombinant non-stereospecific glutathione lyases can be guided by the alignment of the native non-stereospecific glutathione lyases provided in FIG. 5.

Amino acid additions in the recombinant enzymes of the invention, including the recombinant non-stereospecific glutathione lyases, may comprise the addition of any amino acid on the N-terminus, the C-terminus, or both the N-terminus and C-terminus of any native enzyme.

The added amino acids may comprise fusion tags. A number of fusion tags are known in the art. Some fusion tags are used for protein detection. These include green fluorescent protein (GFP) and its many variants (Tsien 1998). Some fusion tags are used for increasing expression and solubility of proteins. These include maltose binding protein (MBP), small ubiquitin-like modifier (SUMO), and glutathione S-transferase (GST), among others (Bell et al. 2013, Butt et al. 2005). Some fusion tags, sometimes referred to as "affinity tags," are used for purification, detection with antibodies, or other uses. A number of affinity tags are known in the art. Exemplary affinity tags include the His tag, the Strep II tag, the T7 tag, the FLAG tag, the S tag, the HA tag, the c-Myc tag, the dihydrofolate reductase (DHFR) tag, the chitin binding domain tag, the calmodulin binding domain tag, and the cellulose binding domain tag. The sequences of each of these tags are well-known in the art.

The recombinant enzymes of the invention, including the recombinant non-stereospecific glutathione lyases, may comprise a peptide cleavage sequence. The peptide cleavage sequence is preferably disposed between the enzyme portion and any fusion tag attached thereto. This permits separation of the fusion tag from the target protein, which may be useful for certain applications. The peptide cleavage sequence may be a recognition sequence for a site-specific peptidase. A number of site-specific peptidases are known in the art. These include Arg-C proteinase, Asp-N endopeptidase, Asp-N endopeptidase+N-terminal glu, BNPS-Skatole, caspase1, caspase2, caspase3, caspase4, caspase5, caspase6, caspase7, caspase8, caspase9, caspase10, chymotrypsin-high specificity (C-term to [FYW], not before P), chymotrypsin-low specificity (C-term to [FYWML], not before P), clostripain (clostridiopeptidase B), CNBr, enterokinase, factor Xa, formic acid, glutamyl endopeptidase, granzymeB, hydroxylamine, iodosobenzoic acid, Lys-C, Lys-N, NTCB (2-nitro-5-thiocyanobenzoic acid), neutrophil elastase, pepsin (pH 1.3), pepsin (pH>2), proline-endopeptidase, proteinase K, SUMO proteases (Ulp1, Senp2, and SUMOstar), staphylococcal peptidase I, subtilisin BPN, tobacco etch virus (TEV) protease, thermolysin, thrombin, and trypsin, and variants thereof, among others. The cleavage recognition sites for these and other site-specific peptidases are well known in the art. Exemplary peptide cleavage sequences include the ExxYxQ↓(G/S) recognition sequence of TEV (and AcTEV and ProTEV), the LVPR↓G recognition sequence of thrombin, the IEGR↓x recognition sequence of factor Xa, and the DDDDK↓x recognition sequence of enterokinase.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLE 1

Nu-Class Glutathione-S-transferases can Act as Glutathione Lyases in the Bacterial Pathway for Breaking β-Aryl Ether Bonds in Lignin Summary As a major component of plant cells walls, lignin is a potential renewable source of valuable chemicals. Several sphingomonad bacteria have been identified that can use glutathione to break the β-aryl ether bond commonly found between phenylpropanoid units of the lignin heteropolymer. To explore bacterial strategies for depolymerizing lignin, we tested the abilities of three sphingomonads to metabolize the β-aryl ether containing dimeric aromatic compound guaiacylglycerol-β-guaiacyl ether (GGE). We found that *Novosphingobium aromaticivorans* metabolized GGE at amongst the fastest rates thus far reported. After the β-aryl ether bond of GGE is broken, the glutathione moiety must be removed from the resultant phenylpropanoid conjugate (α-glutathionyl-β-hydroxypropio-vanillone (GS-HPV)). We found that a Nu-class glutathione-S-transferase (GST) is necessary and sufficient for removing glutathione from both the R and S stereoisomers of GS-HPV in *N. aromaticivorans*. To investigate the prevalence of this glutathione lyase activity within related proteins, we tested Nu-class GSTs from *Sphingobium* sp. SYK-6 and *Escherichia coli* and found that they also cleave both stereoisomers of GS-HPV. We solved the crystal structure of the *N. aromaticivorans* Nu-class GST and used it to develop models for how this enzyme binds and cleaves both stereoisomers of GS-HPV.

Significance

There is considerable interest is identifying biological strategies to produce valuable products from renewable resources. The non-edible, lignocellulosic, fraction of plant biomass has been identified as a renewable source of bio-based products, but the properties of the aromatic polymer lignin present a major hurdle in realizing this goal. Here, we describe a novel role for a Nu-class glutathione-S-transferase (GST) in cleavage of the β-aryl ether bond that connects many aromatic units in lignin. We show that homologues of this enzyme from other bacteria also have this activity, suggesting that this function may be common throughout this widespread class of enzymes. Structural and biochemical analysis of Nu-class GSTs are used to model substrate binding and cleavage by these enzymes.

Introduction

As society looks to diversify its sources of fuels and chemicals, there are compelling reasons to develop renewable sources for them. Lignocellulosic plant biomass is the most abundant renewable material on Earth, so it is a promising but underutilized feedstock for generating products currently derived from petroleum or other non-renewable sources. Lignin, which can compose ~25% of plant biomass (U.S. DOE 2015), is a phenylpropanoid heteropolymer containing several classes of covalent linkages, including a majority of β-aryl ether (β-O-4) bonds (Adler 1977). The properties of lignin create challenges to using it as an industrial raw material. Because of its abundance and potential value, there is interest in developing economical and environmentally sustainable methods to depolymerize lignin to its aromatic substituents. We are interested in analyzing biological processes for lignin depolymerization and conversion to valuable chemicals.

Figure 1:
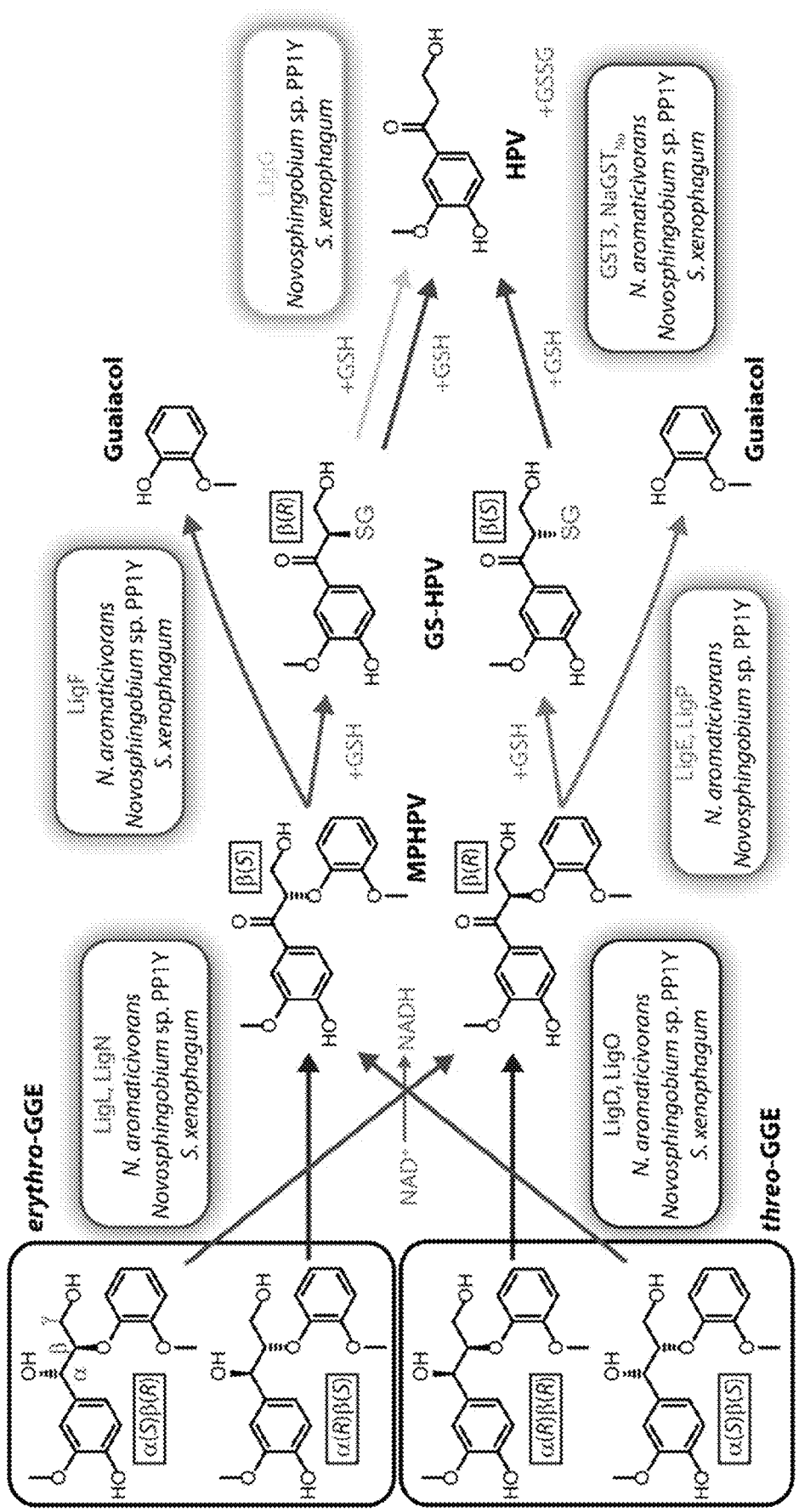
FIG. 1 shows the sphingomonadales β-etherase pathway, used to break the β-aryl ether (β-O-4) bond of compounds such as guaiacylglycerol-β-guaiacyl ether (GGE). Names of enzymes catalyzing each reaction are taken from *Sphingobium* sp. SYK-6 (LigLNDOFEPG; Masai et al. 2003, Sato et al. 2009; Tanamura et al. 2011), *Novosphingobium* sp. MBESO4 (GST3) (Ohta et al. 2015), or *Novosphingobium aromaticivorans* (NaGST$_{Nu}$) (Example 1); the color of each enzyme name matches the arrow color of the reaction it catalyzes. Below each enzyme is listed which of the three sphingomonads investigated in Example 1 (*Novosphingobium* sp. PP1Y, *Novosphingobium aromaticivorans*, and *Sphingobium xenophagum*) are predicted to contain that enzyme. The α, β, and γ carbons of GGE are labeled in the topmost molecule, and the stereochemical designations of all chiral molecules are shown. As shown, metabolism of GGE begins with the stereoselective, NAD⁺-dependent oxidation (by LigD, LigO, LigL, LigN) of the β-aryl alcohol into the α-ketone, β-(2-methoxyphenoxy)-γ-hydroxypropiovanillone (MPHPV) (Sato et al. 2009). β(S)- and ββ(R)-MPHPV are then cleaved by stereospecific glutathione (GSH)-dependent β-etherases (e.g., LigF, LigE/P) to yield the β(R)- and β(S)-stereoisomers of the glutathione conjugate β-glutathionyl-γ-hydroxypropiovanillone (GS-HPV) and guaiacol (Masai et al. 2003, Gall and Kim et al. 2014). GSH-dependent enzymes that remove the glutathione moiety from GS-HPV to form hydroxypropiovanillone (HPV) and glutathione disulfide (GSSG) have been identified in vitro: LigG reacts specifically with β(R)-GS-HPV (Masai et al. 2003), whereas GST3 and NaGST$_{Nu}$ react with both the β(R)- and β(S)-stereoisomers (Ohta et al. 2015).

The β-etherase pathway of sphingomonadales bacteria, which cleaves the β-aryl ether bond (FIG. 1), is a promising route for lignin depolymerization. Although several species are known to contain this pathway (Masai et al. 1989, Palamuru et al. 2015, Ohta et al. 2015), characterizing the strategies and proteins employed could help to develop biological systems for depolymerizing lignin. In this work, we tested sphingomonads predicted to contain the β-etherase pathway (Ohta et al. 2015), and found that *N. aromaticivorans* most rapidly and completely metabolized the dimeric aromatic compound guaiacylglycerol-β-guaiacyl ether (GGE; FIG. 1). We also found that the Saro_2595 gene of *N. aromaticivorans* encodes a previously uncharacterized Nu-class glutathione-S-transferase (named here NaGST$_{Nu}$) that is capable of cleaving glutathione from both the β(R)- and β(S)-stereoisomers of the pathway intermediate β-glutathionyl-γ-hydroxypropiovanillone (GS-HPV; FIG. 1) in vitro, and we show that it is the sole enzyme in *N. aromaticivorans* required for this reaction in vivo.

Nu-class GSTs are found in many organisms (Stourman et al. 2011; Mashiyama et al., 2014), but their physiological roles are unknown. Although the *Escherichia coli* Nu-class GSTs ecYfcG and ecYghU can reduce the disulfide bond of 2-hydroxyethyl disulfide in vitro (Stourman et al. 2011, Wadington et al. 2009, Wadington et al. 2010), the physiological relevance of this reaction has not been established. To test the prevalence of the glutathione lyase activity in Nu-class GSTs, we assayed ecYghU, ecYfcG, and a Nu-class GST from *Sphingobium* sp. SYK-6 (encoded by SLG_04120; named here SYK6GST$_{Nu}$), and found that they also cleave β(R)- and β(S)-GS-HPV in vitro. Furthermore, ecYghU complements growth of an *N. aromaticivorans* ΔNaGST$_{Nu}$ mutant, showing that it is active in vivo.

Crystal structures reported here show that NaGST$_{Nu}$ is similar to ecYghU (Stourman et al. 2011) and *Streptococcus sanguinis* SK36 YghU (Patskovsky et al.), although there are notable differences in the channels leading to the active sites. We propose a mechanism for the glutathione lyase activity of the Nu-class GSTs and use molecular modeling to show how the active site channels of these enzymes can accommodate the β(R)- and β(S)-stereoisomers of GS-HPV.

Indeed, the approach to the active site of these Nu-class GSTs can accommodate a variety of GSH-conjugated substrates, independent of C—S bond stereochemistry, including other GSH-conjugates derived from lignin depolymerization, or ones that might be found in organisms that do not metabolize lignin.

General Materials and Methods

Bacterial strains and growth media. Strains used are listed in Table 1. Unless otherwise noted, *E. coli* cultures were grown in Lysogeny Broth (LB), and shaken at ~200 rpm at 37° C. For routine storage and manipulation, sphingomonad cultures were grown in LB at 30° C. GluSis is a modification of Sistrom's minimal medium (Sistrom 1962) in which the succinate has been replaced by 22.6 mM glucose. Standard Mineral Base (SMB) (Stanier et al. 1966) contains 20 mM $Na_2HPO_4$, 20 mM $KH_2PO_4$, 1 g/L $(NH_4)_2SO_4$, and 20 mL Hutner's vitamin-free concentrated base (adapted from (Cohen et al. 1957), but lacking nicotinic acid, thiamin, and biotin) per liter, final pH 6.8. SMB was supplemented with carbon sources as described below. Where needed to select for plasmids, media were supplemented with 50 µg/mL kanamycin and/or 10 µg/mL chloramphenicol.

TABLE 1

Bacterial strains and plasmids used.

| Strains | Relevant characteristics | References |
|---|---|---|
| *Novosphingobium aromaticivorans* strains | | |
| DSM 12444 | Wild-type; also called F199 | Fredrickson et al. 1991 |
| 12444Δ1879 | DSM 12444 ΔSaro_1879 | This study |
| 12444Δ2595 | 12444Δ1879 ΔSaro_2595 | This study |
| 12444ecyghU | 12444Δ2595 containing *E. coli* yghU at the Saro_2595 locus | This study |
| *Novosphingobium* sp. PP1Y | Wild-type | Notomista et al. 2011 |
| *Sphingobium xenophagum* NBRC 107872 | Wild-type; also called $BN6^T$ and DSM $6383^T$ | Stolz et al. 2000; Pal et al. 2006 |
| *Escherichia coli* strains | | |
| DH5α | F- Φ80lacZ ΔM15 Δ(lacZYA-argF) U169 recA1 endA1 hsdR17 (rK−, mK+) phoA supE44 λ − thi-1 gyrA96 relA1 | Bethesda Research Laboratories Taylor (1993) |
| S17-1 | recA pro hsdR RP4-2-Tc::Mu-Km::Tn7 | Simon et al. 1983 |
| Turbo | F' proA⁺B⁺ lacI$^q$ ΔlacZM15/ fhuA2 Δ(lac-proAB) glnV galK16 galE15 R(zgb-210::Tn10)Tet$^S$ endA1 thi-1 Δ(hsdS-mcrB)5 | New England Biolabs |
| NEB 5-alpha Competent *E. coli* | fhuA2 Δ(argF-lacZ)U169 phoA glnV44 Φ80Δ(lacZ)M15 gyrA96 recA1 relA1 endA1 thi-1 hsdR17 | New England Biolabs |
| E. cloni 10 G | F- mcrA Δ(mrr-hsdRMS-mcrBC) endA1 recA1 Φ 80dlacZΔM15ΔlacX74 araD139 Δ(ara,leu)7697galU galK rpsL nupG λ − tonA (StrR) | Lucigen |
| B834 | F- hsdS metE gal ompT | Wood 1966; Doherty 1995 |
| Plasmids | | |
| pK18mobsacB | pMB1ori sacB kan$^R$ mobT oriT(RP4) lacZα | Schafer et al. 1994 |
| pK18msB-MCS1 | pK18mobsacB lacking the multiple cloning site | Present example |
| pVP302K | lac promoter lacI, Tev site rtxA (*V. cholera*) kan$^R$; coding sequence for 8 × His-tag | Supplemental Materials of Gall and Ralph et al. 2014 |
| pRARE2 | p15a ori camR; tRNA genes for 7 rare codons in *E. coli* | Novagen |
| pK18msB/ΔSaro1879 | pK18mobsacB containing genomic regions flanking Saro_1879 | Present example |
| pK18msB/ΔSaro2595 | pK18mobsacB containing genomic regions flanking Saro_2595 | Present example |
| pK18msB/ecyghU-Δ2595 | pK18mobsacB containing *E. coli* yghU between the Saro_2595 flanking regions | Present example |
| pVP302K/Ctag-2595 | pVP302K containing Saro_2595 upstream of rtxA and His-tag sequence | Present example |
| pVP302K/Untagged2595 | pVP302K containing Saro_2595 | Present example |
| pVP302K/Ntag-2595 | pVP302K containing Saro_2595 downstream of His-tag coding sequence and Tev protease site | Present example |
| pVP302K/Ntag-ecyghU | pVP302K containing yghU downstream of His-tag coding sequence and Tev protease site | Present example |

TABLE 1-continued

Bacterial strains and plasmids used.

| Strains | Relevant characteristics | References |
|---|---|---|
| pVP302K/Ntag-ecyfcG | pVP302K containing yfcG downstream of His-tag coding sequence and Tev protease site | Present example |
| pVP302K/Ntag-SLG_04120 | pVP302K containing SLG_04120 downstream of His-tag coding sequence and Tev protease site | Present example |

Construction of defined *N. aromaticivorans* mutants. We deleted Saro_1879 from the *Novosphingobium aromaticivorans* DSM 12444 genome to create a strain (12444Δ1879) amenable to genomic modifications using a sacB-containing vector. We used 12444Δ1879 to generate strains in which Saro_2595 was deleted from the genome (12444Δ2595) and in which Saro_2595 was replaced in the genome by the *E. coli* yghU gene (12444ecyghU).

Sphingomonad growth experiments. Cell densities were measured using a Klett-Summerson photoelectric colorimeter with a red filter. For *N. aromaticivorans*, 1 Klett Unit (KU) is equal to ~8×10$^6$ cells/mL (Table 2). Experimental cultures of *N. aromaticivorans* and *Novosphingobium* sp. PP1Y were grown in SMB containing either vanillate or GGE alone (4 mM and 3 mM, respectively), or a combination of vanillate and GGE (4 mM and 1.5 mM, respectively). For *S. xenophagum* cultures, vanillate was replaced by glucose, since we found this strain to be unable to metabolize vanillate. *N. aromaticivorans* was also grown in SMB containing 200 µM GGE. Starter cultures were grown in SMB with 4 mM vanillate or glucose, and cells were pelleted and washed with PBS (10 mM Na$_2$HPO$_4$, 1.8 mM KH$_2$PO$_4$, 137 mM NaCl, 2.7 mM KCl; pH=7.4). Pellets were resuspended into culture medium and used to inoculate experimental cultures to initial cell densities of <5 KU.

Cultures were incubated at 30° C., in 125 mL conical flasks containing 20-40 mL of medium and shaken at ~200 rpm. Aliquots (400-600 µL) were removed at specified time points and filtered through 0.22 µm syringe tip filters (e.g., Whatman Puradisc filters, GE Healthcare, Piscataway, N.J.) before HPLC analysis of extracellular aromatics. Every culture was grown at least three times; data shown are from representative cultures.

TABLE 2

Relationship between Klett Units (KU) and colony forming units (CFUs) for *Novosphingobium aromaticivorans* +/− sucrose (CFU mL$^{-1}$ KU$^{-1}$).

| | −sucrose | +sucrose |
|---|---|---|
| DSM 12444 | 8.0 (±3.2) × 10$^6$ | 0 |
| 12444Δ1879 | 8.1 (±1.7) × 10$^6$ | 7.3 (±3.4) × 10$^6$ |

To acquire these data, cultures of *Novosphingobium aromaticivorans* DSM 12444 and 12444Δ1879, were grown in liquid medium. Cell densities were measured using a Klett-Summerson photoelectric colorimeter with a red filter. Cultures were diluted, then plated onto solid media +/−10% sucrose.

Enzyme purifications. Genes Saro_2595, *E. coli* yghU, *E. coli* yfcG, and SLG_04120 from *Sphingobium* sp. SYK-6 (codon-optimized for expression in *E. coli*) were individually cloned into plasmid pVP302K (Gall and Ralph et al. 2014) so that transcripts from the plasmids would be translated into proteins containing a His$_8$-tag connected to the N-terminus via a tobacco etch virus (TEV) protease recognition site. Recombinant proteins were expressed in *E. coli* B834 (Wood 1966, Doherty et al. 1995) containing plasmid pRARE2 (Novagen, Madison, Wis.) grown for ~24 h at 27° C. in ZYM-5052 Autoinduction Medium (Studier 2005) containing kanamycin and chloramphenicol. Recombinant proteins were purified essentially as described previously (Gall and Kim et al. 2014); see below for modifications to the procedure. After removal of His$_8$-tags using TEV protease, recombinant proteins retained a Ser-Ala-Ile-Ala-Gly-peptide on their N-termini, derived from the linker between the protein and the TEV protease recognition site. Recombinant LigE and LigF1 from *N. aromaticivorans* were purified as previously described (Gall and Ralph et al. 2014).

Kinetics analysis of GS-HPV cleavage. The Reaction Buffer (RB) consisted of 25 mM Tris-HCl (pH 8.5) and 25 mM NaCl. The β(R)- and β(S)-stereoisomers of GS-HPV were separately generated by incubating racemic MPHPV (0.46 mM) in RB with 5 mM reduced glutathione (GSH) and either 38 µg/mL LigF1 or 36 µg/mL LigE, respectively, for several h. This sample, containing a single GS-HPV stereoisomer, guaiacol, and the unreacted MPHPV stereoisomer, was diluted with RB to achieve the desired concentration of GS-HPV for the time course reaction (0.005, 0.011, 0.022, 0.096, or 0.193 mM). An additional 5 mM GSH (dissolved in RB) was added prior to initiation of each time course. At time zero, 100 µL of the indicated enzyme sample (resuspended in RB) was combined with 1800 µL of the diluted GS-HPV reaction mixture to achieve final concentrations of 8 nM NaGST$_{Nu}$, 195 nM ecYghU, 195 nM ecYfcG, or 47 nM (for β(R)-GS-HPV reactions) or 18 nM (for β(S)-GS-HPV reactions) SYK6GST$_{Nu}$. Assays were performed at 25° C., and at specified time points, 300 µL of the reaction was removed and combined with 100 µL 1 M HCl (Acros Organics; Geel, Belgium) to stop the reaction before HPLC analysis to quantify HPV formed.

*N. aromaticivorans* crude cell extract assays. *N. aromaticivorans* cells were grown in 500 mL conical flasks containing 267 mL SMB medium with 4 mM vanillate and 1 mM GGE. When cell densities reached ~1×10$^9$ cells/mL, cells were lysed by the sonication procedure used to generate *E. coli* lysates for protein purification. Samples were centrifuged at 7000×g for 15 minutes, and the supernatants were used as crude cell extracts.

Assays containing 50 mM Tris-HCl (pH 8.0), 50 mM NaCl, 10 mM GSH, 0.407 mM racemic MPHPV (a mixture of the β(R)- and β(S)-isomers) and cellular extract from 12444Δ1879 or 12444Δ2595 (final concentrations of 269 and 186 µg protein/mL, respectively) were performed at 30° C. At defined time points, 300 µL aliquots were combined with 100 µL 1 M HCl to stop the reaction before HPLC analysis. At the indicated time, recombinant NaGST$_{Nu}$ (30

µg protein/mL) was added to the 12444Δ2595 cell extract reaction, along with an additional 10 mM GSH.

HPLC analysis. After extracellular aromatics were identified using LC-MS, routine analysis and quantification of aromatics were performed using an Ultra AQ C18 5 µm column (Restek, Bellefonte, Pa.) attached to a System Gold HPLC (Beckman Coulter, Brea, Calif.) with running buffers and chromatography conditions described in FIG. 14. The eluent was analyzed for light absorbance between 191 and 600 nm, and absorbances at 280 nm were used for quantification of aromatic metabolites by comparing peak areas to those of standards (retention times of measured metabolites are shown in FIG. 15).

Production of cDNA libraries from *N. aromaticivorans* cultures and real-time PCR. *N. aromaticivorans* cultures were grown in 120 mL of SMB containing either 4 mM vanillate or 4 mM vanillate and 1 mM GGE. When the cultures reached densities of ~8×10$^8$ cells/mL, 40 mL were removed and combined with 5.71 mL ice-cold Stop Solution (95% ethanol, 5% acid phenol: chloroform (5:1 solution, pH 4.5)). These mixtures were centrifuged at 4° C. for 12 min at 6,000×g. Cell pellets were resuspended into 2 mL Lysis Solution (2% SDS, 16 mM EDTA in RNase-free water), then incubated at 65° C. for 5 min. RNA purification and cDNA synthesis were performed as previously described (Tavano et al. 2005), using SuperScript III reverse transcriptase (Thermo Fisher Scientific, Waltham, Mass.) to construct the cDNA library.

Real-time PCR was performed on a 7500 Real Time PCR System (Applied Biosystems, Forest City, Calif.) using SYBR Green JumpStart Taq ReadyMix (Sigma-Aldrich, St. Louis, Mo.). Primers used to detect transcripts are contained in Table 3. Transcript levels were normalized to those of Saro_0141 (rpoZ, coding for the RNA polymerase omega subunit).

TABLE 3

Primers used for RT qPCR of *Novosphingobium aromaticivorans* genes.

| Transcript assayed for | Primers |
|---|---|
| Saro_0141 (rpoZ) | 5'-GAGATCGCGGAAGAAACCGTGC-3' (SEQ ID NO: 48) <br> 5'-GATTTCATCCACCTCGTCGTCGTC-3' (SEQ ID NO: 49) |
| Saro_0205 (ligD) | 5'-CAACATCAAGTCGAACATCGCGGAAG-3' (SEQ ID NO: 50) <br> 5'-CTGGTGGATCGAATGCAGCGAG-3' (SEQ ID NO: 51) |
| Saro_0793 (ligO) | 5'-GATCGAGGAATCTTCCTACGACGACTG-3' (SEQ ID NO: 52) <br> 5'-GTTTACCACGCCGTGGAGGTTCAC-3' (SEQ ID NO: 53) |
| Saro_0794 (ligN) | 5'-CATATCGTCTGCACCGCTTCGATGTC-3' (SEQ ID NO: 54) <br> 5'-GCAGAATGCCGAGCAGATCACG-3' (SEQ ID NO: 55) |
| Saro_1875 (ligL) | 5'-CCATGTCGTCAACACCGCATCG-3' (SEQ ID NO: 56) <br> 5'-CATGTTCTCGGTCAGGTTCAGCAC-3' (SEQ ID NO: 57) |
| Saro_2091 (ligF) | 5'-GCTGCTGACGGTGTTCGAGAAG-3' (SEQ ID NO: 58) <br> 5'-CTTGAACCAGTCGGTGTGATGCTC-3' (SEQ ID NO: 59) |
| Saro_2405 (ligP) | 5'-CATCGTCGAATACCTCGATGCCAAGTATC-3' (SEQ ID NO: 60) <br> 5'-GTCCTGGCAGAAGCAGAACATCCAC-3' (SEQ ID NO: 61) |
| Saro_2595 | 5'-CCACGATCATGCTGGAAGAACTGCTC-3' (SEQ ID NO: 62) <br> 5'-GATTCGAAGACGCGGAACGGTTCAG-3' (SEQ ID NO: 63) |

Determination of chemical oxygen demand (COD). Initial culture COD values were obtained either from uninoculated medium, or from inoculated medium that was immediately passed through a 0.22 µm filter. Final COD values were obtained when cultures reached their maximum cell densities. For these samples, we analyzed the COD of both the entire culture (cells and medium) and the filtered medium. The difference in COD between the unfiltered and filtered final samples is defined as the COD of cellular biomass. Samples were diluted as needed and combined with High Range COD Digestion Solution (Hach, Loveland, CO). The mixtures were heated to 150° C. for 120 min to oxidize the materials before absorbances were measured at 600 nm. Standards with known COD values were analyzed in parallel.

Chemicals. Vanillate, guaiacol, reduced L-glutathione (GSH), and 2,3-dichloro-5,6-dicyano-p-benzoquinone (DDQ) were purchased from Sigma-Aldrich (St. Louis, Mo.). erythro-Guaiacylglycerol-β-guaiacyl ether (erythro-GGE) was purchased from TCI America (Portland, Oreg.).

A racemic mixture of β-(2-methoxyphenoxy)-γ-hydroxypropiovanillone (MPHPV) was synthesized by dissolving erythro-GGE into ethyl acetate (Fisher Scientific), then slowly adding 1.25 molar equivalents of 2,3-dichloro-5,6-dicyano-p-benzoquinone (DDQ) and stirring for 30 min. The reaction was washed three times with saturated NaHCO$_3$ to remove DDQH$_2$ formed during the reaction. The MPHPV was purified via flash chromatography using hexane/ethyl acetate=1/3, as previously described (Gall and Kim et al. 2014), then crystallized from the eluent via solvent evaporation.

Hydroxypropiovanillone (HPV) was synthesized as previously described for synthesis of β-deoxy-α-veratrylglycerone, except using 4-O-benzyl-acetovanillone as starting material, rather than acetoveratrone (Gall and Kim et al. 2014). Synthesis of HPV required an additional debenzylation step that was unnecessary in the synthesis of β-deoxy-α-veratrylglycerone.

Structural analysis of NaGST$_{Nu}$ and molecular modeling. NaGST$_{Nu}$ was screened for crystal formation against several commercial screens at 277 and 293K using a TTP Labtech Mosquito® crystallization robot. The best diffracting ammonium acetate precipitated crystal was obtained at 293K, by mixing 0.2 µL of protein solution (277 µM protein preincubated for 50 min with 10 mM GSH (neutralized with NaOH)) with 0.2 µL of reservoir solution (4 M ammonium acetate buffered with 100 mM sodium acetate, pH 4.6). This crystal was mounted directly from the growth solution by drawing it through a layer of fomblin oil, thinning the surrounding liquid with a paper wick, and was plunged into liquid nitrogen. The best diffracting ammonium sulfate precipitated crystal was obtained at 293K using 0.13 µL of protein solution and 85 nL of reservoir solution (1.35 M ammonium sulfate, 0.1 M lithium sulfate, and 0.1 M bis-trispropane, pH 7.5). This crystal was cryopreserved by adding 0.5 µL of a solution composed of 2 parts reservoir solution and one part neat glycerol to the droplet containing the crystal, and equilibrating for 11 min prior to looping and plunging into liquid nitrogen.

Diffraction data were obtained at the GM/CA beam-line at Argonne National Laboratory with an Eiger 16M detector (Casanas et al. 2016). Data were collected on the ammonium acetate and ammonium sulfate crystal forms using 1.033 Å (for 1.45 Å resolution) or 0.7749 Å (for 1.25 Å resolution) X-rays, respectively. Diffraction data were reduced using XDS (Kabsch 2010). Both crystals belonged to space group $P2_12_12_1$ with a predicted solvent content of 60%. The structure was solved by molecular replacement with Phaser (McCoy et al. 2007) in the Phenix suite (Adams et al. 2010), using a search model based on PDB ID 3C8E:A (ecYghU (Stourman et al. 2011)) modified with phenix.sculptor (Bunkóczi et al. 2011), based on primary sequence alignment. Structure solution revealed two copies of the protein per asymmetric unit, with strong electron density present for the paired active site glutathione molecules. Phenix.refine (Afonine et al. 2012) and COOT (Emsley et al. 2004) were alternatively used to refine the structure and fit the model to electron density maps.

For modeling β(R)- and β(S)-GS-HPV and their syringyl phenylpropanoid analogues into the active sites of $NaGST_{Nu}$ and ecYghU, the PyMOL Builder function (The PyMOL Molecular Graphics System, Version 1.8.2.1) was used to create molecules of GS-HPV or GS-syringyl by adding atoms onto the GSH2 molecule bound in each active site. Atoms were added so as to visually minimize steric clash with the proteins. The potential energies of the protein-GS-phenylpropanoid complexes were minimized using the Minimize Structure function of UCSF Chimera (Pettersen et al. 2004). For the energy minimization, all of the atoms of the protein-GS-phenylpropanoid complex were held rigid except for those of the phenylpropanoid moiety and the Cys sidechain of GSH2. One-hundred steepest descent steps were run, followed by twenty conjugate gradient steps, and all step sizes were 0.05 Å.

Recipes for media components:
  Hutner's vitamin-free Concentrated Base (Cohen-Bazire et al. 1957) (per 500 mL):
    5 g Nitrilotriacetic acid
    14.78 g $MgSO_4 \cdot 7H_2O$
    1.67 g $CaCl_2 \cdot 2H_2O$
    4.625 mg $(NH_4)_6Mo_7O_{24} \cdot 4H_2O$
    49.5 mg $FeSO_4 \cdot 7H_2O$
    25 mL Metals "44"
  Metals "44" (per 500 mL):
    1.25 g EDTA (free acid) [Add this first; use 10 M NaOH to help dissolve it.]
    5.475 g $ZnSO_4 \cdot 7H_2O$
    2.5 g $FeSO_4 \cdot 7H_2O$
    0.77 g $MnSO_4 \cdot H_2O$
    0.196 g $CuSO_4 \cdot 5H_2O$
    0.125 g $Co(NO_3)_2 \cdot 6H_2O$
    0.0885 g $Na_2B_4O_7 \cdot 10H_2O$ Construction of defined *N. aromaticivorans* mutants. *N. aromaticivorans* has been reported to use sucrose as sole carbon source (Stolz et al. 2000), but we found it to be incapable of growing in the presence of >10% sucrose (Table 2). We also noticed that the gene Saro_1879 is annotated as sacB, whose product, levansucrase, makes sucrose inhibitory to growth of many Gram-negative bacteria (Gay et al. 1985). To create an *N. aromaticivorans* strain that we could modify using a sacB-containing plasmid, we deleted Saro_1879 from its genome. To do this, we constructed plasmid pK18msB/ΔSaro1879, in which genomic DNA from upstream and downstream of Saro_1879 was cloned into pK18msB-MCS1 (for details of plasmid construction, see below). This plasmid was mobilized into *N. aromaticivorans* via electroporation using a single 2.5 kV pulse in a 0.2 cm cuvette in a MicroPulser apparatus (Bio-Rad, Hercules, Calif.). *N. aromaticivorans* was made electrocompetent by washing exponential phase cells from LB cultures twice with ice-cold 0.5 M glucose, then resuspending the cells into 10% glycerol. Transformants in which the plasmid was integrated into the genome via homologous recombination (single crossovers) were selected for by growth on solid LB containing kanamycin. These strains were grown in liquid LB to allow plasmid loss via homologous recombination, then plated on solid LB containing 10% sucrose to select for sucrose-tolerance. Sucrose-tolerant strains in which Saro_1879 had been deleted from the genome were confirmed by PCR amplification and sequencing of genomic DNA. One of these strains (12444Δ1879) was used as the parent strain for subsequent genetic modifications.

To inactivate Saro_2595, we electroporated plasmid pK18msB/ΔSaro2595 (in which genomic DNA from upstream and downstream of Saro_2595 was cloned into pK18msB-MCS1) into strain 12444Δ1879, and a strain lacking the Saro_2595 gene (referred to as 12444Δ2595) was isolated via the process described above for deleting Saro_1879.

To generate a strain (referred to as 12444ecyghU) in which Saro_2595 was replaced in the *N. aromaticivorans* genome with the *E. coli* yghU gene, we constructed plasmid pK18msB/ecyghU-Δ2595, in which yghU (amplified from *E. coli* DH5a genomic DNA) was cloned into pK18msB/ΔSaro2595. This plasmid was mobilized into 12444Δ2595 via conjugation from *E. coli* S17-1. Transconjugants (single crossovers) of *N. aromaticivorans* were isolated on solid GluSis containing kanamycin. After growth in liquid GluSis, strains that lost the plasmid and retained the yghU gene at the native Saro_2595 locus were isolated on solid GluSis medium containing sucrose. The presence of the yghU gene in the genome was confirmed via PCR and sequencing.

Purification of recombinant proteins. Recombinant proteins were purified as described previously (Gall and Kim et al. 2014), except that cells were lysed by sonication, first using a Branson Sonifier 450 (Branson Ultrasonics, Danbury, Conn.) (duty cycle 50%, output level 6, for six rounds of 1-2 min), then a Qsonica Q500 with a cup horn attachment (Qsonica, Newtown, Conn.) (60% amplitude for 10 minutes with cycles of 10 s on, 10 s off). His-tagged proteins were purified from lysates over a column packed with $Ni^{2+}$-NTA resin (Qiagen, Hilden, Germany) attached to an AKTAprime plus FPLC (GE Healthcare Life Sciences), then incubated with TEV protease to remove the His-tag. The protease reaction mixture was passed through a $Ni^{2+}$-NTA column to separate the recombinant protein from the cleaved $His_8$-tag and TEV protease (which also contained a His-tag). Procedures to Construct Plasmids for Genomic Modifications for *N. aromaticivorans* and for Purifying Enzymes Biological reagents. All PCR reactions were performed with Herculase II polymerase (Agilent Technologies, Santa Clara, Calif.). Primers were phosphorylated with polynucleotide kinase from Promega (Madison, Wis.). All other enzymes were from New England Biolabs (Ipswich, Mass.). All primers were from Integrated DNA Technologies (Coralville, Iowa). See Table 4.

TABLE 4

Primers used in genomic modifications and enzyme expression.

| Name | Sequence | Notes |
| --- | --- | --- |
| pK18msB AseI ampl F | 5'-CTGTCGTGCCAGCTGCATTAATG-3' (SEQ ID NO: 64) | AseI site (underlined) native to template |
| pK18msB - MCS XbaI R | 5'-GAACAtcTAGAAAGCCAGTCCGCAGAAAC-3' (SEQ ID NO: 65) | XbaI site (underlined); lowercase bases do not match template |
| Saro1879 lvnsucr ampl F AseI | 5'-CCCGAattaATCGTGACGGTATCAACCTCC-3' (SEQ ID NO: 66) | AseI site (underlined); lowercase bases do not match template |
| Saro1879 lvnsucr ampl R XbaI | 5'-GTTTCGGtCtAGATCGAGCTGACCGAAATC-3' (SEQ ID NO: 67) | XbaI site (underlined); lowercase bases do not match template |
| Saro_2595 amp AseI for | 5'-GTCGatTAatAGTCCGAGATCGAGGCTGC-3' (SEQ ID NO: 68) | AseI site (underlined); lowercase bases do not match template |
| Saro_2595 amp XbaI rev | 5'-CGACtctAGaCAGAGCCTGAACGAAGTC-3' (SEQ ID NO: 69) | XbaI site (underlined); lowercase bases do not match template |
| Saro1879 lvnsucr del REV | 5'-CCGACTTTCTTGAAACAGATTTGGCTTAAGAC-3' (SEQ ID NO: 70) | |
| Saro1879 lvnsucr del FOR | 5'-GTTCATGCTTAACTTCGATGGCGAGC-3' (SEQ ID NO: 71) | |
| Saro_2595 del rev | 5'-CCTGCTCCTTGGGGATATTGTTAGTGTTG-3' (SEQ ID NO: 72) | |
| Saro_2595 del for | 5'-GGAATCGTTGCAAGCGATCGTCAAG-3' (SEQ ID NO: 73) | |
| D2595pK18-ecYghU F | 5'-GGAGCAGGCGATGACAGACAATACTTATCAGCCCGCGAAAG-3' (SEQ ID NO: 74) | underlined region matches sequence in pK18msB/ΔSaro2595 |
| D2595pK18-ecYghU R | 5'-CGAGGCGGGTTTACCCCTGACGCTTATCTTCCGTATTCGTC-3' (SEQ ID NO: 75) | underlined region matches sequence in pK18msB/ΔSaro2595 |
| ecYghU-D2595pK18 F | 5'-TCAGGGGTAAACCCGCCTCGAGACCGGCGAAC-3' (SEQ ID NO: 76) | underlined region matches sequence in yghU |
| ecYghU-D2595pK18 R | 5'-TGTCTGTCATcgCCTGCTCCTTGGGGATATTGTTAGTG-3' (SEQ ID NO: 77) | underlined region matches sequence in yghU; lowercase bases are not present in pK18msB/ΔSaro2595, but are present in the *N. aromaticivorans* genome |
| Saro2595 Ctag PciI F | 5'-GCAGGacATGTCCTCAGAGTACGTTCC-3' (SEQ ID NO: 78) | PciI site (underlined); lowercase bases do not match template |
| Saro2595 Ctag BsaI R | 5'-GTTatctgcgagaccACGATCGCTTGCAACGATTC-3' (SEQ ID NO: 79) | BsaI site (underlined); lowercase bases do not match template |
| pVP302K Ctag BsaI F | 5'-CTGCGGTCTCGCAGATGGTAAAATTCTG-3' (SEQ ID NO: 80) | BsaI site (underlined) |

TABLE 4-continued

Primers used in genomic modifications and enzyme expression.

| Name | Sequence | Notes |
| --- | --- | --- |
| pVP302K Ctag NcoI R | 5'-GGTGATGTC<u>CCATGG</u>TTAATTTCTCCTC TTTAATG-3' (SEQ ID NO: 81) | NcoI site (underlined) |
| Ctag 2595-pVP add Stop R | 5'-<u>tca</u>gaagcccttgACGATCGCTTGCAACGA TTC-3' (SEQ ID NO: 82) | lowercase bases do not match pCtag-2595/pVP302K; underlined bases are stop codon |
| pVP302K Ntag HindIII F | 5'-CATTAA<u>aAGc</u>TTAAACGAATTCGGACT CGGTACGC-3' (SEQ ID NO: 83) | HindIII site (underlined); lowercase bases do not match template |
| 2595-pVP C to Ntag F | 5'-ca<u>agcgaaaatctgtatttcagagcgcgatcgcagga</u>ATGTCCTCAGAGTACGTTCC-3' (SEQ ID NO: 84) | lowercase bases do not match template; bold ATG is Saro_2595 start site; underlined region is Tev protease recognition site |
| pVP302 C to Ntag R | 5'-ccaatgc<u>atggtgatggtgatgatggtgatgtcccat</u>GGTTAATTTCTCCTCTTTAATG-3' (SEQ ID NO: 85) | lowercase bases do not match template; compliment of coding region for 8X-Histidine tag is underlined |
| pVP302K-ecYghU F | 5'-<u>GATCGCAGGA</u>ATGACAGACAATACTT ATCAGCCCGCGAAAG-3' (SEQ ID NO: 86) | underlined region matches sequence in pVP302K |
| pVP302K-ecYghU R | 5'-<u>CGGCTTTCTGT</u>TACCCCTGACGCTTATC TTCCGTATTCGTC-3' (SEQ ID NO: 87) | underlined region matches sequence in pVP302K |
| ecYghU-pVP302K F | 5'-<u>TCAGGGGTAA</u>CAGAAAGCCGAAAATA ACAAAGTTAGCCTGAGCTG-3' (SEQ ID NO: 88) | underlined region matches sequence in yghU |
| ecYghU-pVP302K R yghU | 5'-<u>TGTCTGTCATT</u>CCTGCGATCGCGCTCT GAAAATACAGATTTTCG-3' (SEQ ID NO: 89) | underlined region matches sequence in |
| pVP302K-HiFi-ATW-R | 5'-TCCTGCGATCGCGCTCTGAAAATACAG ATTTTCG-3' (SEQ ID NO: 90) | |
| pVP302K-HiFi-ATW-F | 5'-CAGAAAGCCGAAAATAACAAAGTTAG CCTGAGCTG-3' (SEQ ID NO: 91) | |
| ecYfcG-pVP-Ntag-HiFi-F | 5'-gtatttcagagcgcgatcgcaggaATGATCGATCTCTATTTCGCCCCGACAC-3' (SEQ ID NO: 92) | lowercase region complementary to "pVP302K-HiFi-ATW-R" |
| ecYfcG-pVP-Ntag-HiFi-R | 5'-ctaactttgttattttcggctttctgTTAACTATCCGAACGCTCATCACCGAGTTG-3' (SEQ ID NO: 93) | lowercase region complementary to "pVP302K-HiFi-ATW-F" |
| SYK6 yghU pVP fix R | 5'-gttattttcggctttctgttaagCTTCGGTCTTCG-3' (SEQ ID NO: 94) | Lowercase region complementary to "SYK6 yghU pVP fix F" |
| SYK6 yghU pVP fix F | 5'-cttaacagaaagccgaaaataacAAAGTTAGCCTGAG-3' (SEQ ID NO: 95) | Lowercase region complementary to "SYK6 yghU pVP fix R" |

Construction of pK18msB-MCS1. Plasmid pK18mobsacB (Schafer et al. 1994) was amplified via PCR with phosphorylated primers "pK18msB AseI ampl F" and "pK18msB-MCS XbaI R". The product was circularized with T4 DNA ligase, then transformed into *E. coli* DH5α. The final 5278-base pair (bp) plasmid, pK18msB-MCS1, is similar to pK18mobsacB, except that the multiple cloning site has been removed, and a new XbaI site is 24 bp from one of the plasmid's native AseI sites (with the other native AseI site removed).

Plasmids for deleting Saro_1879 or Saro_2595. Regions of *N. aromaticivorans* genomic DNA containing either Saro_1879 or Saro_2595, along with ~1300-1600 bp flanking regions upstream and downstream of each gene, were separately amplified via PCR using the primer pairs "Saro1879 lvnsucr ampl F AseI"/"Saro1879 lvnsucr ampl R XbaI" and "Saro_2595 amp AseI for"/"Saro_2595 amp XbaI rev". The amplified DNA fragments were digested with AseI and XbaI, then ligated with T4 DNA ligase into AseI- and XbaI-digested pK18msB-MCS1. The resulting plasmids (pK18msB/Saro1879 and pK18msB/Saro2595) were transformed into *E. coli* (strain DH5a for the Saro_1879 plasmid and Turbo for the Saro_2595 plasmid). PCR was performed on the purified plasmids using the phosphorylated primer pairs "Saro1879 lvnsucr del REV"/"Saro1879 lvnsucr del FOR" or "Saro_2595 del rev"/"Saro_2595 del for" to generate linear plasmids lacking the majority of the Saro_1879 and Saro_2595 coding regions, respectively. These DNA fragments were circularized with T4 DNA ligase to form plasmids pK18msB/ΔSaro1879 and pK18msB/ΔSaro2595.

Plasmid for incorporating *E. coli* yghU into the *N. aromaticivorans* genome. The yghU gene (locus tag Ga0077588_1407) was amplified from *E. coli* DH5a genomic DNA using primers "D2595pK18-ecYghU F" and "D2595pK18-ecYghU R", which each contain a sequence on their 5' end that is complementary to a region in the plasmid pK18msB/ΔSaro2595. pK18msB/ΔSaro2595 was amplified with the primers "ecYghU-D2595pK18 F" and "ecYghU-D2595pK18 R", which each contain a sequence on their 5' ends that is complementary to *E. coli* yghU, to generate a linear fragment in which pK18msB-MCS1 contains the regions flanking Saro_2595 in the *N. aromaticivorans* genome, along with the regions complementary to yghU.

The PCR amplified fragments were connected using NEBuilder HiFi DNA Assembly Master Mix (New England Biolabs) (using 81 ng of the linear pK18msB/ΔSaro2595 fragment and 22 ng of the yghU fragment) and transformed into NEB 5-alpha competent *E. coli* (New England Biolabs). The resulting plasmid (pK18msB/ecyghU-Δ2595) consisted of pK18msB-MCS1 containing the *E. coli* yghU gene flanked by regions that flank Saro_2595 in the *N. aromaticivorans* genome (i.e., with the start and stop codons positioned where the respective codons of Saro_2595 would naturally be).

Enzyme Expression Plasmids

Recombinant Saro_2595. Saro_2595 was amplified from *N. aromaticivorans* genomic DNA with the primers "Saro2595 Ctag PciI F" and "Saro2595 Ctag BsaI R". This fragment was digested with PciI and BsaI. The expression vector pVP302K (Gall and Ralph et al. 2014) was amplified using the primers "pVP302K Ctag BsaI F" and "pVP302K Ctag NcoI R". This fragment was digested with BsaI and NcoI. The digested fragments were ligated using T4 DNA ligase, generating plasmid pVP302K/Ctag-2595, which consists of a T5 promoter followed by the coding sequences of Saro_2595, the RtxA protease from *Vibrio cholerae*, and an 8X-Histidine tag.

pVP302K/Ctag-2595 was amplified using phosphorylated primers "Ctag 2595-pVP add Stop R" and "pVP302K Ntag HindIII F". This fragment was circularized using T4 DNA ligase to generate plasmid pVP302K/Untagged2595, in which a stop codon has been introduced directly after Saro_2595. pVP302K/Untagged2595 was amplified via PCR using phosphorylated primers "2595-pVP C to Ntag F" and "pVP302 C to Ntag R". This fragment was circularized using T4 DNA ligase to generate plasmid pVP302K/Ntag-2595, which contains a T5 promoter followed by coding sequences for a His$_8$ tag, a tobacco etch virus (Tev) protease recognition site and Saro_2595.

Recombinant *E. coli* YghU. The yghU gene was amplified from *E. coli* DH5a genomic DNA using the primers "pVP302K-ecYghU F" and "pVP302K-ecYghU R". pVP302K was amplified by PCR using the primers "ecYghU-pVP302K F" and "ecYghU-pVP302K R". The two amplified fragments, with ends that are complementary to each other, were concurrently transformed (94 ng linear pVP302K, 168 ng yghU gene, in 4 μL TE buffer) into *E. cloni* 10G chemically competent cells (Lucigen, Middleton, Wis.). The fragments were combined via homologous recombination in vivo (Bubeck et al. 1993), and the resulting plasmid, pVP302K/Ntag-ecyghU, was purified from the cells and verified via Sanger sequencing.

Recombinant *E. coli* YfcG. The yfcG gene was amplified from *E. coli* DH5α genomic DNA using the primers "ecYfcG-pVP-Ntag-HiFi-F" and "ecYfcG-pVP-Ntag-HiFi-R". pVP302K was amplified via PCR using the primers "pVP302K-HiFi-ATW-R" and "pVP302K-HiFi-ATW-F". The two amplified fragments, with ends that are complementary to each other, were combined using NEBuilder HiFi DNA Assembly Master Mix (New England Biolabs) (100 ng linear pVP302K, 48 ng yghU gene) and transformed into NEB 5-alpha competent *E. coli* (New England Biolabs). The resulting plasmid, pVP302K/Ntag-ecyfcG, was purified and verified via sequencing.

Recombinant SLG_04120. A fragment containing the SLG_04120 gene, codon-optimized for *E. coli*, with ends complementary to pVP302K, was ordered as a gBlock from New England Biolabs. The sequence of the fragment was:

(SEQ ID NO: 96)
```
5'-GTATTTTCAGAGCGCGATCGCAGGAATGGCCGACTCAGATCCATCCA
TGAATCAGCCGACGGGTTACGTCCCGCCGAAAGTTTGGACCTGGGACAAA
GAGAACGGCGGTCAGTTCAGCAATATCAACGCCCCTACGGCTGGTGCGCG
CCAGGACGTCACGCTCCCTGTAGGGGAGCACCCTATCCAATTATATAGTC
TCGGCACTCCGAATGGTCAGAAAGTTACTATCATGTTGGAAGAACTGCTG
GCTGCTGGCTTTGATGCTGAGTATGACGCCTGGCTCATCAAAATCTACAC
AGGCGAGCAATTCGGATCTGATTTCGTCGCCATTAACCCTAATAGCAAAA
TTCCGGCTATGATGGACCATGGTCTCGATCCGCCGCTCCGTTTATTTGAG
TCTGGTTCTATGTTAGTTTATCTGGCCGAAAAGTTTGGCGCATTCCTCCC
GACCGAAATCCGCAAACGTACGGAAACCTTTAACTGGCTCATGTGGCAGA
TGGGTTCTGCTCCTTTTGTGGGTGGTGGCTTTGGCCACTTCTATGCGTAC
GCCCCATTTAAAATCGAATATGCCATTGATCGTTACGCGATGGAAACCAA
```

-continued

```
GCGCCAACTGGACGTTCTGGATAAAAATCTGGCCGATCGTGAATTTATGA

TCGGCGATGAAATCACCATCGCAGATTTTGCGATTTTCCCTTGGTACGGC

TCGATTATGCGTGGCGGTTACAACGCGCAAGAATTCTTGAGCACTCACGA

GTACCGTAACGTTGATCGCTGGGTTACGCAGCTTTCTGAACGTACGGGCG

TAAAGCGTGGTCTCCTTGTCAATTCCGCGGGTCGCCCGGGAGGTGGCATT

GCGGAACGCCATAGCGCGGCTGATTTAGACGCGTCGATTAAAGCGGCTGA

ACAAGAGGCCGCGAAGACCGAAGCTtAACAGAAAGCCGAAAATAACAAAG

TTAG-3'
(underlined regions match sequences in pVP302K)
``` pVP302K was amplified via PCR using the primers "pVP302K-HiFi-ATW-R" and "pVP302K-HiFi-ATW-F".

The amplified pVP302K fragment was combined with SLG_04120 gBlock using ligation-free cloning: fragments were mixed (57 ng linear pVP302K, 84 ng SLG_04120, in 4 μL TE buffer), then transformed into E. cloni 10G competent cells (Lucigen, Middleton, Wis.). DNA sequencing was used to identify a plasmid containing the correct DNA sequence for SLG_04120 in pVP302K, resulting in plasmid pVP302K/Ntag-SLG_04120.

Identification and Quantification of Extracellular Metabolites

Initial identification using LC-MS. Compounds were separated on a Phenomenex PFP 250×4.6-mm column attached to an Accela LC pump equipped with a PDA UV detector. Running buffers A (5 mM formic acid and 5% acetonitrile in $H_2O$) and B (methanol) were initially at 82.5% and 17.5%, respectively. Buffer B was held at 17.5% for 18 minutes, then increased to 50% over 5 minutes, held at 50% for 3 minutes, then returned to initial conditions and re-equilibrated for 4 minutes. Flow rate was 1 mL per minute. UV absorbance data from 190-500 nm at 5 Hz and single wavelength data at 254 nm (20 Hz, 9 nm bandwidth) were collected.

Samples were analyzed by high resolution, tandem mass spectrometry using a Thermo Scientific Q Exactive Orbitrap mass spectrometer. The mass spectrometer was operated in fast polarity switching mode with acquisition of MS/MS spectra of the two most abundant precursor ions from the preceding MS1 scan (50-750 Th). Resolution was 35,000 at 200 Th for MS1 scans and 17,500 at 200 Th for MS/MS scans. Capillary voltage was set at 4000V in both polarities, sheath gas at 50 units, auxiliary gas at 20 units, probe heater at 350° C., inlet capillary at 325° C., and the S-Lens at 50 units. AGC target was 1e6 for MS1 scans and 2e5 for MS/MS scans with a maximum injection time of 50 ms. The isolation width for MS/MS scans was set to 2 Th and a 5 s dynamic exclusion time was used.

Elemental compositions of the metabolites were derived from the mass measurements. From the MS/MS fragmentation patterns and previous data, we provisionally identified the metabolites. We used standards to confirm these putative identifications by matching retention times and mass spectra.

Results

GGE metabolism by sphingomonads. Genomic sequences predict (Ohta et al. 2015) that N. aromaticivorans DSM 12444 (Fredrickson et al. 1991, Fredrickson et al. 1995), Novosphingobium sp. PP1Y (Notomista et al. 2011), and Sphingobium xenophagum NBRC 107872 (Stolz et al. 2000) contain genes that encode enzymes required to metabolize guaiacylglycerol-β-guaiacyl (GGE) via the bacterial β-etherase pathway (FIG. 1). To test this, we fed these bacteria erythro-GGE (FIG. 1), either as sole carbon source or in the presence of another organic molecule.

Figure 2A:
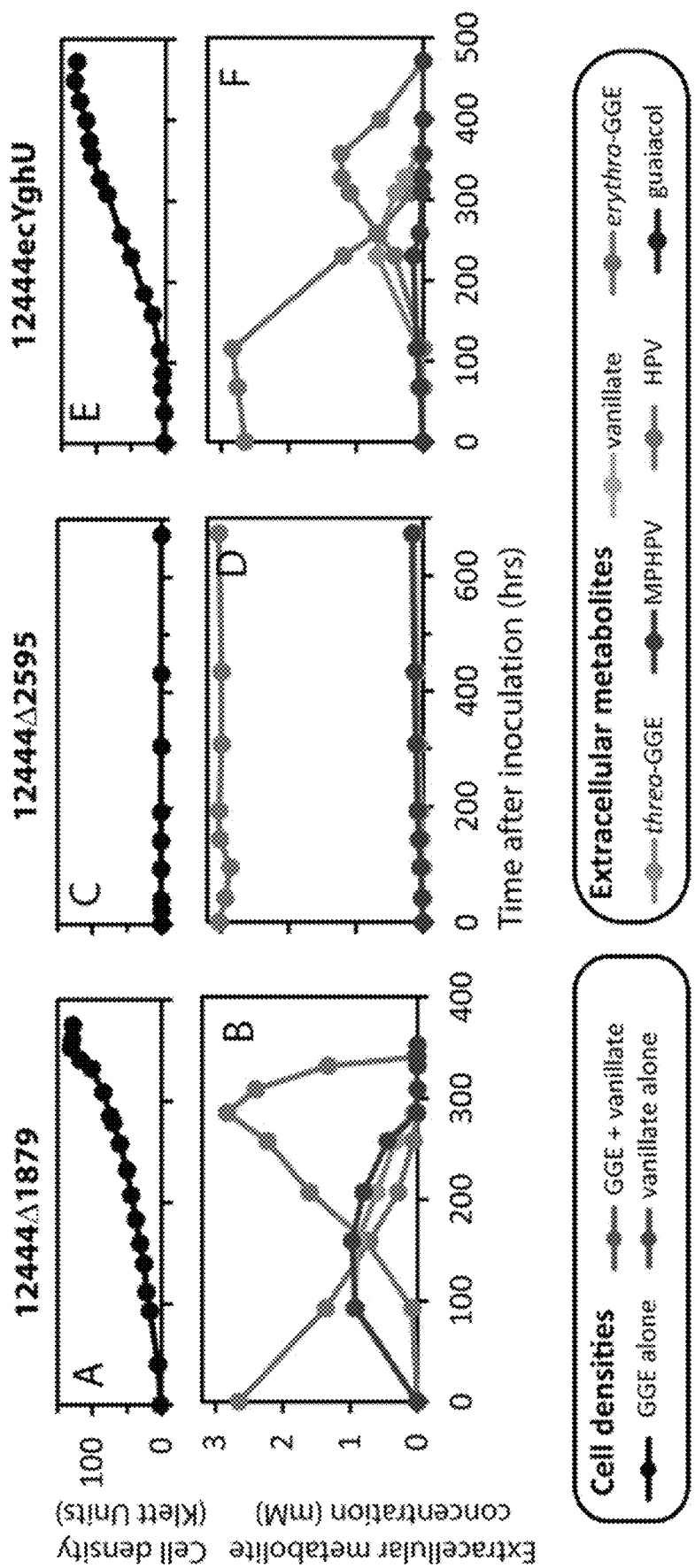
FIGS. 2A and 2B show cell densities and extracellular metabolite concentrations of *N. aromaticivorans* cultures grown in SMB containing 3 mM GGE (FIG. 2A, panels A-F), or 4 mM vanillate and 1.5 mM GGE (FIG. 2B, panels G-L). Data are shown for strains 12444Δ1879 (panels A,B, G,H), 12444Δ2595 (panels C,D,I,J), and 12444ecyghU (panels E,F,K,L). The y-axes of panels H, J, and L use different scales. For comparison, cell density data for cultures grown in SMB containing 4 mM vanillate only are included in panels G, I, and K.
Figure 2B:
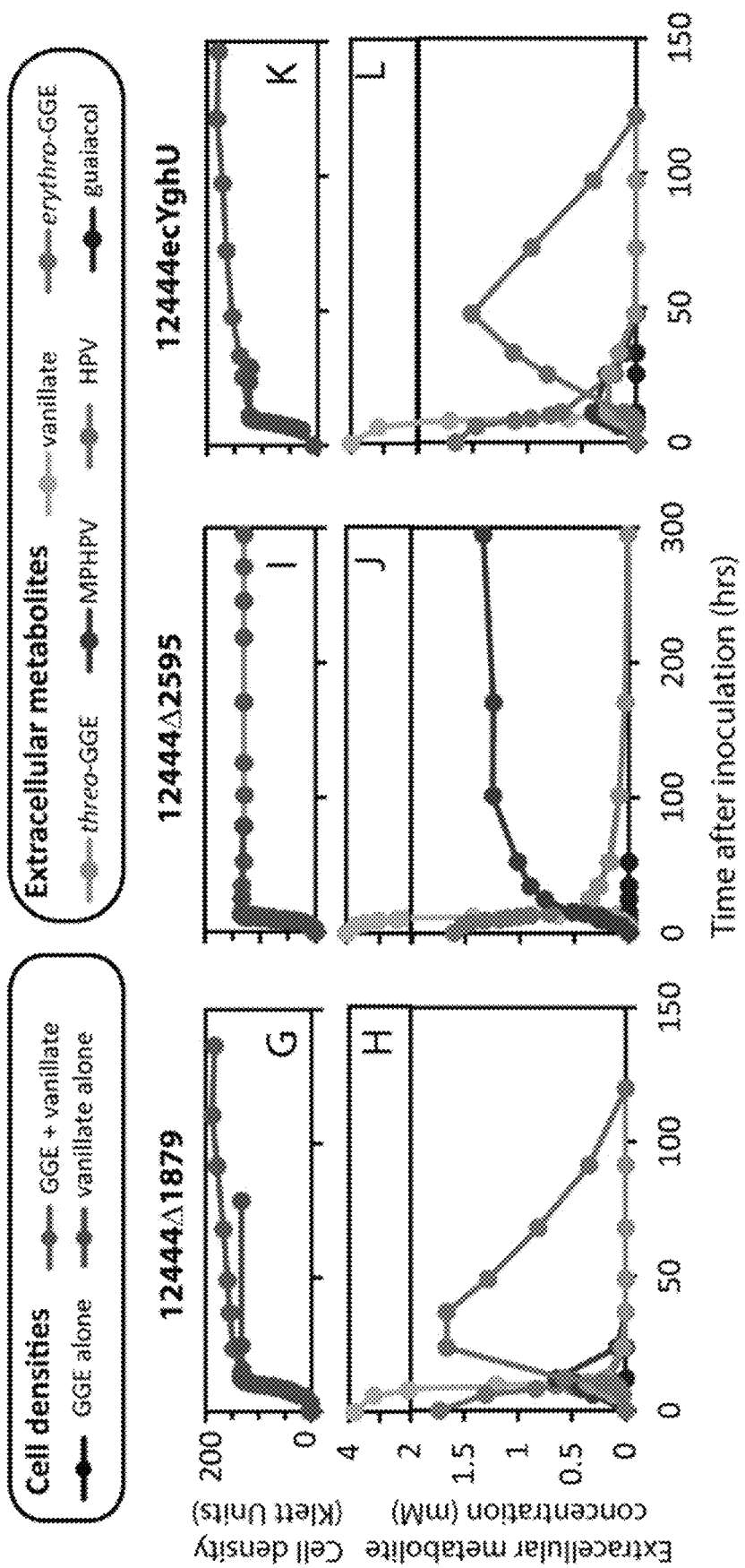
Figure 3:
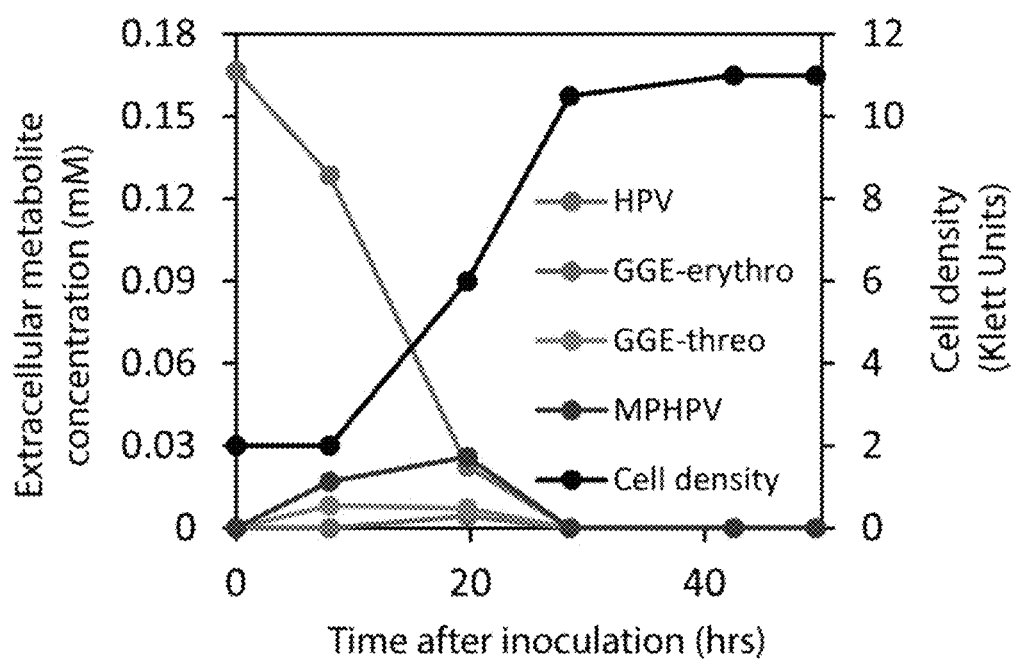
FIG. 3 shows growth and extracellular metabolite levels in a representative culture of *Novosphingobium aromaticivorans* 12444Δ1879 in SMB containing 200 μM GGE. The rate of GGE metabolism by *N. aromaticivorans* (~200 μM within ~30 h) is comparable to that of *Erythrobacter* sp. SG61-1L (~200 μM within ~60 h, though this strain apparently cannot further metabolize guaiacol; Palamuru et al. 2015) and *Novosphingobium* sp. MBESO4 (~900 μM within ~40 h, though this strain apparently cannot assimilate carbon from GGE into cell material; Ohta et al. 2015).

We found that N. aromaticivorans 12444Δ1879 metabolized erythro-GGE and assimilated it into cell material when fed GGE alone (FIG. 2A (panels A,B) and FIG. 3) or GGE plus vanillate (FIG. 2B (panels G,H) and Table 5). β-Etherase pathway intermediates threo-GGE, MPHPV, and HPV transiently appeared in the media of both cultures (FIGS. 2A and 2B (panels B,H) and FIG. 3), whereas the pathway intermediate guaiacol was only detected in the medium of the culture fed GGE plus vanillate (FIG. 2B (panel H)). The predicted pathway intermediate GS-HPV was not detected in the medium of either culture.

Compared to N. aromaticivorans, Novosphingobium sp. PP1Y grew significantly slower in medium containing only GGE (FIG. 4A (panels A,B)). The maximum cell density and amount of COD incorporated into biomass were the same when Novosphingobium sp. PP1Y was fed either GGE plus vanillate or vanillate only (FIG. 4A (panels E,F) and Table 5), suggesting that this strain did not convert a significant amount of GGE into biomass in the presence of vanillate. S. xenophagum did not assimilate GGE into cell material in any culture tested (based on cell density and COD measurements; FIG. 4B (panels C,G) and Table 5), although low levels of some β-etherase pathway intermediates were observed in its culture media (FIG. 4B (panels D,H)).

TABLE 5

Chemical oxygen demand (COD) analysis of bacterial cultures.[a]

| Strain | Carbon sources | Initial COD[b] | Final COD (biomass)[c] | Final COD (Soluble)[d] | % COD incorporated into biomass[e] | % COD lost from the culture[f] |
|---|---|---|---|---|---|---|
| N. aromaticivorans 12444Δ1879 | 3 mM GGE (FIG. 2A (A, B)) | 2100 ± 100 | 480 ± 70 | 500 ± 100 | 22% | 53% |
| | 4 mM vanillate (FIG. 2B (G)) | 1300 ± 100 | 530 ± 40 | 280 ± 80 | 41% | 37% |
| | 4 mM vanillate, 1.5 mM GGE (FIG. 2B(G, H)) | 2170 ± 80 | 720 ± 80 | 340 ± 60 | 33% | 51% |
| Novophingobium sp. PP1Y | 4 mM vanillate (FIG. 4A(E)) | 1200 ± 100 | 420 ± 20 | 240 ± 30 | 36% | 44% |
| | 4 mM vanillate, 1.5 mM GGE (FIG. 4A (E, F)) | 2070 ± 90 | 420 ± 20 | 1080 ± 20 | 20% | 28% |

TABLE 5-continued

Chemical oxygen demand (COD) analysis of bacterial cultures.[a]

| Strain | Carbon sources | Initial COD[b] | Final COD (biomass)[c] | Final COD (Soluble)[d] | % COD incorporated into biomass[e] | % COD lost from the culture[f] |
|---|---|---|---|---|---|---|
| S. xenophagum NBRC 107872 | 4 mM glucose (FIG. 4B (G)) | 1040 ± 30 | 490 ± 30 | 340 ± 20 | 47% | 20% |
| | 4 mM glucose, 1.5 mM GGE (FIG. 4B(G, H)) | 1970 ± 50 | 460 ± 30 | 1270 ± 30 | 23% | 12% |
| N. aromaticivorans 12444Δ2595 | 3 mM GGE (FIG. 2A (C, D)) | 2090 ± 40 | 30 ± 100 | 1900 ± 300 | 1% | 6% |
| | 4 mM vanillate (FIG. 2B (I)) | 1300 ± 200 | 550 ± 90 | 330 ± 70 | 41% | 34% |
| | 4 mM vanillate, 1.5 mM GGE (FIG. 2B (I, J)) | 2200 ± 100 | 520 ± 80 | 1200 ± 100 | 23% | 24% |
| N. aromaticivorans 12444ecyghU | 3 mM GGE (FIG. 2A (E, F)) | 2200 ± 90 | 500 ± 100 | 500 ± 100 | 23% | 52% |
| | 4 mM vanillate (FIG. 2B (K)) | 1400 ± 300 | 570 ± 50 | 430 ± 50 | 42% | 26% |
| | 4 mM vanillate, 1.5 mM GGE (FIG. 2B (K, L)) | 2400 ± 100 | 600 ± 100 | 450 ± 80 | 26% | 55% |

[a]Units of COD are mg/L
[b]Initial COD is that of the medium before inoculation.
[c]Final COD (biomass) is the difference between the unfiltered and filtered final samples.
[d]Final COD (soluble) is the COD remaining in the medium after filtering the final sample.
[e]% COD incorporated into biomass is the ratio of Final COD (biomass) to Initial COD.
[f]% COD lost = 1 − (Final COD (biomass) + Final COD (soluble))/Initial COD. It is assumed that the lost COD represents the electrons in the system that were combined with oxygen during cell growth.

Transcripts of predicted β-etherase pathway genes increase in abundance when N. aromaticivorans grows in the presence of GGE. Since N. aromaticivorans metabolized GGE, we investigated the expression of genes predicted to be involved in the β-etherase pathway in this organism. With the exception of ligL, transcription levels of the genes we tested were increased in cells grown in the presence of GGE versus its absence (Table 6). Among the GGE-induced transcripts was one derived from Saro_2595, which encodes a Nu-class glutathione-S-transferase (named here NaGST$_{Nu}$).

TABLE 6

Fold-changes of transcript levels in N. aromaticivorans cultures grown in vanillate with or without GGE.[a]

| Gene | Homologue[b] | Fold-change[c] |
|---|---|---|
| Saro_0205 | SLG_08640, LigD (77.6%) | 11 ± 3 |
| Saro_0793 | SLG_35880, LigO (41.5%) | 6 ± 2 |
| Saro_0794 | SLG_35900, LigN (44.7%) | 9 ± 1 |
| Saro_1875 | SLG_33660, LigL (48.7%) | 1 ± 1 |
| Saro_2091 | SLG_08650, LigF (59.1%) | 8 ± 1 |
| Saro_2405 | SLG_32600, LigP (65.9%) | 17 ± 9 |
| Saro_2595 | MBENS4_2527, GST3 (37.6%) | 8 ± 2 |

[a]Transcript levels for each culture were normalized to those of Saro_0141 (rpoZ).
[b]Homologue is the gene that codes for a product from Sphingobium sp. SYK-6 (SLG) or Novosphingobium sp. MBES04 (MBENS4) with the highest % amino acid identity to the product of the indicated N. aromaticivorans (Saro) gene.
[c]Fold-change is the ratio of the normalized transcript level in cells grown in the presence of GGE to that in cells grown in the absence of GGE.

NaGST$_{Nu}$ cleaves β(R)- and β(S)-GS-HPV. NaGST$_{Nu}$ is 38% identical in amino acid sequence to Novosphingobium sp. MBES04 GST3 (FIG. 5), which can cleave both β(R)- and β(S)-GS-HPV into HPV in vitro (FIG. 1; (Ohta et al. 2015)). Since N. aromaticivorans lacks any homologues of LigG (the enzyme from Sphingobium sp. SYK-6 that cleaves the β(R)-stereoisomer of GS-HPV (FIG. 1; (Masai et al. 2003)), we tested whether NaGST$_{Nu}$ could cleave both β(R)- and β(S)-GS-HPV in N. aromaticivorans. We found that recombinant NaGST$_{Nu}$ cleaved both β(R)- and β(S)-GS-HPV in vitro (FIG. 6). Kinetic analysis of NaGST$_{Nu}$ showed that it had slightly higher k$_{cat}$ and ~5-fold higher K$_M$ with β(R)-GS-HPV than with β(S)-GS-HPV, resulting in a ~4-fold higher k$_{cat}$/K$_M$ with the β(S)-isomer (Table 7).

TABLE 7

Kinetic parameters for the enzymatic conversion of GS-HPV into HPV.[a]

| Protein | GS-HPV[b] | k$_{cat}$ (s$^{-1}$) | K$_M$ (μm) | k$_{cat}$/K$_M$ (mM$^{-1}$s$^{-1}$) |
|---|---|---|---|---|
| NaGST$_{Nu}$ (8 nM) | β(R) | 80 ± 10 | 40 ± 6 | 1900 ± 400 |
| SYK6GST$_{Nu}$ (47 nM) | β(R) | 13 ± 1 | 55 ± 7 | 240 ± 40 |
| ecYghU (195 nM) | β(R) | 0.43 ± 0.03 | 28 ± 4 | 16 ± 3 |
| ecYfcG (195 nM) | β(R) | 0.04 ± 0.01 | 160 ± 60 | 0.2 ± 0.1 |
| NaGST$_{Nu}$ (8 nM) | β(S) | 57 ± 9 | 8 ± 3 | 8000 ± 3000 |
| SYK6GST$_{Nu}$ (18 nM) | β(S) | 30 ± 5 | 11 ± 2 | 2700 ± 700 |
| ecYghU (195 nM) | β(S) | 0.29 ± 0.03 | 12 ± 3 | 24 ± 6 |
| ecYfcG (195 nM) | β(S) | 0.017 ± 0.004 | 130 ± 40 | 0.14 ± 0.06 |

[a]Kinetic data are from fits shown in FIG. 6
[b]Stereoisomer of GS-HPV used in reaction (see FIG. 1)

NaGST$_{Nu}$ is necessary for GGE metabolism in vivo. To test for an in vivo role of NaGST$_{Nu}$, we generated an N. aromaticivorans mutant lacking Saro_2595 (12444Δ2595). Unlike its parent strain (12444Δ1879), 12444Δ2595 did not incorporate significant GGE into cell material in any culture (based on cell density and COD measurements; FIGS. 2A and B (panels C,I)) and Table 5). When provided only erythro-GGE, 12444Δ2595 produced only a small amount of MPHPV and threo-GGE in the medium (FIG. 2A (panel D)). When 12444Δ2595 was fed both vanillate and erythro-GGE, it completely metabolized the vanillate, and converted almost all of the GGE into MPHPV (FIG. 2B (panel J)). A small amount of guaiacol also appeared in the medium of this culture, suggesting that some MPHPV was cleaved by 12444Δ2595. However, unlike the situation for the parent strain, no extracellular HPV was detected in the 12444Δ2595 culture (FIGS. 2A and 2B (panels D,J)). These results show that NaGST$_{Nu}$ is necessary for complete GGE metabolism by *N. aromaticivorans*.

NaGST$_{Nu}$ is sufficient for conversion of GS-HPV into HPV in *N. aromaticivorans*. To determine which step in the β-etherase pathway requires NaGST$_{Nu}$, we incubated cell extracts of 12444Δ2595 and its parent strain (12444Δ1879) with racemic MPHPV and GSH. With the 12444Δ1879 extract, MPHPV was converted to roughly equimolar amounts of guaiacol and HPV, along with a small amount of GS-HPV (FIG. 7 (A)). In contrast, the 12444Δ2595 extract incompletely cleaved MPHPV, producing roughly equimolar amounts of guaiacol and GS-HPV along with a low level of HPV (~2% of the level of GS-HPV formed; FIG. 7 (B)). Thus, it appeared that the 12444Δ2595 extract was defective in the conversion of GS-HPV into HPV. When recombinant NaGST$_{Nu}$ was added to the 12444Δ2595 extract (FIG. 7 (B)), the GS-HPV disappeared, with a concomitant increase in HPV, showing that the defect in GS-HPV cleavage by 12444Δ2595 extract was caused by the lack of NaGST$_{Nu}$.

NaGST$_{Nu}$ homologues cleave β(R)- and β(S)-GS-HPV. The GST Nu-class is a widespread protein family (Stourman et al. 2011, Mashiyama et al. 2014). Indeed, a non-redundant BLAST search of the NCBI database using NaGST$_{Nu}$ as query identified over 1,000 proteins with amino acid identities of >61% and E-values <2.0×10$^{-124}$. Besides GST3 from *Novosphingobium* sp. MBESO4 (Ohta et al. 2015), the only other Nu-class GSTs that have been analyzed for catalytic activity are *E. coli* ecYghU and ecYfcG (61% and 42% amino acid sequence identity with NaGST$_{Nu}$, respectively; FIG. 5). The roles of these enzymes are unknown, but they are reported to have disulfide bond oxidoreductase activity in vitro (Stourman et al. 2011, Wadington et al. 2009, Wadington et al. 2010, Mashiyama et al. 2014). Though *E. coli* is not known to metabolize lignin-derived GSH adducts, we found that recombinant ecYghU and ecYfcG were both able to cleave β(R)- and β(S)-GS-HPV in vitro (FIG. 6). While the K$_M$ values for ecYghU were comparable to those of NaGST$_{Nu}$ (Table 7), its k$_{cat}$ values were much lower than those of NaGST$_{Nu}$, resulting in k$_{cat}$/K$_M$ values for ecYghU with GS-HPV ~100-fold lower than those of NaGST$_{Nu}$ under our assay conditions (Table 7). For ecYfcG, K$_M$ values were ~10-fold higher and k$_{cat}$ values were ~10-fold lower than those of ecYghU, leading to k$_{cat}$/K$_M$ values with GS-HPV ~100-fold lower for ecYfcG than for ecYghU.

To test whether ecYghU can function in the β-etherase pathway in vivo, we created a strain of *N. aromaticivorans* in which Saro_2595 was replaced in the genome by the *E. coli* yghU gene. The resulting strain, 12444ecyghU, metabolized GGE slower than 12444Δ1879 (the strain containing NaGST$_{Nu}$; FIGS. 2A and 2B), but still removed all of the GGE from the medium and assimilated it into biomass, whereas 12444Δ2595 could not (FIGS. 2A and 2B (panels E,F,K,L); Table 5). This shows that ecYghU can substitute for NaGST$_{Nu}$ in the *N. aromaticivorans* β-etherase pathway.

Although the sphingomonad *Sphingobium* sp. SYK-6 can metabolize GGE (Palamuru et al. 2015, Sato et al. 2009), no enzyme capable of cleaving β(S)-GS-HPV has been identified in this organism (Masai et al. 2003). We tested a recombinant version of the Nu-class GST from *Sphingobium* sp. SYK-6, coded for by SLG_04120 and named here SYK6GST$_{Nu}$, and found that it cleaved both β(S)- and β(R)-GS-HPV in vitro (FIG. 6). SYK6GST$_{Nu}$ had higher k$_{cat}$ and lower K$_M$ with β(S)-GS-HPV than with β(R)-GS-HPV, leading to a ~10-fold greater k$_{cat}$/K$_M$ with the β(S)-isomer (Table 7). Thus, SYK6GST$_{Nu}$ could cleave β(S)-GS-HPV and potentially contribute, along with LigG, to β(R)-GS-HPV cleavage in *Sphingobium* sp. SYK-6 (Masai et al. 2003).

Structural characterization of NaGST$_{Nu}$. We solved two structures of NaGST$_{Nu}$, crystallized under different conditions, with resolutions of 1.25 (pdb 5uuo) and 1.45 (pdb 5uun) Å (Table 8). The structures align with each other with an RMS distance of 0.108 over 7381 atoms. NaGST$_{Nu}$ is a homo-dimer; each subunit contains a characteristic N-terminal GST (thioredoxin-like) domain (Val39 to Gly129), a C-terminal GST domain (Ser135 to Leu257), and a C-terminal extension not present in most other characterized classes of GSTs (Val258 to Phe288)*(FIG. 8 (A)).

TABLE 8

Statistics for the crystal structure determinations of NaGST$_{Nu}$.

| | | |
|---|---|---|
| PDB entry | 5uuo | 5uun |
| Precipitant | Ammonium sulfate | Ammonium acetate |
| Wavelength | 0.7749 | 1.033 |
| Resolution range | 29.36-1.25 (1.295-1.25) | 43.97-1.45 (1.502-1.45) |
| Space group | P 21 21 21 | P 21 21 21 |
| Unit cell | 68.81 70.39 168.23 | 68.59 70.64 168.57 |
| | 90 90 90 | 90 90 90 |
| Total reflections | 3049254 (309691) | 1854065 (113574) |
| Unique reflections | 225346 (22262) | 140421 (11067) |
| Multiplicity | 13.5 (13.9) | 13.2 (10.3) |
| Completeness (%) | 99.91 (99.70) | 96.48 (76.88) |
| Mean I/sigma(I) | 23.67 (1.96) | 36.36 (8.82) |
| Wilson B-factor | 16.03 | 13.23 |
| R-Merge | 0.05235 (1.297) | 0.04367 (0.2047) |
| R-Means | 0.05445 (1.346) | 0.04544 (0.2159) |
| R-Pim | 0.01485 (0.3565) | 0.01239 (0.06599) |
| CC1/2 | 1 (0.841) | 1 (0.986) |
| CC* | 1 (0.956) | 1 (0.997) |
| Reflections used in refinement | 225262 (22242) | 140408 (11066) |

TABLE 8-continued

Statistics for the crystal structure determinations of NaGST$_{Nu}$.

| | | |
|---|---|---|
| Reflections used for R-free | 1963 (197) | 1852 (154) |
| R-Work | 0.1303 (0.2607) | 0.1357 (0.206) |
| R-Free | 0.1324 (0.2979) | 0.1365 (0.1595) |
| CC(work) | 0.978 (0.913) | 0.978 (0.971) |
| CC(free) | 0.988 (0.851) | 0.975 (0.9363) |
| Non-H atoms | 5658 | 5852 |
| Macromolecules | 4626 | 4628 |
| Ligands | 252 | 244 |
| Solvent | 780 | 980 |
| Protein residues | 569 | 1040 |
| RMS(bonds) | 0.007 | 0.008 |
| RMS(angles) | 1.02 | 1.08 |
| Ramachandran favored/allowed/outliers (%) | 93.75/2.30/0.35 | 96.82/2.65/0.53 |
| Rotamer outliers (%) | 0.43 | 0.43 |
| Clashscore | 1.89 | 2.13 |
| Average B-factor | 22.39 | 19.61 |
| B-Factor macromolecules/ligands/solvent | 20.02/26.98/34.97 | 16.91/19.017/33.64 |
| No. TLS groups | 9 | 9 |

*The residue numbers used here for NaGST$_{Nu}$ are for the native protein represented by SEQ ID NO: 18; residues numbers in the pdb entries differ by +5 since the protein used for crystallization contained an N-thermal extention left after proteolytic removal of the His$_8$-tag.
Statistics for the highest-resolution shell are shown in parentheses.

The structure of NaGST$_{Nu}$ is most similar to those of the Nu-class GSTs ecYghU (pdb 3c8e (Stourman et al. 2011), with an RMSD of 0.49 Å over 3116 atoms) and *Streptococcus sanguinis* SK36 YghU (ssYghU; pdb 4mzw (Patskovsky et al.), with an RMSD of 0.58 Å over 3004 atoms). In NaGST$_{Nu}$, ecYghU, and ssYghU, a short channel leads from the active site pocket to the solvent (FIGS. 9 and 12). In other structurally characterized Nu-class GSTs, including ecYfcG (pdb 3gx0 (Wadington et al. 2009)), the active site is more solvent exposed, since these proteins lack N-terminal residues that contribute to the channel walls in the other proteins (FIG. 5; Supplemental Materials of Thuillier et al. 2013).

The active site electron density in NaGST$_{Nu}$ was modeled as a mixed population of GSH1 and GSH2 thiols with an S-S distance of 2.4 Å (~60% occupancy) and GS-SG disulfide with an S-S distance of 2.0 Å (~40% occupancy) (FIG. 8 (B)). Since the crystallization solutions initially contained only GSH, the disulfide likely formed via adventitious oxidation of the closely situated GSH thiols during the crystallization period (~4 weeks), or during X-ray diffraction data collection. For comparison, ecYghU shows a dithiol configuration with HS-SH distance of 2.8 Å (Stourman et al. 2011), whereas ssYghU and ecYfcG each show a disulfide configuration with S-S distance of 2.1 Å (Wadington et al. 2009, Patskovsky et al.).

In NaGST$_{Nu}$, seven residues make close contacts with GSH1 (Thr51, Asn53, Gln86, Lys99, Ile100, Glu116, and Ser117) and three residues make close contacts with GSH2 (Asn25, Asn53, and Arg177 from the opposite chain in the dimer) (FIG. 8 (B)). These residues and contacts to the GSHs are conserved in the YghU structures ((Stourman et al. 2011, Patskovsky et al.); ecYfcG is missing an analogue of Asn25, as it is truncated at its N-terminus relative to the other proteins (FIG. 5). The conserved threonine forms a hydrogen-bond with the GSH1 thiol that is characteristic of Nu-class GSTs (Stourman et al. 2011) (FIG. 8 (B); 3.0 Å interatomic distance for Thr 51 in NaGST$_{Nu}$). ecYghU is predicted to have one additional interaction with GSH1 (via Gln151 (Stourman et al. 2011)) not present in NaGST$_{Nu}$, ssYghU, or ecYfcG (which contain Val150, Thr148, and Val105 at this position, respectively).

Alignment of the individual subunits of NaGST$_{Nu}$, ecYghU and ssYghU shows four different configurations for their C-termini (FIG. 9 (A)): two for NaGST$_{Nu}$ (FIG. 9 (B,C)) and one each for ecYghU (FIG. 9 (D)) and ssYghU (FIG. 9 (E)). The C-terminal region of ecYfcG is in essentially the same configuration as that of ssYghU, though the last eleven residues of ecYfcG are not present in its crystal structure. The two NaGST$_{Nu}$ subunits differ in the positioning of residues Leu258 to Phe288, with Phe288 being distant from the active site channel in one subunit (5uun open, FIG. 9 (B)), and near the channel entrance in the other (5uun closed, FIG. 9 (C)), a difference of ~18 Å. The closed NaGST$_{Nu}$ configuration is stabilized by hydrogen-bonds between the sidechain amide of Lys262 and the carbonyl oxygen of Lys286, and the sidechain amide of Lys286 and the carbonyl oxygen of Arg220. The open configuration lacks these interactions and the sidechain of Arg220 has two rotamer positions. The sizes of the active site channel opening in the open and closed configurations of NaGST$_{Nu}$ are ~18 Å$^2$ and ~11 Å$^2$, respectively (FIG. 9 (B,C)). For comparison, the area of active site access for both ecYghU and ssYghU is ~25 Å$^2$ (FIG. 9 (D,E)). The placement of helices-10 and 11 in ecYghU (FIG. 9 (D)), and the truncated C-terminal sequence of ssYghU (FIG. 9 (D), FIG. 5), make it is unlikely that either of these C-termini can occupy a position similar to that seen in NaGST$_{Nu}$.

Modeling of β(R)- and β(S)-GS-HPV into the GSH2 position in the NaGST$_{Nu}$ active site predicts that their HPV moieties extend into the active site channel in different orientations (FIG. 10 (A)). The channel interior includes the phenol groups of Tyr166 and Tyr224, and the carboxylate of Phe288 in the closed configuration. Our models predict that these three residues interact differently with β(R)- and β(S)-GS-HPV. With the less reactive β(R)-GS-HPV, Tyr166 is predicted to provide a long interaction (4 Å) with the α-ketone, whereas Tyr224 hydrogen-bonds to the γ-hydroxyl (3.1 Å), which in turn hydrogen-bonds to the Å-ketone (FIG. 10 (B)). With the more reactive β(S)-GS-HPV, Tyr166 is predicted to provide a cation-π interaction with its aromatic ring (average distance 3.4 Å), whereas Tyr224 provides a hydrogen-bond to its γ-hydroxyl (FIG. 10 (C)). Phe288 is also predicted to hydrogen-bond with the phenolic group of both β(R)- and β(S)-GS-HPV in the closed configuration of NaGST$_{Nu}$.

Discussion

In developing bio-based systems to depolymerize lignin, optimized cellular and enzyme catalysts are needed. In this study, we tested sphingomonads for the ability to break the β-aryl ether bond commonly found in lignin (FIG. 1), and characterized a Nu-class glutathione-S-transferase from *N. aromaticivorans* that acts as a glutathione lyase in the β-etherase pathway (NaGST$_{Nu}$). Our finding that other Nu-class GSTs also catalyze this reaction provides important insight into the function of this enzyme family in lignin depolymerization and possibly metabolism of other compounds that proceed via GSH-conjugates.

Differences in GGE metabolism. We found that *N. aromaticivorans* was the most effective species studied here at metabolizing the dimeric aromatic compound GGE and assimilating it into cellular material. The rate of GGE metabolism by *N. aromaticivorans* is comparable to those of *Erythrobacter* sp. SG61-1L (Palamuru et al. 2015) and *Novosphingobium* sp. MBESO4 (Ohta et al. 2015) (FIG. 3). *Sphingobium* sp. SYK-6 (Palamuru et al. 2015), *Novosphingobium* sp. PP1Y (FIG. 4A), and *S. xenophagum* (FIG. 4B) are slower and/or less efficient at metabolizing GGE, even though they each contain enzymes implicated in the β-etherase pathway.

GGE metabolism by *N. aromaticivorans*. The appearance of extracellular MPHPV, threo-GGE, and HPV in *N. aromaticivorans* cultures suggests that it excretes these β-etherase pathway intermediates (FIGS. 2A and 2B). The appearance of threo-GGE in cultures fed erythro-GGE shows that GGE oxidation is reversible in vivo, as was previously found for *Pseudomonas acidovorans* D3 (Vicuña et al. 1987). The low level of extracellular guaiacol, and the absence of extracellular GS-HPV in GGE-fed cultures suggest that MPHPV cleavage occurred intracellularly, as was proposed for *Novosphingobium* sp. MBESO4 (Ohta et al. 2015), and which was expected, based on the requirement for GSH for this reaction (FIG. 1). Since the conversion of GS-HPV into HPV also requires GSH, this reaction also likely occurred intracellularly. The relatively late uptake of HPV from the media (FIGS. 2A and 2B (panels B,H)) suggests that *N. aromaticivorans* metabolized and assimilated guaiacol before HPV. In contrast, *Erythrobacter* sp. SG61-1L metabolized HPV, but not guaiacol (Palamura et al. 2015), and *Pseudomonas acidovorans* E-3 consumed the guaiacol only after consuming the phenylpropanoid formed from splitting veratrylglycerol-β-guaiacyl ether (Crawford et al. 1973). This shows that species use different strategies for metabolizing β-etherase pathway intermediates, a feature that could be useful in developing strains that produce specific pathway intermediates.

Bacterial metabolism of HPV has been proposed to proceed through acetovanillone, vanillin, vanillate, and protocatechuate (Crawford et al., 1973; Masai et al., 2007; Palamuru et al., 2015; Vicuña et al., 1987), and metabolism of guaiacol has been proposed to proceed through catechol (Crawford et al., 1973). However, we failed to detect any of these compounds in *N. aromaticivorans* culture media, suggesting that aromatic intermediates downstream of HPV and guaiacol were retained within the cells upon formation.

Nu-class GSTs can function as glutathione lyases. We found that NaGST$_{Nu}$, SYK6GST$_{Nu}$, ecYghU, and ecYfcG cleave the GS-moiety from both β(R)- and β(S)-GS-HPV, though with a wide range of catalytic efficiencies ($k_{cat}/K_M$) (at least $10^4$-fold; Table 7). Thus, along with GST3 from *Novosphingobium* sp. MBESO4 (Ohta et al., 2015), all five of the Nu-class GSTs that have been tested for GS-HPV cleavage show glutathione lyase (deglutathionylation) activity with both stereoisomers of this substrate. Phylogenetic analysis of Nu-class GSTs shows these enzymes lie in widely separate sub-clades, suggesting that this activity may be widespread throughout this large class of proteins (FIG. 13).

Proposed mechanism for the Nu-class GST glutathione lyase reaction. We modeled the GS-moiety of GS-HPV into the GSH2 active site position of NaGST$_{Nu}$ (FIG. 8 (B)), with the HPV moieties of β(R)- and β(S)-GS-HPV extending into the active site channel in different orientations (FIG. 10(A) and FIG. 12 (A,B)). We propose a mechanism for the glutathione lyase reaction (FIG. 11) in which the thiol of the GSH1 molecule (FIG. 8 (B)) is activated by hydrogen-bonding with the conserved active site threonine (Thr51), which has moderate reactivity as a base at pH 8.5 (FIG. 11 (A)). The activated GS1 thiol attacks the GS- of GS-HPV to form a disulfide GS-SG. In our proposed mechanism, the lyase reaction (C—S bond cleavage) is facilitated by polarization of the GS-HPV α-ketone by interactions involving Tyr166 and Tyr224 (which are highly conserved amongst many Nu-class GSTs; FIG. 5), and the γ-hydroxyl of HPV, with different interactions for the two GS-HPV stereoisomers (FIG. 11 (A)). With β(R)-GS-HPV, Tyr166 is predicted to provide a long interaction (3.9 Å) with the α-ketone, while Tyr224 hydrogen-bonds to the γ-hydroxyl (3.1 Å), which in turn hydrogen-bonds to the α-ketone (FIGS. 10 (B) and 11 (A)). Tyr166 is predicted to provide a cation-π interaction with the aromatic ring of the tighter binding β(S)-GS-HPV (average distance 3.4 Å), while Tyr224 provides a hydrogen-bond to its γ-hydroxyl (FIGS. 10 (C) and 11 (A)). Phe288 is also predicted to hydrogen-bond with the phenolic group of both β(R)- and β(S)-GS-HPV in the closed C-terminal configuration of NaGST$_{Nu}$ (FIGS. 10 (B,C) and 11). ecYfcG lacks analogues of these Tyr residues (FIG. 5), which may contribute to its diminished catalytic capability ($k_{cat}/K_M$ values ~$10^4$-fold lower than those of NaGST$_{Nu}$; Table 7). In the absence of a redox cofactor, we propose that a transient enolate (FIG. 11 (B)) stores the 2e$^-$ reducing equivalents released by disulfide bond formation as an incipient carbanion. Due to active site steric constraints, our model places the reactive portion (S—C$_\beta$—(C$_\alpha$=O)-aryl) of both β(R)- and β(S)-GS-HPV into roughly planar configurations in the NaGST$_{Nu}$ channel (FIG. 10 and FIG. 12 (A,B)), which should promote the formation of the enolate intermediate (FIG. 11 (B)). In contrast, steric constraints in the ecYghU active site channel resulting from differences between its channel interior and that of NaGST$_{Nu}$ place these reactive GS-HPV atoms ~45° out of alignment in our ecYghU models (FIG. 12 (C,D)), providing a possible explanation for the slower reactivity of ecYghU with GS-HPV compared to NaGST$_{Nu}$ (ecYghU has values of $k_{cat}/K_M$ ~100-fold lower than those of NaGST$_{Nu}$; Table 7). Collapse of the proposed enolate intermediate proceeds with carbanion trapping of a solvent-derived proton, corresponding to reduction of the carbon atom originally containing the thioether bond (FIG. 11 (C)).

This proposed mechanism for Nu-class GSTs with GS-HPV is different from that proposed for the omega class GST LigG, in which β(R)-GS-HPV initially forms a mixed disulfide with a cysteine residue, releasing the HPV moiety (Pereira et al. 2016). A GSH molecule then enters the LigG active site and combines with the enzyme bound GS-moiety to form GSSG. A side chain thiol is unlikely to be involved in Nu-class glutathione lyase activity, since NaGST$_{Nu}$ only contains one cysteine, which is ~21 Å away from the active site, and SYK6GST$_{Nu}$ and ecYghU do not contain any cysteine residues.

NaGST$_{Nu}$ converts β(R)- and β(S)-GS-HPV into HPV in *N. aromaticivorans*. Although GST3 from *Novosphingobium* sp. MBES04 can convert β(R)- and β(S)-GS-HPV into HPV in vitro (Ohta et al. 2015), a physiological role in the β-etherase pathway has not been established. The inability of *N. aromaticivorans* 12444Δ2595 to completely metabolize GGE (FIGS. 2A and 2B (panels C,D,I,J)) shows that NaGST$_{Nu}$ is necessary for the β-etherase pathway in *N. aromaticivorans*. Unexpectedly, we found that 12444Δ2595 accumulated extracellular MPHPV. Cleavage of MPHPV into guaiacol and GS-HPV is catalyzed by LigF and LigE/P (FIG. 1), enzymes that are likely expressed in 12444Δ2595, since crude extract from this strain can cleave MPHPV (FIG. 7 (B)). We hypothesize that without NaGST$_{Nu}$, GS-HPV accumulates intracellularly in 12444Δ2595, and cells become limited for the GSH that is needed to cleave MPHPV.

It is unclear whether the trace amount of HPV formed in assays using 12444Δ2595 extract (FIG. 7 (B)) resulted from activity of an unknown enzyme or spontaneous cleavage of GS-HPV. In any event, addition of recombinant NaGST$_{Nu}$ to the 12444Δ2595 extract resulted in the complete conversion of GS-HPV into HPV (FIG. 7 (B)), providing the first demonstration of a single enzyme being sufficient for one of the steps of the β-etherase pathway in vivo.

The role of Nu-class GSTs in the β-etherase pathway. The ability of Nu-class GSTs to cleave both β(R)- and β(S)-GS-HPV raises the question of why some species contain both this enzyme and LigG (e.g. *Sphingobium* sp. SYK-6), which is specific for the β(R)-isomer (FIG. 1). Our data show that both NaGST$_{Nu}$ and SYK6GST$_{Nu}$ have a higher k$_{cat}$/K$_M$ value with β(S)-GS-HPV than with the β(R)-isomer (Table 7). For NaGST$_{Nu}$, this difference in k$_{cat}$/K$_M$ values between the stereoisomers was ~4-fold and the values (~8000 and ~1900 mM$^{-1}$s$^{-1}$ for the β(S)- and β(R)-isomers, respectively) are both greater than that reported for LigG with β(R)-GS-HPV (1700 mM$^{-1}$s$^{-1}$ (Pereira et al. 2016)). For SYK6GST$_{Nu}$, the difference in k$_{cat}$/K$_M$ values between the isomers is ~10-fold, and the value with β(R)-GS-HPV (~240 mM$^{-1}$s$^{-1}$) is lower than that reported for LigG. These observations suggest that SYK6GST$_{Nu}$ likely cleaves β(S)-GS-HPV in *Sphingobium* sp. SYK-6, but that LigG may play a role in cleaving β(R)-GS-HPV in that organism. Although cell extract from a *Sphingobium* sp. SYK-6 ΔLigG mutant completely cleaved a racemic GS-HPV sample (since the lysate presumably contained active SYK6GST$_{Nu}$) the physiological effect of deleting LigG was not reported (Masai et al. 2003). Perhaps organisms like *N. aromaticivorans* that lack LigG need Nu-class GSTs to have higher efficiencies toward β(R)-GS-HPV than Nu-class GSTs in species that contain a stereospecific enzyme like LigG.

The potential role(s) of Nu-class GSTs in bacteria that do not contain the β-etherase pathway.

Many organisms contain Nu-class GSTs, including those not known or predicted to use the β-etherase pathway (Mashiyama et al., 2014; Stourman et al., 2011). Whereas several of these enzymes have been found to have disulfide bond reductase activity in vitro, the physiological roles of most of these proteins are unknown (Mashiyama et al., 2014; Stourman et al., 2011). We found that ecYghU and ecYfcG from *E. coli*, an organism not known to metabolize lignin-derived phenylpropanoids, can cleave both β(R)- and β(S)-GS-HPV in vitro, though with lower catalytic efficiencies than NaGST$_{Nu}$ and SYK6GST$_{Nu}$ (Table 2). The fact that ecYghU can replace NaGST$_{Nu}$ in *N. aromaticivorans* (FIGS. 2A and 2B (panels E,F,K,L)) shows that it can indeed function as a glutathione lyase in vivo. The relatively low k$_{cat}$/K$_M$ values of ecYghU and ecYfcG in cleavage of GS-HPV compared to NaGST$_{Nu}$ and SYK6GST$_{Nu}$ could reflect the fact that GS-HPV is not a natural substrate for the *E. coli* enzymes. Although the overall structures of Nu-class GSTs are similar, differences in the residues surrounding the active sites (as seen between NaGST$_{Nu}$ and ecYghU, for example; FIG. 12) could make enzymes from other organisms better suited for binding and cleaving other GS-conjugates that they more commonly encounter.

Conclusion

This work shows that *N. aromaticivorans* can rapidly and completely metabolize the β-aryl ether-containing compound GGE, and that the Nu-class glutathione-S-transferase NaGST$_{Nu}$ plays a direct role in this process. The following example illustrates that NaGST$_{Nu}$ can participate in cleavage of bona fide lignin oligomers in vitro, indicating utility of this enzyme in converting biomass into valuable chemicals. NaGST$_{Nu}$ and other Nu-class GSTs can cleave both the β(R)- and β(S)-stereoisomers of the β-etherase pathway intermediate GS-HPV, in contrast to the other characterized enzymes in the pathway, which are stereospecific (FIG. 1). Our finding that ecYghU also cleaves GS-HPV shows that Nu-class GSTs from organisms lacking the β-etherase pathway can nevertheless act as racemic glutathione lyases.

EXAMPLE 2

In Vitro Enzymatic Release Of Syringyl, Guaiacyl, and Tricin Units from Lignin

Summary

New information and processes are needed to derive valuable compounds from renewable resources. Lignin is an abundant, heterogeneous, and racemic polymer in terrestrial plants, and it is comprised predominantly of guaiacyl and syringyl monoaromatic phenylpropanoid units that are covalently linked together in a purely chemical radical coupling polymerization process. In addition, the plant secondary metabolite, tricin, is a recently found and abundant lignin monomer in grasses. The most prevalent type of inter-unit linkage between guaiacyl, syringyl, and tricin units is the β-ether linkage. Previous studies have shown that enzymes in the bacterial β-etherase pathway catalyze glutathione-dependent cleavage of β-ether bonds in dimeric β-ether lignin model compounds, resulting in the release of monoaromatic products, the reduction of nicotinamide adenine dinucleotide (NAD$^+$) to NADH, and the oxidation of glutathione (GSH) to glutathione disulfide (GSSG). To date, however, it remains unclear whether the known β-etherase enzymes are active on lignin polymers. Here, we report on enzymes that catalyze β-ether cleavage from model compounds and bona fide lignin, under conditions that recycle the cosubstrates NAD$^+$ and GSH. Guaiacyl, syringyl and tricin derivatives were identified as reaction products when different model compounds or lignin fractions were used as substrates. These results provide the first demonstration of an in vitro enzymatic system that can recycle NAD$^+$ and GSH while releasing aromatic monomers from model compounds as well as natural and engineered lignin oligomers. These findings can improve the ability to produce valuable aromatic compounds from a renewable resource like lignin.

Introduction

There is economic and environmental interest in using renewable resources as raw materials for production of chemicals that are currently derived from fossil fuels. Lignin, a renewable resource that accounts for ~15-30% (dry weight) of vascular plant cell walls (Higuchi 1980, Lewis et al. 1990), is comprised of aromatic compounds that may be valuable commodities for the biofuel, chemical, cosmetic, food, and pharmaceutical industries (Sinha et al. 2008). Consequently, intensive efforts are currently aimed at developing chemical, enzymatic and hybrid methods for deriving simpler and lower molecular weight products from lignin (Gall et al. 2017).

The lignin backbone is predominantly composed of guaiacyl (G) and syringyl (S) phenylpropanoid units (FIG. 16 (A)) that derive from the monomers coniferyl and sinapyl alcohol that become covalently linked during lignification via radical coupling reactions, primarily by endwise addition of a monomer (radical) to the phenolic end of the growing polymer (radical). G and S units are inter-linked by a variety of chemical bonds by which the units are characterized: resinols (β-β), 4-O-5-diaryl ethers, phenylcoumarans (β-5), and β-O-4-aryl ethers (termed β-ethers hereafter)] (Adler 1977, Adler 1957, Adler 1955). In grasses, the flavone tricin (T units, FIG. 16 (A)) begins a chain and is covalently linked to the next unit via a 4-O-β-ether bond (Lan et al. 2016, Lan et al. 2015, del Rio et al. 2012). Given that approximately 50-70% of all inter-unit linkages in lignin are β-ethers (Adler 1977, Adler 1957, Adler 1955), cleavage of these bonds is crucial for processes aiming to derive valuable low molecular weight compounds from lignin in high yields. The formation of β-ether linkages during lignification generates a racemic lignin product containing both β(R)- and β(S)-carbons that, after re-aromatization of the quinone methide intermediate by proton-assisted water addition, are adjacent to either α(R)- or α(S)-configured benzylic alcohols (Akiyama et al. 2002, Sugimoto et al. 2002, Ralph et al. 1999). Each unit therefore has 4 optical isomers and two 'real' isomers—the so-designated threo and erythro (or syn and anti) isomers. Lignin depolymerization via β-ether bond cleavage has been demonstrated with chemical *catalysis* (Rahimi et al. 2013, Rahimi et al. 2014). In addition, cytoplasmic enzymes in a sphingomonad β-etherase pathway have been identified that oxidize and cleave model β-ether linked aromatic dimers (Masai et al. 2007).

The β-etherase pathway is present in *Sphingobium* sp. strain SYK-6 and other sphingomonads (e.g., *Novosphingobium* spp.) (Masai et al. 2007, Gall and Ralph et al. 2014). The diaromatic β-ether-linked guaiacylglycerol-β-guaiacyl ether (GGE, FIG. 16 (B)) lignin model compound has been used as a substrate to identify the following three enzymatic steps in cleavage of β-ether linkages in vitro (Gall and Ralph et al. 2014, Masai et al. 2003, Sato et al. 2009, Tanamura et al. 2010, Gall and Kim et al. 2014): (1) a set of dehydrogenases catalyze nicotinamide adenine dinucleotide ($NAD^+$)-dependent α-oxidation of GGE to GGE-ketone and NADH (Sato et al. 2009, Masai and Kubota et al. 1993), (2) β-etherases that are members of the glutathione S-transferase superfamily, carry out glutathione (GSH)-dependent cleavage of GGE-ketone, releasing guaiacol and β-S-glutathionyl-γ-hydroxy-propiovanillone (GS-HPV) (Masai et al. 2003, Gall and Kim et al. 2014, Masai and Katayama et al. 1993), and (3) one or more glutathione lyases catalyze GSH-dependent cleavage of GS-HPV, yielding glutathione disulfide (GSSG) and γ-hydroxypropiovanillone (HPV) (Masai et al. 2003, Gall and Kim et al. 2014, Rosini et al. 2016, Kontur et al. 2018).

The use for multiple enzymes at some of the pathway's steps is attributable to the existence of both R- and S-configured chiral centers in lignin (Akiyama et al. 2002, Sugimoto et al. 2002, Ralph et al. 1999). The known $NAD^+$-dependent dehydrogenases (LigD, LigL, LigN, and LigO) exhibit strict stereospecificity at the α position with indifference to the configuration at the β position (Sato et al. 2009). With model diaromatic substrates, LigD and LigO are active on the R-configured α-epimers, whereas LigL and LigN are active on the S-configured α-epimers. Because the combined activity of these dehydrogenases eliminates the chiral center at α, GGE-ketone exists as two β-enantiomers that are cleaved by stereospecific β-etherases LigE, LigP and LigF, each of which catalyzes the release of guaiacol with chiral inversion at the β position, and one of two β-epimers of GS-HPV (LigE and LigP convert β(R)-GGE-ketone to β(S)-GS-HPV and LigF converts β(S)-GGE-ketone to β(R)-GS-HPV) (Gall and Kim et al. 2014). The final step is the GSH-dependent cleavage of the GS-HPV epimers, yielding GSSG and HPV as coproducts. LigG has been shown to cleave both β(R)-GS-HPV and β(S)-GS-HPV (Rosini et al. 2016), although it appears to have a strong preference for the former (Masai et al. 2003, Gall and Kim et al. 2014). Recently, a GSH transferase from *Novosphingobium aromaticivorans* DSM12444 ($NaGST_{Nu}$; Saro_2595 in GenBank assembly GCA_000013325.1) (Kontur et al. 2018) has been shown to have high activity with β(R)-GS-HPV and β(S)-GS-HPV both in vivo and in vitro, producing HPV and GSSG as products (FIG. 16 (B)).

Despite what is known about the activity of individual β-etherase pathway enzymes with model diaromatic compounds, there is little information on their function with lignin oligomers. In vivo activity may be limited to aromatic dimers or small lignin oligomers due to restrictions in transporting large polymers into the bacterial cytoplasm where the β-etherase pathway enzymes are found. To better understand the function of β-etherase pathway enzymes, we sought to use a minimal set of enzymes to develop a coupled in vitro assay capable of releasing G, S and T aromatic monomers and recycling the cosubstrates $NAD^+$ and GSH. Here we demonstrate complete conversion of GGE to guaiacol and HPV in a reaction containing LigD, LigN, LigE, LigF, $NaGST_{Nu}$, and the *Allochromatium vinosum* DSM180 GSH reductase (AvGR), which catalyzes NADH-dependent reduction of GSSG (FIG. 16 (B)) (Reiter et al. 2013). We also show that this same combination of enzymes releases tricin from the model compound guaiacylglycerol-β-tricin ether (GTE, FIG. 16 (C)). In addition, we show that the same combination of enzymes releases G, S, and T units from bona fide lignin oligomers; this is the first report to demonstrate the release of tricin from lignin units by biological methods. We discuss new insights gained from this study and its implications for the future production of these and possibly other valuable products from lignin.

Methods

General. GGE was purchased from TCI America (Portland, Oreg.). Tricin, GTE, GTE-ketone, HPV, γ-hydroxypropiosyringone (HPS) and GGE-ketone were synthesized by previously described methods (Adler et al. 1955, Lan et al. 2015, Masai et al. 1989). All other chemicals were purchased from Sigma-Aldrich (St. Louis, Mo.). Methods to isolate and characterize maize (Zea mays) corn stover (MCS) and hybrid poplar (HP) lignin samples were described previously (Lan et al. 2015, Stewart et al. 2009, Shuai et al. 2016). $^1H$ and $^{13}C$ NMR spectra were recorded on a Bruker Biospin (Billerica, Mass.) AVANCE 700 MHz spectrometer fitted with a cryogenically-cooled 5-mm quadruple-resonance $^1H/^{31}P/^{13}C/^{15}N$ QCI gradient probe with inverse geometry (proton coils closest to the sample). Manipulation of DNA and preparation of *Escherichia coli* transformant cultures were carried out according to previously described methods (Moore 2003). All lig genes from *Sphingobium* sp. strain SYK-6, as well as those encoding AvGR from *A. vinosum* DSM180 were codon optimized for expression in *E. coli* and obtained from GeneArt® (Life Technologies). NaGST$_{Nu}$ was amplified and cloned from *N. aromaticivorans* DSM12444 genomic DNA (Kontur et al. 2018).

Plasmid and protein preparation. Procedures for cloning, recombinant expression and purification of Tev protease, LigE, LigF, LigG, and NaGST$_{Nu}$ are described elsewhere (Gall and Kim et al. 2014, Kontur et al. 2017). Codon-optimized ligD, ligN and genes AvGR were cloned into plasmid pVP302K (Gall and Kim et al. 2014) via the PCR overlap method (Shevchuk et al. 2004, Bryksin et al. 2010, Horton et al. 2013, Horton 1993). Expression and purification of LigD, LigN, NaGST$_{Nu}$, and AvGR followed similar procedures as those used previously (Gall and Kim et al. 2014). Briefly, *E. coli* strain B834 cultures, transformed with expression plasmids, were grown aerobically overnight in 1 L of auto-induction ZYM-5052 medium (Studier 2005) supplemented with 100 μg mL$^{-1}$ kanamycin. Cells were pelleted and extracts prepared via compression and sonication. Histidine-tagged proteins were purified from cell lysates via Ni-NTA affinity chromatography with QIAGEN Ni-NTA resin. His-tagged Tev protease was used to liberate N-terminal His-tags and a second round of Ni-NTA affinity chromatography was used to remove the tag and Tev protease before separation by size-exclusion chromatography. Protein preparations were concentrated and frozen with liquid $N_2$.

Enzyme assays. In vitro enzyme assays containing LigD, LigN, LigE, LigF, NaGST$_{Nu}$ (or LigG), and AvGR (or a subset of those enzymes) were conducted in assay buffer (25 mM Tris, 2.0% DMSO, pH 8.0). The concentration of each enzyme was 50 μg mL$^{-1}$ in all assays. When GGE (6 mM) was the substrate, the initial cosubstrate concentrations were 2 mM NAD$^+$ and 4 mM GSH. When GTE (1 mM) was the substrate, the initial cosubstrate concentrations were 5 mM NAD$^+$ and 5 mM GSH. When an isolated lignin sample was used as the substrate (2.2 mg mL$^{-1}$), the initial cosubstrate concentrations were 2 mM NAD$^+$ and 4 mM GSH. Enzyme assays (1 mL or larger volume as needed) were carried out (in duplicate) as follows: (1) the substrate (GGE, GTE, or lignin) was dissolved in DMSO (50-times concentrated above the intended assay concentration) and 20 μL of the solution were added to a 2 mL vial, (2) 880 μL of 25.6 mM Tris pH 11.5 (where the acidic effect of GSH drops the pH to 8.0 after addition of 5 mM GSH), (3) 50 μL of a stock solution in 25 mM Tris containing NAD$^+$ and GSH (each is 20-times concentrated above the intended assay concentration), and (4) 50 μL of 20-times concentrated mixture of the desired enzymes. At indicated time points, 150 μL samples were removed from an assay and enzymatic activity was abolished by pipetting into 5 μL of 5 M phosphoric acid. GGE, guaiacol, HPV, and HPS concentrations were quantified for each time point [see below] using a linear regression of known standards for each compound.

Preparative gel-permeation chromatography (GPC). GPC of lignin samples was carried out using a Beckman 125NM solvent delivery module equipped with a Beckman 168 UV detector (λ=280 nm) and a 30 mL Bio-Rad Bio Bead S-X3 column (a neutral, porous styrene-divinylbenzene copolymer). Dimethylformamide (DMF) was used as the mobile phase at a flow rate of 1.0 mL min$^{-1}$. Between 20 and 50 mg of lignin was dissolved in a minimal amount of DMF, injected into the mobile phase, and 1 mL fractions were collected until UV absorption decreased to baseline levels. Fractions were then subjected to analytical GPC to estimate their average molecular weight (MW). The DMF was evaporated in vacuo in order to recover material used for enzyme assays.

Analytical GPC. Analytical GPC of lignin samples was carried out with a Shimadzu Prominence Ultra Fast Liquid Chromatography system (LC-20AD pumps, SIL-20AC HT autosampler, CTO-20A column oven and CBM-20A controller) and using two TSKgel Alpha-2500 (300×7.8 mm; Tosoh Bioscience) columns at 40° C. Samples (10 μL injection volume) containing approximately 1 mg mL$^{-1}$ of isolated or GPC-fractionated lignin were injected into a mobile phase (100 μM LiBr in DMF) at a flow rate of 0.3 mL min$^{-1}$ with a run length of 90 min. An SPD-M20A photodiode array detector (λ=200 nm) was used for the determination of elution times that were subsequently converted to MW values using regression analysis of ReadyCal-Kit Polystyrene standards.

$C_{18}$-Chromatography. $C_{18}$-Chromatographic separations were carried out using a Beckman 125NM solvent delivery module equipped with a Beckman 168 UV detector. 150 μL samples from enzyme assays were collected and 20 μL aliquots were injected into either a 4×120 mm Restek Ultra Aqueous $C_{18}$-reversed stationary phase column, or a 4.6× 250 mm Phenomenex Luna 5u $C_{18}$(2)-reversed stationary phase column with a 1.0 mL min$^{-1}$ mobile phase composed of a mixture of an aqueous buffer (5 mM formic acid in 95/5 $H_2O$/acetonitrile) and methanol. Samples from enzyme assays using GTE as the substrate were analyzed on the Phenomenex column to improve separation of GTE and tricin. All other $C_{18}$-chromatographic separations were carried out using the Restek column. For the Restek column, the methanol fraction of the buffer (with water as the remainder) was adjusted as follows: 0-6 min, 30% methanol; 6-15 min, gradient from 30 to 80% methanol; 15-27 min, 80% methanol; 27-28 min, gradient from 80 to 30% methanol; 28-33 min, 30% methanol. For the Phenomenex column, the gradient system was as follows: 0-6 min, 10% methanol; 6-50 min, gradient from 10 to 90% methanol; 50-63 min, 90% methanol; 63-64 min, gradient from 90 to 10% methanol; 64-70 min, 10% methanol.

Results

Design of a Coupled In Vitro Assay for Cleavage of β-Ether-Linked Diaromatic Compounds.

As an initial substrate for this assay we used erythro-GGE, which is a mixture of enantiomers (αR,βS)-GGE and (αS,βR)-GGE that has been used extensively as a substrate with β-etherase pathway enzymes vitro (Gall and Ralph et al. 2014, Masai et al. 2003, Sato et al. 2009, Tanamura et al. 2010, Gall and Kim et al. 2014). We used recombinant preparations of LigD and LigN as these dehydrogenases are reported to be sufficient for the NAD$^+$-dependent oxidation of R- and S-configured α-anomers of erythro-GGE in vitro (Sato et al. 2009). The assay also contained recombinant preparations of LigE and LigF that have been shown to separately catalyze the GSH-dependent conversion of a racemic mixture of GGE to guaiacol and the S- and R-epimers of GSH-HPV (Gall and Kim et al. 2014). NaGST$_{Nu}$ was present to catalyze the GSH-dependent cleavage of the GSH-HPV epimers to HPV and GSSG. The properties of individual enzymes (FIG. 16 (B)) predicts that this coupled system will require equimolar concentrations of GGE and NAD$^+$ and twice as much GSH for complete conversion of GGE to HPV and guaiacol.

In an attempt to reduce the amount of added NAD$^+$ and GSH that would be needed for full conversion of diaromatic substrate to products, some reactions included recombinant AvGR, which catalyzes the NADH-dependent reduction of GSSG (Reiter et al. 2013), thereby recycling the cosubstrates NAD$^+$ and GSH for continued conversion of the β-ether substrates. This cosubstrate recycling system was tested with 6 mM erythro-GGE and limiting concentrations of NAD$^+$ (2 mM) and GSH (4 mM) (FIG. 17A (panel A)). Using a mixture of LigD, LigN, LigE, LigF, and NaGST$_{Nu}$ (without AvGR), we observed that erythro-GGE was partially converted to HPV and guaiacol (FIG. 17A (panel B)). Quantification of this assay revealed that the erythro-GGE concentration decreased from 6.0 mM to 3.8 mM at the end of the assay, whereas the HPV and guaiacol concentrations were each 2.0 mM, the NAD$^+$ levels were non-detectable, and the threo-GGE [a mixture of enantiomers (αR,βR)-GGE and (αS,βS)-GGE] concentration increased to 0.1 mM presumably due to the reported reversibility of the LigD/LigN reactions (Pereira et al. 2016). Thus, the final GGE concentration (3.9 mM, the sum of erythro-GGE and threo-GGE concentrations) was consistent with consumption of 2.0 mM NAD$^+$. In addition, the production of 2.0 mM (each) of HPV and guaiacol was consistent with the consumption of 4.0 mM GSH, where 2.0 mM GSH was consumed in the LigE/LigF reactions and an additional 2.0 mM GSH was consumed in the NaGST$_{Nu}$ reaction.

To test the impact of AvGR on this assay, we added it to a parallel in vitro reaction. In the presence of AvGR (FIG. 17A (panel C)), we found that GGE was completely consumed along with the appearance of equimolar amounts of HPV and guaiacol (6.0 mM each) without a detectable change in the NAD$^+$ concentration or accumulation of any β-etherase pathway intermediates by the time of the assay's conclusion. To determine if any β-etherase pathway intermediates accumulated over the course of the assay, we tested for time-dependent changes in the concentrations of the substrate, known pathway intermediates and products in a parallel reaction (FIG. 18). We found that as erythro-GGE degradation occurs there is a time-dependent accumulation and depletion of GGE-ketone and threo-GGE and, eventually, complete equimolar conversion of the substrate to HPV and guaiacol (FIG. 17A (panels A-C)). From these results, we conclude that the combination of LigD, LigN, LigE, LigF, NaGST$_{Nu}$, and AvGR is sufficient to process all of the chiral centers in a β-ether substrate such as erythro-GGE. In addition, we conclude that the presence of AvGR is sufficient to recycle the cosubstrates NAD$^+$ and GSH that are needed for cleavage of β-ether bonds in a model diaromatic compound such as erythro-GGE.

From information available in the literature, it has remained unclear whether the GSH lyase from *Sphingobium* strain SYK-6, LigG, exhibits a preference for β(R)-GS-HPV (Masai et al. 2003, Gall and Kim et al. 2014), or is capable of cleaving the thioether linkages in both β(R)-GS-HPV and β(S)-GS-HPV (Rosini et al. 2016). As the presence of NaGST$_{Nu}$ resulted in cleavage of both β(R)-GS-HPV and β(S)-GS-HPV in this coupled reaction system (FIG. 17A (panels A-C)), we sought to use this in vitro assay to test the activity of LigG under identical conditions. When we performed an assay using 6.0 mM erythro-GGE, 2.0 mM NAD$^+$, and 4.0 mM GSH, as well as the mixture of LigD, LigN, LigE, LigF, and LigG (without AvGR), we observed partial conversion of GGE to HPV and guaiacol (FIG. 17B (panel D)). At the end of this assay, the total GGE concentration (4.0 mM, the sum of erythro-GGE and threo-GGE concentrations) was expected based on the consumption of 2.0 mM NAD$^+$. Further, the production of 2.0 mM (each) of HPV and guaiacol was consistent with the consumption of 4.0 mM GSH (2.0 mM GSH consumed by each of the LigE/LigF and LigG reaction steps). When we added AvGR to a parallel reaction that contained GGE (6.0 mM), NAD$^+$ (2 mM), GSH (4 mM) and a combination of LigD, LigN, LigE, LigF, and LigG, we did not observe complete conversion of GGE to HPV and guaiacol (FIG. 17B (panel E)). Instead, we detected the diaromatic substrate (erythro-GGE), threo-GGE, GS-HPV, and GGE-ketone (0.7 mM). In contrast to what is found when NaGST$_{Nu}$ was present under identical reaction conditions, the presence of LigG led to incomplete utilization of the diaromatic substrate and the accumulation of β-etherase pathway intermediates. From these results we conclude that LigG is not able to completely cleave both β-epimers of GS-HPV in vitro. Consequently, all subsequent assays were performed using NaGST$_{Nu}$ as a source of GSH lyase activity.

Production of Tricin from GTE In Vitro.

In grasses, the flavone tricin (T, FIG. 16 (A)) is covalently linked to one end of lignin, via a β-ether bond (Lan et al. 2016, Lan et al. 2015, Lan et al. 2014). Although β-etherase pathway enzymes have been shown to cleave β-ether-linked diaromatic model compounds containing G and S monomers, to date there is no published data on their ability to remove the diaromatic flavonoid T units from any substrate. Thus, we sought to test the ability of the coupled assay to cleave GTE (FIG. 16 (C)), a model compound containing a β-ether linked tricin moiety. HPLC analysis of the synthetic GTE (FIG. 19A (A)) indicated that it contained a 6:1 ratio of erythro-GTE [(αR,βS)-GTE and (αS,βR)-GTE] (to threo-GTE [(αR,βR)-GTE and (αS,βS)-GTE], which was consistent with the NMR analysis of this material (Lan et al. 2016).

When we incubated 1.0 mM GTE, 5.0 mM NAD$^+$, 5.0 mM GSH with the combination of LigD, LigN, LigE, LigF and NaGST$_{Nu}$ (FIG. 19B (B)) we observed the complete conversion of GTE to tricin and HPV. This result predicts that LigD and LigN oxidize GTE to form GTE-ketone, LigE and LigF catalyze β-ether cleavage in GTE-ketone to form GS-HPV and tricin, and NaGST$_{Nu}$ releases HPV from GS-HPV (FIG. 16 (C)), suggesting that the larger β-ether-linked flavone model was able to access the active sites in LigD, LigN, LigE, and LigF. To further test this hypothesis, we assayed for the presence of the expected β-etherase pathway intermediates, GS-HPV and GTE-ketone, from GTE. By performing a parallel reaction containing the same substrates and only LigD, LigN, LigE, and LigF (FIG. 19B (C)), we observed that GTE was degraded and tricin was produced. However, in this assay, there was no detectable production of HPV and we observed accumulation of GS-HPV. These findings indicate that the absence of NaGST$_{Nu}$ prevented the conversion of GS-HPV to HPV (FIG. 16 (C)). Finally, in an assay containing only the enzymes LigD and LigN (FIG. 19B (D)), we found that GTE was almost completely converted to GTE-ketone, as expected from the NAD$^+$-dependent α-oxidation activity of GTE. Together, the data show for the first time that T units can be derived from β-ether-linked model compounds in vitro using enzymes, cosubstrates and intermediates that are known to be part of the β-etherase pathway (FIG. 16).

Release of G, S, and T Units from Lignin Oligomers.

With the coupled enzymatic system in place, we tested it for activity with lignin oligomers. First, we tested if a mixture of LigD, LigN, LigE, LigF, NaGST$_{Nu}$, and AvGR produced S units from a high-syringyl hybrid poplar (HP)

lignin polymer (Stewart et al. 2009, Shuai et al. 2016). To ensure that the test was performed with lignin oligomers rather than low-MW material, we fractionated the HP lignin by GPC and pooled the high-MW fractions (FIG. 20, Table 9) for use as a substrate (FIG. 21 (A-B)). From 2.2 mg mL$^{-1}$ lignin oligomers having MW between 9,000 and 12,000 (with 2 mM NAD$^+$ and 4 mM GSH), we detected the production of 1.0 mM HPS, the HPV analog expected to be produced by cleavage of β-ether bonds from a syringyl unit at one end of the lignin chain. We also detected the formation of an unknown product in this reaction (FIG. 21 (B)), which could be either a chemically modified S unit released from the HP lignin or a GS-linked intermediate product. Furthermore, syringaresinol, a dimeric unit in the HP lignin polymer (Stewart et al. 2009), was not detected as a product of the enzymatic reaction.

TABLE 9

Estimated size of the HP lignin fractions after preparative GPC (size distributions are shown in FIG. 9-2). Size was determined from analytical GPC and is reported in Da and the corresponding polymer length is reported in number of units, based on the MW of syringaresinol (418.44) and β-ether-linked syringyl units (228.24). Asterisks highlight fractions that were pooled and used as the substrate in enzyme assays.

|  | Average MW | Average Length (Units) |
| --- | --- | --- |
| Original sample, pre-fractionation | 8,665 | 38.3 |
| Fraction 1* | 11,550 | 51.0 |
| Fraction 2* | 10,780 | 47.6 |
| Fraction 3* | 9,340 | 41.3 |
| Fraction 4 | 7,240 | 32.0 |
| Fraction 5 | 5,200 | 23.0 |
| Fraction 6 | 3,720 | 16.5 |
| Fraction 7 | 2,660 | 11.8 |
| Fraction 8 | 1,910 | 8.5 |
| Fraction 9 | 1,280 | 5.8 |

Given the ability of the enzymatic assay to release HPS from HP lignin, we also tested for the release of aromatic monomers from a more complex lignin, such as the one derived from maize corn stover (MCS) (Lan et al. 2016, Lan et al. 2015). To generate substrates for these assays, we used preparative GPC to size-fractionate MCS lignin (FIG. 22, Table 10) and tested materials with different apparent MW values as the source of lignin oligomer substrates for enzyme assays (FIGS. 23A and 23B). To test for activity with these samples, we incubated LigD, LigN, LigE, LigF, NaGST$_{Nu}$, and AvGR with MCS lignin oligomers (2.2 mg mL$^{-1}$), 2.0 mM NAD$^+$ and 4.0 mM GSH (FIG. 23A (panel A)). In these experiments, we detected release of HPV and HPS in assays using lignin oligomers with average MW ranging from 460 to 10,710 (FIG. 22). The highest concentrations of HPV (0.4 mM) and HPS (0.1 mM) were observed with lignin oligomers having an average MW of 1,390 (FIG. 23B (panel D)) as the substrate. In general, larger lignin oligomers resulted in lower accumulation of HPV and HPS. In addition, similar to the observations with HP lignin, unknown products were detected in most of the enzymatic reactions with the different lignin fractions (FIGS. 23A and 23B). Tricin was only observed as a reaction product when using the lowest MW fraction tested (MW=460, FIG. 23B (panel F)). In sum, we conclude from these experiments that a combination of LigD, LigN, LigE, LigF, NaGST$_{Nu}$, and AvGR can release some, but not all, G, S and T units from MCS lignin oligomers.

TABLE 10

Estimated size of the MCS lignin fractions after preparative GPC (size distributions are shown in FIG. 5). Size was determined from analytical GPC and is reported in Da and the corresponding polymer length is reported in number of units, based on the crude assumption that the average unit has a MW of 210. Asterisks highlight fractions that were used as the substrate in enzyme assays.

|  | Average MW | Average Length (Units) |
| --- | --- | --- |
| Original sample, pre-fractionation | 5,980 | 28.5 |
| Fraction 1* | 10,710 | 51.0 |
| Fraction 2 | 9,860 | 46.9 |
| Fraction 3 | 8,320 | 39.6 |
| Fraction 4 | 6,690 | 31.9 |
| Fraction 5* | 5,370 | 25.6 |
| Fraction 6 | 3,930 | 18.7 |
| Fraction 7 | 2,110 | 10.1 |
| Fraction 8* | 1,390 | 6.6 |
| Fraction 11 | 880 | 4.2 |
| Fraction 14* | 660 | 3.1 |
| Fraction 17* | 460 | 2.2 |

Discussion

In order to use a polymer like lignin as a source of valuable aromatics and other chemicals it is necessary to develop new or improve on existing depolymerization strategies. There has been considerable interest in exploring the use of the bacterial β-etherase pathway for the biological production of aromatics from this renewable plant polymer. There is now a large amount of information on the types of model diaromatic substrates recognized by individual β-etherase enzymes in vitro, the products of their activity, and their structural or functional relationships to other known enzymes (Pereira et al. 2016, Helmich et al. 2016). Despite this, information is lacking on their activity with lignin oligomers. In addition, as these are cytoplasmic enzymes, it is plausible that they evolved to break down β-ether links only in the smaller lignin oligomers that could be transported inside the cells. In this work, we sought to develop a coupled in vitro system containing a set of β-etherase pathway enzymes that was capable of releasing monoaromatic compounds when incubated with different substrates. We reasoned that such a system would provide additional information on the β-etherase enzymes and aid in studies aimed at determining the requirements for release of valuable aromatics from bona fide lignin oligomers.

In this study, we identified a minimum set of enzymes (LigD, LigN, LigE, LigF, NaGST$_{Nu}$, and AvGR) that is capable of cleaving β-ether linkages and completely converting model diaromatic compounds to aromatic monomers. We further showed that this coupled in vitro assay system is capable of stoichiometric production of monoaromatic products from model diaromatics in the presence of limiting amounts of the cosubstrates NAD$^+$ and GSH. The ability to recycle NAD$^+$ and GSH reduces the need for expensive cofactors and increases the future utility of a coupled enzyme system for processing lignin oligomers in vitro. Finally, we showed that this coupled enzyme system has activity with fractionated lignin oligomers. Below we summarize the new information gained from using this assay with widely used or new model β-ether linked substrates as well as lignin oligomers of different sizes.

Insights Gained from using the Coupled Assay with Diaromatic Compounds.

Using GGE as a substrate, we demonstrated that the GSH reductase AvGR is capable of recycling the cosubstrates NAD$^+$ and GSH, enabling the β-etherase enzymes to completely cleave GGE in the presence of sub-stoichiometric amounts of these cofactors (FIG. 17A (panels A-C)). The *A. vinosum* DSM180 AvGR is well-suited for this purpose, as most glutathione reductases described in the literature use NADPH instead of NADH as an electron donor (Reiter et al. 2014). When AvGR was not present in an assay in which GGE concentrations were greater than those of NAD$^+$ and GSH, there was incomplete hydrolysis of this diaromatic substrate, accumulation of β-etherase pathway intermediates, and depletion of NAD$^+$, as expected if the reaction was cofactor limited.

We were also able to detect the release of tricin when GTE was used as a substrate in this assay, showing for the first time that β-etherase pathway enzymes are capable of β-ether bond cleavage in a substrate bearing a large flavonoid moiety. This further shows that the β-etherase pathway enzymes are not limited to substrates containing only G and S monoaromatic units. In prior research, we had demonstrated the ability of LigE and LigF to cleave G-G, G-S, S-G, and S-S dimer models (Gall and Ralph et al. 2014, Gall and Kim et al. 2014), so this result extends the knowledge of the diversity of substrates for these enzymes to the G-T dimers. Thus, although the β-etherase pathway enzymes are thought to be highly stereospecific, they are also capable of recognizing the many different configurations of β-ether linked aromatics potentially present in lignin. With the results of these and previous findings combined (Gall and Ralph et al. 2014, Gall and Kim et al. 2014), we conclude that the minimal set of enzymes used in this study is sufficient to enable the β-etherase pathway in vitro to release of G, S, and T units from compounds modeling β-ether units in lignin.

This coupled assay also allowed us to directly compare the ability of LigG and NaGST$_{Nu}$ to function in the β-etherase pathway. We found that the presence of NaGST$_{Nu}$, AvGR, along with LigD, LigN, LigE, and LigF, was sufficient to allow complete conversion of GGE to HPV and guaiacol (FIG. 17A (panels A-C)). This is consistent with our prediction that NaGST$_{Nu}$ can accommodate both GS-HPV epimers in its active site (Kontur et al. 2018) and the ability of this enzyme to produce stoichiometric amounts of HPV from GGE when added to this coupled assay. In contrast when LigG replaced NaGST$_{Nu}$ under otherwise identical assay conditions, there was incomplete hydrolysis of GGE to HPV and guaiacol, with significant accumulation of GGE-ketone and lower amounts of GS-HPV (FIGS. 17A and 17B (panels A,D-E)). Thus, although it has been suggested that LigG can hydrolyze both β-epimers of GS-HPV (Rosini et al. 2016), this result, along with those published previously (Gall and Kim et al. 2014), support the hypothesis that LigG has a strong preference for β(R)-GS-HPV. This direct comparison of substrate conversion to products in assays that differ only in the addition of LigG or NaGST$_{Nu}$ allows us to conclude that use of the latter enzyme has advantages owing to its greater ability to release HPV from both GS-HPV epimers under comparable conditions in vitro.

Release of Aromatic Monomers from Lignin Oligomers In Vitro.

The features of this coupled β-etherase assay allowed us to begin testing the ability to remove monomer aromatics from bona fide lignin. Lignin is a heterogeneous, high molecular weight polymer, with only limited solubility under the aqueous buffer conditions used for this assay. Consequently, to increase our chances of observing aromatic products under the conditions used for the coupled assay, we used several different lignin oligomers. We also fractionated these materials to test for release of aromatics from different sized lignin oligomers. This has provided several important new insights into the activity of β-etherase enzymes with lignin oligomers and identified opportunities for increasing our understanding of this pathway.

We tested the ability of this enzyme mixture to cleave lignin oligomers that were derived from an engineered poplar line that contains a high content of S units (Stewart et al. 2009). HPS was detected as a product when high molecular weight fractions of the HP lignin were used as the substrate. This provides direct proof that the enzyme mixture will cleave aromatic oligomers containing S units and that this set of β-etherase pathway enzymes are active with lignin oligomers. Given that the vast majority of the aromatic units in HP lignin are S units (Stewart et al. 2009), we estimate that the oligomers used in the enzymatic assay had between 40 and 50 aromatic units (Table 9). With the concentration of lignin oligomer used in this assay (~2.2 mg mL$^{-1}$), complete substrate degradation would yield ~8 mM HPS. The measured HPS concentration in this assay was 1.0 mM, resulting in a 12.5% yield of HPS from HP lignin. Thus, it appears that the mixture of enzymes used in this study, although sufficient for complete cleavage of model diaromatic compounds, and of some β-ether links in HP lignin, is not capable of complete cleavage of all the β-ether linkages in the HP lignin oligomers. It is possible that a heretofore undescribed protein is required to further process these lignin oligomers, or that inhibition of enzyme activity was caused by the presence of some of the high MW oligomers. Although our findings with the model dimers, and previous research, indicate that LigD and LigN are sufficient for complete oxidation of diaromatic compounds (FIGS. 17A and 17B) (Sato et al. 2009, Hishiyama et al. 2012), it is possible that the seemingly redundant dehydrogenases LigO and LigL have a higher affinity for higher MW lignin oligomers. Similarly, LigP, a GSH-S-transferase with apparent redundant activity with LigE (Tanamura et al. 2010), may be of interest for the optimization of in vitro lignin depolymerization.

In the assays using HP lignin as a substrate, we did not detect syringaresinol as a product, even though this dimer is found in low abundance in this polymer (Stewart et al. 2009). Existing models for the composition of HP lignin predict that syringaresinol is primarily internal to the polymer (Stewart et al. 2009). Thus, it is possible that the failure to detect syringaresinol as a reaction product reflects the inability of the tested β-etherase enzymes to access and cleave β-ether bonds that are adjacent to a syringaresinol moiety or that the enzymes exhibited only limited exolytic activity, thus never reaching the syringaresinol unit.

Having established that the coupled enzymatic assay exhibited β-etherase catalytic activity with high-MW fractions of the HP lignin oligomers, we tested a more complex lignin sample from corn stover as a substrate (MCS lignin). Fractionation of this lignin was also carried out and experiments with a wider array of lignin fractions were conducted to test for the release of the major aromatic monomers present in this material (G, S and T units). The detection of HPV, HPS, and tricin from different MCS lignin fractions confirms the observations with the β-ether linked models that the enzyme set used was active in the release of G, S, and T units from lignin. However, tricin was only observed with the lignin fraction having an average MW of 460 (FIG. 22). Using a crude assumption that the average aromatic unit in lignin has a MW of 210 and the known MW of tricin (330), this fraction represents mostly lignin dimers or a T unit with at most one or two other S or G unit. Thus, the ability of the enzymes to cleave the β-ether linkage next to a flavonoid moiety appears restricted to lower MW oligomers. In contrast, HPS and HPV were released from MCS lignin in assays using all of the fractions tested (FIGS. 23A and 23B), which we estimate to encompass a range of oligomers from dimers to 50-unit oligomers (Table 10). The highest measured concentration of HPS and HPV corresponded to the lignin fraction with average MW of 1,390, or ~7 aromatic units (Table 10). Using the same assumption of 210 as the average MW of an aromatic unit in lignin, and the mass of lignin used in the assay (2.2 mg mL$^{-1}$), we estimate a yield of HPS plus HPV of ~5%, which is lower than the estimated HPS yield from HP lignin. This lower release of substrates from MCS than HP lignin likely reflects the more heterogeneous and complex structure of the MCS lignin sample and potential inability of the β-etherase pathway enzymes to access and cleave all β-ether bonds in the polymer.

Taken together, the findings presented here reveal new and exciting features of the β-etherase pathway enzymes. We identified tricin as a valuable flavonoid that can be enzymatically cleaved from β-ether linked models and from low-MW lignin fractions. We also demonstrated β-etherase activity with intact lignin oligomers of varying sizes, some of which might even be too large to be transported into cells. These findings therefore provide the first demonstration that in vitro depolymerization of lignin is possible with β-etherase enzymes, an important step towards the development of biotechnological applications designed to derive high-value monomeric compounds from bona fide lignin polymers. The activity of this set of enzymes on oligomeric substrates provides an opportunity to develop and optimize conditions for aromatic release from lignin fractions derived from biomass deconstruction chemistries that are or will be used by industry.

Abbreviations

NAD$^+$, nicotinamide adenine dinucleotide; NADH, reduced nicotinamide adenine di-nucleotide; GSH, glutathione; GSSG, glutathione disulfide; GS-HPV, β-S-glutathionyl-γ-hydroxypropiovanillone; GS-HPS, β-S-glutathionyl-γ-hydroxypropiosyringone; HPV, γ-hydroxypropiovanillone; HPS, γ-hydroxypropiosyringone; GGE, guaiacylglycerol-β-guaiacyl ether; GGE-ketone, α-oxidized GGE; GTE, guaiacylglycerol-β-tricin ether; GTE-ketone, α-oxidized GTE; NaGST$_{Nu}$, Novosphingobium aromaticivorans strain DSM12444 glutathione lyase; AvGR, Allochromatium vinosum DSM180 glutathione reductase; GPC, gel-permeation chromatography.

EXAMPLE 3

A Heterodimeric β-Etherase Capable of Sterospecifically Breaking the β-Aryl Ether Bond Commonly Found in Lignin Summary This example describes a newly identified enzyme that can cleave the major β-aryl ether linkage in plant lignin. Lignin is a heterogeneous polymer of aromatic units that can constitute as much as 30% of a plant's dry cell weight, making it one of the most abundant renewable materials on Earth. Currently, there are few economical uses for lignin; the polymer is typically disposed of or burned for energy. The aromatic compounds that make up lignin could potentially be used in the chemical, cosmetic, food, and pharmaceutical industries; however, due largely to its irregular, covalently bonded structure, lignin has historically been difficult to depolymerize. Consequently, intensive efforts are currently aimed at developing chemical, enzymatic, and hybrid methods for deriving simpler and lower molecular weight products from lignin.

Some sphingomonad bacteria (e.g. Novosphingobium aromaticivorans) can break the bonds between aromatic units in the lignin polymer, including the β-aryl ether (β-O-4) bond, the most common linkage between aromatic units in lignin (typically >50% of the total linkages). The sphingomonad pathway for breaking the β-aryl ether bond involves three initial steps. First, the α-hydroxyl is oxidized by one of several stereospecific NAD$^+$-dependent dehydrogenases (LigL, LigN, LigD, LigO). Next, stereospecific β-etherases (LigF, LigE, LigP) replace the β-ether bond of the resulting α-ketone with a thioether bond involving glutathione (GSH), releasing a glutathione conjugated phenylpropanoid. Finally, the glutathione moiety is removed from the GS-phenylpropanoid by either a stereospecific (i.e. LigG) or non-stereospecific (i.e. GST$_{Nu}$) glutathione lyase. All of the characterized GSH-dependent β-etherases in this pathway function as homodimers.

The β-etherases that react with a particular stereoisomer of the β-aryl ether bond are similar in amino acid sequence to each other. These β-aryl etherases fall into distinct groups that cleave either the R-(LigE and LigP homodimers) or the S-stereoisomers (LigF homodimers), and the enzymes that cleave the two different stereoisomers of the β-aryl ether bond are phylogenetically distinct from each other. We report here a heterodimeric β-aryl etherase (BaeA, comprised of the Saro_2872 and Saro_2873 proteins) that cleaves the R-stereoisomer of the β-aryl ether bond (like LigE and LigP), but is composed of polypeptides that are more similar in sequence to (but still phylogenetically distinct from) the enzymes in the LigF group.

This expands the known range of enzymes capable of breaking the β-aryl ether bond commonly found in lignin, some of which may have kinetic or other properties better suited to operating within an in vitro lignin depolymerization system than the previously characterized LigE and LigP enzymes.

Construction of N. aromaticivorans Mutants

Biological reagents. All PCR reactions were performed with Herculase II polymerase (Agilent Technologies, Santa Clara, Calif.). Primers were phosphorylated with polynucleotide kinase from Promega (Madison, Wis.). All other enzymes were from New England Biolabs (Ipswich, Mass.). All primers were from Integrated DNA Technologies (Coralville, Iowa).

For cloning using the NEBuilder HiFi Assembly system (New England Biolabs), plasmid pK18msB-MCS (Schafer et al. 1994) was amplified using primers "pK18msB AseI ampl F" and "pK18msB-MCS XbaI R" to generate the linear fragment pK18msB-MCS (see Example 1 above).

Strains. The strains used in the present example are presented in Table 11.

TABLE 11

Novosphingobium aromaticivorans strains used in this example.

| Strain | Genotype | Reference |
|---|---|---|
| 12444Δ1879 | DSM 12444 ΔSaro_1879 | Examples above |
| 12444ΔligE | 12444Δ1879 ΔSaro_2405 | This example |
| 12444Δ2872 | 12444Δ1879 ΔSaro_2872 | This example |
| 12444Δ2873 | 12444Δ1879 ΔSaro_2873 | This example |
| 12444ΔligEΔ2872 | 12444Δ1879 ΔSaro_2405 ΔSaro_2872 | This example |

TABLE 12

Primers used in genomic modifications and enzyme expression.

| Name | Sequence | Notes |
| --- | --- | --- |
| pK18msB AseI ampl F | 5'-CTGTCGTGCCAGCTGCATTAATG-3' (SEQ ID NO: 64) | AseI site (underlined) native to template |
| pK18msB - MCS XbaI R | 5'-GAACAtcTAGAAAGCCAGTCCGCAGAAAC-3' (SEQ ID NO: 65) | XbaI site (underlined); lowercase bases do not match template |
| pK18-ligE OvExt F | 5'-GTTTCTGCGGACTGGCTTTCTAGATGTTCC AGTGCTCTACAACCAGTCGTACCACATG-3' (SEQ ID NO: 97) | Underlined region is complementary to pK18msB-MCS |
| pK18-ligE OvExt R | 5'-CGATTCATTAATGCAGCTGGCACGACAGCG AGTTGAACGAAACCTCCTCGTTCATG-3' (SEQ ID NO: 98) | Underlined region is complementary to pK18msB-MCS |
| Saro2405 ligE del F | 5'-GCATCACCGAAGGCATGAAGAAGTAAACG-3' (SEQ ID NO: 99) | |
| Saro2405 ligE del R | 5'-GTGACTCAATTGCCGTCACCCTGAACTTG-3' (SEQ ID NO: 100) | |
| Saro_2872 ampl AseI F2 | 5'-CATCattaATTCGACCTGGCCATAGGACTG-3' (SEQ ID NO: 101) | AseI site (underlined); lowercase bases do not match template |
| Saro_2872 ampl XbaI R | 5'-taGttCtaGACCATCTTTTCCGCTGGAGC-3' (SEQ ID NO: 102) | XbaI site (underlined); lowercase bases do not match template |
| Saro_2872 del R | 5'-GCTTGTCAAGGCCTGGCTTGC-3' (SEQ ID NO: 103) | |
| Saro_2872 del F | 5'-TtATCCCTCGATCTCCGCCATGATGAG-3' (SEQ ID NO: 104) | lowercase base does not match template |
| Saro_2873-pk18 hifi ampl R | 5'-GTTTCTGCGGACTGGCTTTCTAGATGTTCCC TACAAGGGAGGGCAGTGAAATGAAGC-3' (SEQ ID NO: 105) | Underlined region is complementary to pK18msB-MCS |
| Saro_2873 hifi del F | 5'-CATCCCTCGATCTCGTCCATCCGCTGCCCA TCC-3' (SEQ ID NO: 106) | Underlined region is complementary to Saro_2873 hifi del R |
| Saro_2873-pk18 hifi ampl F | 5'-CGATTCATTAATGCAGCTGGCACGACAGG GACGAATGATAGACCAGCCACTTCAGG-3' (SEQ ID NO: 107) | Underlined region is complementary to pK18msB-MCS |
| Saro_2873 hifi del R | 5'-GATGGACGAGATCGAGGGATGAGCGCGCT TCTTTTACC-3' (SEQ ID NO: 108) | Underlined region is complementary to Saro_2873 hifi del F |
| Saro2872 Ctag BsaI F | 5'-GGCatctgcgaGaccTCCCCAACGGTTGATTTC AG-3' (SEQ ID NO: 109) | BsaI site (underlined); lowercase bases do not match template |
| Saro2872 Ctag BspHI R | 5'-CGAGtcATGAGCGCGCTTCTTTACCACG-3' (SEQ ID NO: 110) | BspHI site (underlined); lowercase bases do not match template |
| pVP302K Ctag BsaI F | 5'-CTGCGGTCTCGCAGATGGTAAAATTCTG-3' (SEQ ID NO: 80) | BsaI site (underlined) |
| pVP302K Ctag NcoI R | 5'-GGTGATGTCCCATGGTTAATTTCTCCTCTTT AATG-3' (SEQ ID NO: 81) | NcoI site (underlined) |

TABLE 12-continued

Primers used in genomic modifications and enzyme expression.

| Name | Sequence | Notes |
|---|---|---|
| Ctag 2872-pVP add Stop R | 5'-CGAGttaTCCCCAACGGTTGATTTCAGG-3' (SEQ ID NO: 111) | lowercase bases do not match template |
| pVP302K Ntag HindIII F | 5'-CATTAAaAGcTTAAACGAATTCGGACTCGG TACGC-3' (SEQ ID NO: 83) | HindIII site (underlined); lowercase bases do not match template |
| 2872-pVP C to Ntag F | 5'-caagcgaaaatctgtattttcagagcgcgatcgcaggaATGAGC GCGCTTCTTTACCACG-3' (SEQ ID NO: 112) | lowercase bases do not match template |
| pVP302 C to Ntag R | 5'-ccaatgcatggtgatggtgatgatggtgatgtcccatGGTTAATT TCTCCTCTTTAATG-3' (SEQ ID NO: 85) | lowercase bases do not match template |
| Saro2872 gNtag R | 5'-caagcgaaaatctgtattttcagagcgcgatcgcaggaAGCGCG CTTCTTTACCACGG-3' (SEQ ID NO: 113) | lowercase bases do not match template |
| Saro2872 gNtag F | 5'-ccaatgcatggtgatggtgatgatggtgatgtaTCATCCCTCG ATCTCCGCCATGATG-3' (SEQ ID NO: 114) | lowercase bases do not match template |
| 2872-3_pVP_HiFi_F | 5'-CTAACTTTGTTATTTTCGGCTTTCTGTTATC CCCAACGGTTGATTTCAGG-3' (SEQ ID NO: 115) | Underlined region is complementary to pVP302K |
| Saro2872-3NOTAG_pVP_HiFi_R | 5'-GAATTCATTAAAGAGGAGAAATTAACCAT GGACGAGGTAAGCCTCTATCATTGG-3' (SEQ ID NO: 116) | Underlined region is complementary to pVP302K |
| pVP302K-HiFi-noTag-R | 5'-GGTTAATTTCTCCTCTTTAATGAATTCTGTG TGAAATTG-3' (SEQ ID NO: 117) | |
| pVP302K-HiFi-ATW-F | 5'-CAGAAAGCCGAAAATAACAAAGTTAGCCT GAGCTG-3' (SEQ ID NO: 91) | |
| Saro2872-3Ntag_pVP_HiFi_R | 5'-GTATTTTCAGAGCGCGATCGCAGGAATGG ACGAGGTAAGCCTCTATCATTGG-3' (SEQ ID NO: 118) | Underlined region is complementary to pVP302K |
| pVP302K-HiFi-ATW-R | 5'-TCCTGCGATCGCGCTCTGAAAATACAGATT TTCG-3' (SEQ ID NO: 90) | |
| Saro2872-S14A_R | 5'-CGCGgCGCTCACCGTTCTTGC-3' (SEQ ID NO: 119) | Lowercase g introduces S→A mutation in underlined codon |
| Saro2872-S14A_F | 5'-CCGTTGGGCTCGCCGTGGTAAAGAAG-3' (SEQ ID NO: 120) | |
| Saro2873-S15A_R | 5'-GCAAGCCGATGCTCGCGTTGATG-3' (SEQ ID NO: 121) | |
| Saro2873-S15A_F | 5'-CAGcGTTGGCATTGGGTTCCCAATGATAG AG-3' (SEQ ID NO: 122) | Lowercase c introduces S→A mutation in underlined codon |
| Saro2873-N14A_F | 5'-CAGAGgcGGCATTGGGTTCCCAATGATAG AG-3' (SEQ ID NO: 123) | Lowercase gc introduces N→A mutation in underlined codon |
| pEU-HiFi-ATW-R | 5'-GTGATGATGATGATGATGTCCCATTAAC-3' (SEQ ID NO: 124) | |
| pEU-HiFi-ATW-F | 5'-TAGTTTAAACGAATTCGAGCTCGG-3' (SEQ ID NO: 125) | |
| Saro2872-pEU2394-HiFi-F | 5'-GGACATCATCATCATATCACGCATTGGCA AGCGAAAATCTGTATTTTCAG-3' (SEQ ID NO: 126) | Underlined region is complementary to pEU |
| Saro2872-pEU2394-HiFi-R | 5'-CCGAGCTCGAATTCGTTTAAACTACGAGTT ATCCCCAACGGTTGATTTCAGG-3' (SEQ ID NO: 127) | Underlined region is complementary to pEU |

TABLE 12-continued

Primers used in genomic modifications and enzyme expression.

| Name | Sequence | Notes |
| --- | --- | --- |
| pEU-2872-fix-R | 5'-<u>CATTAACTAACTAGTGTAGTTGTAGAATGT</u>AAAATGTAATGTTGTTGTTGTTTG-3' (SEQ ID NO: 128) | Underlined region was missing in originally created pEU-2872 |
| pEU-2872-fix-F | 5'-GGACATCATCATCATCATCACGCATTGG-3' (SEQ ID NO: 129) | |
| Saro_2873-pEU_HiFi-F | 5'-<u>CAACTACACTAGTTAGTTAATGGA</u>CGAGGTAAGCCTCTATCATTGG-3' (SEQ ID NO: 130) | Underlined region is complementary to pEU |
| Saro_2873-pEU_HiFi-R | 5'-<u>CGAGCTCGAATTCGTTTAAACTACT</u>CATCCCTCGATCTCCGCCATG-3' (SEQ ID NO: 131) | Underlined region is complementary to pEU |
| pEU2394 F | 5'-GTAGTTTAAACGAATTCGAGCTCGGTACC-3' (SEQ ID NO: 132) | |

Plasmid for deleting Saro_2405. A 3844 bp region of the N. aromaticivorans genome extending from 1501 bp upstream of Saro_2405 to 1503 bp downstream of the gene was amplified from purified genomic DNA using primers "pK18-ligE OvExt F" and "pK18-ligE OvExt R", which contain 5' ends that are complementary to the ends of linearized pK18msB-MCS. The genomic DNA fragment was combined with linearized pK18msB-MCS using the NEBuilder HiFi Assembly system to produce plasmid pK18msB-ligE. This plasmid was amplified using kinase phosphorylated primers "Saro2405 ligE del F" and "Saro2405 ligE del R" to produce a linear fragment in which the majority of Saro_2405 (including the start codon) was missing. This linear fragment was circularized using T4 DNA Ligase to generate plasmid pK18msB-ΔligE.

Plasmid for deleting Saro_2872. A ~2813 bp region of the N. aromaticivorans genome extending from 1073 bp upstream of Saro_2872 to 954 bp downstream of the gene was amplified from purified genomic DNA using primers "Saro_2872 ampl AseI F2" and "Saro_2872 ampl XbaI R", which contain recognition sites for the restriction enzymes AseI or XbaI, respectively, incorporated into their 5' ends. The resulting fragment was digested with AseI and XbaI, then ligated with pK18msB-MCS that had been digested with AseI and XbaI, using T4 DNA Ligase, to form plasmid pK18msB-Saro2872. This plasmid was amplified using kinase phosphorylated primers "Saro_2872 del R" and "Saro_2872 del F" to produce a linear fragment in which the majority of Saro_2872 was missing. Since the start codon of Saro_2872 overlaps with the stop codon of Saro_2873, "Saro_2872 del F" contains a single base mismatch with pK18msB-Saro2872, to inactivate the Saro_2872 start codon, while preserving the Saro_2873 stop codon. This linear fragment was circularized using T4 DNA Ligase to generate plasmid pK18msB-ΔSaro2872.

Plasmid for deleting Saro_2873. ~1100 bp regions from upstream and downstream of Saro_2873 in the N. aromaticivorans genome were separately amplified from purified genomic DNA using primer sets "Saro_2873-pk18 hifi ampl R" and "Saro_2873 hifi del F", and "Saro_2873-pk18 hifi ampl F" and "Saro_2873 hifi del R", respectively. These two fragments were combined with linearized pK18msB-MCS using the NEBuilder HiFi Assembly system to produce plasmid pK18msB-ΔSaro2873, in which the regions that naturally flank Saro_2873 in the genome are adjacent to each other.

Deleting genes from the N. aromaticivorans genome. Deletion plasmids were separately mobilized into N. aromaticivorans via conjugation with Escherichia coli S17-1. For the conjugation, cultures of E. coli S17-1 harboring the plasmid and N. aromaticivorans were grown up overnight in Lysogeny Broth containing kanamycin or GluSis, respectively. Cultures were subcultured and allowed to resume exponential growth before being harvested by centrifugation. E. coli and N. aromaticivorans cell pellets were washed in lysogeny broth, then resuspended together into 90 μL lysogeny broth. Conjugations were allowed to proceed overnight at 30° C. The following day, the conjugations were outgrown in GluSis at 30° C. for >1 h, then plated onto solid GluSis with kanamycin to select for N. aromaticivorans cells in which the plasmid had incorporated into the genome via homologous recombination (single crossovers). Single crossovers were confirmed through the inability to immediately grow on GluSis containing 10% sucrose.

Single crossovers were cultured in 5 mL of GluSis containing 10% sucrose and shaken at 30° C. until growth commenced (usually after several days), which signified loss of the plasmid from the genome via a second round of homologous recombination. These cultures were streaked onto solid GluSis+10% sucrose to isolate individual strains that has lost the plasmid (double crossovers), and plasmid loss was confirmed by the inability to grow on GluSis+kanamycin. The absences of the desired genes were confirmed via PCR performed on isolated genomic DNA and Sanger sequencing.

Bacterial Growth Media

E. coli cultures used for cloning were grown in lysogeny broth (LB), and shaken at ~200 rpm at 37° C. For routine storage and manipulation, N. aromaticivorans cultures were grown in LB or GluSis at 30° C. GluSis is a modification of Sistrom's minimal medium in which the succinate has been replaced by 22.6 mM glucose (see Example 1, above). N. aromaticivorans growth experiments used Standard Mineral Base (SMB) minimal medium, as described in Example 1, except at pH 7.0. Where needed to select for plasmids, media were supplemented with 100 μg/mL ampicillin, 50 μg/mL kanamycin, or 20 μg/mL chloramphenicol.

*N. aromaticivorans* Growth Experiments

Starter cultures of *N. aromaticivorans* were grown in 4 mL SMB containing 4 mM vanillate. Experimental cultures were grown in 20-30 mL of SMB containing 3 mM vanillate and 1 mM GGE, in 125 mL conical growth flasks shaken at 200 rpm at 30° C. Aliquots (400-600 μL) were removed at specified time points and filtered through 0.22 μm syringe tip filters (e.g. Whatman Puradisc filters, GE Healthcare) before HPLC analysis of extracellular aromatics. Every culture was grown at least three times; data shown are from representative cultures.

For the 12444ΔligEΔ2872 and 12444ΔligEΔ2873 cultures, we filtered >2 mL for the final time points. These samples still contained MPHPV; to determine which stereoisomer(s) of MPHPV remained present, the samples were split into three 400 uL aliquots and combined with 5 mM GSH and either $H_2O$, recombinant LigE (90 μg/mL), or recombinant LigF1 (147 μg/mL), and incubated at 30° C. for 1 h. These samples were then analyzed via HPLC as described below.

Expression and Purification of Recombinant Proteins

Plasmid for expressing recombinant Saro_2872. Saro_2872 was amplified from *N. aromaticivorans* genomic DNA with the primers "Saro2872 Ctag BsaI F" and "Saro2872 Ctag BspHI R". This fragment was digested with restriction enzymes BspHI and BsaI. The expression vector pVP302K (Gall and Ralph et al. 2014) was amplified using the primers "pVP302K Ctag BsaI F" and "pVP302K Ctag NcoI R", and the resulting fragment was digested with BsaI and NcoI. The digested fragments were ligated using T4 DNA ligase, generating plasmid pVP302K/Ctag-2872, which consists of a T5 promoter followed by the coding sequences of Saro_2872 (absent the stop codon), the RtxA protease from *Vibrio cholerae*, and a $His_8$ tag.

pVP302K/Ctag-2872 was amplified using kinase phosphorylated primers "Ctag 2872-pVP add Stop R" and "pVP302K Ntag HindIII F". This fragment was circularized using T4 DNA ligase to generate plasmid pVP302K/Untagged2872, in which a stop codon has been introduced directly after Saro_2872.

pVP302K/Untagged2872 was amplified via PCR using kinase phosphorylated primers "2872-pVP C to Ntag F" and "pVP302 C to Ntag R". The amplified fragment was circularized using T4 DNA ligase to generate plasmid pVP302K/Ntag-2872, which contains a T5 promoter followed by coding sequences for a $His_8$-tag, a tobacco etch virus (Tev) protease recognition site and Saro_2872.

Plasmids for expressing recombinant Saro_2872 and Saro_2873 together (BaeA).

To express BaeA containing a $His_8$-tag on the N-terminus of Saro_2872:

We first generated a strain of *N. aromaticivorans* in which a coding sequence for a $His_8$-tag was incorporated into the genome so that cellular copies of Saro_2872 protein would contain a $His_8$-tag on their N-terminus. pK18msB-Saro2872 was amplified via PCR using kinase phosphorylated primers "Saro2872 gNtag R" and "Saro2872 gNtag F", to generate a fragment containing Saro_2873 (with its stop codon), followed by a coding sequence for a $His_8$-tag, then a Tev protease recognition site, then Saro_2872 (missing its native start codon). This fragment was circularized using T4 DNA ligase to generate plasmid pK18msB-$H_8$Saro2872. pK18msB-$H_8$Saro2872 was mobilized into strain 12444Δ2872 via conjugation from *E. coli* S17-1, and a strain of *N. aromaticivorans* (12444-$H_8$2872) containing the coding sequence for Saro_2872 containing an N-terminal $His_8$-tag was generated and isolated using homologous recombination as described above for generating deletion mutants.

We ran PCR using genomic DNA from strain 12444-$H_8$2872 as template with primers "2872-3pVP_HiFi_F" and "Saro2872-3NOTAG_pVP_HiFi_R" to generate a fragment containing the coding sequence for Saro_2873 (with stop codon intact), followed by the coding sequence for a $His_8$-tag, then for Saro_2872 (missing its start codon), with extensions on the ends of the fragment that are complementary to plasmid pVP302K. pVP302K was amplified via PCR using the primers "pVP302K-HiFi-noTag-R" and "pVP302K-HiFi-ATW-F". These two fragments were combined using the NEBuilder HiFi Assembly system to create plasmid pVP302K/2873-H2872.

To express BaeA containing a $His_8$-tag on the N-terminus of Saro_2873:

We ran PCR using genomic DNA from strain 12444Δ1879 as template with primers "2872-3_pVP_HiFi_F" and "Saro2872-3Ntag_pVP_HiFi_R" to generate a fragment containing the native genomic organization of the Saro_2873 and Saro_2872 genes, with extensions on the ends of the fragment that are complementary to plasmid pVP302K. pVP302K was amplified via PCR using the primers "pVP302K-HiFi-ATW-R" and "pVP302K-HiFi-ATW-F". These two fragments were combined using the NEBuilder HiFi Assembly system to create plasmid pVP302K/H2873-2872.

To express BaeA mutants:

To generate mutant 2:S14A, pVP302K/2873-H2872 was amplified by kinase phosphorylated primers "Saro2872-S14A_R" and "Saro2872-S14A_F". To generate mutant 3:S15A, pVP302K/H2873-2872 was amplified by kinase phosphorylated primers "Saro2873-S15A_R" and "Saro2873-S15A_F". To generate mutant 3:N14A, pVP302K/2873-H2872 was amplified by kinase phosphorylated primers "Saro2873-S15A_R" and "Saro2873-N14A_F". These linear fragments were separately circularized using T4 DNA ligase to generate plasmids pVP302K/2873-H2872(S14A), pVP302K/H2873(S15A)-2872, and pVP302K/2873(N14A)-H2872, respectively.

To generate mutant 2:14A/3:S15A, pVP302K/2873-H2872(S14A) was amplified by kinase phosphorylated primers "Saro2873-S15A_R" and "Saro2873-S15A_F". The linear fragment was circularized using T4 DNA ligase to generate plasmid pVP302K/2873(S15A)-H2872(S14A).

Plasmids for expressing recombinant Saro_2873. We amplified plasmids pVP302K/2873-H2872 and pVP302K/H2873-2872 via PCR using kinase phosphorylated primers "pVP302K-HiFi-ATW-F" and "Saro_2872 del F". These linear fragments were separately circularized using T4 DNA ligase to generate plasmids pVP302K/Untagged2873 and pVP302K/Ntag-2873, respectively.

Expression and purification of recombinant enzymes. Recombinant proteins were expressed using the plasmids described above in *E. coli* B834 containing plasmid pRARE2 (Novagen) grown for ~25 hours at 25° C. in ZYM-5052 Autoinduction Medium containing kanamycin and chloramphenicol. Recombinant proteins were purified using a $Ni^{2+}$-NTA column as described in Example 1 above, except using gravity-flow columns instead of an FPLC system. After removal of $His_8$-tags using Tev protease, recombinant proteins retained a Ser-Ala-Ile-Ala-Gly-peptide on their N-termini, derived from the linker between the protein and the Tev protease recognition site. Recombinant LigF1 was purified as previously described (Gall and Ralph et al. 2014).

Recombinant enzyme concentrations were determined via the Bradford method (absorbance at 595 nm), using known concentrations of bovine serum albumin as standards (Thermo Scientific) and protein assay dye reagent from Biorad.

Cell-Free Synthesis Of Saro_2872 And Saro_2873

Plasmid for expressing Saro_2872 in a cell-free system. Plasmid pEU-NGFP (Goren et al. 2009) was amplified via PCR using primers "pEU-HiFi-ATW-R" and "pEU-HiFi-ATW-F" to generate a linear fragment in which the gene for Green Fluorescent Protein has been removed. pVP302K/Ntag-2872 was amplified via PCR using primers "Saro2872-pEU2394-HiFi-F" and "Saro2872-pEU2394-HiFi-R" to generate a linear fragment containing the coding sequence for the Tev protease recognition site followed by Saro_2872. These linear fragments were combined using the NEBuilder HiFi Assembly system to create a plasmid that was missing a short sequence upstream of the translational start site. To add this sequence, we amplified the plasmid using kinase phosphorylated primers "pEU-2872-fix-R" and "pEU-2872-fix-F". The linear fragment was circularized using T4 DNA ligase to form plasmid pEU-H2872, which contains a sequence for a $His_6$-tag, followed by a Tev protease recognition site, then Saro_2872.

Plasmid for expressing Saro_2873 in a cell-free system. N. aromaticivorans genomic DNA was amplified via PCR using primers "Saro_2873-pEU_HiFi-F" and "Saro_2873-pEU_HiFi-R" to generate a linear fragment containing Saro_2873 with ends that are complementary to pEU. pEU-H2872 was amplified via PCR using primers "pEU-2872-fix-R" and "pEU2394 F" to generate a linear fragment in which the sequences for the $His_6$-tag, the Tev protease recognition site, and Saro_2872 were removed. These linear fragments were combined using the NEBuilder HiFi Assembly system to create plasmid pEU-2873.

Cell-free protein synthesis. Cell-free protein synthesis was run essentially as previously described (Makino et al. 2014). The Saro_2872 polypeptide contained a $His_6$-tag and a Tev protease recognition site on its N-terminus that were not removed. The Saro_2873 polypeptide was synthesized in its native form. Synthesized polypeptides were not purified from the synthesis reaction mixture; assays for enzymatic activity were performed by adding aliquots directly from the synthesis reaction. Concentrations of the Saro_2872 and Saro_2873 polypeptides in the reaction mixtures were approximated using the intensities of the bands in an SDS-PAGE gel.

Assays to Determine Activities and Stereospecificties of Saro_2872 and Saro_2873

0.1 mM racemic (β(S) and β(R)) MPHPV was combined with 5.8 mM glutathione (GSH) in reaction buffer (RB; 25 mM Tris-HCl (pH 8.0) and 25 mM NaCl). Cell-free protein synthesis mixtures containing Saro_2872 and Saro_2873 were added individually or together to the MPHPV/GSH solutions to achieve concentrations of ~24 nM of each polypeptide. These 625 µL reactions were incubated at 30° C. for 24 h to several days. Each was then split into 190 µL aliquots and combined with an additional 2.3 mM GSH and either $H_2O$, 151 µg/mL LigE (Saro_2405), or 184 µg/mL LigF1 (Saro_2091). These 212 µL reactions were incubated at 30° C. for several hours, then analyzed via HPLC.

Kinetics of the enzymatic cleavage of β(R)-MPHPV. Various concentrations of racemic MPHPV (equal amounts of the β(S)- and β(R)-stereoisomers) were combined with 5 mM GSH in RB. At time zero, 100 µL of a given enzyme in RB+5 mM GSH was combined with 1000 µL of the racemic MPHPV/GSH sample at 25° C. (both samples were equilibrated to 25° C. before mixing). Final concentrations of β(R)-MPHPV in each reaction were 0.0045, 0.010, 0.017, 0.068, or 0.13 mM. Final enzyme concentrations were 18 nM BaeA, 23 nM BaeA (2:S14A), 22 nM BaeA (3:S15A), 24 nM BaeA (2:S14A/3:S15A), 98 nM BaeA (3N14A), or 70 nM LigE (Saro_2405) (all concentrations are for the dimeric enzyme, except for LigE, which is the concentration of the monomer). At specified time points, 200 µL of a reaction was removed and combined with 40 µL of 1 M HCl (Acros Organics) to stop the reaction before HPLC analysis to quantify GS-HPV formed. Control experiments were allowed to proceed for several hours to ensure that only the β(R)-MPHPV in the reaction mixtures was being reacted with in these experiments.

HPLC analysis. Analysis and quantification of aromatic compounds were performed using an Ultra AQ C18 5 µm column (Restek) attached to a System Gold HPLC (Beckman Coulter) with running buffers and methods described in Example 1. The eluent was analyzed for light absorbance between 191 and 600 nm, and absorbances at 280 nm were used for quantification of aromatic metabolites by comparing peak areas to those of standards.

Results

An N. aromaticivorans Saro_2405 (ligE) deletion mutant can completely metabolize erythro-GGE. LigE from N. aromaticivorans is capable of stereospecifically breaking the β-aryl ether bond of the β(R) stereoisomers of MPHPV and other di-aromatic compounds in vitro. To investigate the in vivo role of LigE in N. aromaticivorans, we constructed a strain in which the gene for LigE (Saro_2405) was deleted from the genome (12444ΔligE), and grew it, along with its parent strain (12444Δ1879), in a medium containing vanillate and erythro-GGE.

As expected from the examples provided above, 12444Δ1879 completely consumed both the vanillate and the GGE. Metabolism of GGE proceeded through several intermediates, including both β(R) and β(S) MPHPV, which transiently appeared in the medium, then were taken back up by the cells (FIG. 24, panel A). Consistent with our examples above, only a trace amount of guaiacol appeared in the extracellular medium, and the glutathione conjugate GS-HPV was never observed in the medium.

As the gene product of Saro_2405 is the only predicted homologue of LigE and LigP in N. aromaticivorans, and LigE and LigP are the only sphingomonad enzymes known to be capable of breaking the β(R) stereoisomer of the β-aryl ether bond, we expected that strain 12444ΔligE would be incapable of fully metabolizing erythro-GGE. However, although MPHPV consistently disappeared from the medium slower for 12444ΔligE than for 12444Δ1879, 12444ΔligE was capable of completely removing racemic MPHPV from the medium (FIG. 24, panel B). As MPHPV disappeared from the medium, HPV accumulated in the medium up to a concentration roughly equal to the initial erythro-GGE concentration, suggesting that essentially all of the GGE was metabolized through MPHPV and into HPV. These results suggest that 12444ΔligE contains an enzyme capable of breaking the β-aryl ether bond of β(R)-MPHPV.

Saro_2872 and Saro_2873 are required for cleavage of β(R)-MPHPV in N. aromaticivorans 12444ΔligE. As LigE, LigP, and LigF are all classified as glutathione S-transferases, we expected that a glutathione S-transferase was reacting with β(R)-MPHPV in the 12444ΔligE strain. We thus investigated Saro_2872 and Saro_2873, which are annotated as coding for glutathione-S-transferases and are located in a gene cluster with Saro_2865, which codes for one of the two LigF isoforms in N. aromaticivorans. We separately deleted Saro_2872 and Saro_2873 from the genome of 12444ΔligE and found that neither of the resulting strains, 12444ΔligEΔ2872 and 12444ΔligEΔ2873, respectively, could fully metabolize erythro-GGE (FIG. 24, panels D and E). Each strain accumulated MPHPV in its medium to a concentration roughly one-half of the medium's initial erythro-GGE concentration, suggesting that they were deficient in metabolizing MPHPV.

Our method of analysis does not distinguish between the β(R) and β(S) stereoisomers of MPHPV. Therefore, to determine which stereoisomer(s) of MPHPV remained unreacted in the media of the 12444ΔligEΔ2872 and 12444ΔligEΔ2873 cultures, the spent media were filtered, and individual aliquots were combined with $H_2O$, or recombinant LigF or LigE, which are known to react stereospecifically with the β(S) or β(R) isomers of MPHPV, respectively (FIG. 25, panels F-K). Addition of LigF to the spent media samples resulted in the conversion of a small amount (<10%) of MPHPV into GS-HPV and guaiacol (FIG. 25, panels G,J), suggesting that some of the unconsumed MPHPV was the β(S) isomer. However, addition of LigE resulted in conversion of most of the MPHPV into GS-HPV and guaiacol (FIG. 25, panels H,K), suggesting that a large fraction of the MPHPV was the β(R) isomer. These results suggest that 12444ΔligE requires both Saro_2872 and Saro_2873 for complete metabolism of MPHPV, particularly the β(R) isomer.

To determine whether both Saro_2872 and Saro_2873 are necessary for complete metabolism of MPHPV in an *N. aromaticivorans* strain with a functional LigE, we deleted Saro_2872 from 12444Δ1879. The resulting strain (12444Δ2872) was capable of fully metabolizing erythro-GGE (FIG. 24, panel C), though it removed the MPHPV from the medium slower than 12444Δ1879 (FIG. 24, panel A), similar to 12444ΔligE (FIG. 24, panel B). Thus, it appears that either LigE or a combination of Saro_2872 and Saro_2873 is sufficient for completely metabolizing β(R)-MPHPV.

The Saro_2872 and Saro_2873 polypeptides form a heterodimer that is stereospecific for β(R)-MPHPV. As our genetic results suggested that the Saro_2872 and Saro_2873 gene products contribute to cleavage of β(R)-MPHPV in *N. aromaticivorans*, we sought to express these proteins and test them for this activity in vitro.

Initial attempts to individually express and purify the Saro_2872 and Saro_2873 polypeptides recombinantly in *Escherichia coli* were unsuccessful. We thus separately expressed each polypeptide using a cell-free protein synthesis system. When the polypeptides were individually combined with racemic (β(R) and β(S)) MPHPV, a trace amount of GS-HPV appeared in the reactions (<1% of the initial MPHPV concentration), but essentially all of the MPHPV remained unreacted (FIG. 26, panels A-C), even after several days.

The lack of activity of the Saro_2872 and Saro_2873 polypeptides, and our observation that the Saro_2872 and Saro_2873 ORFs overlap in the *N. aromaticivorans* genome, led us to hypothesize that the polypeptides may form a heterodimer. Indeed, when we combined the separately prepared Saro_2872 and Saro_2873 polypeptides with each other and with racemic MPHPV, half of the MPHPV was converted into GS-HPV and guaiacol (FIG. 26, panel D). To determine which stereoisomer(s) of MPHPV remained unreacted in this reaction, we split the reaction mixture and added recombinant LigE (Saro_2405) or LigF1 (Saro_2091). Upon addition of LigE, no change in the amounts of MPHPV, GS-HPV, or guaiacol was observed (FIG. 26, panel E). Upon addition of LigF1, the remaining MPHPV in the reaction mixture was converted into GS-HPV and guaiacol (FIG. 26, panel F), suggesting that the MPHPV remaining after the reaction of racemic MPHPV with the mixture of Saro_2872 and Saro_2873 was the β(S) stereoisomer.

To generate larger amounts of the Saro_2872-Saro_2873 complex than was possible with the cell-free system, we attempted to express the Saro_2872 and Saro_2873 polypeptides together from a single expression vector in *E. coli*. Despite the fact that only one of the polypeptides contained a $His_8$-tag on its N-terminus, two polypeptides from the *E. coli* cell lysate, corresponding to the expected sizes of Saro_2872 and Saro_2873, reversibly bound to a $Ni^{2+}$-NTA column, consistent with Saro_2872 and Saro_2873 forming a heterodimer. Indeed, the purified recombinant protein ran as a single peak that corresponded to a dimer in gel permeation chromatography experiments (FIG. 27).

In reactions similar to those performed with the cell-free generated polypeptides, we found that the recombinantly generated Saro_2872-Saro_2873 complex reacted specifically with β(R)-MPHPV, and did not react with β(S)-MPHPV. Because the Saro_2872-Saro_2873 heterodimer is a β-aryl etherase, we call the heterodimer BaeA. The fact that BaeA has the same stereospecificity as LigE (for β(R)-MPHPV) is curious, as both Saro_2872 and Saro_2873 cluster much closer to the previously characterized LigF enzymes than to the previously characterized LigE enzymes in a phylogenetic analysis (FIG. 28). This finding likely has implications for the evolution of the enzymatic ability to break the two stereoisomers of the β-aryl ether bond of lignin.

The Saro_2873 subunit is much more catalytically active than the Saro_2872 subunit in BaeA. We sought to gain insight into the relative activities of the Saro_2872 and Saro_2873 subunits in BaeA by independently inactivating one or the other of the subunits. Previous work found that LigF from *Sphingobium* sp. SYK-6 (SLG_08650) contains a serine residue in its active site ($Ser^{14}$) that is important for reacting with β(S)-(1'-formyl-3'-methoxyphenoxy)-γ-hydroxypropioveratrone (an analogue of MPHPV): mutation of the serine had a dramatic effect on the reaction rate, although it was unclear whether the effect was from changes in substrate binding, turnover, or both (Helmich et al. 2016). This serine residue is conserved in all the previously characterized LigF enzymes, and in both Saro_2872 ($Ser^{14}$) and Saro_2873 ($Ser^{15}$) (FIG. 29). We mutated these serines into alanines separately (2:S14A and 3:S15A) and together (2:S14A/3:S15A) in BaeA and assayed the variant enzymes in vitro, along with wild-type BaeA. As we did not know the relative activities of the two subunits in BaeA, we initially calculated kinetic parameters for the enzymes using the concentrations of the dimers (and not the total concentrations of the individual putative active sites).

Wild-type BaeA and the three serine mutants all had the same $k_{cat}$ value, suggesting that these serine residues are not involved in enzymatic turnover (Table 13). However, the variants in which $Ser^{15}$ in Saro_2873 was mutated (3:S15A and 2:S14A/3:S15A) had $K_M$ values that were 5 to 6-fold higher than that of the wild-type enzyme, suggesting that these variants bound the substrate weaker than the wild-type enzyme. The 2:S14A variant had the same $K_M$ value as the wild-type enzyme, which, along with the lack of an effect on $k_{cat}$, implies that $Ser^{14}$ in Saro_2872 is not involved in catalysis by BaeA.

TABLE 13

Kinetic parameters for the enzymatic conversion of β(R)-MPHPV into GS-HPV

| Protein | $k_{cat}$ (s$^{-1}$) | $K_M$ (μM) | $k_{cat}/K_M$ (mM$^{-1}$s$^{-1}$) |
|---|---|---|---|
| BaeA | 2.9 ± 0.3 | 20 ± 3 | 150 ± 30 |
| BaeA (2:S14A) | 2.8 ± 0.2 | 22 ± 3 | 130 ± 20 |
| BaeA (3:S15A) | 2.4 ± 0.3 | 100 ± 20 | 23 ± 6 |
| BaeA (2:S14A/3:S15A) | 2.8 ± 0.5 | 120 ± 30 | 23 ± 8 |
| BaeA (3:N14A) | 0.14 ± 0.02 | 250 ± 60 | 0.5 ± 0.2 |
| LigE | 0.68 ± 0.06 | 7 ± 1 | 100 ± 20 |

Analysis of the structure of LigF from *Sphingobium* sp. SYK-6 (PDB 4xt0) shows that the side-chain amide nitrogen of Asn$^{13}$ is within hydrogen-bonding distance (3.3 Å) of the bound glutathione thiol group; an analogous asparagine is present in all of the previously characterized LigF enzymes, and in Saro_2873 (Asn$^{14}$) (FIG. 29). (Saro_2872 has an Ala in this position (FIG. 29).) Active site asparagine residues are known or predicted to be involved in catalysis in other glutathione S-transferases. We mutated Asn$^{14}$ in Saro_2873 into Ala and found that the resulting BaeA variant (3:N14A) had a $k_{cat}$ value ~20-fold lower and a $K_M$ value ~12.5-fold higher than wild-type BaeA (Table 13), suggesting that this residue is critical in both substrate binding and turnover in BaeA. We assume that mutation of this residue only affects the active site of the Saro_2873 subunit and does not have any long range effects on the active site of Saro_2872 or the overall folding or structure of the dimer; indeed, all mutant versions of BaeA used in this study ran as dimers in gel permeation chromatography (FIG. 27), similar to the wild-type enzyme, suggesting that the mutations did not affect the overall folding of the proteins or the binding between subunits.

The fact that mutation of a single residue in the Saro_2873 subunit had such a dramatic effect on the overall catalysis of BaeA suggests that Saro_2873 is the catalytically dominant subunit of the dimer, and that, if the Saro_2872 subunit has any activity in BaeA, it is <~5% of the activity of the Saro_2873 subunit.

Catalytic comparison of BaeA and LigE. To directly compare catalysis between BaeA and LigE (Saro_2405), we also analyzed recombinant LigE in our in vitro reaction system. We found that LigE had a ~4-fold lower $k_{cat}$ value and a ~3-fold lower $K_M$ value than BaeA, leading to a catalytic efficiency ($k_{cat}/K_M$) for LigE that is slightly lower than that of BaeA (Table 13).

REFERENCES

Adams, P. D., Afonine, P. V., Bunkóczi, G., Chen, V. B., Davis, I. W., Echols, N., Headd, J. J., Hung, L.-W., Kapral, G. J., Grosse-Kunstleve, R. W., et al. (2010). PHENIX: a comprehensive Python-based system for macromolecular structure solution. *Acta Crystallogr. D Biol. Crystallogr.* 66, 213-221.
Adler E (1977) Lignin chemistry—past, present and future. *Wood Sci Technol* 11(3):169-218.
Adler E: Structural elements of lignin. *Industrial & Engineering Chemistry* 1957, 49:1377-1383.
Adler E, Eriksoo E: Guaiacylglycerol and its β-guaiacyl ether. *Acta chemica Scandinavica* 1955, 9:341-342.
Afonine, P. V., Grosse-Kunstleve, R. W., Echols, N., Headd, J. J., Moriarty, N. W., Mustyakimov, M., Terwilliger, T. C., Urzhumtsev, A., Zwart, P. H., and Adams, P. D. (2012). Towards automated crystallographic structure refinement with phenix sefine. *Acta Crystallogr. D Biol. Crystallogr.* 68, 352-367.
Akiyama T, Sugimoto T, Matsumoto Y, Meshitsuka G: Erythro/threo ratio of β-O-4 structures as an important structural characteristic of lignin. I: Improvement of ozonation method for the quantitative analysis of lignin side-chain structure. *Journal of Wood Science* 2002, 48:210-215.
Bubeck P, Winkler M, Bautsch W (1993) Rapid cloning by homologous recombination in vivo. *Nucleic Acids Res* 21(15):3601-3602.
Bunkóczi, G., and Read, R. J. (2011). Improvement of molecular-replacement models with Sculptor. *Acta Crystallogr. D Biol. Crystallogr.* 67, 303-312.
Bryksin A V, Matsumura I: Overlap extension PCR cloning: a simple and reliable way to create recombinant plasmids. *Biotechniques* 2010, 48:463-465.
Casanas, A., Warshamanage, R., Finke, A. D., Panepucci, E., Olieric, V., Nöll, A., Tampé, R., Brandstetter, S., Förster, A., Mueller, M., et al. (2016). EIGER detector: application in macromolecular crystallography. *Acta Crystallogr D Struct Biol* 72, 1036-1048.
Cohen-Bazire G, Sistrom W R, Stanier R Y (1957) Kinetic studies of pigment synthesis by non-sulfur purple bacteria. *J Cell Comp Physiol* 49(1):25-68.
Crawford R L, Kirk T K, Harkin J M, McCoy E (1973) Bacterial cleavage of an arylglycerol-β-aryl ether bond. *Appl Microbiol* 25(2):322-324.
del Rio J C, Rencoret J, Prinsen P, Martinez A T, Ralph J, Gutierrez A: Structural characterization of wheat straw lignin as revealed by analytical pyrolysis, 2D-NMR, and reductive cleavage method. *Journal of Agricultural and Food Chemistry* 2012, 60:5922-5935.
Doherty A J, Ashford S R, Brannigan J A, Wigley D B (1995) A superior host strain for the over-expression of cloned genes using the T7 promoter based vectors. *Nucleic Acids Res* 23(11):2074-2075.
Emsley, P., and Cowtan, K. (2004). Coot: model-building tools for molecular graphics. *Acta Crystallogr. D Biol. Crystallogr.* 60, 2126-2132.
Fredrickson J K, Brockman F J, Workman D J, Li S W, Stevens T O (1991) Isolation and characterization of a subsurface bacterium capable of growth on toluene, naphthalene, and other aromatic compounds. *Appl Environ Microbiol* 57(3):796-803.
Fredrickson J K, et al. (1995) Aromatic-degrading *Sphingomonas* isolates from the deep subsurface. *Appl Environ Microbiol* 61(5):1917-1922.
Gall D L, Kim H, Lu F, Donohue T J, Noguera D R, Ralph J: Stereochemical features of glutathione-dependent enzymes in the *Sphingobium* sp. strain SYK-6 β-aryl etherase pathway. *J Biol Chem* 2014, 289:8656-8667.
Gall D L, Ralph J, Donohue T J, Noguera D R: A group of sequence-related sphingomonad enzymes catalyzes cleavage of β-aryl ether linkages in lignin β-guaiacyl and β-syringyl ether dimers. *Environmental Science & Technology* 2014, 48:12454-12463.
Gall D L, Ralph J, Donohue T J, Noguera D R: Biochemical transformation of lignin for deriving valued commodities from lignocellulose. (*In Review*). *Current Opinion in Biotechnology* 2017.
Gay P, Le Coq D, Steinmetz M, Berkelman T, Kado C I: Positive selection procedure for entrapment of insertion sequence elements in gram-negative bacteria. *J Bacteriol* 1985, 164(2):918-921.

Goren M A, Nozawa A, Makino S, Wrobel R, Fox B G: Cell-free translation of integral membrane proteins into unilamelar liposomes. *Meth. Enzymol.* 2009, 463:647-673.

Grabber J H, Ralph J, Hatfield R D, Quideau S, Kuster T, Pell A N. Dehydrogenation polymer-cell wall complexes as a model for lignified grass walls. *J. Agric. Food Chem.,* 1996, 44(6):1453-1459.

Helmich K E, Pereira J H, Gall D L, Heins R A, McAndrew R P, Bingman C, Deng K, Holland K C, Noguera D R, Simmons B A, et al.: Structural basis of stereospecificity in the bacterial enzymatic cleavage of β-aryl ether bonds in lignin. *Journal of Biological Chemistry* 2016, 291: 5234-5246.

Higuchi T: Lignin structure and morphological distribution in plant cell walls. In *Lignin biodegradation: microbiology, chemistry and potential applications*. Edited by Kirk T K, Higuchi T, Chang H: CRC Press; 1980:1-20. vol I.

Hishiyama S, Otsuka Y, Nakamura M, Ohara S, Kajita S, Masai E, Katayama Y: Convenient synthesis of chiral lignin model compounds via optical resolution: four stereoisomers of guaiacylglycerol-β-guaiacyl ether and both enantiomers of 3-hydroxy-1-(4-hydroxy-3-methoxyphenyl)-2-(2-methoxy-phenoxy)-propan-1-one (erone). *Tetrahedron Letters* 2012, 53:842-845.

Horton R M: In vitro recombination and mutagenesis of DNA:SOEing together tailor-made genes. *Methods in molecular biology* (Clifton, N.J.) 1993, 15:251-261.

Horton R M, Cai Z, Ho S N, Pease L R: Gene splicing by overlap extension: tailor-made genes using the polymerase chain reaction. *Biotechniques* 2013, 54:129-133.

Kabsch, W. (2010). XDS. *Acta Crystallogr. D Biol. Crystallogr.* 66, 125-132.

Katoh K, Misawa K, Kuma K, Miyata T. MAFFT: a novel method for rapid multiple sequence alignment based on fast Fourier transform. *Nucleic Acids Res.* 2002, 9(14): 3059-3066.

Kontur W S, Bingman C A, Olmsted C N, Wassarman D R, Ulbrich A, Gall D L, Smith R W, Yusko L M, Fox B G, Noguera D R, Coon J J, Donohue T J: Novosphingobium aromaticivorans uses a Nu-class glutathione S-transferase as a glutathione lyase in breaking the β-aryl ether bond of lignin. *J. Biol. Chem.* 2018, 293: 4955-4968.

Lan W, Lu F C, Morreel K, Rencoret J, Del Rio J C, Zakai U, Jones D, Zhu Y M, Boerjan W, Ralph J: Tricin: A novel monomer in grass lignins. *Abstracts of Papers of the American Chemical Society* 2014, 247.

Lan W, Lu F C, Regner M, Zhu Y M, Rencoret J, Ralph S A, Zakai U I, Morreel K, Boerjan W, Ralph J: Tricin, a flavonoid monomer in monocot lignification. *Plant Physiology* 2015, 167:1284-U1265.

Lan W, Morreel K, Lu F C, Rencoret J, del Rio J C, Voorend W, Vermerris W, Boerjan W, Ralph J: Maize tricin-oligolignol metabolites and their implications for monocot lignification. *Plant Physiology* 2016, 171:810-820.

Larkin M A, Blackshields G, Brown N P, Chenna R, McGettigan P A, McWilliam H, Valentin F, Wallace I M, Wilm A, Lopez R, Thompson J D, Gibson T J, Higgins D G. (2007). Clustal W and Clustal X version 2.0. *Bioinformatics*, 23, 2947-2948.

Lewis N G, Yamamoto E: Lignin—occurrence, biogenesis and biodegradation. *Annual Review of Plant Physiology and Plant Molecular Biology* 1990, 41:455-496.

Makino S, Beebe E T, Markley J L, Fox B G: Cell-free protein synthesis for functional and structural studies. *Methods Mol. Biol.* 2014, 1091:161-178.

Masai E, Katayama Y, Nishikawa S, Yamasaki M, Morohoshi N, Haraguchi T: Detection and localization of a new enzyme catalyzing the β-aryl ether cleavage in the soil bacterium (*Pseudomonas paucimobilis* SYK-6). *Febs Letters* 1989, 249:348-352.

Masai E, Kubota S, Katayama Y, Kawai S, Yamasaki M, Morohoshi N: Characterization of the Cα-dehydrogenase gene involved in the cleavage of β-aryl ether by *Pseudomonas paucimobilis*. *Bioscience Biotechnology and Biochemistry* 1993, 57:1655-1659.

Masai E, Katayama Y, Kubota S, Kawai S, Yamasaki M, Morohoshi N: A bacterial enzyme degrading the model lignin compound β-etherase is a member of the glutathione-S-transferase superfamily. *Febs Letters* 1993, 323: 135-140.

Masai E, Ichimura A, Sato Y, Miyauchi K, Katayama Y, Fukuda M: Roles of the enantioselective glutathione S-transferases in cleavage of β-aryl ether. *Journal of Bacteriology* 2003, 185:1768-1775.

Masai E, Katayama Y, Fukuda M (2007) Genetic and biochemical investigations on bacterial catabolic pathways for lignin-derived aromatic compounds. *Biosci Biotechnol Biochem* 71(1):1-15.

Mashiyama, S. T., Malabanan, M. M., Akiva, E., Bhosle, R., Branch, M. C., Hillerich, B., Jagessar, K., Kim, J., Patskovsky, Y., Seidel, R. D., et al. (2014). Large-scale determination of sequence, structure, and function relationships in cytosolic glutathione transferases across the biosphere. *PLoS Biol.* 12, e1001843.

McCoy, A. J., Grosse-Kunstleve, R. W., Adams, P. D., Winn, M. D., Storoni, L. C., and Read, R. J. (2007). Phaser crystallographic software. *J Appl Crystallogr* 40, 658-674.

Moore D D: Current protocols in molecular biology. Edited by Ausubel F M, Brent R, Kingston R E, Moore D D, Seidman J G, Smith J A, Struhl K: John Wiley & Sons; 2003.

Notomista E, et al. (2011) The marine isolate *Novosphingobium* sp. PP1Y shows specific adaptation to use the aromatic fraction of fuels as the sole carbon and energy source. *Microb Ecol* 61(3):582-594.

Ohta Y, Nishi S, Hasegawa R, Hatada Y (2015) Combination of six enzymes of a marine *Novosphingobium* converts the stereoisomers of β-O-4 lignin model dimers into the respective monomers. *Sci Rep* 5:15105.

Palamuru S, et al. (2015) Phylogenetic and kinetic characterization of a suite of dehydrogenases from a newly isolated bacterium, strain SG61-1L, that catalyze the turnover of guaiacylglycerol-β-guaiacyl ether stereoisomers. *Appl Environ Microbiol* 81(23):8164-8176.

Pal, R., Bhasin, V. K., and Lal, R. (2006). Proposal to reclassify [Sphingomonas] xenophaga Stolz et al. 2000 and [Sphingomonas] taejonensis Lee et al. 2001 as *Sphingobium xenophagum* comb. nov. and *Sphingopyxis taejonensis* comb. nov., respectively. *Int. J. Syst. Evol. Microbiol.* 56, 667-670.

Patskovsky Y, et al. PDB ID: 4mzw Crystal structure of nu-class glutathione transferase Yghu from *Streptococcus sanguinis* SK36, complex with glutathione disulfide, target EFI-507286. doi:10.2210/pdb4mzw/pdb.

Pereira J H, Heins R A, Gall D L, McAndrew R P, Deng K, Holland K C, Donohue T J, Noguera D R, Simmons B A, Sale K L, et al.: Structural and biochemical characterization of the early and late enzymes in the lignin β-aryl ether cleavage pathway from *Sphingobium* sp. SYK-6. *Journal of Biological Chemistry* 2016, 291:10228-10238.

Pettersen E F, et al. (2004) UCSF Chimera—a visualization system for exploratory research and analysis. *J Comput Chem* 25(13):1605-1612.

The PyMOL Molecular Graphics System, Version 1.8.2.1 Schrödinger, LLC Available at: https://www.pymol.org/.

Rahimi A, Azarpira A, Kim H, Ralph J, Stahl S S: Chemoselective metal-free aerobic alcohol oxidation in lignin. *Journal of the American Chemical Society* 2013, 135:6415-6418.

Rahimi A, Ulbrich A, Coon J J, Stahl S S: Formic-acid-induced depolymerization of oxidized lignin to aromatics. *Nature* 2014, 515:249-252.

Ralph J, Peng J P, Lu F C, Hatfield R D, Helm R F: Are lignins optically active? *Journal of Agricultural and Food Chemistry* 1999, 47:2991-2996.

Reiter J, Strittmatter H, Wiemann L O, Schieder D, Sieber V: Enzymatic cleavage of lignin β-O-4 aryl ether bonds via net internal hydrogen transfer. *Green Chemistry* 2013, 15:1373-1381.

Reiter J, Pick A, Wiemann L O, Schieder D, Sieber V: A novel natural NADH and NADPH dependent glutathione reductase as tool in biotechnological applications. *JSM Biotechnol Bioeng* 2014, 2:1028-1035.

Rosini E, Allegretti C, Melis R, Cerioli L, Conti G, Pollegioni L, D'Arrigo P: Cascade enzymatic cleavage of the β-O-4 linkage in a lignin model compound. *Catalysis Science & Technology* 2016, 6:2195-2205.

Santos R B, Hart P, Jameel H, Chang H. Wood based lignin reactions important to the biorefinery and pulp and paper industries. *BioResources* 2013, 8(1):1456-1477.

Sato Y, et al. (2009) Identification of three alcohol dehydrogenase genes involved in the stereospecific catabolism of arylglycerol-β-aryl ether by *Sphingobium* sp. strain SYK-6. *Appl Environ Microbiol* 75(16):5195-5201.

Schäfer, A., Tauch, A., Jager, W., Kalinowski, J., Thierbach, G., and Pühler, A. (1994). Small mobilizable multipurpose cloning vectors derived from the *Escherichia coli* plasmids pK18 and pK19: selection of defined deletions in the chromosome of *Corynebacterium glutamicum*. *Gene* 145, 69-73.

Shevchuk N A, Bryksin A V, Nusinovich Y A, Cabello F C, Sutherland M, Ladisch S: Construction of long DNA molecules using long PCR-based fusion of several fragments simultaneously. *Nucleic Acids Research* 2004, 32.

Shuai L, Amiri M T, Questell-Santiago Y M, Héroguel F, Li Y, Kim H, Meilan R, Chapple C, Ralph J, Luterbacher J S: Stabilization with formaldehyde facilitates the high-yield production of monomers from lignin during integrated biomass depolymerization. *Science* 2016, 354 (6310):329-333.

Simon, R., Priefer, U., and Pühler, A. (1983). A Broad Host Range Mobilization System for In Vivo Genetic Engineering: Transposon Mutagenesis in Gram Negative Bacteria. *Nat Biotech* 1, 784-791.

Sinha A K, Sharma U K, Sharma N: A comprehensive review on vanilla flavor: Extraction, isolation and quantification of vanillin and others constituents. *International Journal of Food Sciences and Nutrition* 2008, 59:299-326.

Sistrom W R (1962) The kinetics of the synthesis of photopigments in *Rhodopseudomonas spheroides*. *J Gen Microbiol* 28:607-616.

Stanier R Y, Palleroni N J, Doudoroff M (1966) The aerobic pseudomonads: a taxonomic study. *J Gen Microbiol* 43(2):159-271.

Stewart J J, Akiyama T, Chapple C, Ralph J, Mansfield S D: The effects on lignin structure of overexpression of ferulate 5-hydroxylase in hybrid poplar. *Plant Physiology* 2009, 150:621-635.

Stolz A, et al. (2000) Description of *Sphingomonas xenophaga* sp. nov. for strains BN6$^T$ and N,N which degrade xenobiotic aromatic compounds. *Int J Syst Evol Microbiol* 50 Pt 1:35-41.

Stourman N V, et al. (2011) Structure and function of YghU, a nu-class glutathione transferase related to YfcG from *Escherichia coli*. *Biochemistry* 50(7):1274-1281.

Studier F W (2005) Protein production by auto-induction in high density shaking cultures. *Protein Expr Purif* 41(1): 207-234.

Sugimoto T, Akiyama T, Matsumoto Y, Meshitsuka G: The erythro/threo ratio of β-O-4 structures as an important structural characteristic of lignin—Part 2. Changes in erythro/threo (E/T) ratio of β-O-4 structures during delignification reactions. *Holzforschung* 2002, 56:416-421.

Tanamura K, Kasai D, Nakamura M, Katayama Y, Fukuda M, Masai E: Identification of the third glutathione S-transferase gene involved in the stereospecific cleavage of β-aryl ether in *Sphingobium* sp. strain SYK-6. *Journal of* Biotechnology 2010, 150:S235-S235.

Tavano C L, Podevels A M, Donohue T J (2005) Identification of genes required for recycling reducing power during photosynthetic growth. *J Bacteriol* 187(15):5249-5258.

Taylor, R. G., Walker, D. C., and McInnes, R. R. (1993). *E. coli* host strains significantly affect the quality of small scale plasmid DNA preparations used for sequencing. *Nucleic Acids Res.* 21, 1677-1678

Thuillier, A., Roret, T., Favier, F., Gelhaye, E., Jacquot, J.-P., Didierjean, C., and Morel-Rouhier, M. (2013). Atypical features of a Ure2p glutathione transferase from *Phanerochaete chrysosporium*. *FEBS Lett.* 587, 2125-2130.

Tsien R Y. (1998) The green fluorescent protein. *Annu Rev Biochem.* 67:509-44.

U.S. DOE (2015) Lignocellulose Biomass for Advanced Biofuels and Bioproducts: Workshop Report, DOE/SC-0170. U.S. Department of Energy Office of Science. Available at: http://genomicscience.energy.gov/biofuels/lignocellulose/ [Accessed May 17, 2017].

Vicuña R, González B, Mozuch M D, Kirk T K (1987) Metabolism of lignin model compounds of the arylglycerol-β-aryl ether type by *Pseudomonas acidovorans* D(3). *Appl Environ Microbiol* 53(11):2605-2609.

Wadington M C, Ladner J E, Stourman N V, Harp J M, Armstrong R N (2009) Analysis of the structure and function of YfcG from *Escherichia coli* reveals an efficient and unique disulfide bond reductase. *Biochemistry* 48(28):6559-6561.

Wadington M C, Ladner J E, Stourman N V, Harp J M, Armstrong R N (2010) Correction to Analysis of the structure and function of YfcG from *Escherichia coli* reveals an efficient and unique disulfide bond reductase. *Biochemistry* 49(50):10765.

Wood W B (1966) Host specificity of DNA produced by *Escherichia coli*: bacterial mutations affecting the restriction and modification of DNA. *J Mol Biol* 16(1):118-133.

Exemplary Versions of the Invention

Various exemplary versions of the invention are as follows.

Version 1: A method of processing lignin, comprising contacting lignin comprising β-O-4 ether linkages in vitro with:
- a dehydrogenase comprising at least one of LigD, LigO, LigN, and LigL;
- a β-etherase comprising at least one of LigE, LigF, LigP, and an enzyme comprising a first polypeptide having an amino acid sequence of SEQ ID NO:40 or an amino acid sequence at least about 95% identical thereto and a second polypeptide having an amino acid sequence of SEQ ID NO:42 or an amino acid sequence at least about 95% identical thereto; and
- a glutathione lyase comprising any one or more of LigG and a non-stereospecific glutathione lyase comprising an amino acid sequence at least about 80%, 85%, 90%, or 95% identical to any of:

SEQ ID NO: 18 (NaGST$_{Nu}$);

residues 21-313 of SEQ ID NO: 20 (recombinant NaGST$_{Nu}$);

SEQ ID NO: 22 (SYK6GST$_{Nu}$);

residues 21-324 of SEQ ID NO: 24 (recombinant SYK6GST$_{Nu}$);

SEQ ID NO: 26 (ecYghU);

residues 21-313 of SEQ ID NO: 28 (recombinant ecYghU);

SEQ ID NO: 30 (ecYfcG);

SEQ ID NO: 32 (ssYghU);

SEQ ID NO: 34 (GST3);
and

SEQ ID NO: 36 (PcUre2pB1).

Version 2. The method of version 1, wherein the glutathione lyase comprises the non-stereospecific glutathione lyase.

Version 3. The method of version 1, wherein the glutathione lyase comprises the non-stereospecific glutathione lyase and the non-stereospecific glutathione lyase comprises an amino acid sequence at least about 80%, 85%, 90%, or 95% identical to any of:

SEQ ID NO: 18 (NaGST$_{Nu}$);

residues 21-313 of SEQ ID NO: 20 (recombinant NaGST$_{Nu}$);

SEQ ID NO: 22 (SYK6GST$_{Nu}$);

residues 21-324 of SEQ ID NO: 24 (recombinant SYK6GST$_{Nu}$);

SEQ ID NO: 26 (ecYghU);

residues 21-313 of SEQ ID NO: 28 (recombinant ecYghU);

SEQ ID NO: 30 (ecYfcG);

SEQ ID NO: 32 (ssYghU);

SEQ ID NO: 34 (GST3);
and

SEQ ID NO: 36 (PcUre2pB1).

Version 4. The method of version 1, wherein the glutathione lyase comprises the non-stereospecific glutathione lyase and the non-stereospecific glutathione lyase comprises an amino acid sequence at least about 80%, 85%, 90%, or 95% identical to any of:

SEQ ID NO: 18 (NaGST$_{Nu}$);

residues 21-313 of SEQ ID NO: 20 (recombinant NaGST$_{Nu}$);

SEQ ID NO: 22 (SYK6GST$_{Nu}$);

residues 21-324 of SEQ ID NO: 24 (recombinant SYK6GST$_{Nu}$);

SEQ ID NO: 26 (ecYghU);
and
residues 21-313 of SEQ ID NO:28 (recombinant ecYghU).

Version 5. The method of version 1, wherein the glutathione lyase comprises the non-stereospecific glutathione lyase and the non-stereospecific glutathione lyase comprises an amino acid sequence at least about 90% or 95% identical to any of:

SEQ ID NO: 18 (NaGST$_{Nu}$);

residues 21-313 of SEQ ID NO: 20 (recombinant NaGST$_{Nu}$);

SEQ ID NO: 22 (SYK6GST$_{Nu}$);

residues 21-324 of SEQ ID NO: 24 (recombinant SYK6GST$_{Nu}$);

SEQ ID NO: 26 (ecYghU);
and residues 21-313 of SEQ ID NO: 28 (recombinant ecYghU).

Version 6. The method of any one of versions 1-5, wherein the non-stereospecific glutathione lyase comprises at least one, at least two, at least three, at least four, at least five, at least six, at least seven, or all of:
- threonine or a conservative variant of threonine at a position corresponding to position 51 of SEQ ID NO:18 (NaGST$_{Nu}$);
- asparagine or a conservative variant of asparagine at a position corresponding to position 53 of SEQ ID NO:18 (NaGST$_{Nu}$);

glutamine or a conservative variant of glutamine at a position corresponding to position 86 of SEQ ID NO:18 (NaGST$_{Nu}$);

lysine, a conservative variant of lysine, arginine, or a conservative variant of arginine at a position corresponding to position 99 of SEQ ID NO:18 (NaGST$_{Nu}$);

isoleucine or a conservative variant of isoleucine at a position corresponding to position 100 of SEQ ID NO:18 (NaGST$_{Nu}$);

glutamate or a conservative variant of glutamate at a position corresponding to position 116 of SEQ ID NO:18 (NaGST$_{Nu}$);

serine, threonine, a conservative variant of serine, or a conservative variant of threonine at a position corresponding to position 117 of SEQ ID NO:18 (NaGST$_{Nu}$);

arginine or a conservative variant of arginine at a position corresponding to position 177 of SEQ ID NO:18 (NaGST$_{Nu}$).

Version 7. The method of any one of versions 1-5, wherein the non-stereospecific glutathione lyase comprises at least one, at least two, at least three, at least four, at least five, at least six, at least seven, at least eight, at least nine, at least ten, or all of:

asparagine or a conservative variant of asparagine at a position corresponding to position 25 of SEQ ID NO:18 (NaGST$_{Nu}$);

threonine or a conservative variant of threonine at a position corresponding to position 51 of SEQ ID NO:18 (NaGST$_{Nu}$);

asparagine or a conservative variant of asparagine at a position corresponding to position 53 of SEQ ID NO:18 (NaGST$_{Nu}$);

glutamine or a conservative variant of glutamine at a position corresponding to position 86 of SEQ ID NO:18 (NaGST$_{Nu}$);

lysine, a conservative variant of lysine, arginine, or a conservative variant of arginine at a position corresponding to position 99 of SEQ ID NO:18 (NaGST$_{Nu}$);

isoleucine or a conservative variant of isoleucine at a position corresponding to position 100 of SEQ ID NO:18 (NaGST$_{Nu}$);

glutamate or a conservative variant of glutamate at a position corresponding to position 116 of SEQ ID NO:18 (NaGST$_{Nu}$);

serine, threonine, a conservative variant of serine, or a conservative variant of threonine at a position corresponding to position 117 of SEQ ID NO:18 (NaGST$_{Nu}$);

tyrosine or a conservative variant of tyrosine at a position corresponding to position 166 of SEQ ID NO:18 (NaGST$_{Nu}$);

arginine or a conservative variant of arginine at a position corresponding to position 177 of SEQ ID NO:18 (NaGST$_{Nu}$); and tyrosine or a conservative variant of tyrosine at a position corresponding to position 224 of SEQ ID NO:18 (NaGST$_{Nu}$).

Version 8. The method of any one of versions 1-8, wherein the contacting occurs in the presence of a glutathione (GSH) reductase that catalyzes reduction of glutathione disulfide (GSSG).

Version 9. The method of version 8, wherein the GSH reductase comprises an amino acid sequence at least about 95% identical to SEQ ID NO:38 (AvGR).

Version 10. The method of any one of versions 1-9, wherein the contacting releases at least one of a monomeric phenylpropanoid unit and a monomeric flavone.

Version 11. The method of any one of versions 1-10, wherein the contacting releases at least one of a monomeric guaiacyl phenylpropanoid unit, a monomeric syringyl phenylpropanoid unit, a monomeric p-hydroxyphenyl phenylpropanoid unit, and a monomeric tricin unit.

Version 12. The method of any one of versions 1-11, wherein the lignin comprises an average molecular weight (MW) of from about 600 to about 20,000.

Version 13. A composition, comprising:

lignin comprising β-O-4 ether linkages;

a dehydrogenase comprising at least one of LigD, LigO, LigN, and LigL;

a β-etherase comprising at least one of LigE, LigF, LigP, and an enzyme comprising a first polypeptide having an amino acid sequence of SEQ ID NO:40 or an amino acid sequence at least about 95% identical thereto and a second polypeptide having an amino acid sequence of SEQ ID NO:42 or an amino acid sequence at least about 95% identical thereto; and a glutathione lyase comprising any one or more of LigG and a non-stereospecific glutathione lyase comprising an amino acid sequence at least about 80%, 85%, 90%, or 95% identical to any of:

```
SEQ ID NO: 18 (NaGST_{Nu});

residues 21-313 of SEQ ID NO: 20 (recombinant

NaGST_{Nu});

SEQ ID NO: 22 (SYK6GST_{Nu});

residues 21-324 of SEQ ID NO: 24 (recombinant

SYK6GST_{Nu});

SEQ ID NO: 26 (ecYghU);

residues 21-313 of SEQ ID NO: 28 (recombinant ecYghU);

SEQ ID NO: 30 (ecYfcG);

SEQ ID NO: 32 (ssYghU);

SEQ ID NO: 34 (GST3);
and

SEQ ID NO: 36 (PcUre2pB1).
```

Version 14. The composition of version 13, wherein the glutathione lyase comprises the non-stereospecific glutathione lyase.

Version 15. The composition of version 13, wherein the glutathione lyase comprises the non-stereospecific glutathione lyase and the non-stereospecific glutathione lyase comprises an amino acid sequence at least about 80%, 85%, 90%, or 95% identical to any of:

```
SEQ ID NO: 18 (NaGST_{Nu});

residues 21-313 of SEQ ID NO: 20 (recombinant

NaGST_{Nu});
```

```
SEQ ID NO: 22 (SYK6GST_Nu);

residues 21-324 of SEQ ID NO: 24 (recombinant

SYK6GST_Nu);

SEQ ID NO: 26 (ecYghU);

residues 21-313 of SEQ ID NO: 28 (recombinant ecYghU);

SEQ ID NO: 30 (ecYfcG);

SEQ ID NO: 32 (ssYghU);

SEQ ID NO: 34 (GST3);
and

SEQ ID NO: 36 (PcUre2pB1).
```

Version 16. The composition of version 13, wherein the glutathione lyase comprises the non-stereospecific glutathione lyase and the non-stereospecific glutathione lyase comprises an amino acid sequence at least about 80%, 85%, 90%, or 95% identical to any of:

```
SEQ ID NO: 18 (NaGST_Nu);

residues 21-313 of SEQ ID NO: 20 (recombinant

NaGST_Nu);

SEQ ID NO: 22 (SYK6GST_Nu);

residues 21-324 of SEQ ID NO: 24 (recombinant

SYK6GST_Nu);

SEQ ID NO: 26 (ecYghU);
and residues 21-313 of SEQ ID NO: 28 (recombinant ecYghU).
```

Version 17. The composition of version 13, wherein the glutathione lyase comprises the non-stereospecific glutathione lyase and the non-stereospecific glutathione lyase comprises an amino acid sequence at least about 90% or 95% identical to any of:

```
SEQ ID NO: 18 (NaGST_Nu);

residues 21-313 of SEQ ID NO: 20 (recombinant

NaGST_Nu);

SEQ ID NO: 22 (SYK6GST_Nu);

residues 21-324 of SEQ ID NO: 24 (recombinant

SYK6GST_Nu);

SEQ ID NO: 26 (ecYghU);
and residues 21-313 of SEQ ID NO: 28 (recombinant ecYghU).
```

Version 18. The composition of any one of versions 13-17, wherein the non-stereospecific glutathione lyase comprises at least one, at least two, at least three, at least four, at least five, at least six, at least seven, or all of:

threonine or a conservative variant of threonine at a position corresponding to position 51 of SEQ ID NO:18 (NaGST_Nu);

asparagine or a conservative variant of asparagine at a position corresponding to position 53 of SEQ ID NO:18 (NaGST_Nu);

glutamine or a conservative variant of glutamine at a position corresponding to position 86 of SEQ ID NO:18 (NaGST_Nu);

lysine, a conservative variant of lysine, arginine, or a conservative variant of arginine at a position corresponding to position 99 of SEQ ID NO:18 (NaGST_Nu);

isoleucine or a conservative variant of isoleucine at a position corresponding to position 100 of SEQ ID NO:18 (NaGST_Nu);

glutamate or a conservative variant of glutamate at a position corresponding to position 116 of SEQ ID NO:18 (NaGST_Nu);

serine, threonine, a conservative variant of serine, or a conservative variant of threonine at a position corresponding to position 117 of SEQ ID NO:18 (NaGST_Nu);

arginine or a conservative variant of arginine at a position corresponding to position 177 of SEQ ID NO:18 (NaGST_Nu).

Version 19. The composition of any one of versions 13-17, wherein the non-stereospecific glutathione lyase comprises at least one, at least two, at least three, at least four, at least five, at least six, at least seven, at least eight, at least nine, at least ten, or all of:

asparagine or a conservative variant of asparagine at a position corresponding to position 25 of SEQ ID NO:18 (NaGST_Nu);

threonine or a conservative variant of threonine at a position corresponding to position 51 of SEQ ID NO:18 (NaGST_Nu);

asparagine or a conservative variant of asparagine at a position corresponding to position 53 of SEQ ID NO:18 (NaGST_Nu);

glutamine or a conservative variant of glutamine at a position corresponding to position 86 of SEQ ID NO:18 (NaGST_Nu);

lysine, a conservative variant of lysine, arginine, or a conservative variant of arginine at a position corresponding to position 99 of SEQ ID NO:18 (NaGST_Nu);

isoleucine or a conservative variant of isoleucine at a position corresponding to position 100 of SEQ ID NO:18 (NaGST_Nu);

glutamate or a conservative variant of glutamate at a position corresponding to position 116 of SEQ ID NO:18 (NaGST_Nu);

serine, threonine, a conservative variant of serine, or a conservative variant of threonine at a position corresponding to position 117 of SEQ ID NO:18 (NaGST_Nu);

tyrosine or a conservative variant of tyrosine at a position corresponding to position 166 of SEQ ID NO:18 (NaGST_Nu);

arginine or a conservative variant of arginine at a position corresponding to position 177 of SEQ ID NO:18 (NaGST_Nu); and tyrosine or a conservative variant of tyrosine at a position corresponding to position 224 of SEQ ID NO:18 (NaGST_Nu).

Version 20. The composition of any one of versions 13-19, further comprising a glutathione (GSH) reductase that catalyzes reduction of glutathione disulfide (GSSG).

Version 21. The composition of version 20, wherein the GSH reductase comprises an amino acid sequence at least about 95% identical to SEQ ID NO:38 (AvGR).

Version 22. A method of chemical conversion, comprising contacting a first compound in vitro with a non-stereospecific glutathione lyase to yield a second compound, wherein:

the non-stereospecific glutathione lyase comprises an amino acid sequence at least about 80%, 85%, 90%, or 95% identical to any of:

```
SEQ ID NO: 18 (NaGST_{Nu});

residues 21-313 of SEQ ID NO: 20 (recombinant

NaGST_{Nu});

SEQ ID NO: 22 (SYK6GST_{Nu});

residues 21-324 of SEQ ID NO: 24 (recombinant

SYK6GST_{Nu});

SEQ ID NO: 26 (ecYghU);

residues 21-313 of SEQ ID NO: 28 (recombinant ecYghU);

SEQ ID NO: 30 (ecYfcG);

SEQ ID NO: 32 (ssYghU);

SEQ ID NO: 34 (GST3);
and

SEQ ID NO: 36 (PcUre2pB1)
``` the first compound has a structure of Formula I or a salt thereof:

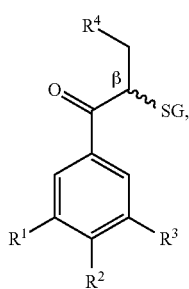

(I)

wherein:
R$^1$, R$^2$, and R$^3$ are each independently —H, —OH, —O-alkyl, —O-lignin, or -lignin;
R$^4$ is —H, —OH, —SH, —COOH, —SO$_3$H, or —O-lignin; and
SG is glutathione bound in an S or R configuration; and
the second compound has a structure of Formula II or a salt thereof:

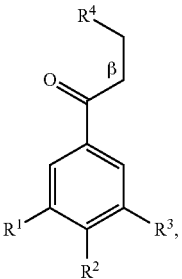

(II)

wherein R$^1$, R$^2$, R$^3$, and R$^4$ are as defined above.

Version 23. The method of version 22, wherein:
R$^1$ in Formula I and Formula II is —H or —OCH$_3$;
R$^2$ in Formula I and Formula II is —OH;
R$^3$ in Formula I and Formula II is —H or —OCH$_3$; and
R$^4$ in Formula I and Formula II is —OH.

Version 24. The method of any one of versions 22-23, wherein the non-stereospecific glutathione lyase comprises an amino acid sequence at least about 80%, 85%, 90%, or 95% identical to any of:

```
SEQ ID NO: 18 (NaGST_{Nu});

residues 21-313 of SEQ ID NO: 20 (recombinant

NaGST_{Nu});

SEQ ID NO: 22 (SYK6GST_{Nu});

residues 21-324 of SEQ ID NO: 24 (recombinant

SYK6GST_{Nu});

SEQ ID NO: 26 (ecYghU);
and residues 21-313 of SEQ ID NO: 28 (recombinant ecYghU).
```

Version 25. The method of any one of versions 22-23, wherein the non-stereospecific glutathione lyase comprises an amino acid sequence at least about 90% or 95% identical to any of:

```
SEQ ID NO: 18 (NaGST_{Nu});

residues 21-313 of SEQ ID NO: 20 (recombinant

NaGST_{Nu});

SEQ ID NO: 22 (SYK6GST_{Nu});

residues 21-324 of SEQ ID NO: 24 (recombinant

SYK6GST_{Nu});

SEQ ID NO: 26 (ecYghU);
and residues 21-313 of SEQ ID NO: 28 (recombinant ecYghU).
```

Version 26. The method of any one of versions 22-25, wherein the non-stereospecific glutathione lyase comprises at least one, at least two, at least three, at least four, at least five, at least six, at least seven, or all of:

threonine or a conservative variant of threonine at a position corresponding to position 51 of SEQ ID NO:18 (NaGST$_{Nu}$);

asparagine or a conservative variant of asparagine at a position corresponding to position 53 of SEQ ID NO:18 (NaGST$_{Nu}$);

glutamine or a conservative variant of glutamine at a position corresponding to position 86 of SEQ ID NO:18 (NaGST$_{Nu}$);

lysine, a conservative variant of lysine, arginine, or a conservative variant of arginine at a position corresponding to position 99 of SEQ ID NO:18 (NaGST$_{Nu}$);

isoleucine or a conservative variant of isoleucine at a position corresponding to position 100 of SEQ ID NO:18 (NaGST$_{Nu}$);

glutamate or a conservative variant of glutamate at a position corresponding to position 116 of SEQ ID NO:18 (NaGST$_{Nu}$);

serine, threonine, a conservative variant of serine, or a conservative variant of threonine at a position corresponding to position 117 of SEQ ID NO:18 (NaGST$_{Nu}$);

arginine or a conservative variant of arginine at a position corresponding to position 177 of SEQ ID NO:18 (NaGST$_{Nu}$).

Version 27. The method of any one of versions 22-25, wherein the non-stereospecific glutathione lyase comprises at least one, at least two, at least three, at least four, at least five, at least six, at least seven, at least eight, at least nine, at least ten, or all of:

asparagine or a conservative variant of asparagine at a position corresponding to position 25 of SEQ ID NO:18 (NaGST$_{Nu}$);

threonine or a conservative variant of threonine at a position corresponding to position 51 of SEQ ID NO:18 (NaGST$_{Nu}$);

asparagine or a conservative variant of asparagine at a position corresponding to position 53 of SEQ ID NO:18 (NaGST$_{Nu}$);

glutamine or a conservative variant of glutamine at a position corresponding to position 86 of SEQ ID NO:18 (NaGST$_{Nu}$);

lysine, a conservative variant of lysine, arginine, or a conservative variant of arginine at a position corresponding to position 99 of SEQ ID NO:18 (NaGST$_{Nu}$);

isoleucine or a conservative variant of isoleucine at a position corresponding to position 100 of SEQ ID NO:18 (NaGST$_{Nu}$);

glutamate or a conservative variant of glutamate at a position corresponding to position 116 of SEQ ID NO:18 (NaGST$_{Nu}$);

serine, threonine, a conservative variant of serine, or a conservative variant of threonine at a position corresponding to position 117 of SEQ ID NO:18 (NaGST$_{Nu}$);

tyrosine or a conservative variant of tyrosine at a position corresponding to position 166 of SEQ ID NO:18 (NaGST$_{Nu}$);

arginine or a conservative variant of arginine at a position corresponding to position 177 of SEQ ID NO:18 (NaGST$_{Nu}$); and tyrosine or a conservative variant of tyrosine at a position corresponding to position 224 of SEQ ID NO:18 (NaGST$_{Nu}$).

Version 28. The method of any of versions 22-27, wherein the contacting occurs in the presence of a glutathione (GSH) reductase that catalyzes reduction of glutathione disulfide (GSSG).

Version 29. The method of version 28, wherein the GSH reductase comprises an amino acid sequence at least about 95% identical to SEQ ID NO:38 (AvGR).

Version 30. The method of any one of versions 22-29, further comprising contacting lignin comprising β-O-4 ether linkages in vitro with enzymes to generate the first compound, wherein the enzymes comprise:

a dehydrogenase comprising at least one of LigD, LigO, LigN, and LigL; and a β-etherase comprising at least one of LigE, LigF, LigP, and an enzyme comprising a first polypeptide having an amino acid sequence of SEQ ID NO:40 or an amino acid sequence at least about 95% identical thereto and a second polypeptide having an amino acid sequence of SEQ ID NO:42 or an amino acid sequence at least about 95% identical thereto.

Version 31. A recombinant non-stereospecific glutathione lyase comprising an amino acid sequence at least about 80%, 85%, 90%, or 95% identical to any of:

```
SEQ ID NO: 18 (NaGST_{Nu});

residues 21-313 of SEQ ID NO: 20 (recombinant

NaGST_{Nu});

SEQ ID NO: 22 (SYK6GST_{Nu});
and residues 21-324 of SEQ ID NO: 24 (recombinant

SYK6GST_{Nu}).
```

Version 32. The glutathione lyase of version 31, comprising an amino acid sequence at least about 80%, 85%, 90%, or 95% identical to any of:

```
SEQ ID NO: 18 (NaGST_{Nu});

residues 21-313 of SEQ ID NO: 20 (recombinant

NaGST_{Nu});

SEQ ID NO: 22 (SYK6GST_{Nu});
and residues 21-324 of SEQ ID NO: 24 (recombinant

SYK6GST_{Nu}).
```

Version 33. The glutathione lyase of version 31, comprising an amino acid sequence at least about 90% or 95% identical to any of:

```
SEQ ID NO: 18 (NaGST_{Nu});

residues 21-313 of SEQ ID NO: 20 (recombinant

NaGST_{Nu});

SEQ ID NO: 22 (SYK6GST_{Nu});
and residues 21-324 of SEQ ID NO: 24 (recombinant

SYK6GST_{Nu}).
```

Version 34. The glutathione lyase of any one of versions 31-33, wherein the non-stereospecific glutathione lyase comprises at least one, at least two, at least three, at least four, at least five, at least six, at least seven, or all of:
- threonine or a conservative variant of threonine at a position corresponding to position 51 of SEQ ID NO:18 (NaGST$_{Nu}$);
- asparagine or a conservative variant of asparagine at a position corresponding to position 53 of SEQ ID NO:18 (NaGST$_{Nu}$);
- glutamine or a conservative variant of glutamine at a position corresponding to position 86 of SEQ ID NO:18 (NaGST$_{Nu}$);
- lysine, a conservative variant of lysine, arginine, or a conservative variant of arginine at a position corresponding to position 99 of SEQ ID NO:18 (NaGST$_{Nu}$);
- isoleucine or a conservative variant of isoleucine at a position corresponding to position 100 of SEQ ID NO:18 (NaGST$_{Nu}$);
- glutamate or a conservative variant of glutamate at a position corresponding to position 116 of SEQ ID NO:18 (NaGST$_{Nu}$);
- serine, threonine, a conservative variant of serine, or a conservative variant of threonine at a position corresponding to position 117 of SEQ ID NO:18 (NaGST$_{Nu}$);
- arginine or a conservative variant of arginine at a position corresponding to position 177 of SEQ ID NO:18 (NaGST$_{Nu}$).

Version 35. The glutathione lyase of any one of versions 31-33, wherein the non-stereospecific glutathione lyase comprises at least one, at least two, at least three, at least four, at least five, at least six, at least seven, at least eight, at least nine, at least ten, or all of:
- asparagine or a conservative variant of asparagine at a position corresponding to position 25 of SEQ ID NO:18 (NaGST$_{Nu}$);
- threonine or a conservative variant of threonine at a position corresponding to position 51 of SEQ ID NO:18 (NaGST$_{Nu}$);
- asparagine or a conservative variant of asparagine at a position corresponding to position 53 of SEQ ID NO:18 (NaGST$_{Nu}$);
- glutamine or a conservative variant of glutamine at a position corresponding to position 86 of SEQ ID NO:18 (NaGST$_{Nu}$);
- lysine, a conservative variant of lysine, arginine, or a conservative variant of arginine at a position corresponding to position 99 of SEQ ID NO:18 (NaGST$_{Nu}$);
- isoleucine or a conservative variant of isoleucine at a position corresponding to position 100 of SEQ ID NO:18 (NaGST$_{Nu}$);
- glutamate or a conservative variant of glutamate at a position corresponding to position 116 of SEQ ID NO:18 (NaGST$_{Nu}$);
- serine, threonine, a conservative variant of serine, or a conservative variant of threonine at a position corresponding to position 117 of SEQ ID NO:18 (NaGST$_{Nu}$);
- tyrosine or a conservative variant of tyrosine at a position corresponding to position 166 of SEQ ID NO:18 (NaGST$_{Nu}$);
- arginine or a conservative variant of arginine at a position corresponding to position 177 of SEQ ID NO:18 (NaGST$_{Nu}$); and
- tyrosine or a conservative variant of tyrosine at a position corresponding to position 224 of SEQ ID NO:18 (NaGST$_{Nu}$).

Version 36. The glutathione lyase of any one of versions 31-35, wherein the glutathione lyase comprises at least one non-native modification selected from the group consisting of an amino acid addition, an amino acid deletion, and an amino acid substitution.

---

We claim:

1. A method of chemical conversion, comprising contacting a first compound in vitro with a non-stereospecific glutathione lyase to yield a second compound, wherein:
the non-stereospecific glutathione lyase comprises:
an amino acid sequence at least 80% identical to any of:

SEQ ID NO: 18 (NaGST$_{Nu}$);

residues 21-313 of SEQ ID NO: 20 (recombinant NaGST$_{Nu}$);

SEQ ID NO: 22 (SYK6GST$_{Nu}$);

residues 21-324 of SEQ ID NO: 24 (recombinant SYK6GST$_{Nu}$);

SEQ ID NO: 26 (ecYghU);

residues 21-313 of SEQ ID NO: 28 (recombinant ecYghU);

SEQ ID NO: 30 (ecYfcG);

SEQ ID NO: 32 (ssYghU); and

SEQ ID NO: 36 (PcUre2pB 1);

and at least four of:
threonine or a conservative variant of threonine at a position corresponding to position 51 of SEQ ID NO:18 (NaGST$_{Nu}$);
asparagine or a conservative variant of asparagine at a position corresponding to position 53 of SEQ ID NO:18 (NaGST$_{Nu}$);
glutamine or a conservative variant of glutamine at a position corresponding to position 86 of SEQ ID NO:18 (NaGST$_{Nu}$);
lysine, a conservative variant of lysine, arginine, or a conservative variant of arginine at a position corresponding to position 99 of SEQ ID NO:18 (NaGST$_{Nu}$);
isoleucine or a conservative variant of isoleucine at a position corresponding to position 100 of SEQ ID NO:18 (NaGST$_{Nu}$);
glutamate or a conservative variant of glutamate at a position corresponding to position 116 of SEQ ID NO:18 (NaGST$_{Nu}$);
serine, threonine, a conservative variant of serine, or a conservative variant of threonine at a position corresponding to position 117 of SEQ ID NO:18 (NaGST$_{Nu}$); and
arginine or a conservative variant of arginine at a position corresponding to position 177 of SEQ ID NO:18 (NaGST$_{Nu}$);

the first compound has a structure of Formula I or a salt thereof:

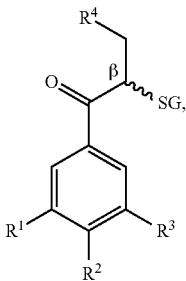
(I)

wherein:
R¹, R², and R³ are each independently —H, —OH, —O-alkyl, —O-lignin, or -lignin;
R⁴ is —H, —OH, —SH, —COOH, —SO₃H, or —O-lignin; and
SG is glutathione bound in an S or R configuration; and the second compound has a structure of Formula II or a salt thereof:

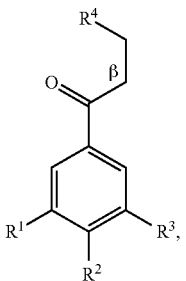
(II)

wherein:
R¹, R², and R³ are each independently —H, —OH, —O-alkyl, —O-lignin, or -lignin; and
R⁴ is —H, —OH, —SH, —COOH, —SO₃H, or —O-lignin.

2. The method of claim 1, wherein the non-stereospecific glutathione lyase comprises an amino acid sequence at least about 85% identical to any of:

```
SEQ ID NO: 18 (NaGST_Nu);

residues 21-313 of SEQ ID NO: 20 (recombinant

NaGST_Nu);

SEQ ID NO: 22 (SYK6GST_Nu);

residues 21-324 of SEQ ID NO: 24 (recombinant

SYK6GST_Nu);

SEQ ID NO: 26 (ecYghU);

residues 21-313 of SEQ ID NO: 28 (recombinant ecYghU);

SEQ ID NO: 30 (ecYfcG);

SEQ ID NO: 32 (ssYghU);
and

SEQ ID NO: 36 (PcUre2pB1).
```

3. The method of claim 1, wherein the non-stereospecific glutathione lyase comprises an amino acid sequence at least about 90% identical to any of:

```
SEQ ID NO: 18 (NaGST_Nu);

residues 21-313 of SEQ ID NO: 20 (recombinant

NaGST_Nu);

SEQ ID NO: 22 (SYK6GST_Nu);

residues 21-324 of SEQ ID NO: 24 (recombinant

SYK6GST_Nu);

SEQ ID NO: 26 (ecYghU);

residues 21-313 of SEQ ID NO: 28 (recombinant ecYghU);

SEQ ID NO: 30 (ecYfcG);

SEQ ID NO: 32 (ssYghU);
and

SEQ ID NO: 36 (PcUre2pB1).
```

4. The method of claim 1, wherein the non-stereospecific glutathione lyase comprises an amino acid sequence at least about 95% identical to any of:

```
SEQ ID NO: 18 (NaGST_Nu);

residues 21-313 of SEQ ID NO: 20 (recombinant

NaGST_Nu);

SEQ ID NO: 22 (SYK6GST_Nu);

residues 21-324 of SEQ ID NO: 24 (recombinant

SYK6GST_Nu);

SEQ ID NO: 26 (ecYghU);

residues 21-313 of SEQ ID NO: 28 (recombinant ecYghU);

SEQ ID NO: 30 (ecYfcG);

SEQ ID NO: 32 (ssYghU);
and

SEQ ID NO: 36 (PcUre2pB1).
```

5. The method of claim 1, wherein the non-stereospecific glutathione lyase comprises at least seven of:
asparagine or a conservative variant of asparagine at a position corresponding to position 25 of SEQ ID NO:18 (NaGST_Nu);
threonine or a conservative variant of threonine at a position corresponding to position 51 of SEQ ID NO:18 (NaGST_Nu);
asparagine or a conservative variant of asparagine at a position corresponding to position 53 of SEQ ID NO:18 (NaGST_Nu);

glutamine or a conservative variant of glutamine at a position corresponding to position 86 of SEQ ID NO:18 (NaGST$_{Nu}$);

lysine, a conservative variant of lysine, arginine, or a conservative variant of arginine at a position corresponding to position 99 of SEQ ID NO:18 (NaGST$_{Nu}$);

isoleucine or a conservative variant of isoleucine at a position corresponding to position 100 of SEQ ID NO:18 (NaGST$_{Nu}$);

glutamate or a conservative variant of glutamate at a position corresponding to position 116 of SEQ ID NO:18 (NaGST$_{Nu}$);

serine, threonine, a conservative variant of serine, or a conservative variant of threonine at a position corresponding to position 117 of SEQ ID NO:18 (NaGST$_{Nu}$);

tyrosine or a conservative variant of tyrosine at a position corresponding to position 166 of SEQ ID NO:18 (NaGST$_{Nu}$);

arginine or a conservative variant of arginine at a position corresponding to position 177 of SEQ ID NO:18 (NaGST$_{Nu}$); and tyrosine or a conservative variant of tyrosine at a position corresponding to position 224 of SEQ ID NO:18 (NaGST$_{Nu}$).

6. The method of claim 1, wherein the contacting occurs in the presence of a glutathione (GSH) reductase that catalyzes reduction of glutathione disulfide (GSSG).

7. The method of claim 6, wherein the GSH reductase comprises an amino acid sequence at least about 95% identical to SEQ ID NO:38 (AvGR).

8. The method of claim 1, wherein the non-stereospecific glutathione lyase comprises an amino acid sequence at least 80% identical to any of:

```
SEQ ID NO: 18 (NaGST_Nu);

residues 21-313 of SEQ ID NO: 20 (recombinant

NaGST_Nu);

SEQ ID NO: 22 (SYK6GST_Nu);

residues 21-324 of SEQ ID NO: 24 (recombinant

SYK6GST_Nu);

SEQ ID NO: 26 (ecYghU);

residues 21-313 of SEQ ID NO: 28 (recombinant ecYghU);
and

SEQ ID NO: 32 (ssYghU).
```

9. The method of claim 8, wherein the non-stereospecific glutathione lyase comprises an amino acid sequence at least about 85% identical to any of:

```
SEQ ID NO: 18 (NaGST_Nu);

residues 21-313 of SEQ ID NO: 20 (recombinant

NaGST_Nu);
```

```
SEQ ID NO: 22 (SYK6GST_Nu);

residues 21-324 of SEQ ID NO: 24 (recombinant

SYK6GST_Nu);

SEQ ID NO: 26 (ecYghU);

residues 21-313 of SEQ ID NO: 28 (recombinant ecYghU);
and

SEQ ID NO: 32 (ssYghU).
```

10. The method of claim 8, wherein the non-stereospecific glutathione lyase comprises an amino acid sequence at least about 90% identical to any of:

```
SEQ ID NO: 18 (NaGST_Nu);

residues 21-313 of SEQ ID NO: 20 (recombinant

NaGST_Nu);

SEQ ID NO: 22 (SYK6GST_Nu);

residues 21-324 of SEQ ID NO: 24 (recombinant

SYK6GST_Nu);

SEQ ID NO: 26 (ecYghU);

residues 21-313 of SEQ ID NO: 28 (recombinant ecYghU);
and

SEQ ID NO: 32 (ssYghU).
```

11. The method of claim 8, wherein the non-stereospecific glutathione lyase comprises an amino acid sequence at least about 95% identical to any of:

```
SEQ ID NO: 18 (NaGST_Nu);

residues 21-313 of SEQ ID NO: 20 (recombinant

NaGST_Nu);

SEQ ID NO: 22 (SYK6GST_Nu);

residues 21-324 of SEQ ID NO: 24 (recombinant

SYK6GST_Nu);

SEQ ID NO: 26 (ecYghU);

residues 21-313 of SEQ ID NO: 28 (recombinant ecYghU);
and

SEQ ID NO: 32 (ssYghU).
```

12. The method of claim 8, wherein the non-stereospecific glutathione lyase comprises at least seven of:

asparagine or a conservative variant of asparagine at a position corresponding to position 25 of SEQ ID NO:18 (NaGST$_{Nu}$);

threonine or a conservative variant of threonine at a position corresponding to position 51 of SEQ ID NO:18 (NaGST$_{Nu}$);

asparagine or a conservative variant of asparagine at a position corresponding to position 53 of SEQ ID NO:18 (NaGST$_{Nu}$);

glutamine or a conservative variant of glutamine at a position corresponding to position 86 of SEQ ID NO:18 (NaGST$_{Nu}$);

lysine, a conservative variant of lysine, arginine, or a conservative variant of arginine at a position corresponding to position 99 of SEQ ID NO:18 (NaGST$_{Nu}$);

isoleucine or a conservative variant of isoleucine at a position corresponding to position 100 of SEQ ID NO:18 (NaGST$_{Nu}$);

glutamate or a conservative variant of glutamate at a position corresponding to position 116 of SEQ ID NO:18 (NaGST$_{Nu}$);

serine, threonine, a conservative variant of serine, or a conservative variant of threonine at a position corresponding to position 117 of SEQ ID NO:18 (NaGST$_{Nu}$);

tyrosine or a conservative variant of tyrosine at a position corresponding to position 166 of SEQ ID NO:18 (NaGST$_{Nu}$);

arginine or a conservative variant of arginine at a position corresponding to position 177 of SEQ ID NO:18 (NaGST$_{Nu}$); and tyrosine or a conservative variant of tyrosine at a position corresponding to position 224 of SEQ ID NO:18 (NaGST$_{Nu}$).

13. The method of claim 8, wherein the contacting occurs in the presence of a glutathione (GSH) reductase that catalyzes reduction of glutathione disulfide (GSSG).

14. The method of claim 13, wherein the GSH reductase comprises an amino acid sequence at least about 95% identical to SEQ ID NO:38 (AvGR).

15. The method of claim 1, wherein the non-stereospecific glutathione lyase comprises an amino acid sequence at least 80% identical to any of:

```
SEQ ID NO: 18 (NaGST_Nu);

residues 21-313 of SEQ ID NO: 20 (recombinant

NaGST_Nu);

SEQ ID NO: 22 (SYK6GST_Nu);

residues 21-324 of SEQ ID NO: 24 (recombinant

SYK6GST_Nu);

SEQ ID NO: 26 (ecYghU);
and residues 21-313 of SEQ ID NO: 28 (recombinant ecYghU).
```

16. The method of claim 15, wherein the non-stereospecific glutathione lyase comprises an amino acid sequence at least about 85% identical to any of:

```
SEQ ID NO: 18 (NaGST_Nu);

residues 21-313 of SEQ ID NO: 20 (recombinant

NaGST_Nu);
```

```
SEQ ID NO: 22 (SYK6GST_Nu);

residues 21-324 of SEQ ID NO: 24 (recombinant

SYK6GST_Nu);

SEQ ID NO: 26 (ecYghU);
and residues 21-313 of SEQ ID NO: 28 (recombinant ecYghU).
```

17. The method of claim 15, wherein the non-stereospecific glutathione lyase comprises an amino acid sequence at least about 90% identical to any of:

```
SEQ ID NO: 18 (NaGST_Nu);

residues 21-313 of SEQ ID NO: 20 (recombinant

NaGST_Nu);

SEQ ID NO: 22 (SYK6GST_Nu);

residues 21-324 of SEQ ID NO: 24 (recombinant

SYK6GST_Nu);

SEQ ID NO: 26 (ecYghU);
and residues 21-313 of SEQ ID NO: 28 (recombinant ecYghU).
```

18. The method of claim 15, wherein the non-stereospecific glutathione lyase comprises an amino acid sequence at least about 95% identical to any of:

```
SEQ ID NO: 18 (NaGST_Nu);

residues 21-313 of SEQ ID NO: 20 (recombinant

NaGST_Nu);

SEQ ID NO: 22 (SYK6GST_Nu);

residues 21-324 of SEQ ID NO: 24 (recombinant

SYK6GST_Nu);

SEQ ID NO: 26 (ecYghU);
and residues 21-313 of SEQ ID NO: 28 (recombinant ecYghU).
```

19. The method of claim 15, wherein the non-stereospecific glutathione lyase comprises at least seven of:

asparagine or a conservative variant of asparagine at a position corresponding to position 25 of SEQ ID NO:18 (NaGST$_{Nu}$);

threonine or a conservative variant of threonine at a position corresponding to position 51 of SEQ ID NO:18 (NaGST$_{Nu}$);

asparagine or a conservative variant of asparagine at a position corresponding to position 53 of SEQ ID NO:18 (NaGST$_{Nu}$);

glutamine or a conservative variant of glutamine at a position corresponding to position 86 of SEQ ID NO:18 (NaGST$_{Nu}$);

lysine, a conservative variant of lysine, arginine, or a conservative variant of arginine at a position corresponding to position 99 of SEQ ID NO:18 (NaGST$_{Nu}$);

isoleucine or a conservative variant of isoleucine at a position corresponding to position 100 of SEQ ID NO:18 (NaGST$_{Nu}$);

glutamate or a conservative variant of glutamate at a position corresponding to position 116 of SEQ ID NO:18 (NaGST$_{Nu}$);

serine, threonine, a conservative variant of serine, or a conservative variant of threonine at a position corresponding to position 117 of SEQ ID NO:18 (NaGST$_{Nu}$);

tyrosine or a conservative variant of tyrosine at a position corresponding to position 166 of SEQ ID NO:18 (NaGST$_{Nu}$);

arginine or a conservative variant of arginine at a position corresponding to position 177 of SEQ ID NO:18 (NaGST$_{Nu}$); and tyrosine or a conservative variant of tyrosine at a position corresponding to position 224 of SEQ ID NO:18 (NaGST$_{Nu}$).

20. The method of claim 15, wherein the contacting occurs in the presence of a glutathione (GSH) reductase that catalyzes reduction of glutathione disulfide (GSSG).

21. The method of claim 20, wherein the GSH reductase comprises an amino acid sequence at least about 95% identical to SEQ ID NO:38 (AvGR).

* * * * *

SEQUENCE LISTING

```
<160> NUMBER OF SEQ ID NOS: 132

<210> SEQ ID NO 1
<211> LENGTH: 918
<212> TYPE: DNA
<213> ORGANISM: Sphingobium sp. SYK-6

<400> SEQUENCE: 1
atgaaggatt tccaggatca ggtcgcgttc atcacgggcg gcgcgtcggg cgccggcttc      60
ggccaggcga aagtgttcgg tcaggcaggc gcgaagatcg tggtggcgga cgtgcgggcc     120
gaagcggtcg agaaggccgt cgccgagctg gaagggctcg ggatcaccgc gcatggcatc     180
gtgctcgata tcatggaccg cgaggcctat gcccgggcgg cggacgaagt ggaggccgtg     240
ttcggccagg cgccgacgct tctctccaac accgctggcg tgaacagctt cgggccgatc     300
gagaagacca cttatgatga tttcgactgg atcatcggcg tcaatctgaa cggcgtcatc     360
aacggcatgg tgaccttcgt gccgcgcatg atcgcgagcg ggcggccggg gcacatcgtc     420
accgtctcgt cgctcggcgg cttcatgggg agcgcgctcg ccgggcccta ttcggcggcc     480
aaggcggcca gcatcaatct gatggaaggc tatcggcagg ggctagagaa atacggcatc     540
ggcgtctccg tctgcacgcc ggccaacatc aagtcgaaca tcgcggaagc ctcgcgcctg     600
cgtcccgcga aatacggcac cagcggctat gtggagaacg aggaatcgat tgcctcgctg     660
```

-continued

```
cactccattc accagcacgg gctcgagccg agaagctgg cggaagcgat caagaaggt      720 gtcgaggaca atgctctcta catcattccc tatcccgaag tgcgcgaagg actggagaag    780
cattttcagg ccatcatcga ttcggtcgcg ccgatggaga gcgatccgga aggcgcccgc    840
cagcgggtcg aggcactgat ggcctgggga cgggaccgca cgcgggtctt cgccgagggc    900
gacaagaaag gcgcctga                                                  918
```

<210> SEQ ID NO 2
<211> LENGTH: 305
<212> TYPE: PRT
<213> ORGANISM: Sphingobium sp. SYK-6

<400> SEQUENCE: 2

```
Met Lys Asp Phe Gln Asp Gln Val Ala Phe Ile Thr Gly Gly Ala Ser
1               5                   10                  15

Gly Ala Gly Phe Gly Gln Ala Lys Val Phe Gly Gln Ala Gly Ala Lys
            20                  25                  30

Ile Val Val Ala Asp Val Arg Ala Glu Ala Val Glu Lys Ala Val Ala
        35                  40                  45

Glu Leu Glu Gly Leu Gly Ile Thr Ala His Gly Ile Val Leu Asp Ile
    50                  55                  60

Met Asp Arg Glu Ala Tyr Ala Arg Ala Ala Asp Glu Val Glu Ala Val
65                  70                  75                  80

Phe Gly Gln Ala Pro Thr Leu Leu Ser Asn Thr Ala Gly Val Asn Ser
                85                  90                  95

Phe Gly Pro Ile Glu Lys Thr Thr Tyr Asp Asp Phe Asp Trp Ile Ile
            100                 105                 110

Gly Val Asn Leu Asn Gly Val Ile Asn Gly Met Val Thr Phe Val Pro
        115                 120                 125

Arg Met Ile Ala Ser Gly Arg Pro Gly His Ile Val Thr Val Ser Ser
130                 135                 140

Leu Gly Gly Phe Met Gly Ser Ala Leu Ala Gly Pro Tyr Ser Ala Ala
145                 150                 155                 160

Lys Ala Ala Ser Ile Asn Leu Met Glu Gly Tyr Arg Gln Gly Leu Glu
                165                 170                 175

Lys Tyr Gly Ile Gly Val Ser Val Cys Thr Pro Ala Asn Ile Lys Ser
            180                 185                 190

Asn Ile Ala Glu Ala Ser Arg Leu Arg Pro Ala Lys Tyr Gly Thr Ser
        195                 200                 205

Gly Tyr Val Glu Asn Glu Glu Ser Ile Ala Ser Leu His Ser Ile His
    210                 215                 220

Gln His Gly Leu Glu Pro Glu Lys Leu Ala Glu Ala Ile Lys Lys Gly
225                 230                 235                 240

Val Glu Asp Asn Ala Leu Tyr Ile Ile Pro Tyr Pro Glu Val Arg Glu
                245                 250                 255

Gly Leu Glu Lys His Phe Gln Ala Ile Ile Asp Ser Val Ala Pro Met
            260                 265                 270

Glu Ser Asp Pro Glu Gly Ala Arg Gln Arg Val Glu Ala Leu Met Ala
        275                 280                 285

Trp Gly Arg Asp Arg Thr Arg Val Phe Ala Glu Gly Asp Lys Lys Gly
    290                 295                 300

Ala
305
```

-continued

<210> SEQ ID NO 3
<211> LENGTH: 894
<212> TYPE: DNA
<213> ORGANISM: Sphingobium sp. SYK-6

<400> SEQUENCE: 3

| | | | | | |
|---|---|---|---|---|---|
| gtgcaggatc | tggaagggaa | agtcgcgttc | gtcaccggcg | ggggatcggg | ggtggcgctc | 60 |
| ggccaggcca | aggtgcttgc | cgaggaagcg | cagatgaagg | tggtgatcgc | cgacatccgg | 120 |
| caggaccatc | tcgacgaagc | gatgggctat | ttcagccaga | agaatgtcgc | cgtccacccc | 180 |
| gtccgcctcg | acctgacgga | tcgcgccgcc | tatgcggccg | ccgtcgacga | ggccgagcag | 240 |
| gtgttcggac | ccgtcgacct | gctgtgcaac | accgccgggg | tcagccagtt | cggccccatc | 300 |
| gagaaagcga | cgtttgacga | ctgggactgg | cagatggacg | tcaacgtgaa | tggcgtcatc | 360 |
| aacggcgtga | tgactgtcat | gccgcgcatg | atcgagcggg | ggcagggcgg | tcacatcctc | 420 |
| atcaccgcgt | cgatgtccgc | tttcgtggcg | ctgcccacga | cgggaatcta | ctgcacgacc | 480 |
| aaatatgccg | tgcgcggcct | tgccgaatcg | ctccgggtgg | aaatgccgaa | atacaatatc | 540 |
| ggcgtctcat | tgctttgccc | cggcggcgtg | aacaccaaca | tccaccggtc | ggtcgaagcc | 600 |
| cggccggaga | aatatggcaa | taccggctat | atgggcgcg | acgaggccgt | gttcgccggg | 660 |
| ctcaagcgcg | tgatcgagca | cggcttcgac | ccggtcgatc | tcggccgcgt | ggtgctcgat | 720 |
| gccgtgcgca | acgatcggtt | ctgggtgttg | ccctatcccg | agttcgctga | ggggcagaaa | 780 |
| gcgcgggatc | aggaagtcat | cgacgccatg | atgtcctatg | cggaccaccc | ggactatgcg | 840 |
| cgccgcatga | agatccgcga | gcagatgaag | cgggacatgc | cgggtagcga | ttga | 894 |

<210> SEQ ID NO 4
<211> LENGTH: 297
<212> TYPE: PRT
<213> ORGANISM: Sphingobium sp. SYK-6

<400> SEQUENCE: 4

Met Gln Asp Leu Glu Gly Lys Val Ala Phe Val Thr Gly Gly Ser
1               5                   10                  15

Gly Val Ala Leu Gly Gln Ala Lys Val Leu Ala Glu Glu Ala Gln Met
            20                  25                  30

Lys Val Val Ile Ala Asp Ile Arg Gln Asp His Leu Asp Glu Ala Met
        35                  40                  45

Gly Tyr Phe Ser Gln Lys Asn Val Ala Val His Pro Val Arg Leu Asp
    50                  55                  60

Leu Thr Asp Arg Ala Ala Tyr Ala Ala Ala Val Asp Glu Ala Glu Gln
65                  70                  75                  80

Val Phe Gly Pro Val Asp Leu Leu Cys Asn Thr Ala Gly Val Ser Gln
                85                  90                  95

Phe Gly Pro Ile Glu Lys Ala Thr Phe Asp Asp Trp Asp Trp Gln Met
            100                 105                 110

Asp Val Asn Val Asn Gly Val Ile Asn Gly Val Met Thr Val Met Pro
        115                 120                 125

Arg Met Ile Glu Arg Gly Gln Gly Gly His Ile Leu Ile Thr Ala Ser
    130                 135                 140

Met Ser Ala Phe Val Ala Leu Pro Thr Thr Gly Ile Tyr Cys Thr Thr
145                 150                 155                 160

Lys Tyr Ala Val Arg Gly Leu Ala Glu Ser Leu Arg Val Glu Met Pro
                165                 170                 175

Lys Tyr Asn Ile Gly Val Ser Leu Leu Cys Pro Gly Gly Val Asn Thr

```
                180               185               190
Asn Ile His Arg Ser Val Glu Ala Arg Pro Glu Lys Tyr Gly Asn Thr
                195                   200                   205
Gly Tyr Tyr Gly Arg Asp Glu Ala Val Phe Ala Gly Leu Lys Arg Val
    210                   215                   220
Ile Glu His Gly Phe Asp Pro Val Asp Leu Gly Arg Val Val Leu Asp
225                   230                   235                   240
Ala Val Arg Asn Asp Arg Phe Trp Val Leu Pro Tyr Pro Glu Phe Ala
                245                   250                   255
Glu Gly Gln Lys Ala Arg Asp Gln Glu Val Ile Asp Ala Met Met Ser
                260                   265                   270
Tyr Ala Asp His Pro Asp Tyr Ala Arg Arg Met Lys Ile Arg Glu Gln
                275                   280                   285
Met Lys Arg Asp Met Pro Gly Ser Asp
    290                   295
```

<210> SEQ ID NO 5
<211> LENGTH: 936
<212> TYPE: DNA
<213> ORGANISM: Sphingobium sp. SYK-6

<400> SEQUENCE: 5

```
atgttggacg taagcggcaa gaccgccttc atcaccggcg gtgccagcgg catgggctgg    60
ggcatggcca aggcctttgg cgaggcaggc atgaaggtga tcatcgccga cattcgccag   120
gacgccctcg atcaggccat ggagggcttt tcgaagacca tcttgccgt tcactccatc    180
ctgctcgacg tgaccagccg cgacggctgg gccagggccg cggatgaagc cgaagagcgg   240
ttcggcaaca tccatgtcct cgcgctcaat gccggggtgg gcaccggcgg atcgatgctg   300
acggccacct acaaggactg ggatttcaac atgggcgtca atgtgggggg cgtcgtcaat   360
ggcctcgtca ccatgctgcc gcgcatgctg ccccatggcg aggaaggcca gctcgtcgtc   420
acctcctcca ccggaggctt ctccgcggta ggcggcgccg ggctctactg tgccgccaaa   480
tattgcgtgg ccggcatgtt cgagagtctg gcgacggacc tgcgcggcac cgcgctcggc   540
gcctccgtct tcttccccgg cccggtgcag acccagctcg gcatctcgac gcaggcgacc   600
cggcccgagc atctgcgcaa cgaggcgccg ccgcctccgc cgccagcgt gggcgctcag    660
caggacaagc gccccgcgcc gggcttcgac ccgagcctgt tcatgaccag cgaggaagtg   720
ggccagcgcg tgctgcgcgg catccgccgg cgcgacctgt tcatcatgac ccatccggaa   780
ttcacgaaag catcgaggc gcgcaacaac gcactgctgc gggccattcc ggtcgaggcg    840
cccaacgagg cgcgggccaa tctggtcgcc cagttcggca ccctcatgta caacccgatc   900
tacgatgggc agcagccgct cgacgagccg ctctga                             936
```

<210> SEQ ID NO 6
<211> LENGTH: 311
<212> TYPE: PRT
<213> ORGANISM: Sphingobium sp. SYK-6

<400> SEQUENCE: 6

```
Met Leu Asp Val Ser Gly Lys Thr Ala Phe Ile Thr Gly Gly Ala Ser
1               5                   10                  15
Gly Met Gly Trp Gly Met Ala Lys Ala Phe Gly Glu Ala Gly Met Lys
            20                  25                  30
Val Ile Ile Ala Asp Ile Arg Gln Asp Ala Leu Asp Gln Ala Met Glu
        35                  40                  45
```

Gly Phe Ser Lys Thr Asn Leu Ala Val His Ser Ile Leu Leu Asp Val
 50                  55                  60

Thr Ser Arg Asp Gly Trp Ala Arg Ala Ala Asp Glu Ala Glu Glu Arg
 65                  70                  75                  80

Phe Gly Asn Ile His Val Leu Ala Leu Asn Ala Gly Val Gly Thr Gly
                 85                  90                  95

Gly Ser Met Leu Thr Ala Thr Tyr Lys Asp Trp Asp Phe Asn Met Gly
            100                 105                 110

Val Asn Val Gly Gly Val Val Asn Gly Leu Val Thr Met Leu Pro Arg
            115                 120                 125

Met Leu Ala His Gly Glu Glu Gly Gln Leu Val Val Thr Ser Ser Thr
            130                 135                 140

Gly Gly Phe Ser Ala Val Gly Gly Ala Gly Leu Tyr Cys Ala Ala Lys
145                 150                 155                 160

Tyr Cys Val Ala Gly Met Phe Glu Ser Leu Ala Thr Asp Leu Arg Gly
                165                 170                 175

Thr Ala Leu Gly Ala Ser Val Phe Phe Pro Gly Pro Val Gln Thr Gln
            180                 185                 190

Leu Gly Ile Ser Thr Gln Ala Thr Arg Pro Glu His Leu Arg Asn Glu
            195                 200                 205

Ala Pro Pro Pro Pro Ala Ser Val Gly Ala Gln Gln Asp Lys Arg
210                 215                 220

Pro Ala Pro Gly Phe Asp Pro Ser Leu Phe Met Thr Ser Glu Glu Val
225                 230                 235                 240

Gly Gln Arg Val Leu Arg Gly Ile Arg Arg Asp Leu Phe Ile Met
                245                 250                 255

Thr His Pro Glu Phe Thr Lys Gly Ile Glu Ala Arg Asn Asn Ala Leu
            260                 265                 270

Leu Arg Ala Ile Pro Val Glu Ala Pro Asn Glu Ala Arg Ala Asn Leu
            275                 280                 285

Val Ala Gln Phe Gly Thr Leu Met Tyr Asn Pro Ile Tyr Asp Gly Gln
            290                 295                 300

Gln Pro Leu Asp Glu Pro Leu
305                 310

<210> SEQ ID NO 7
<211> LENGTH: 870
<212> TYPE: DNA
<213> ORGANISM: Sphingobium sp. SYK-6

<400> SEQUENCE: 7
atggacatcg cagggaccac ggcgttcatc acgggcggcg cgagcggcat cggcttcggc      60
atcgcgcagc gcctgctggc caatggcgcg cggctggtgc ttgcagatat ccggcaggat     120
catctcgacg aagccaggca gttcttcgag gagcgccagc aggggcgcaa tgtccatacc     180
atccgcctgg acgtctccga tcgggcgcag atggcggagg ccgccaggga atgcgaggcg     240
gtgatgggcg ggccggacat cctcatcaac aatgccggca tcgatccgtc aggccccttc     300
aaggacgcga cgtatcagga ttgggattat gggctcgcca tcaatctcat ggggccgatc     360
aatggcatca tggcgttcac gcccggcatg cgggcacgcg ggcgtggcgg gcacatcgtc     420
aacacggcct cgctggcggg ccttacgccc atgccgagct tcatggccat ctatgcgact     480
gccaaggccg ccgtcatcac cttgaccgag accatccggg acagcatggc ggaggataat     540
atcggcgtca ccgtgctcat gcccggtccg atcaagagcc gcatccacga atccgggcag     600

```
aaccggcccg aacgcttccg cgcgggcagc gggctggcgg aaaccgagca gcagctcgcg      660
aagcgcgtgg tggcggacaa ctggatggaa cccaccgagg tggggacat gattgtcgac       720 gccatcgttc acaacaagct gtatgtctcg acccacggca actggcggga gacttgcgaa      780
gcgcggttcc aggccctgct cgactccatg ccggaggcca ggccgttcga tttcggcgcg      840
tcgctggcgg tgccgaagga agaggcctga                                       870
```

<210> SEQ ID NO 8
<211> LENGTH: 289
<212> TYPE: PRT
<213> ORGANISM: Sphingobium sp. SYK-6

<400> SEQUENCE: 8

```
Met Asp Ile Ala Gly Thr Thr Ala Phe Ile Thr Gly Gly Ala Ser Gly
1               5                   10                  15

Ile Gly Phe Gly Ile Ala Gln Arg Leu Leu Ala Asn Gly Ala Arg Leu
            20                  25                  30

Val Leu Ala Asp Ile Arg Gln Asp His Leu Asp Glu Ala Arg Gln Phe
        35                  40                  45

Phe Glu Glu Arg Gln Gln Gly Arg Asn Val His Thr Ile Arg Leu Asp
    50                  55                  60

Val Ser Asp Arg Ala Gln Met Ala Glu Ala Ala Arg Glu Cys Glu Ala
65                  70                  75                  80

Val Met Gly Gly Pro Asp Ile Leu Ile Asn Asn Ala Gly Ile Asp Pro
                85                  90                  95

Ser Gly Pro Phe Lys Asp Ala Thr Tyr Gln Asp Trp Asp Tyr Gly Leu
            100                 105                 110

Ala Ile Asn Leu Met Gly Pro Ile Asn Gly Ile Met Ala Phe Thr Pro
        115                 120                 125

Gly Met Arg Ala Arg Gly Arg Gly Gly His Ile Val Asn Thr Ala Ser
    130                 135                 140

Leu Ala Gly Leu Thr Pro Met Pro Ser Phe Met Ala Ile Tyr Ala Thr
145                 150                 155                 160

Ala Lys Ala Ala Val Ile Thr Leu Thr Glu Thr Ile Arg Asp Ser Met
                165                 170                 175

Ala Glu Asp Asn Ile Gly Val Thr Val Leu Met Pro Gly Pro Ile Lys
            180                 185                 190

Ser Arg Ile His Glu Ser Gly Gln Asn Arg Pro Glu Arg Phe Arg Ala
        195                 200                 205

Gly Ser Gly Leu Ala Glu Thr Glu Gln Gln Leu Ala Lys Arg Val Val
    210                 215                 220

Ala Asp Asn Trp Met Glu Pro Thr Glu Val Gly Asp Met Ile Val Asp
225                 230                 235                 240

Ala Ile Val His Asn Lys Leu Tyr Val Ser Thr His Gly Asn Trp Arg
                245                 250                 255

Glu Thr Cys Glu Ala Arg Phe Gln Ala Leu Leu Asp Ser Met Pro Glu
            260                 265                 270

Ala Arg Pro Phe Asp Phe Gly Ala Ser Leu Ala Val Pro Lys Glu Glu
        275                 280                 285

Ala
```

<210> SEQ ID NO 9
<211> LENGTH: 846
<212> TYPE: DNA

<213> ORGANISM: Sphingobium sp. SYK-6

<400> SEQUENCE: 9

```
atggccagga acaacaccat cactctgtat gacctgcagc tggagtccgg ctgcacgatc      60
agcccctatg tctggcgcac caaatatgcg ctcaagcaca agggcttcga catcgacatc     120
gtgcccggcg gcttcaccgg cattcttgag cggaccggcg gccggtccga gcgcgtgccg     180
gtcatcgtgg acgatggcga gtgggtgctc gacagctggg tgatcgcgga atatctcgac     240
gagaaatatc ccgatcgccc catgctgttc gagggcccga cccagaagaa cctcatgaag     300
ttcctggaca actggctgtg gtccacggcg gtgggcccgt ggttccgctg ctatatcctc     360
gattatcatg atctctcgct gccgcaggac cgcgattatg tgcgctggag ccgcgagcag     420
tggttcctgg gcgggcagcg cctggaagac gtgcaggccg gccgcgagga tcggctgccg     480
ctcgtgccgc cgacgctcga gcccttccgc cgcattctcg cggaaaccaa gtggcttggc     540
ggcgaccagc cgaacttcgc ggactattcc gcgctggcgg tgtttctctg gaccgcgtcc     600
gtcgcccgca cgccgccgct gaccgaggat gatccgctgc gggactggct ggaccgtggc     660
ttcgacctgt tgatgggct ggggcggcat cccggcatga acccgctgtt cgggctcaag     720
ctgcgggaag cgaccccga gcctttcgtc cggcagaccg gccccgcggg cgctggcggg     780
caggcgctca caaggggcc gcagaccacg aagatgccgc cgcgcgtcgc cgagaaagcg     840
gactga                                                                846
```

<210> SEQ ID NO 10
<211> LENGTH: 281
<212> TYPE: PRT
<213> ORGANISM: Sphingobium sp. SYK-6

<400> SEQUENCE: 10

```
Met Ala Arg Asn Asn Thr Ile Thr Leu Tyr Asp Leu Gln Leu Glu Ser
1               5                   10                  15

Gly Cys Thr Ile Ser Pro Tyr Val Trp Arg Thr Lys Tyr Ala Leu Lys
            20                  25                  30

His Lys Gly Phe Asp Ile Asp Ile Val Pro Gly Gly Phe Thr Gly Ile
        35                  40                  45

Leu Glu Arg Thr Gly Gly Arg Ser Glu Arg Val Pro Val Ile Val Asp
    50                  55                  60

Asp Gly Glu Trp Val Leu Asp Ser Trp Val Ile Ala Glu Tyr Leu Asp
65                  70                  75                  80

Glu Lys Tyr Pro Asp Arg Pro Met Leu Phe Glu Gly Pro Thr Gln Lys
                85                  90                  95

Asn Leu Met Lys Phe Leu Asp Asn Trp Leu Trp Ser Thr Ala Val Gly
            100                 105                 110

Pro Trp Phe Arg Cys Tyr Ile Leu Asp Tyr His Asp Leu Ser Leu Pro
        115                 120                 125

Gln Asp Arg Asp Tyr Val Arg Trp Ser Arg Glu Gln Trp Phe Leu Gly
    130                 135                 140

Gly Gln Arg Leu Glu Asp Val Gln Ala Gly Arg Glu Asp Arg Leu Pro
145                 150                 155                 160

Leu Val Pro Pro Thr Leu Glu Pro Phe Arg Arg Ile Leu Ala Glu Thr
                165                 170                 175

Lys Trp Leu Gly Gly Asp Gln Pro Asn Phe Ala Asp Tyr Ser Ala Leu
            180                 185                 190

Ala Val Phe Leu Trp Thr Ala Ser Val Ala Arg Thr Pro Pro Leu Thr
```

-continued

```
                195                 200                 205
Glu Asp Asp Pro Leu Arg Asp Trp Leu Asp Arg Gly Phe Asp Leu Phe
    210                 215                 220
Asp Gly Leu Gly Arg His Pro Gly Met Asn Pro Leu Phe Gly Leu Lys
225                 230                 235                 240
Leu Arg Glu Gly Asp Pro Glu Pro Phe Val Arg Gln Thr Gly Pro Ala
                245                 250                 255
Gly Ala Gly Gln Ala Leu Asn Lys Gly Pro Gln Thr Thr Lys Met
                260                 265                 270
Pro Pro Arg Val Ala Glu Lys Ala Asp
                275                 280
```

<210> SEQ ID NO 11
<211> LENGTH: 774
<212> TYPE: DNA
<213> ORGANISM: Sphingobium sp. SYK-6

<400> SEQUENCE: 11

```
atgacgttga aactctacag cttcggtccc ggggcgaact cgctcaagcc gctcgcgacg      60
ctctacgaga agggcctcga attcgagcag gtcttcgtcg atccgagcaa gttcgagcag     120
cattcggact ggttcaagaa gatcaatccg cgcggtcagg tgccggcgct ctggcatgac     180
ggcaaggtcg tcaccgaatc gacggtgatc tgcgaatatc tggaggacgt gttccccgag     240
tccggcaatt cgctgcgccc ggccgacccc ttcaagcgcg ccgaaatgcg ggtgtggacc     300
aagtgggtcg atgaatattt ctgctggtgc gtctccacca tcggctgggc cttcggcatc     360
aaggcgatcg cgcagaagat gagcgacgag gaattcgagg agcacatcaa caagaatgtg     420
ccgatccccg agcagcagct caaatggcgc gcgcgcgcgca acggattccc gcaggagatg     480
ctggacgagg aattccgcaa ggtcggcgtc tcggtggcgc ggctggaaga gacgctctcg     540
aagcaggact atctggtcga cacgggttac agcctcgcgg acatctgcaa tttcgccatc     600
gccaatggcc tgcagcgccc cggcggcttc ttcggcgact atgtgaacca ggaaaagacg     660
cccggcctgt gcgcctggct cgaccggatc aatgcgcgtc cggcgatcaa ggaaatgttc     720
gagaaatcga gcgcgagga cctgctcaag cggcagaacg agaaagtcgc ctga           774
```

<210> SEQ ID NO 12
<211> LENGTH: 257
<212> TYPE: PRT
<213> ORGANISM: Sphingobium sp. SYK-6

<400> SEQUENCE: 12

```
Met Thr Leu Lys Leu Tyr Ser Phe Gly Pro Gly Ala Asn Ser Leu Lys
1               5                   10                  15
Pro Leu Ala Thr Leu Tyr Glu Lys Gly Leu Glu Phe Glu Gln Val Phe
                20                  25                  30
Val Asp Pro Ser Lys Phe Glu Gln His Ser Asp Trp Phe Lys Lys Ile
            35                  40                  45
Asn Pro Arg Gly Gln Val Pro Ala Leu Trp His Asp Gly Lys Val Val
        50                  55                  60
Thr Glu Ser Thr Val Ile Cys Glu Tyr Leu Glu Asp Val Phe Pro Glu
65                  70                  75                  80
Ser Gly Asn Ser Leu Arg Pro Ala Asp Pro Phe Lys Arg Ala Glu Met
                85                  90                  95
Arg Val Trp Thr Lys Trp Val Asp Glu Tyr Phe Cys Trp Cys Val Ser
                100                 105                 110
```

```
Thr Ile Gly Trp Ala Phe Gly Ile Lys Ala Ile Ala Gln Lys Met Ser
            115                 120                 125

Asp Glu Glu Phe Glu Glu His Ile Asn Lys Asn Val Pro Ile Pro Glu
        130                 135                 140

Gln Gln Leu Lys Trp Arg Arg Ala Arg Asn Gly Phe Pro Gln Glu Met
145                 150                 155                 160

Leu Asp Glu Glu Phe Arg Lys Val Gly Val Ser Val Ala Arg Leu Glu
                165                 170                 175

Glu Thr Leu Ser Lys Gln Asp Tyr Leu Val Asp Thr Gly Tyr Ser Leu
            180                 185                 190

Ala Asp Ile Cys Asn Phe Ala Ile Ala Asn Gly Leu Gln Arg Pro Gly
            195                 200                 205

Gly Phe Phe Gly Asp Tyr Val Asn Gln Glu Lys Thr Pro Gly Leu Cys
        210                 215                 220

Ala Trp Leu Asp Arg Ile Asn Ala Arg Pro Ala Ile Lys Glu Met Phe
225                 230                 235                 240

Glu Lys Ser Lys Arg Glu Asp Leu Leu Lys Arg Gln Asn Glu Lys Val
                245                 250                 255

Ala

<210> SEQ ID NO 13
<211> LENGTH: 846
<212> TYPE: DNA
<213> ORGANISM: Sphingobium sp. SYK-6

<400> SEQUENCE: 13
atggcaaaag acaacaagat caccatctac gatctggcgc tggcgagcgg tgcgacgatc      60
agcccattcg tatgggcgac caaatatgcc atcgcgcaca agggcttcga gctggacatc     120
gtgcccggcg gcttttccgg cattcccgag cggaccggcg gtgtgaccga cgcctcccg     180
gcgatcgtcg atgacgggaa atgggtgctc gatagctggc tgatcgccga gtatctcgac     240
gagacctatc ccgagcggcc gaccctcatc ccgcacgcca gcgtcaaggc gctcacgcaa     300
ggcatggaag cttggctgtg gggcgccgcc atcagcccgt ggatgacctg cttcatcaag     360
cagtatcggg accgctcgct gccgcaggat catgagtatg tgaccacctc gcgcgagcgt     420
atgttcggtc gcaagatcga ggacatcatc gtgggccgcg aggaccgcat tcccaaagtg     480
ccgccgacgc tgcagctgct cgcaacgtg ctggcggaga caagtggct gggtggcgac      540
acgcccaatt atgcggactt ccgcctgctc gccgtgttcc tgttcaccgc tcggtcgcc     600
gacacgccgg tcctgaccga tgacgacccg ctgcgcgact ggatcgagcg cggcttcgat     660
ctctacggcg gctgggccg gcatcccggc ctctcgccca tcttcggcct gcaactgcgc     720
gagggcgatc ccgagccctt catcaagggc ggcgccgtgg gcggcctcgc cacgcgcaac     780
accggcccca gtcgaccgc cgccgagacc gcgcgcctca gggcgagaa ggcgccggcc     840
gcctga                                                                846

<210> SEQ ID NO 14
<211> LENGTH: 281
<212> TYPE: PRT
<213> ORGANISM: Sphingobium sp. SYK-6

<400> SEQUENCE: 14

Met Ala Lys Asp Asn Lys Ile Thr Ile Tyr Asp Leu Ala Leu Ala Ser
1               5                  10                  15
```

```
Gly Ala Thr Ile Ser Pro Phe Val Ala Thr Lys Tyr Ala Ile Ala
                20                  25                  30

His Lys Gly Phe Glu Leu Asp Ile Val Pro Gly Gly Phe Ser Gly Ile
             35                  40                  45

Pro Glu Arg Thr Gly Val Thr Glu Arg Leu Pro Ala Ile Val Asp
 50                  55                  60

Asp Gly Lys Trp Val Leu Asp Ser Trp Leu Ile Ala Glu Tyr Leu Asp
 65                  70                  75                  80

Glu Thr Tyr Pro Glu Arg Pro Thr Leu Ile Pro His Ala Ser Val Lys
                 85                  90                  95

Ala Leu Thr Gln Gly Met Glu Ala Trp Leu Trp Gly Ala Ala Ile Ser
                100                 105                 110

Pro Trp Met Thr Cys Phe Ile Lys Gln Tyr Arg Asp Arg Ser Leu Pro
                115                 120                 125

Gln Asp His Glu Tyr Val Thr Thr Ser Arg Glu Arg Met Phe Gly Arg
        130                 135                 140

Lys Ile Glu Asp Ile Ile Val Gly Arg Glu Asp Arg Ile Pro Lys Val
145                 150                 155                 160

Pro Pro Thr Leu Gln Leu Leu Arg Asn Val Leu Ala Glu Asn Lys Trp
                165                 170                 175

Leu Gly Gly Asp Thr Pro Asn Tyr Ala Asp Phe Arg Leu Leu Ala Val
                180                 185                 190

Phe Leu Phe Thr Ala Ser Val Ala Asp Thr Pro Val Leu Thr Asp Asp
            195                 200                 205

Asp Pro Leu Arg Asp Trp Ile Glu Arg Gly Phe Asp Leu Tyr Gly Gly
210                 215                 220

Leu Gly Arg His Pro Gly Leu Ser Pro Ile Phe Gly Leu Gln Leu Arg
225                 230                 235                 240

Glu Gly Asp Pro Glu Pro Phe Ile Lys Gly Ala Val Gly Gly Leu
                245                 250                 255

Ala Thr Arg Asn Thr Gly Pro Lys Ser Thr Ala Ala Glu Thr Ala Arg
            260                 265                 270

Leu Lys Gly Glu Lys Ala Pro Ala Ala
            275                 280

<210> SEQ ID NO 15
<211> LENGTH: 798
<212> TYPE: DNA
<213> ORGANISM: Sphingobium sp. SYK-6

<400> SEQUENCE: 15
atggccgagc cacaggaact gacgatctat cacattcccg gctgccccctt ctccgagcgt     60 gtggaaatca tgctcgagct caagggcctg cgcatgaagg atgtcgagat cgacattccc    120
aagccgcgcc cggactggct gcttgccaag acgggcggca cgaccgcgct tccgcttctc    180
gacgtcgaga tggcgagag cctcaaggaa agcatggtca tcctgcgcta tctggagcag    240 cgctacccccg agccggcggt ggcgcatccc gatcccttct gtcacgcggt ggaaggcatg    300
ctggccgagc tggccgggcc ttttccggc gcgggctacc ggatgatcct caaccgggag    360
atcggcaagc gcgaggagat gcgtgccgct gtcgatgccg agttcggcaa ggtggacgcg    420
ttcctcaagc gttatgcgac cggcagcgac ttcctgttcg acgatcgctt cggctgggcg    480
gaagtggctt tcacgccgat gttcaagcgc ctgtggttcc tggactatta tgaagattat    540
gaagtgccgg ccaatttcga ccgggtgctg cgctggcgcg cggcgtgcac ggcgcatccg    600
```

```
gccgcgcaat atcgctcgaa ggaagagttg ctgaagctct attatgacta cacgcagggc      660
ggcggcaatg ccgcattcc cgagggcgc agcatttcca gcttctcgcc ggatgtcgac        720
tggcgtacgc gcccgatgcc gccccgcgac aaatgggac atgcggcgac cgacgcggaa      780
ctgggcctca cccgctga                                                     798
```

<210> SEQ ID NO 16
<211> LENGTH: 265
<212> TYPE: PRT
<213> ORGANISM: Sphingobium sp. SYK-6

<400> SEQUENCE: 16

```
Met Ala Glu Pro Gln Glu Leu Thr Ile Tyr His Ile Pro Gly Cys Pro
1               5                   10                  15

Phe Ser Glu Arg Val Glu Ile Met Leu Glu Leu Lys Gly Leu Arg Met
            20                  25                  30

Lys Asp Val Glu Ile Asp Ile Ser Lys Pro Arg Pro Asp Trp Leu Leu
        35                  40                  45

Ala Lys Thr Gly Gly Thr Thr Ala Leu Pro Leu Leu Asp Val Glu Asn
    50                  55                  60

Gly Glu Ser Leu Lys Glu Ser Met Val Ile Leu Arg Tyr Leu Glu Gln
65                  70                  75                  80

Arg Tyr Pro Glu Pro Ala Val Ala His Pro Asp Pro Phe Cys His Ala
                85                  90                  95

Val Glu Gly Met Leu Ala Glu Leu Ala Gly Pro Phe Ser Gly Ala Gly
            100                 105                 110

Tyr Arg Met Ile Leu Asn Arg Glu Ile Gly Lys Arg Glu Glu Met Arg
        115                 120                 125

Ala Ala Val Asp Ala Glu Phe Gly Lys Val Asp Ala Phe Leu Lys Arg
    130                 135                 140

Tyr Ala Thr Gly Ser Asp Phe Leu Phe Asp Asp Arg Phe Gly Trp Ala
145                 150                 155                 160

Glu Val Ala Phe Thr Pro Met Phe Lys Arg Leu Trp Phe Leu Asp Tyr
                165                 170                 175

Tyr Glu Asp Tyr Glu Val Pro Ala Asn Phe Asp Arg Val Leu Arg Trp
            180                 185                 190

Arg Ala Ala Cys Thr Ala His Pro Ala Ala Gln Tyr Arg Ser Lys Glu
        195                 200                 205

Glu Leu Leu Lys Leu Tyr Tyr Asp Tyr Thr Gln Gly Gly Asn Gly
    210                 215                 220

Arg Ile Pro Glu Gly Arg Ser Ile Ser Ser Phe Ser Pro Asp Val Asp
225                 230                 235                 240

Trp Arg Thr Arg Pro Met Pro Pro Arg Asp Lys Trp Gly His Ala Ala
                245                 250                 255

Thr Asp Ala Glu Leu Gly Leu Thr Arg
            260                 265
```

<210> SEQ ID NO 17
<211> LENGTH: 867
<212> TYPE: DNA
<213> ORGANISM: Novosphingobium aromaticivorans

<400> SEQUENCE: 17

```
atgtcctcag agtacgttcc cccgaaggtc tggaagtggg acaaggccaa cggcggcgcc      60
ttcgccagcg tcaaccgccc agtcgccggc ccgacgagcg agcgcgaact gccggtcggc     120
```

-continued

```
aagcatcctt tccaggtcta ttcgctcggc acgcccaacg ggcagaaggc cacgatcatg      180
ctggaagaac tgctccagct gggcttttcc gaggccgagt acgacgcctg gctgatcaag      240
atcttcgaag gcgaccagtt caccagcggc ttcgtcgaca tcaatccgaa ctccaagatc      300
ccggccatgg tcgaccgctc gggccctgaa ccgttccgcg tcttcgaatc cggcgccatt      360
ctgatgcacc ttgctgaaaa gtttggcgtt ttcctgccaa cttccggccc cgcccgcgcc      420
gagtgcctat cctggctgtt ctggcaggtc ggctccgccc cgttcatcgg cggcggcttc      480
ggccacttct acaactacgc cccgatcaag atcgagtacg cgatcgatcg ctatgccatg      540
gaaaccaagc gccttttcga cgtggccaac cgtcgcctcg cggaaagccg ctatcttgcg      600
ggggacgaat acacgatcgc cgaccttgcc acctacacct ggttcggcaa catctaccgc      660
ggcgaagcct acggcgaggc ggcgaccttc ctgtcgatgc acgaatacga acacgtcggc      720
cgctgggtcg gcgagatcga cgcgaggccg ggggtgctgc gggggcggtt ggtgaactcc      780
agcaagggcc tggcagagcg tcacgacgcg agcgatttcg acgccctccc gccggaatcg      840
ttgcaagcga tcgtcaaggg cttctga                                         867
```

<210> SEQ ID NO 18
<211> LENGTH: 288
<212> TYPE: PRT
<213> ORGANISM: Novosphingobium aromaticivorans

<400> SEQUENCE: 18

```
Met Ser Ser Glu Tyr Val Pro Pro Lys Val Trp Lys Trp Asp Lys Ala
1               5                   10                  15

Asn Gly Gly Ala Phe Ala Ser Val Asn Arg Pro Val Ala Gly Pro Thr
            20                  25                  30

Ser Glu Arg Glu Leu Pro Val Gly Lys His Pro Phe Gln Val Tyr Ser
        35                  40                  45

Leu Gly Thr Pro Asn Gly Gln Lys Ala Thr Ile Met Leu Glu Glu Leu
    50                  55                  60

Leu Gln Leu Gly Phe Ser Glu Ala Glu Tyr Asp Ala Trp Leu Ile Lys
65                  70                  75                  80

Ile Phe Glu Gly Asp Gln Phe Thr Ser Gly Phe Val Asp Ile Asn Pro
                85                  90                  95

Asn Ser Lys Ile Pro Ala Met Val Asp Arg Ser Gly Pro Glu Pro Phe
            100                 105                 110

Arg Val Phe Glu Ser Gly Ala Ile Leu Met His Leu Ala Glu Lys Phe
        115                 120                 125

Gly Val Phe Leu Pro Thr Ser Gly Pro Ala Arg Ala Glu Cys Leu Ser
    130                 135                 140

Trp Leu Phe Trp Gln Val Gly Ser Ala Pro Phe Ile Gly Gly Gly Phe
145                 150                 155                 160

Gly His Phe Tyr Asn Tyr Ala Pro Ile Lys Ile Glu Tyr Ala Ile Asp
                165                 170                 175

Arg Tyr Ala Met Glu Thr Lys Arg Leu Phe Asp Val Ala Asn Arg Arg
            180                 185                 190

Leu Ala Glu Ser Arg Tyr Leu Ala Gly Asp Glu Tyr Thr Ile Ala Asp
        195                 200                 205

Leu Ala Thr Tyr Thr Trp Phe Gly Asn Ile Tyr Arg Gly Glu Ala Tyr
    210                 215                 220

Gly Glu Ala Ala Thr Phe Leu Ser Met His Glu Tyr Glu His Val Gly
225                 230                 235                 240
```

Arg Trp Val Gly Glu Ile Asp Ala Arg Pro Gly Val Leu Arg Gly Arg
                245                 250                 255

Leu Val Asn Ser Ser Lys Gly Leu Ala Glu Arg His Asp Ala Ser Asp
        260                 265                 270

Phe Asp Ala Leu Pro Pro Glu Ser Leu Gln Ala Ile Val Lys Gly Phe
    275                 280                 285

<210> SEQ ID NO 19
<211> LENGTH: 942
<212> TYPE: DNA
<213> ORGANISM: Artificial Sequence
<220> FEATURE:
<223> OTHER INFORMATION: NaGSTNu (Recombinant)

<400> SEQUENCE: 19

| | | | | | |
|---|---|---|---|---|---|
| atgggacatc | accatcatca | ccatcaccat | gcattggcaa | gcgaaaatct | gtattttcag | 60 |
| agcgcgatcg | caggaatgtc | ctcagagtac | gttcccccga | aggtctggaa | gtgggacaag | 120 |
| gccaacggcg | cgccttcgc | cagcgtcaac | cgcccagtcg | ccggcccgac | gagcgagcgc | 180 |
| gaactgccgg | tcggcaagca | tcctttccag | gtctattcgc | tcggcacgcc | caacgggcag | 240 |
| aaggccacga | tcatgctgga | agaactgctc | cagctgggct | tttccgaggc | cgagtacgac | 300 |
| gcctggctga | tcaagatctt | cgaaggcgac | cagttcacca | gcggcttcgt | cgacatcaat | 360 |
| ccgaactcca | agatcccggc | catggtcgac | cgctcgggcc | ctgaaccgtt | ccgcgtcttc | 420 |
| gaatccggcg | ccattctgat | gaccttgct | gaaaagtttg | gcgttttcct | gccaacttcc | 480 |
| ggccccgccc | gcgccgagtg | cctatcctgg | ctgttctggc | aggtcggctc | cgccccgttc | 540 |
| atcggcggcg | gcttcggcca | cttctacaac | tacgccccga | tcaagatcga | gtacgcgatc | 600 |
| gatcgctatg | ccatggaaac | caagcgcctt | ttcgacgtgg | ccaaccgtcg | cctcgcggaa | 660 |
| agccgctatc | ttgcggggga | cgaatacacg | atcgccgacc | ttgccaccta | cacctggttc | 720 |
| ggcaacatct | accgcggcga | agcctacggc | gaggcggcga | ccttcctgtc | gatgcacgaa | 780 |
| tacgaacacg | tcggccgctg | ggtcggcgag | atcgacgcga | ggccgggggt | gctgcggggg | 840 |
| cggttggtga | actccagcaa | gggcctggca | gagcgtcacg | acgcgagcga | tttcgacgcc | 900 |
| ctcccgccgg | aatcgttgca | agcgatcgtc | aagggcttct | ga | | 942 |

<210> SEQ ID NO 20
<211> LENGTH: 313
<212> TYPE: PRT
<213> ORGANISM: Artificial Sequence
<220> FEATURE:
<223> OTHER INFORMATION: NaGSTNu (Recombinant)

<400> SEQUENCE: 20

Met Gly His His His His His His His Ala Leu Ala Ser Glu Asn
1               5                   10                  15

Leu Tyr Phe Gln Ser Ala Ile Ala Gly Met Ser Ser Glu Tyr Val Pro
            20                  25                  30

Pro Lys Val Trp Lys Trp Asp Lys Ala Asn Gly Gly Ala Phe Ala Ser
        35                  40                  45

Val Asn Arg Pro Val Ala Gly Pro Thr Ser Glu Arg Glu Leu Pro Val
    50                  55                  60

Gly Lys His Pro Phe Gln Val Tyr Ser Leu Gly Thr Pro Asn Gly Gln
65                  70                  75                  80

Lys Ala Thr Ile Met Leu Glu Glu Leu Leu Gln Leu Gly Phe Ser Glu
                85                  90                  95

```
Ala Glu Tyr Asp Ala Trp Leu Ile Lys Ile Phe Glu Gly Asp Gln Phe
            100                 105                 110

Thr Ser Gly Phe Val Asp Ile Asn Pro Asn Ser Lys Ile Pro Ala Met
        115                 120                 125

Val Asp Arg Ser Gly Pro Glu Pro Phe Arg Val Phe Glu Ser Gly Ala
    130                 135                 140

Ile Leu Met His Leu Ala Glu Lys Phe Gly Val Phe Leu Pro Thr Ser
145                 150                 155                 160

Gly Pro Ala Arg Ala Glu Cys Leu Ser Trp Leu Phe Trp Gln Val Gly
                165                 170                 175

Ser Ala Pro Phe Ile Gly Gly Gly Phe Gly His Phe Tyr Asn Tyr Ala
            180                 185                 190

Pro Ile Lys Ile Glu Tyr Ala Ile Asp Arg Tyr Ala Met Glu Thr Lys
        195                 200                 205

Arg Leu Phe Asp Val Ala Asn Arg Arg Leu Ala Glu Ser Arg Tyr Leu
    210                 215                 220

Ala Gly Asp Glu Tyr Thr Ile Ala Asp Leu Ala Thr Tyr Thr Trp Phe
225                 230                 235                 240

Gly Asn Ile Tyr Arg Gly Glu Ala Tyr Gly Glu Ala Ala Thr Phe Leu
                245                 250                 255

Ser Met His Glu Tyr Glu His Val Gly Arg Trp Val Gly Glu Ile Asp
            260                 265                 270

Ala Arg Pro Gly Val Leu Arg Gly Arg Leu Val Asn Ser Ser Lys Gly
        275                 280                 285

Leu Ala Glu Arg His Asp Ala Ser Asp Phe Asp Ala Leu Pro Pro Glu
    290                 295                 300

Ser Leu Gln Ala Ile Val Lys Gly Phe
305                 310

<210> SEQ ID NO 21
<211> LENGTH: 900
<212> TYPE: DNA
<213> ORGANISM: Sphingobium sp. SYK-6

<400> SEQUENCE: 21
atggccgaca gcgacccctc catgaaccag cctacaggct atgtgccgcc caaggtctgg      60
acctgggaca aggagaatgg cgggcagttc tccaacatca tgcgccgac ggcgggcgcc     120 cggcaggacg tcacgctgcc tgtgggcgag cacccatcc agctctattc gctgggcacg     180
ccgaacggcc agaaagtcac catcatgctc gaggagctgc tggcggcgg tttcgacgcg     240 gaatatgatg cctggctcat caagatctac accggcgagc agttcggcag cgacttcgtc     300
gcgatcaatc ccaacagcaa gatcccggcg atgatggacc atggcttgga cccgccattg     360
cgcctgtttg agagcggatc gatgctggtc tatcttgccg agaagttcgg cgccttcctc     420
cccaccgaga tccgcaagcg caccgagacc ttcaactggc tgatgtggca gatgggttcg     480
gcgccattcg tgggcggcgg attcgggcat ttctatgcct atgcgccgtt caagatcgaa     540
tatgcgatcg accgctatgc catggagacc aagcgccagc tcgacgtgct ggacaagaac     600
ctggccgacc gcgagttcat gatcggcgac gagatcacca ttgcggactt cgccatcttc     660
ccctggtacg gatcgatcat gcgcggcggc tacaatgcgc aggaattcct ctccacccat     720
gaatatcgca atgtcgatcg ctgggtgacg cagctttccg agcgcaccgg ggtcaagcgg     780
ggcctgctcg tgaacagcgc cggccggccg ggcggcggca tcgccgagcg cacagcgcc     840 gccgatctgg acgcgtccat caaggccgcc gagcaagaag ccgcgaagac cgaggcctga     900
```

<210> SEQ ID NO 22
<211> LENGTH: 299
<212> TYPE: PRT
<213> ORGANISM: Sphingobium sp. SYK-6

<400> SEQUENCE: 22

```
Met Ala Asp Ser Asp Pro Ser Met Asn Gln Pro Thr Gly Tyr Val Pro
1               5                   10                  15
Pro Lys Val Trp Thr Trp Asp Lys Glu Asn Gly Gly Gln Phe Ser Asn
            20                  25                  30
Ile Asn Ala Pro Thr Ala Gly Ala Arg Gln Asp Val Thr Leu Pro Val
        35                  40                  45
Gly Glu His Pro Ile Gln Leu Tyr Ser Leu Gly Thr Pro Asn Gly Gln
    50                  55                  60
Lys Val Thr Ile Met Leu Glu Glu Leu Leu Ala Ala Gly Phe Asp Ala
65                  70                  75                  80
Glu Tyr Asp Ala Trp Leu Ile Lys Ile Tyr Thr Gly Glu Gln Phe Gly
                85                  90                  95
Ser Asp Phe Val Ala Ile Asn Pro Asn Ser Lys Ile Pro Ala Met Met
            100                 105                 110
Asp His Gly Leu Asp Pro Pro Leu Arg Leu Phe Glu Ser Gly Ser Met
        115                 120                 125
Leu Val Tyr Leu Ala Glu Lys Phe Gly Ala Phe Leu Pro Thr Glu Ile
    130                 135                 140
Arg Lys Arg Thr Glu Thr Phe Asn Trp Leu Met Trp Gln Met Gly Ser
145                 150                 155                 160
Ala Pro Phe Val Gly Gly Phe Gly His Phe Tyr Ala Tyr Ala Pro
                165                 170                 175
Phe Lys Ile Glu Tyr Ala Ile Asp Arg Tyr Ala Met Glu Thr Lys Arg
            180                 185                 190
Gln Leu Asp Val Leu Asp Lys Asn Leu Ala Asp Arg Glu Phe Met Ile
        195                 200                 205
Gly Asp Glu Ile Thr Ile Ala Asp Phe Ala Ile Phe Pro Trp Tyr Gly
    210                 215                 220
Ser Ile Met Arg Gly Gly Tyr Asn Ala Gln Glu Phe Leu Ser Thr His
225                 230                 235                 240
Glu Tyr Arg Asn Val Asp Arg Trp Val Thr Gln Leu Ser Glu Arg Thr
                245                 250                 255
Gly Val Lys Arg Gly Leu Leu Val Asn Ser Ala Gly Arg Pro Gly Gly
            260                 265                 270
Gly Ile Ala Glu Arg His Ser Ala Ala Asp Leu Asp Ala Ser Ile Lys
        275                 280                 285
Ala Ala Glu Gln Glu Ala Ala Lys Thr Glu Ala
    290                 295
```

<210> SEQ ID NO 23
<211> LENGTH: 975
<212> TYPE: DNA
<213> ORGANISM: Artificial Sequence
<220> FEATURE:
<223> OTHER INFORMATION: SYK6GSTNu (Recombinant)

<400> SEQUENCE: 23

```
atgggacatc accatcatca ccatcaccat gcattggcaa gcgaaaatct gtattttcag      60
agcgcgatcg caggaatggc cgactcagat ccatccatga atcagccgac gggttacgtc     120
```

```
ccgccgaaag tttggacctg ggacaaagag aacggcggtc agttcagcaa tatcaacgcc    180
cctacggctg gtgcgcgcca ggacgtcacg ctccctgtag gggagcaccc tatccaatta    240
tatagtctcg gcactccgaa tggtcagaaa gttactatca tgttggaaga actgctggct    300
gctggctttg atgctgagta tgacgcctgg ctcatcaaaa tctacacagg cgagcaattc    360
ggatctgatt tcgtcgccat taaccctaat agcaaaattc cggctatgat ggaccatggt    420
ctcgatccgc cgctccgttt atttgagtct ggttctatgt tagtttatct ggccgaaaag    480
tttggcgcat tcctcccgac cgaaatccgc aaacgtacgg aaacctttaa ctggctcatg    540
tggcagatgg gttctgctcc ttttgtgggt ggtggctttg gccacttcta tgcgtacgcc    600
ccatttaaaa tcgaatatgc cattgatcgt tacgcgatgg aaaccaagcg ccaactggac    660
gttctggata aaaatctggc cgatcgtgaa tttatgatcg gcgatgaaat caccatcgca    720
gattttgcga ttttcccttg gtacggctcg attatgcgtg gcggttacaa cgcgcaagaa    780
ttcttgagca ctcacgagta ccgtaacgtt gatcgctggg ttacgcagct ttctgaacgt    840
acgggcgtaa agcgtggtct ccttgtcaat tccgcgggtc gcccgggagg tggcattgcg    900
gaacgccata gcgcggctga tttagacgcg tcgattaaag cggctgaaca agaggccgcg    960
aagaccgaag cttaa                                                    975
```

<210> SEQ ID NO 24
<211> LENGTH: 324
<212> TYPE: PRT
<213> ORGANISM: Artificial Sequence
<220> FEATURE:
<223> OTHER INFORMATION: SYK6GSTNu (Recombinant)

<400> SEQUENCE: 24

```
Met Gly His His His His His His His Ala Leu Ala Ser Glu Asn
1               5                   10                  15

Leu Tyr Phe Gln Ser Ala Ile Ala Gly Met Ala Asp Ser Asp Pro Ser
                20                  25                  30

Met Asn Gln Pro Thr Gly Tyr Val Pro Pro Lys Val Trp Thr Trp Asp
            35                  40                  45

Lys Glu Asn Gly Gly Gln Phe Ser Asn Ile Asn Ala Pro Thr Ala Gly
        50                  55                  60

Ala Arg Gln Asp Val Thr Leu Pro Val Gly Glu His Pro Ile Gln Leu
65                  70                  75                  80

Tyr Ser Leu Gly Thr Pro Asn Gly Gln Lys Val Thr Ile Met Leu Glu
                85                  90                  95

Glu Leu Leu Ala Ala Gly Phe Asp Ala Glu Tyr Asp Ala Trp Leu Ile
            100                 105                 110

Lys Ile Tyr Thr Gly Glu Gln Phe Gly Ser Asp Phe Val Ala Ile Asn
        115                 120                 125

Pro Asn Ser Lys Ile Pro Ala Met Met Asp His Gly Leu Asp Pro Pro
    130                 135                 140

Leu Arg Leu Phe Glu Ser Gly Ser Met Leu Val Tyr Leu Ala Glu Lys
145                 150                 155                 160

Phe Gly Ala Phe Leu Pro Thr Glu Ile Arg Lys Arg Thr Glu Thr Phe
                165                 170                 175

Asn Trp Leu Met Trp Gln Met Gly Ser Ala Pro Phe Val Gly Gly Gly
            180                 185                 190

Phe Gly His Phe Tyr Ala Tyr Ala Pro Phe Lys Ile Glu Tyr Ala Ile
        195                 200                 205
```

```
Asp Arg Tyr Ala Met Glu Thr Lys Arg Gln Leu Asp Val Leu Asp Lys
            210                 215                 220

Asn Leu Ala Asp Arg Glu Phe Met Ile Gly Asp Glu Ile Thr Ile Ala
225                 230                 235                 240

Asp Phe Ala Ile Phe Pro Trp Tyr Gly Ser Ile Met Arg Gly Gly Tyr
                245                 250                 255

Asn Ala Gln Glu Phe Leu Ser Thr His Glu Tyr Arg Asn Val Asp Arg
            260                 265                 270

Trp Val Thr Gln Leu Ser Glu Arg Thr Gly Val Lys Arg Gly Leu Leu
        275                 280                 285

Val Asn Ser Ala Gly Arg Pro Gly Gly Ile Ala Glu Arg His Ser
    290                 295                 300

Ala Ala Asp Leu Asp Ala Ser Ile Lys Ala Ala Glu Gln Glu Ala Ala
305                 310                 315                 320

Lys Thr Glu Ala
```

<210> SEQ ID NO 25
<211> LENGTH: 867
<212> TYPE: DNA
<213> ORGANISM: Escherichia coli

<400> SEQUENCE: 25

```
atgacagaca atacttatca gcccgcgaaa gtctggacgt gggataaatc cgctggcggc      60
gcgttcgcca atatcaatcg cccggtttct ggtccgacgc atgaaaaaac gctgcccgtt     120
ggcaaacacc cattgcaact ttattcgctg gaacgccga acggtcagaa agtaacgatt      180
atgcttgagg agctgctggc gctgggcgtt actggtgcag agtacgacgc ctggctgatt     240
cgtattggcg atggcgatca attctccagc ggctttgtcg aagtgaaccc aaactcgaag     300
atcccggcgc tgcgcgatca tacgcataat ccgccgatcc gcgtgtttga atctggttcg     360
atcctgcttt atctggcgga gaaatttggc tacttcctgc cgcaggattt ggcaaagcgt     420
actgaaacga tgaactggct gttctggtta cagggcgcgg caccgttcct cggcggtggt     480
tttggtcact ttaccattta cgcaccggta aagattgagt acgccatcaa ccgctttacc     540
atggaagcca acgtctgctc gacgtgctg ataagcaac tggcgcagca taagtttgtt      600
gcgggcgatg agtacaccat tgcggatatg gcgatttggc cgtggtttgg caacgtggtg    660
ttaggtggtg tgtatgatgc cgctgagttt cttgatgcgg gcagttataa gcatgtacaa    720
cgctgggcga agaagtaggc gaacgtccg gcggtgaaac gtgggcgtat tgttaaccgc     780
accaacggac cgctgaatga gcagttgcat gagcgccatg acgccagtga tttcgagacg    840
aatacggaag ataagcgtca ggggtaa                                         867
```

<210> SEQ ID NO 26
<211> LENGTH: 288
<212> TYPE: PRT
<213> ORGANISM: Escherichia coli

<400> SEQUENCE: 26

```
Met Thr Asp Asn Thr Tyr Gln Pro Ala Lys Val Trp Thr Trp Asp Lys
1               5                   10                  15

Ser Ala Gly Gly Ala Phe Ala Asn Ile Asn Arg Pro Val Ser Gly Pro
            20                  25                  30

Thr His Glu Lys Thr Leu Pro Val Gly Lys His Pro Leu Gln Leu Tyr
        35                  40                  45
```

```
Ser Leu Gly Thr Pro Asn Gly Gln Lys Val Thr Ile Met Leu Glu Glu
     50                  55                  60

Leu Leu Ala Leu Gly Val Thr Gly Ala Glu Tyr Asp Ala Trp Leu Ile
 65                  70                  75                  80

Arg Ile Gly Asp Gly Asp Gln Phe Ser Ser Gly Phe Val Glu Val Asn
                 85                  90                  95

Pro Asn Ser Lys Ile Pro Ala Leu Arg Asp His Thr His Asn Pro Pro
             100                 105                 110

Ile Arg Val Phe Glu Ser Gly Ser Ile Leu Leu Tyr Leu Ala Glu Lys
         115                 120                 125

Phe Gly Tyr Phe Leu Pro Gln Asp Leu Ala Lys Arg Thr Glu Thr Met
130                 135                 140

Asn Trp Leu Phe Trp Leu Gln Gly Ala Ala Pro Phe Leu Gly Gly Gly
145                 150                 155                 160

Phe Gly His Phe Tyr His Tyr Ala Pro Val Lys Ile Glu Tyr Ala Ile
                165                 170                 175

Asn Arg Phe Thr Met Glu Ala Lys Arg Leu Leu Asp Val Leu Asp Lys
             180                 185                 190

Gln Leu Ala Gln His Lys Phe Val Ala Gly Asp Glu Tyr Thr Ile Ala
         195                 200                 205

Asp Met Ala Ile Trp Pro Trp Phe Gly Asn Val Val Leu Gly Gly Val
210                 215                 220

Tyr Asp Ala Ala Glu Phe Leu Asp Ala Gly Ser Tyr Lys His Val Gln
225                 230                 235                 240

Arg Trp Ala Lys Glu Val Gly Glu Arg Pro Ala Val Lys Arg Gly Arg
                245                 250                 255

Ile Val Asn Arg Thr Asn Gly Pro Leu Asn Glu Gln Leu His Glu Arg
             260                 265                 270

His Asp Ala Ser Asp Phe Glu Thr Asn Thr Glu Asp Lys Arg Gln Gly
         275                 280                 285

<210> SEQ ID NO 27
<211> LENGTH: 942
<212> TYPE: DNA
<213> ORGANISM: Artificial Sequence
<220> FEATURE:
<223> OTHER INFORMATION: ecYghU (Recombinant)

<400> SEQUENCE: 27
atgggacatc accatcatca ccatcaccat gcattggcaa gcgaaaatct gtattttcag      60
agcgcgatcg caggaatgac agacaatact tatcagcccg cgaaagtctg dacgtgggat     120
aaatccgctg gcggcgcgtt cgccaatatc aatcgcccgg tttctggtcc gacgcatgaa     180
aaaacgctgc ccgttggcaa acacccattg caactttatt cgctgggaac gccgaacggt     240
cagaaagtaa cgattatgct tgaggagctg ctggcgctgg gcgttactgg tgcagagtac     300
gacgcctggc tgattcgtat tggcgatggc gatcaattct ccagcggctt tgtcgaagtg     360 aacccaaaact cgaagatccc ggcgctgcgc gatcatacgc ataatccgcc gatccgcgtg     420
tttgaatctg gttcgatcct gctttatctg gcggagaaat ttggctactt cctgccgcag     480
gatttggcaa agcgtactga aacgatgaac tggctgttct ggttacaggg cgcggcaccg     540
ttcctcggcg gtggttttgg tcactttttac cattacgcac cggtaaagat tgagtacgcc     600
atcaaccgct ttaccatgga agccaaacgt ctgctcgacg tgctggataa gcaactggcg     660
cagcataagt ttgttgcggg cgatgagtac accattgcgg atatggcgat ttggccgtgg     720
```

-continued

```
tttggcaacg tggtgttagg tggtgtgtat gatgccgctg agtttcttga tgcgggcagt    780
tataagcatg tacaacgctg ggcgaaagaa gtaggcgaac gtccggcggt gaaacgtggg    840
cgtattgtta accgcaccaa cggaccgctg aatgagcagt tgcatgagcg ccatgacgcc    900
agtgatttcg agacgaatac ggaagataag cgtcagggt aa                       942
```

<210> SEQ ID NO 28
<211> LENGTH: 313
<212> TYPE: PRT
<213> ORGANISM: Artificial Sequence
<220> FEATURE:
<223> OTHER INFORMATION: ecYghU (Recombinant)

<400> SEQUENCE: 28

```
Met Gly His His His His His His His Ala Leu Ala Ser Glu Asn
1               5                   10                  15

Leu Tyr Phe Gln Ser Ala Ile Ala Gly Met Thr Asp Asn Thr Tyr Gln
            20                  25                  30

Pro Ala Lys Val Trp Thr Trp Asp Lys Ser Ala Gly Gly Ala Phe Ala
        35                  40                  45

Asn Ile Asn Arg Pro Val Ser Gly Pro Thr His Glu Lys Thr Leu Pro
    50                  55                  60

Val Gly Lys His Pro Leu Gln Leu Tyr Ser Leu Gly Thr Pro Asn Gly
65                  70                  75                  80

Gln Lys Val Thr Ile Met Leu Glu Glu Leu Ala Leu Gly Val Thr
                85                  90                  95

Gly Ala Glu Tyr Asp Ala Trp Leu Ile Arg Ile Gly Asp Gly Asp Gln
            100                 105                 110

Phe Ser Ser Gly Phe Val Glu Val Asn Pro Asn Ser Lys Ile Pro Ala
        115                 120                 125

Leu Arg Asp His Thr His Asn Pro Pro Ile Arg Val Phe Glu Ser Gly
    130                 135                 140

Ser Ile Leu Leu Tyr Leu Ala Glu Lys Phe Gly Tyr Phe Leu Pro Gln
145                 150                 155                 160

Asp Leu Ala Lys Arg Thr Glu Thr Met Asn Trp Leu Phe Trp Leu Gln
                165                 170                 175

Gly Ala Ala Pro Phe Leu Gly Gly Phe Gly His Phe Tyr His Tyr
            180                 185                 190

Ala Pro Val Lys Ile Glu Tyr Ala Ile Asn Arg Phe Thr Met Glu Ala
        195                 200                 205

Lys Arg Leu Leu Asp Val Leu Asp Lys Gln Leu Ala Gln His Lys Phe
    210                 215                 220

Val Ala Gly Asp Glu Tyr Thr Ile Ala Asp Met Ala Ile Trp Pro Trp
225                 230                 235                 240

Phe Gly Asn Val Val Leu Gly Gly Val Tyr Asp Ala Ala Glu Phe Leu
                245                 250                 255

Asp Ala Gly Ser Tyr Lys His Val Gln Arg Trp Ala Lys Glu Val Gly
            260                 265                 270

Glu Arg Pro Ala Val Lys Arg Gly Arg Ile Val Asn Arg Thr Asn Gly
        275                 280                 285

Pro Leu Asn Glu Gln Leu His Glu Arg His Asp Ala Ser Asp Phe Glu
    290                 295                 300

Thr Asn Thr Glu Asp Lys Arg Gln Gly
305                 310
```

```
<210> SEQ ID NO 29
<211> LENGTH: 648
<212> TYPE: DNA
<213> ORGANISM: Escherichia coli

<400> SEQUENCE: 29
atgatcgatc tctatttcgc cccgacaccc aatggtcaca aaattacgct gtttctcgaa      60
gaagcagagc tggattatcg cttgattaag gtagacctgg ggaaaggcgg tcagtttcgt     120
ccggaatttt tgcgcatttc gcccaacaac aaaattccgg caattgttga tcattctcct     180
gccgatggcg gcgaaccgct aagcctcttt gagtctggtg ccatttttgtt gtatctggct    240 gagaaaacag gactcttttt gagtcatgaa acgcgtgagc gcgccgccac attacagtgg     300
ttattctggc aggtaggcgg actggggccg atgcttgggc aaaatcatca ttttaatcac     360
gcagcccccc aaaccattcc ttacgctatt gaacgttatc aggttgaaac tcagcgtctt     420
taccatgtac tgaacaagcg gctggaaaac tcgccctggc tgggaggcga aactacagc     480 attgcggata ttgcctgctg gccgtgggtt aatgcctgga ctcgccagcg aattgaccta     540
gcaatgtatc cggcagtcaa gaactggcat gagcggatcc gttcgcgccc tgccaccggg     600
caggcactgc taaaagcaca actcggtgat gagcgttcgg atagttaa                  648

<210> SEQ ID NO 30
<211> LENGTH: 215
<212> TYPE: PRT
<213> ORGANISM: Escherichia coli

<400> SEQUENCE: 30

Met Ile Asp Leu Tyr Phe Ala Pro Thr Pro Asn Gly His Lys Ile Thr
 1               5                  10                  15

Leu Phe Leu Glu Glu Ala Glu Leu Asp Tyr Arg Leu Ile Lys Val Asp
                20                  25                  30

Leu Gly Lys Gly Gly Gln Phe Arg Pro Glu Phe Leu Arg Ile Ser Pro
        35                  40                  45

Asn Asn Lys Ile Pro Ala Ile Val Asp His Ser Pro Ala Asp Gly Gly
    50                  55                  60

Glu Pro Leu Ser Leu Phe Glu Ser Gly Ala Ile Leu Leu Tyr Leu Ala
65                  70                  75                  80

Glu Lys Thr Gly Leu Phe Leu Ser His Glu Thr Arg Glu Arg Ala Ala
                85                  90                  95

Thr Leu Gln Trp Leu Phe Trp Gln Val Gly Leu Gly Pro Met Leu
            100                 105                 110

Gly Gln Asn His His Phe Asn His Ala Ala Pro Gln Thr Ile Pro Tyr
        115                 120                 125

Ala Ile Glu Arg Tyr Gln Val Glu Thr Gln Arg Leu Tyr His Val Leu
    130                 135                 140

Asn Lys Arg Leu Glu Asn Ser Pro Trp Leu Gly Gly Glu Asn Tyr Ser
145                 150                 155                 160

Ile Ala Asp Ile Ala Cys Trp Pro Trp Val Asn Ala Trp Thr Arg Gln
                165                 170                 175

Arg Ile Asp Leu Ala Met Tyr Pro Ala Val Lys Asn Trp His Glu Arg
            180                 185                 190

Ile Arg Ser Arg Pro Ala Thr Gly Gln Ala Leu Leu Lys Ala Gln Leu
        195                 200                 205

Gly Asp Glu Arg Ser Asp Ser
    210                 215
```

<210> SEQ ID NO 31
<211> LENGTH: 789
<212> TYPE: DNA
<213> ORGANISM: Streptococcus sanguinis

<400> SEQUENCE: 31

| | | | | | |
|---|---|---|---|---|---|
| atgacctatc | aattgccaaa | gtctggtct | gctgcggaca | gcgaccaagg | gaaattttca | 60 |
| ggtatcaatc | agcctactgc | aggcgtgcgt | tttgagcaga | agcttcctgt | cggtaaagaa | 120 |
| ccttttcagc | tgtattcact | gggacacct | aatggagtca | aggtgacgat | tatgctggag | 180 |
| gaactgctgg | cagcaggggt | gacagaggct | acctatgacc | tatataaaat | cagcattatg | 240 |
| gacggcgacc | agtttggctc | agattttgtg | aaaatcaatc | ccaactccaa | gattccggcc | 300 |
| ttgttggacc | agtcaggtca | taagccgatt | cctgtctttg | aatcagcaaa | tatcctgctc | 360 |
| tatctggcag | agaagtttgg | aaagctgatt | ccgtcagatt | tggccggtcg | gactgaggtg | 420 |
| ctcaactggc | tcttctggca | gacaggagcg | gcgcccttct | ggggaggcgg | atttggtcat | 480 |
| ttctttaact | atgctccaga | aaagctagaa | tatccaatta | accgctttac | catggaagcc | 540 |
| aagcgacagc | tggatttatt | ggacaaagaa | ttggctaaga | aagcttatat | agctggagaa | 600 |
| gactacagta | ttgctgatat | tgctatctgg | tcttggtatg | gtcagttagt | gcaggataag | 660 |
| ctctatccag | gcgcagctga | gttcttggat | gctgcatcct | acaaacatct | atctgcttgg | 720 |
| gcggagaaga | ttgcagctcg | tccggcagtc | cagcgcggtt | tagctgctga | gtatcaggaa | 780 |
| atcaaataa | | | | | | 789 |

<210> SEQ ID NO 32
<211> LENGTH: 262
<212> TYPE: PRT
<213> ORGANISM: Streptococcus sanguinis

<400> SEQUENCE: 32

Met Thr Tyr Gln Leu Pro Lys Val Trp Ser Ala Asp Ser Asp Gln
1               5                   10                  15

Gly Lys Phe Ser Gly Ile Asn Gln Pro Thr Ala Gly Val Arg Phe Glu
            20                  25                  30

Gln Lys Leu Pro Val Gly Lys Glu Pro Phe Gln Leu Tyr Ser Leu Gly
        35                  40                  45

Thr Pro Asn Gly Val Lys Val Thr Ile Met Leu Glu Glu Leu Leu Ala
    50                  55                  60

Ala Gly Val Thr Glu Ala Thr Tyr Asp Leu Tyr Lys Ile Ser Ile Met
65                  70                  75                  80

Asp Gly Asp Gln Phe Gly Ser Asp Phe Val Lys Ile Asn Pro Asn Ser
                85                  90                  95

Lys Ile Pro Ala Leu Leu Asp Gln Ser Gly His Lys Pro Ile Pro Val
            100                 105                 110

Phe Glu Ser Ala Asn Ile Leu Leu Tyr Leu Ala Glu Lys Phe Gly Lys
        115                 120                 125

Leu Ile Pro Ser Asp Leu Ala Gly Arg Thr Glu Val Leu Asn Trp Leu
    130                 135                 140

Phe Trp Gln Thr Gly Ala Ala Pro Phe Leu Gly Gly Gly Phe Gly His
145                 150                 155                 160

Phe Phe Asn Tyr Ala Pro Glu Lys Leu Glu Tyr Pro Ile Asn Arg Phe
                165                 170                 175

Thr Met Glu Ala Lys Arg Gln Leu Asp Leu Leu Asp Lys Glu Leu Ala
            180                 185                 190

Lys Lys Ala Tyr Ile Ala Gly Glu Asp Tyr Ser Ile Ala Asp Ile Ala
        195                 200                 205

Ile Trp Ser Trp Tyr Gly Gln Leu Val Gln Asp Lys Leu Tyr Pro Gly
    210                 215                 220

Ala Ala Glu Phe Leu Asp Ala Ala Ser Tyr Lys His Leu Ser Ala Trp
225                 230                 235                 240

Ala Glu Lys Ile Ala Ala Arg Pro Ala Val Gln Arg Gly Leu Ala Ala
            245                 250                 255

Glu Tyr Gln Glu Ile Lys
            260

<210> SEQ ID NO 33
<211> LENGTH: 681
<212> TYPE: DNA
<213> ORGANISM: Novosphingobium sp. MBES04

<400> SEQUENCE: 33
gtgctggaac tgtggacttc ggaaacaccg aatggctgga aaccaccat catgctcgag      60 gagctggacg cgaactacac gttgcgtccg atctcgctga ccaaccgcga gcagaaggaa    120
gactggtatc tcgcccgcaa tcccaacggg cgtatcccca cactgatcga ccatgaggtc    180
gatgccggga acggcggttt tgcggtgttc gaatcgggtg cgatcctgat ctaccttgcc    240
gagaagttcg gccgtttcct gccagccgac acgatgggcc gcagccgcgc gatccagtgg    300
gtgatgtggc agatgtcggg cctcggcccc atgatgggac aggcgaccgt cttcaaccgc    360
tacttcgagc ccaggctgcc cgaggtcatc gaccgctaca cgcgcgagag ccgccgcctc    420
ttcgaagtga tggacacgca cctcgccgac aacgaattcc tcgcgggcga ctattcgatc    480
gccgacatcg cctgcttccc gtgggtgcgc gggcatgact gggcctgcat cgacatggag    540
gggctgcccc acctgcaacg ctggttcgag accatcggtg agcgcccggc cgtccagcgc    600
ggcctgctct tgcccgaacc gcccaaggcg gacgagatgg ccgagaagac gacccgccag    660
ggcaagaaca tcctggcctg a                                              681

<210> SEQ ID NO 34
<211> LENGTH: 226
<212> TYPE: PRT
<213> ORGANISM: Novosphingobium sp. MBES04

<400> SEQUENCE: 34

Met Leu Glu Leu Trp Thr Ser Glu Thr Pro Asn Gly Trp Lys Thr Thr
1               5                   10                  15

Ile Met Leu Glu Glu Leu Asp Ala Asn Tyr Thr Leu Arg Pro Ile Ser
            20                  25                  30

Leu Thr Asn Arg Glu Gln Lys Asp Trp Tyr Leu Ala Arg Asn Pro
        35                  40                  45

Asn Gly Arg Ile Pro Thr Leu Ile Asp His Glu Val Asp Ala Gly Asn
    50                  55                  60

Gly Gly Phe Ala Val Phe Glu Ser Gly Ala Ile Leu Ile Tyr Leu Ala
65                  70                  75                  80

Glu Lys Phe Gly Arg Phe Leu Pro Ala Asp Thr Met Gly Arg Ser Arg
                85                  90                  95

Ala Ile Gln Trp Val Met Trp Gln Met Ser Gly Leu Gly Pro Met Met
            100                 105                 110

Gly Gln Ala Thr Val Phe Asn Arg Tyr Phe Glu Pro Arg Leu Pro Glu
        115                 120                 125

```
Val Ile Asp Arg Tyr Thr Arg Glu Ser Arg Leu Phe Glu Val Met
    130                 135                 140
Asp Thr His Leu Ala Asp Asn Glu Phe Leu Ala Gly Asp Tyr Ser Ile
145                 150                 155                 160
Ala Asp Ile Ala Cys Phe Pro Trp Val Arg Gly His Asp Trp Ala Cys
                165                 170                 175
Ile Asp Met Glu Gly Leu Pro His Leu Gln Arg Trp Phe Glu Thr Ile
            180                 185                 190
Gly Glu Arg Pro Ala Val Gln Arg Gly Leu Leu Pro Glu Pro Pro
        195                 200                 205
Lys Ala Asp Glu Met Ala Glu Lys Thr Thr Arg Gln Gly Lys Asn Ile
    210                 215                 220
Leu Ala
225
```

<210> SEQ ID NO 35
<211> LENGTH: 673
<212> TYPE: DNA
<213> ORGANISM: Phanerochaete chrysosporium

<400> SEQUENCE: 35

```
atggctacca acaccgacaa gcctgttgtc cactacaccg cacctacgcc caatggatgg      60
gtgcccgcta tcctcctgga ggagctgaag gctgtttacg gcggtcccga ctacgagact     120
gttaaaatga gcatcaggga cgcagacatt ggcaaggtcc acaaccaggt caagtcagac     180
tggttcctca gatttgccc taacggccgc attcccgcaa tcacgcacga aggcttcccc     240
gttttcgaga cctctgccat cctcctctat cttgcccagc acttcgacaa ggagaacgcc     300
ttctcgcgcg accccgtcaa ggacccaaag ggctacagcg aggagctgca gtggctattc     360
ttcgctcacg gaggtattgg ccccatgcag ggtcaggcca accatttaa cctttacgcg     420
ccggagaaga tcccatacgc catcaaccgc tacctcaacg agtcgaagcg tctgtaccgc     480
gtcctcgacg accgtctcaa gggccgcgag tatatcctgg gcacgtacgg catcgcagac     540
atcaagatct ttggctgggc gcgcattgcg ccccgcactg gccttgacct cgacgagttc     600
cccaacgtca aggcgtgggt cgagcgcatc gagaagcggc cggctgtcca ggctggcatc     660
aacagctgca act                                                        673
```

<210> SEQ ID NO 36
<211> LENGTH: 224
<212> TYPE: PRT
<213> ORGANISM: Phanerochaete chrysosporium

<400> SEQUENCE: 36

```
Met Ala Thr Asn Thr Asp Lys Pro Val Val His Tyr Thr Ala Pro Thr
1               5                   10                  15
Pro Asn Gly Trp Val Pro Ala Ile Leu Leu Glu Glu Leu Lys Ala Val
            20                  25                  30
Tyr Gly Gly Pro Asp Tyr Glu Thr Val Lys Met Ser Ile Arg Asp Ala
        35                  40                  45
Asp Ile Gly Lys Val His Asn Gln Val Lys Ser Asp Trp Phe Leu Lys
    50                  55                  60
Ile Cys Pro Asn Gly Arg Ile Pro Ala Ile Thr His Glu Gly Phe Pro
65                  70                  75                  80
Val Phe Glu Thr Ser Ala Ile Leu Leu Tyr Leu Ala Gln His Phe Asp
                85                  90                  95
```

```
Lys Glu Asn Ala Phe Ser Arg Asp Pro Val Lys Asp Pro Lys Gly Tyr
            100                 105                 110

Ser Glu Glu Leu Gln Trp Leu Phe Ala His Gly Gly Ile Gly Pro
            115                 120                 125

Met Gln Gly Gln Ala Asn His Phe Asn Leu Tyr Ala Pro Glu Lys Ile
130                 135                 140

Pro Tyr Ala Ile Asn Arg Tyr Leu Asn Glu Ser Lys Arg Leu Tyr Arg
145                 150                 155                 160

Val Leu Asp Asp Arg Leu Lys Gly Arg Glu Tyr Ile Leu Gly Thr Tyr
                165                 170                 175

Gly Ile Ala Asp Ile Lys Ile Phe Gly Trp Ala Arg Ile Ala Pro Arg
            180                 185                 190

Thr Gly Leu Asp Leu Asp Glu Phe Pro Asn Val Lys Ala Trp Val Glu
            195                 200                 205

Arg Ile Glu Lys Arg Pro Ala Val Gln Ala Gly Ile Asn Ser Cys Asn
    210                 215                 220
```

<210> SEQ ID NO 37
<211> LENGTH: 1377
<212> TYPE: DNA
<213> ORGANISM: Allochromatium vinosum

<400> SEQUENCE: 37

```
atgagccagc attttgatct gatcgccatc ggcggcggca gcggcggcct ggcggtcgcc     60
gagaaagcgg cgcagttcgg ccgtcgcgta gccctgatcg aaggcgccaa actgggcggc    120
acctgcgtca acgccggctg tgtacccaag aaggtgatgt ggtatgccgc caatctggcg    180
gcggccgtcg cggatgcgcc cgactacggg atccaggccc gttcggacgg tctcgactgg    240
ggcaagctga tcgccggccg caaccagtac atcgccgaca tcaacggcta ctgggacggc    300
tatgccgaac gcctgggcct cacccggatc gacggcttcg cgcgttttgt cgatgcgcgc    360
acggtcgcgg tcggcgacca gcactacacc gccgaccaca tcgtcatcgc caccggcggc    420
cggccgatcg tgccacgaat gccgggcgct gaactgggca tcacttcgga cggcttcttc    480
gcgctggaag aacagcccaa gcgcgtcgcc atcatcggcg cgggctatat cggcgtggag    540
ctggcgggcg tgctgagcgc gctcggcacc gagatcacca tcgtggcgct ggaagaccgg    600
atgctcgcgc tgttcgatcc gcttatcagc gagaccctgg ccgagaacat gacgctgcat    660
ggcatcgaca tgcacctgca attcgaggtc gccgggatcg agcgcgatga acagggactg    720
gtgctggccg cgcgcgacgg tcagcgtctg accggcttcg atcaggtcat ctgggccgtc    780
gggcgcgcgc ccaacacgcg cgagctgaac ctggaggcgg ccgggatcac ggtcgagcgt    840
agcggtgtca tcccgaccga tgcctggcag aacaccactg ttcccggcat ctatgccatc    900
ggcgacatca ccgggcgcga gccgctgact ccggtagcga tcgccgccgg acggcgtctg    960
gccgaacgcc tgttcaacga caagccggat tcaaagctcg actacgagaa cgtgcccacg   1020
gtggtgttcg ctcatccgcc gatcggcaag gtcggtctga ccgagcctga ggcgcgcgag   1080
cgttacggcg acacgctcac catctatgag accagcttca cgcccatgcg ctacgcgctc   1140
aacgcacacg gacccaagac cgcgatgaag ctggtctgtg ccggtgagga cgagaaggtg   1200
gtcggcatcc atctgatcgg cgatggcgtc gacgagatga tgcagggctt cggtgtggcg   1260
gtgaagatgg gcgcgaccaa ggccgatctc gacaatacgg tcgccatcca tccgtgcagc   1320
gccgaggaac tggtgacgct gaaggtgccg gtgcggcggc cgggtcagtc cggttga      1377
```

<210> SEQ ID NO 38
<211> LENGTH: 458
<212> TYPE: PRT
<213> ORGANISM: Allochromatium vinosum

<400> SEQUENCE: 38

```
Met Ser Gln His Phe Asp Leu Ile Ala Ile Gly Gly Gly Ser Gly Gly
 1               5                  10                  15

Leu Ala Val Ala Glu Lys Ala Ala Gln Phe Gly Arg Arg Val Ala Leu
            20                  25                  30

Ile Glu Gly Ala Lys Leu Gly Gly Thr Cys Val Asn Ala Gly Cys Val
        35                  40                  45

Pro Lys Lys Val Met Trp Tyr Ala Ala Asn Leu Ala Ala Val Ala
 50                  55                  60

Asp Ala Pro Asp Tyr Gly Ile Gln Ala Arg Ser Asp Gly Leu Asp Trp
 65                  70                  75                  80

Gly Lys Leu Ile Ala Gly Arg Asn Gln Tyr Ile Ala Asp Ile Asn Gly
                85                  90                  95

Tyr Trp Asp Gly Tyr Ala Glu Arg Leu Gly Leu Thr Arg Ile Asp Gly
            100                 105                 110

Phe Ala Arg Phe Val Asp Ala Arg Thr Val Ala Val Gly Asp Gln His
        115                 120                 125

Tyr Thr Ala Asp His Ile Val Ile Ala Thr Gly Gly Arg Pro Ile Val
130                 135                 140

Pro Arg Met Pro Gly Ala Glu Leu Gly Ile Thr Ser Asp Gly Phe Phe
145                 150                 155                 160

Ala Leu Glu Glu Gln Pro Lys Arg Val Ala Ile Ile Gly Gly Gly Tyr
                165                 170                 175

Ile Gly Val Glu Leu Ala Gly Val Leu Ser Ala Leu Gly Thr Glu Ile
            180                 185                 190

Thr Ile Val Ala Leu Glu Asp Arg Met Leu Ala Leu Phe Asp Pro Leu
        195                 200                 205

Ile Ser Glu Thr Leu Ala Glu Asn Met Thr Leu His Gly Ile Asp Met
    210                 215                 220

His Leu Gln Phe Glu Val Ala Gly Ile Glu Arg Asp Glu Gln Gly Leu
225                 230                 235                 240

Val Leu Ala Ala Arg Asp Gly Gln Arg Leu Thr Gly Phe Asp Gln Val
                245                 250                 255

Ile Trp Ala Val Gly Arg Ala Pro Asn Thr Arg Glu Leu Asn Leu Glu
            260                 265                 270

Ala Ala Gly Ile Thr Val Glu Arg Ser Gly Val Ile Pro Thr Asp Ala
        275                 280                 285

Trp Gln Asn Thr Thr Val Pro Gly Ile Tyr Ala Ile Gly Asp Ile Thr
    290                 295                 300

Gly Arg Glu Pro Leu Thr Pro Val Ala Ile Ala Ala Gly Arg Arg Leu
305                 310                 315                 320

Ala Glu Arg Leu Phe Asn Asp Lys Pro Asp Ser Lys Leu Asp Tyr Glu
                325                 330                 335

Asn Val Pro Thr Val Val Phe Ala His Pro Pro Ile Gly Lys Val Gly
            340                 345                 350

Leu Thr Glu Pro Glu Ala Arg Glu Arg Tyr Gly Asp Thr Leu Thr Ile
        355                 360                 365

Tyr Glu Thr Ser Phe Thr Pro Met Arg Tyr Ala Leu Asn Ala His Gly
    370                 375                 380
```

```
Pro Lys Thr Ala Met Lys Leu Val Cys Ala Gly Glu Asp Glu Lys Val
385                 390                 395                 400

Val Gly Ile His Leu Ile Gly Asp Gly Val Asp Glu Met Met Gln Gly
                405                 410                 415

Phe Gly Val Ala Val Lys Met Gly Ala Thr Lys Ala Asp Leu Asp Asn
            420                 425                 430

Thr Val Ala Ile His Pro Cys Ser Ala Glu Glu Leu Val Thr Leu Lys
        435                 440                 445

Val Pro Val Arg Arg Pro Gly Gln Ser Gly
    450                 455
```

<210> SEQ ID NO 39
<211> LENGTH: 786
<212> TYPE: DNA
<213> ORGANISM: Novosphingobium aromaticivorans

<400> SEQUENCE: 39

```
atgagcgcgc ttctttacca cggcgagccc aacggcgcgt cgctcaccgt tcttgcggcg    60
cttgcggaaa cgggcctcga tatcgagtgt cgccgcatcg acctcctggc gggcgagcgc   120
cattcgcttc ccggcatcgt cgatcccgtc gcgctcgacc tgtccatcga aggcgaaggt   180
ccggtgctgg tgatcgacgg ggaagcaatg accgaatccg tcttcctcgc caatatctg    240
gacgaggcgg cgggcggggt ggggctccag ccgaccgacg cctatgcgcg ctgggaaatg   300
atgatgtggt gccgccagat caccgagcgc ctctcgcccg ccgcggccct gctcggcaat   360
ctcgccacgt cgcaaagcgc catcgccgcc atcccggccg aggacttcgc cattctcgcc   420
gcacggatcg tttccgacga cctgcgcgag cggtggcagg ccctgaacga cgatgcggtg   480
aacgccgcac aggtcgccga cagcgaaacc aaggtcgccg ccgccgtcga ccgctgcgag   540
aagcagcttg gcgatggacg cgaatggctg atggggactt tctccatcgc cgatctcgtc   600
acctactcgt ggcttgccgg gatggagccg ctccgcctg ccgcctttgc cgatgcaccg    660
cttgtcaagg cctggcttgc ccgcaccgcc gcgcgccctt gcgtgcaggc ggcacttgcc   720
cgggccacca tttccgaacc gctccgcgcc tgggcgccgg ggcctgaaat caaccgttgg   780
ggataa                                                              786
```

<210> SEQ ID NO 40
<211> LENGTH: 261
<212> TYPE: PRT
<213> ORGANISM: Novosphingobium aromaticivorans

<400> SEQUENCE: 40

```
Met Ser Ala Leu Leu Tyr His Gly Glu Pro Asn Gly Ala Ser Leu Thr
1               5                   10                  15

Val Leu Ala Ala Leu Ala Glu Thr Gly Leu Asp Ile Glu Cys Arg Arg
            20                  25                  30

Ile Asp Leu Leu Ala Gly Glu Arg His Ser Leu Pro Gly Ile Val Asp
        35                  40                  45

Pro Val Ala Leu Asp Leu Ser Ile Glu Gly Glu Gly Pro Val Leu Val
    50                  55                  60

Ile Asp Gly Glu Ala Met Thr Glu Ser Val Phe Leu Ala Gln Tyr Leu
65                  70                  75                  80

Asp Glu Ala Ala Gly Gly Val Gly Leu Gln Pro Thr Asp Ala Tyr Ala
                85                  90                  95

Arg Trp Glu Met Met Met Trp Cys Arg Gln Ile Thr Glu Arg Leu Ser
```

```
            100                 105                 110
Pro Ala Ala Leu Leu Gly Asn Leu Ala Thr Ser Gln Ser Ala Ile
        115                 120                 125

Ala Ala Ile Pro Ala Glu Asp Phe Ala Ile Leu Ala Ala Arg Ile Val
    130                 135                 140

Ser Asp Asp Leu Arg Glu Arg Trp Gln Ala Leu Asn Asp Asp Ala Val
145                 150                 155                 160

Asn Ala Ala Gln Val Ala Asp Ser Glu Thr Lys Val Ala Ala Ala Val
                165                 170                 175

Asp Arg Cys Glu Lys Gln Leu Gly Asp Gly Arg Glu Trp Leu Met Gly
            180                 185                 190

Thr Phe Ser Ile Ala Asp Leu Val Thr Tyr Ser Trp Leu Ala Gly Met
        195                 200                 205

Glu Pro Leu Arg Pro Ala Ala Phe Ala Asp Ala Pro Leu Val Lys Ala
    210                 215                 220

Trp Leu Ala Arg Thr Ala Ala Arg Pro Cys Val Gln Ala Ala Leu Ala
225                 230                 235                 240

Arg Ala Thr Ile Ser Glu Pro Leu Arg Ala Trp Ala Pro Gly Pro Glu
                245                 250                 255

Ile Asn Arg Trp Gly
            260

<210> SEQ ID NO 41
<211> LENGTH: 771
<212> TYPE: DNA
<213> ORGANISM: Novosphingobium aromaticivorans

<400> SEQUENCE: 41
atggacgagg taagcctcta tcattgggaa cccaatgcca actctggcaa gccgatgctc      60
gcgttgatgg agaagggcgt gccctttttcc agccattaca tcgacatgct ccagttcgat     120
cagcacaagc cggaatacct tgcgatcaac ccgcaaggca cgatcccggc gatgacgcac     180
aatggccagg tgctgacgga aagcaccgcg atcatggagt acgtgaacga ccgcttcgac     240
gggccggacc tcatgcccgc cgacgcgcag gatcgctggc gcgtgcgctg gtggatgaag     300
ttcatggacc agtggcttgg ccccagtttc tcgatgatcg gctggagcgt gtttgtcggt     360
cccatggtcc gccagcgcga ccccgccgaa cttgccgccg cgatcgaccg tatcccttg      420 cccgaacgcc gcaccgcgtg gcgcaaggcg atcaacggcg acttctcgga aagcgagatg     480
gccgaaagcc gccgccgcgt ggggctgggc atcgccaagc tggaagagga actgggcaag     540
cggccctatg tcggttcgaa ccagtacagc ctggccgaca tcaacatctt caacagcacc     600
tattcgctgc ccatttcccca gcccgatctg gcgggcaagg acaggacgcc gaacatcatg     660
cgctggctca agcgtgtcta cacccgcgaa gcggtgaaga agacctgggc catgggcaag     720
acggaccttg cccatcgcta cggcctcatc atggcggaga tcgagggatg a             771

<210> SEQ ID NO 42
<211> LENGTH: 256
<212> TYPE: PRT
<213> ORGANISM: Novosphingobium aromaticivorans

<400> SEQUENCE: 42

Met Asp Glu Val Ser Leu Tyr His Trp Glu Pro Asn Ala Asn Ser Gly
1               5                   10                  15

Lys Pro Met Leu Ala Leu Met Glu Lys Gly Val Pro Phe Ser Ser His
            20                  25                  30
```

Tyr Ile Asp Met Leu Gln Phe Asp Gln His Lys Pro Glu Tyr Leu Ala
                35                  40                  45

Ile Asn Pro Gln Gly Thr Ile Pro Ala Met Thr His Asn Gly Gln Val
 50                  55                  60

Leu Thr Glu Ser Thr Ala Ile Met Glu Tyr Val Asn Asp Arg Phe Asp
 65                  70                  75                  80

Gly Pro Asp Leu Met Pro Ala Asp Ala Gln Asp Arg Trp Arg Val Arg
                 85                  90                  95

Trp Trp Met Lys Phe Met Asp Gln Trp Leu Gly Pro Ser Phe Ser Met
                100                 105                 110

Ile Gly Trp Ser Val Phe Val Gly Pro Met Val Arg Gln Arg Asp Pro
                115                 120                 125

Ala Glu Leu Ala Ala Ala Ile Asp Arg Ile Pro Leu Pro Glu Arg Arg
                130                 135                 140

Thr Ala Trp Arg Lys Ala Ile Asn Gly Asp Phe Ser Glu Ser Glu Met
145                 150                 155                 160

Ala Glu Ser Arg Arg Arg Val Gly Leu Gly Ile Ala Lys Leu Glu Glu
                165                 170                 175

Glu Leu Gly Lys Arg Pro Tyr Val Gly Ser Asn Gln Tyr Ser Leu Ala
                180                 185                 190

Asp Ile Asn Ile Phe Asn Ser Thr Tyr Ser Leu Pro Ile Ser Gln Pro
                195                 200                 205

Asp Leu Ala Gly Lys Asp Arg Thr Pro Asn Ile Met Arg Trp Leu Lys
                210                 215                 220

Arg Val Tyr Thr Arg Glu Ala Val Lys Lys Thr Trp Ala Met Gly Lys
225                 230                 235                 240

Thr Asp Leu Ala His Arg Tyr Gly Leu Ile Met Ala Glu Ile Glu Gly
                245                 250                 255

<210> SEQ ID NO 43
<211> LENGTH: 258
<212> TYPE: PRT
<213> ORGANISM: Novosphingobium aromaticivorans

<400> SEQUENCE: 43

Met Ala Leu Lys Tyr Tyr His Ala Glu Pro Leu Ala Asn Ser Leu Lys
 1               5                  10                  15

Ser Met Val Pro Leu Lys Glu Lys Gly Leu Ala Tyr Glu Ser Ile Tyr
                 20                  25                  30

Val Asp Leu His Lys Phe Glu Gln His Gln Pro Trp Phe Thr Ala Ile
                 35                  40                  45

Asn Pro Glu Gly Gln Val Pro Val Leu Asp His Asp Gly Thr Ile Ile
 50                  55                  60

Thr His Thr Thr Val Ile Asn Glu Tyr Leu Glu Asp Ala Phe Pro Asp
 65                  70                  75                  80

Ala Gln Pro Ala Asp Ala Pro Leu Arg Pro Arg Asp Pro Val Gly Ala
                 85                  90                  95

Ala Arg Met Arg Tyr Trp Asn Lys Phe Ile Asp Glu His Val Met Asn
                100                 105                 110

Tyr Val Ser Met His Gly Trp His Arg Met Val Gly Val Ile Ala Arg
                115                 120                 125

Asn Ile Ala Ser Gly Asp Phe Glu Lys Leu Leu Glu Ser Ile Pro Leu
                130                 135                 140

Pro Asp Gln Arg Lys Lys Trp Ala Thr Ala Arg Ser Gly Phe Ser Glu

```
            145                 150                 155                 160
        Ala Asp Leu Ala Asn Ala Thr Ala Lys Ile Glu Tyr Ala Leu Asp Lys
                        165                 170                 175

Val Glu Lys Gln Leu Gly Glu Thr Lys Trp Leu Ala Gly Asp Thr Tyr
                        180                 185                 190

Thr Leu Ala Asp Ile Asn Phe Tyr Ser His Cys Gly Ala Met Val Glu
                        195                 200                 205

Arg Met Phe Pro Glu Met Glu Val Ala Arg Arg Ala Pro Arg Leu Cys
                        210                 215                 220

Glu Trp Arg Asp Arg Val Ala Ala Arg Pro Ala Val Ala Glu Ala Leu
        225                 230                 235                 240

Lys Ser Glu Asp Arg Thr Ala Pro Gly Leu Arg Val Trp Ser Gly Glu
                        245                 250                 255

Val Arg

<210> SEQ ID NO 44
<211> LENGTH: 257
<212> TYPE: PRT
<213> ORGANISM: Novosphingobium aromaticivorans

<400> SEQUENCE: 44

Met Val Ile Pro Leu Gly Glu Asp Asn Thr Ile Met Leu Lys Leu Tyr
        1               5                   10                  15

Ser Phe Gly Pro Ala Ala Asn Ser Met Lys Pro Leu Leu Thr Val Phe
                        20                  25                  30

Glu Lys Gly Leu Asp Val Glu Lys His Arg Leu Asp Pro Ala Lys Phe
                        35                  40                  45

Glu His His Thr Asp Trp Phe Lys Ala Ile Asn Pro Arg Gly Gln Val
                        50                  55                  60

Pro Ala Leu Val Asp Gly Asp Lys Val Val Thr Glu Ser Thr Val Ile
        65                  70                  75                  80

Cys Glu Tyr Leu Glu Asp Glu Tyr Pro Thr Glu Val Ala Leu Arg Pro
                        85                  90                  95

Ala Asp Ser Phe Gly Lys Ala Gln Met Arg Ile Trp Thr Lys Trp Val
                        100                 105                 110

Asp Glu Tyr Phe Cys Trp Cys Val Ser Thr Ile Gly Trp His Arg Tyr
                        115                 120                 125

Val Gly Asn Met Val Lys Ser Leu Ser Asp Ala Glu Phe Glu Glu Lys
                        130                 135                 140

Val Lys Ala Ile Pro Val Ile Glu Gln Gln Val Lys Trp Arg Arg Ala
        145                 150                 155                 160

Arg Glu Gly Phe Pro Gln Asp Met Leu Asp Glu Glu Met Arg Lys Ile
                        165                 170                 175

Ala Tyr Ser Val Arg Lys Leu Asp Asp His Leu Ala Asp His Glu Trp
                        180                 185                 190

Leu Val Pro Gly Gln Tyr Thr Leu Ala Asp Ile Cys Asn Phe Ala Ile
                        195                 200                 205

Ala Asn Gly Met Gln Phe Gly Phe Ala Glu Leu Val Asn Lys Gln Asp
                        210                 215                 220

Thr Pro His Leu Val Arg Trp Ile Glu Gln Ile Asn Glu Arg Pro Ala
        225                 230                 235                 240

Val Lys Gln Met Phe Ala Gln Val Glu Leu Glu Lys Leu Gly Pro Arg
                        245                 250                 255

Glu
```

<210> SEQ ID NO 45
<211> LENGTH: 257
<212> TYPE: PRT
<213> ORGANISM: Sphingobium sp. SYK-6

<400> SEQUENCE: 45

Met Thr Leu Lys Leu Tyr Ser Phe Gly Pro Gly Ala Asn Ser Leu Lys
1               5                   10                  15

Pro Leu Ala Thr Leu Tyr Glu Lys Gly Leu Glu Phe Glu Gln Val Phe
            20                  25                  30

Val Asp Pro Ser Lys Phe Glu Gln His Ser Asp Trp Phe Lys Lys Ile
        35                  40                  45

Asn Pro Arg Gly Gln Val Pro Ala Leu Trp His Asp Gly Lys Val Val
    50                  55                  60

Thr Glu Ser Thr Val Ile Cys Glu Tyr Leu Glu Asp Val Phe Pro Glu
65                  70                  75                  80

Ser Gly Asn Ser Leu Arg Pro Ala Asp Pro Phe Lys Arg Ala Glu Met
                85                  90                  95

Arg Val Trp Thr Lys Trp Val Asp Glu Tyr Phe Cys Trp Cys Val Ser
            100                 105                 110

Thr Ile Gly Trp Ala Phe Gly Ile Lys Ala Ile Ala Gln Lys Met Ser
        115                 120                 125

Asp Glu Glu Phe Glu Glu His Ile Asn Lys Asn Val Pro Ile Pro Glu
    130                 135                 140

Gln Gln Leu Lys Trp Arg Arg Ala Arg Asn Gly Phe Pro Gln Glu Met
145                 150                 155                 160

Leu Asp Glu Glu Phe Arg Lys Val Gly Val Ser Val Ala Arg Leu Glu
                165                 170                 175

Glu Thr Leu Ser Lys Gln Asp Tyr Leu Val Asp Thr Gly Tyr Ser Leu
            180                 185                 190

Ala Asp Ile Cys Asn Phe Ala Ile Ala Asn Gly Leu Gln Arg Pro Gly
        195                 200                 205

Gly Phe Phe Gly Asp Tyr Val Asn Gln Glu Lys Thr Pro Gly Leu Cys
    210                 215                 220

Ala Trp Leu Asp Arg Ile Asn Ala Arg Pro Ala Ile Lys Glu Met Phe
225                 230                 235                 240

Glu Lys Ser Lys Arg Glu Asp Leu Leu Lys Arg Gln Asn Glu Lys Val
                245                 250                 255

Ala

<210> SEQ ID NO 46
<211> LENGTH: 250
<212> TYPE: PRT
<213> ORGANISM: Novosphingobium sp. PP1Y

<400> SEQUENCE: 46

Met Leu Thr Leu Tyr Ser Phe Gly Pro Gly Ala Asn Ser Leu Lys Pro
1               5                   10                  15

Leu Leu Ala Leu Tyr Glu Lys Gly Leu Glu Phe Thr Pro Arg Phe Val
            20                  25                  30

Asp Pro Thr Arg Phe Glu His His Glu Glu Trp Phe Lys Lys Ile Asn
        35                  40                  45

Pro Arg Gly Gln Val Pro Ala Leu Asp His Asp Gly His Ile Ile Thr
    50                  55                  60

```
Glu Ser Thr Val Ile Cys Glu Tyr Leu Glu Asp Ala Phe Pro Glu Ala
65                  70                  75                  80

Pro Arg Leu Arg Pro Val Asp Pro Val Met Ile Ala Glu Met Arg Val
                85                  90                  95

Trp Thr Lys Trp Val Asp Glu Tyr Phe Cys Trp Cys Val Ser Thr Ile
            100                 105                 110

Gly Trp Glu Arg Met Ile Gly Pro Met Ala Arg Ala Leu Ser Asp Glu
        115                 120                 125

Glu Phe Glu Ala Lys Val Ala Arg Ile Pro Val Pro Glu Gln Arg Thr
    130                 135                 140

Lys Trp Arg Thr Ala Arg Thr Gly Phe Pro Lys Glu Val Leu Asp Glu
145                 150                 155                 160

Glu Met Arg Lys Ile Gly Val Ser Val Asn Arg Leu Glu Thr Arg Leu
                165                 170                 175

Ala Glu Ser Pro Trp Leu Ala Gly Glu Asn Phe Ser Leu Ala Asp Val
            180                 185                 190

Cys Asn Phe Ala Ile Ala Asn Gly Met Gln Asn Gly Phe Ser Asp Ile
        195                 200                 205

Val Asn Arg Glu Ala Thr Pro His Leu Val Ala Trp Ile Glu Lys Ile
    210                 215                 220

Asn Asp Arg Pro Ala Cys Lys Ala Met Phe Ala Asn Ser Lys Ser Glu
225                 230                 235                 240

Phe Ala Asp Arg Gly Gln Lys Val Thr Ala
                245                 250

<210> SEQ ID NO 47
<211> LENGTH: 256
<212> TYPE: PRT
<213> ORGANISM: Novosphingobium sp. MBES04

<400> SEQUENCE: 47

Met Leu Thr Leu Tyr Ser Phe Gly Pro Gly Ala Asn Ser Leu Lys Pro
1               5                   10                  15

Leu Leu Ala Leu Tyr Glu Lys Gly Leu Glu Phe Thr Pro Arg Phe Val
                20                  25                  30

Asp Pro Thr Lys Phe Glu His His Glu Glu Trp Phe Lys Lys Ile Asn
            35                  40                  45

Pro Arg Gly Gln Val Pro Ala Leu Asp His Asp Gly Asn Val Ile Thr
        50                  55                  60

Glu Ser Thr Val Ile Cys Glu Tyr Leu Glu Asp Ala Phe Pro Asp Ala
65                  70                  75                  80

Pro Arg Leu Arg Pro Thr Asp Pro Val Gln Ile Ala Glu Met Arg Val
                85                  90                  95

Trp Thr Lys Trp Val Asp Glu Tyr Phe Cys Trp Cys Val Ser Thr Ile
            100                 105                 110

Gly Trp Glu Arg Gly Ile Gly Pro Met Ala Arg Ala Leu Ser Asp Glu
        115                 120                 125

Glu Phe Glu Glu Lys Val Lys Arg Ile Pro Ile Pro Glu Gln Gln Ala
    130                 135                 140

Lys Trp Arg Ser Ala Arg Ala Gly Phe Pro Lys Glu Val Leu Asp Glu
145                 150                 155                 160

Glu Met Arg Lys Ile Arg Val Ser Ile Asp Arg Leu Glu Lys Arg Leu
                165                 170                 175

Ser Glu Ser Thr Trp Leu Ala Gly Glu Asp Tyr Thr Leu Ala Asp Ile
            180                 185                 190
```

```
Cys Asn Phe Ala Ile Ala Asn Gly Met Glu Lys Gly Phe Asp Asp Ile
        195                 200                 205

Val Asn Thr Ala Ala Thr Pro Asn Leu Val Ala Trp Ile Glu Arg Ile
    210                 215                 220

Asn Ala Arg Pro Ala Cys Ile Glu Met Phe Ala Lys Ser Lys Ser Glu
225                 230                 235                 240

Phe Ala Ala Arg Lys Pro Phe Ala Lys Ser Glu Glu Gln Ala Gln Ala
                245                 250                 255
```

<210> SEQ ID NO 48
<211> LENGTH: 22
<212> TYPE: DNA
<213> ORGANISM: Artificial Sequence
<220> FEATURE:
<223> OTHER INFORMATION: Saro_0141 (rpoZ) Primer

<400> SEQUENCE: 48
gagatcgcgg aagaaaccgt gc                                    22

<210> SEQ ID NO 49
<211> LENGTH: 24
<212> TYPE: DNA
<213> ORGANISM: Artificial Sequence
<220> FEATURE:
<223> OTHER INFORMATION: Saro_0141 (rpoZ) Primer 2

<400> SEQUENCE: 49
gatttcatcc acctcgtcgt cgtc                                  24

<210> SEQ ID NO 50
<211> LENGTH: 26
<212> TYPE: DNA
<213> ORGANISM: Artificial Sequence
<220> FEATURE:
<223> OTHER INFORMATION: Saro_0205 (ligD) Primer 1

<400> SEQUENCE: 50
caacatcaag tcgaacatcg cggaag                                26

<210> SEQ ID NO 51
<211> LENGTH: 22
<212> TYPE: DNA
<213> ORGANISM: Artificial Sequence
<220> FEATURE:
<223> OTHER INFORMATION: Saro_0205 (ligD) Primer 2

<400> SEQUENCE: 51
ctggtggatc gaatgcagcg ag                                    22

<210> SEQ ID NO 52
<211> LENGTH: 27
<212> TYPE: DNA
<213> ORGANISM: Artificial Sequence
<220> FEATURE:
<223> OTHER INFORMATION: Saro_0793 (ligO) Primer 1

<400> SEQUENCE: 52
gatcgaggaa tcttcctacg acgactg                               27

<210> SEQ ID NO 53
<211> LENGTH: 24
<212> TYPE: DNA
<213> ORGANISM: Artificial Sequence
<220> FEATURE:

```
<223> OTHER INFORMATION: Saro_0793 (ligO) Primer 2

<400> SEQUENCE: 53
gtttaccacg ccgtggaggt tcac                                          24

<210> SEQ ID NO 54
<211> LENGTH: 26
<212> TYPE: DNA
<213> ORGANISM: Artificial Sequence
<220> FEATURE:
<223> OTHER INFORMATION: Saro_0794 (ligN) Primer 1

<400> SEQUENCE: 54
catatcgtct gcaccgcttc gatgtc                                        26

<210> SEQ ID NO 55
<211> LENGTH: 22
<212> TYPE: DNA
<213> ORGANISM: Artificial Sequence
<220> FEATURE:
<223> OTHER INFORMATION: Saro_0794 (ligN) Primer 2

<400> SEQUENCE: 55
gcagaatgcc gagcagatca cg                                            22

<210> SEQ ID NO 56
<211> LENGTH: 22
<212> TYPE: DNA
<213> ORGANISM: Artificial Sequence
<220> FEATURE:
<223> OTHER INFORMATION: Saro_1875 (ligL) Primer 1

<400> SEQUENCE: 56
ccatgtcgtc aacaccgcat cg                                            22

<210> SEQ ID NO 57
<211> LENGTH: 24
<212> TYPE: DNA
<213> ORGANISM: Artificial Sequence
<220> FEATURE:
<223> OTHER INFORMATION: Saro_1875 (ligL) Primer 2

<400> SEQUENCE: 57
catgttctcg gtcaggttca gcac                                          24

<210> SEQ ID NO 58
<211> LENGTH: 22
<212> TYPE: DNA
<213> ORGANISM: Artificial Sequence
<220> FEATURE:
<223> OTHER INFORMATION: Saro_2091 (ligF) Primer 1

<400> SEQUENCE: 58
gctgctgacg gtgttcgaga ag                                            22

<210> SEQ ID NO 59
<211> LENGTH: 24
<212> TYPE: DNA
<213> ORGANISM: Artificial Sequence
<220> FEATURE:
<223> OTHER INFORMATION: Saro_2091 (ligF) Primer 2

<400> SEQUENCE: 59
cttgaaccag tcggtgtgat gctc                                          24
```

-continued

```
<210> SEQ ID NO 60
<211> LENGTH: 29
<212> TYPE: DNA
<213> ORGANISM: Artificial Sequence
<220> FEATURE:
<223> OTHER INFORMATION: Saro_2405 (ligP) Primer 1

<400> SEQUENCE: 60
catcgtcgaa tacctcgatg ccaagtatc                                    29

<210> SEQ ID NO 61
<211> LENGTH: 25
<212> TYPE: DNA
<213> ORGANISM: Artificial Sequence
<220> FEATURE:
<223> OTHER INFORMATION: Saro_2405 (ligP) Primer 2

<400> SEQUENCE: 61
gtcctggcag aagcagaaca tccac                                        25

<210> SEQ ID NO 62
<211> LENGTH: 26
<212> TYPE: DNA
<213> ORGANISM: Artificial Sequence
<220> FEATURE:
<223> OTHER INFORMATION: Saro_2595 Primer 1

<400> SEQUENCE: 62
ccacgatcat gctggaagaa ctgctc                                       26

<210> SEQ ID NO 63
<211> LENGTH: 25
<212> TYPE: DNA
<213> ORGANISM: Artificial Sequence
<220> FEATURE:
<223> OTHER INFORMATION: Saro_2595 Primer 2

<400> SEQUENCE: 63
gattcgaaga cgcggaacgg ttcag                                        25

<210> SEQ ID NO 64
<211> LENGTH: 23
<212> TYPE: DNA
<213> ORGANISM: Artificial Sequence
<220> FEATURE:
<223> OTHER INFORMATION: Primer pK18msB AseI ampl F

<400> SEQUENCE: 64
ctgtcgtgcc agctgcatta atg                                          23

<210> SEQ ID NO 65
<211> LENGTH: 29
<212> TYPE: DNA
<213> ORGANISM: Artificial Sequence
<220> FEATURE:
<223> OTHER INFORMATION: Primer pK18msB -MCS XbaI R

<400> SEQUENCE: 65
gaacatctag aaagccagtc cgcagaaac                                    29

<210> SEQ ID NO 66
<211> LENGTH: 30
<212> TYPE: DNA
<213> ORGANISM: Artificial Sequence
<220> FEATURE:
<223> OTHER INFORMATION: Primer Saro1879 lvnsucr ampl F AseI
```

<400> SEQUENCE: 66
cccgaattaa tcgtgacggt atcaacctcc                              30

<210> SEQ ID NO 67
<211> LENGTH: 30
<212> TYPE: DNA
<213> ORGANISM: Artificial Sequence
<220> FEATURE:
<223> OTHER INFORMATION: Primer Saro1879 lvnsucr ampl R XbaI

<400> SEQUENCE: 67
gtttcggtct agatcgagct gaccgaaatc                              30

<210> SEQ ID NO 68
<211> LENGTH: 29
<212> TYPE: DNA
<213> ORGANISM: Artificial Sequence
<220> FEATURE:
<223> OTHER INFORMATION: Primer Saro_2595 amp AseI for

<400> SEQUENCE: 68
gtcgattaat agtccgagat cgaggctgc                               29

<210> SEQ ID NO 69
<211> LENGTH: 28
<212> TYPE: DNA
<213> ORGANISM: Artificial Sequence
<220> FEATURE:
<223> OTHER INFORMATION: Primer Saro_2595 amp XbaI rev

<400> SEQUENCE: 69
cgactctaga cagagcctga acgaagtc                                28

<210> SEQ ID NO 70
<211> LENGTH: 32
<212> TYPE: DNA
<213> ORGANISM: Artificial Sequence
<220> FEATURE:
<223> OTHER INFORMATION: Primer Saro1879 lvnsucr del REV

<400> SEQUENCE: 70
ccgactttct tgaaacagat ttggcttaag ac                           32

<210> SEQ ID NO 71
<211> LENGTH: 26
<212> TYPE: DNA
<213> ORGANISM: Artificial Sequence
<220> FEATURE:
<223> OTHER INFORMATION: Primer Saro1879 lvnsucr del FOR

<400> SEQUENCE: 71
gttcatgctt aacttcgatg gcgagc                                  26

<210> SEQ ID NO 72
<211> LENGTH: 29
<212> TYPE: DNA
<213> ORGANISM: Artificial Sequence
<220> FEATURE:
<223> OTHER INFORMATION: Primer Saro_2595 del rev

<400> SEQUENCE: 72
cctgctcctt ggggatattg ttagtgttg                               29

<210> SEQ ID NO 73
<211> LENGTH: 25

-continued

<210> SEQ ID NO 73
<211> LENGTH: 25
<212> TYPE: DNA
<213> ORGANISM: Artificial Sequence
<220> FEATURE:
<223> OTHER INFORMATION: Primer Saro_2595 del for

<400> SEQUENCE: 73
ggaatcgttg caagcgatcg tcaag                                    25

<210> SEQ ID NO 74
<211> LENGTH: 41
<212> TYPE: DNA
<213> ORGANISM: Artificial Sequence
<220> FEATURE:
<223> OTHER INFORMATION: Primer D2595pK18-ecYghU F

<400> SEQUENCE: 74
ggagcaggcg atgacagaca atacttatca gcccgcgaaa g                  41

<210> SEQ ID NO 75
<211> LENGTH: 41
<212> TYPE: DNA
<213> ORGANISM: Artificial Sequence
<220> FEATURE:
<223> OTHER INFORMATION: Primer D2595pK18-ecYghU R

<400> SEQUENCE: 75
cgaggcgggt ttacccctga cgcttatctt ccgtattcgt c                  41

<210> SEQ ID NO 76
<211> LENGTH: 32
<212> TYPE: DNA
<213> ORGANISM: Artificial Sequence
<220> FEATURE:
<223> OTHER INFORMATION: Primer ecYghU-D2595pK18 F

<400> SEQUENCE: 76 tcagggtaa acccgcctcg agaccggcga ac                             32

<210> SEQ ID NO 77
<211> LENGTH: 38
<212> TYPE: DNA
<213> ORGANISM: Artificial Sequence
<220> FEATURE:
<223> OTHER INFORMATION: Primer ecYghU-D2595pK18 R

<400> SEQUENCE: 77
tgtctgtcat cgcctgctcc ttggggatat tgttagtg                      38

<210> SEQ ID NO 78
<211> LENGTH: 27
<212> TYPE: DNA
<213> ORGANISM: Artificial Sequence
<220> FEATURE:
<223> OTHER INFORMATION: Primer Saro2595 Ctag PciI F

<400> SEQUENCE: 78
gcaggacatg tcctcagagt acgttcc                                  27

<210> SEQ ID NO 79
<211> LENGTH: 35
<212> TYPE: DNA
<213> ORGANISM: Artificial Sequence
<220> FEATURE:
<223> OTHER INFORMATION: Primer Saro2595 Ctag BsaI R

<400> SEQUENCE: 79
gttatctgcg agaccacgat cgcttgcaac gattc                                35

<210> SEQ ID NO 80
<211> LENGTH: 28
<212> TYPE: DNA
<213> ORGANISM: Artificial Sequence
<220> FEATURE:
<223> OTHER INFORMATION: Primer pVP302K Ctag BsaI F

<400> SEQUENCE: 80
ctgcggtctc gcagatggta aaattctg                                       28

<210> SEQ ID NO 81
<211> LENGTH: 35
<212> TYPE: DNA
<213> ORGANISM: Artificial Sequence
<220> FEATURE:
<223> OTHER INFORMATION: GGTGATGTCCCATGGTTAATTTCTCCTCTTTAATG

<400> SEQUENCE: 81
ggtgatgtcc catggttaat ttctcctctt taatg                               35

<210> SEQ ID NO 82
<211> LENGTH: 33
<212> TYPE: DNA
<213> ORGANISM: Artificial Sequence
<220> FEATURE:
<223> OTHER INFORMATION: Primer Ctag 2595-pVP add Stop R

<400> SEQUENCE: 82
tcagaagccc ttgacgatcg cttgcaacga ttc                                 33

<210> SEQ ID NO 83
<211> LENGTH: 35
<212> TYPE: DNA
<213> ORGANISM: Artificial Sequence
<220> FEATURE:
<223> OTHER INFORMATION: Primer pVP302K Ntag HindIII F

<400> SEQUENCE: 83
cattaaaagc ttaaacgaat tcggactcgg tacgc                               35

<210> SEQ ID NO 84
<211> LENGTH: 58
<212> TYPE: DNA
<213> ORGANISM: Artificial Sequence
<220> FEATURE:
<223> OTHER INFORMATION: Primer 2595-pVP C to Ntag F

<400> SEQUENCE: 84
caagcgaaaa tctgtatttt cagagcgcga tcgcaggaat gtcctcagag tacgttcc      58

<210> SEQ ID NO 85
<211> LENGTH: 59
<212> TYPE: DNA
<213> ORGANISM: Artificial Sequence
<220> FEATURE:
<223> OTHER INFORMATION: Primer pVP302 C to Ntag R

<400> SEQUENCE: 85
ccaatgcatg gtgatggtga tgatggtgat gtcccatggt taatttctcc tctttaatg    59

<210> SEQ ID NO 86
<211> LENGTH: 41
<212> TYPE: DNA
<213> ORGANISM: Artificial Sequence

```
<220> FEATURE:
<223> OTHER INFORMATION: Primer pVP302K-ecYghU F

<400> SEQUENCE: 86
gatcgcagga atgacagaca atacttatca gcccgcgaaa g                    41

<210> SEQ ID NO 87
<211> LENGTH: 41
<212> TYPE: DNA
<213> ORGANISM: Artificial Sequence
<220> FEATURE:
<223> OTHER INFORMATION: Primer pVP302K-ecYghU R

<400> SEQUENCE: 87
cggctttctg ttacccctga cgcttatctt ccgtattcgt c                    41

<210> SEQ ID NO 88
<211> LENGTH: 45
<212> TYPE: DNA
<213> ORGANISM: Artificial Sequence
<220> FEATURE:
<223> OTHER INFORMATION: Primer ecYghU-pVP302K F

<400> SEQUENCE: 88
tcaggggtaa cagaaagccg aaaataacaa agttagcctg agctg                45

<210> SEQ ID NO 89
<211> LENGTH: 44
<212> TYPE: DNA
<213> ORGANISM: Artificial Sequence
<220> FEATURE:
<223> OTHER INFORMATION: Primer ecYghU-pVP302K R

<400> SEQUENCE: 89
tgtctgtcat tcctgcgatc gcgctctgaa aatacagatt ttcg                 44

<210> SEQ ID NO 90
<211> LENGTH: 34
<212> TYPE: DNA
<213> ORGANISM: Artificial Sequence
<220> FEATURE:
<223> OTHER INFORMATION: Primer pVP302K-HiFi-ATW-R

<400> SEQUENCE: 90
tcctgcgatc gcgctctgaa aatacagatt ttcg                            34

<210> SEQ ID NO 91
<211> LENGTH: 35
<212> TYPE: DNA
<213> ORGANISM: Artificial Sequence
<220> FEATURE:
<223> OTHER INFORMATION: Primer pVP302K-HiFi-ATW-F

<400> SEQUENCE: 91
cagaaagccg aaaataacaa agttagcctg agctg                           35

<210> SEQ ID NO 92
<211> LENGTH: 53
<212> TYPE: DNA
<213> ORGANISM: Artificial Sequence
<220> FEATURE:
<223> OTHER INFORMATION: Primer ecYfcG-pVP-Ntag-HiFi-F

<400> SEQUENCE: 92
gtattttcag agcgcgatcg caggaatgat cgatctctat ttcgcccga cac         53
```

<210> SEQ ID NO 93
<211> LENGTH: 56
<212> TYPE: DNA
<213> ORGANISM: Artificial Sequence
<220> FEATURE:
<223> OTHER INFORMATION: Primer ecYfcG-pVP-Ntag-HiFi-R

<400> SEQUENCE: 93
ctaactttgt tattttcggc tttctgttaa ctatccgaac gctcatcacc gagttg    56

<210> SEQ ID NO 94
<211> LENGTH: 35
<212> TYPE: DNA
<213> ORGANISM: Artificial Sequence
<220> FEATURE:
<223> OTHER INFORMATION: Primer SYK6 yghU pVP fix R

<400> SEQUENCE: 94
gttattttcg gctttctgtt aagcttcggt cttcg    35

<210> SEQ ID NO 95
<211> LENGTH: 37
<212> TYPE: DNA
<213> ORGANISM: Artificial Sequence
<220> FEATURE:
<223> OTHER INFORMATION: Primer SYK6 yghU pVP fix F

<400> SEQUENCE: 95
cttaacagaa agccgaaaat aacaaagtta gcctgag    37

<210> SEQ ID NO 96
<211> LENGTH: 951
<212> TYPE: DNA
<213> ORGANISM: Artificial Sequence
<220> FEATURE:
<223> OTHER INFORMATION: Codon-optimized SLG_04120 gene fragment

<400> SEQUENCE: 96
gtattttcag agcgcgatcg caggaatggc cgactcagat ccatccatga atcagccgac    60
gggttacgtc ccgccgaaag tttggacctg ggacaaagag aacggcggtc agttcagcaa    120
tatcaacgcc cctacggctg tgcgcgcca ggacgtcacg ctccctgtag gggagcaccc    180
tatccaatta tatagtctcg gcactccgaa tggtcagaaa gttactatca tgttggaaga    240
actgctggct gctggctttg atgctgagta tgacgcctgg ctcatcaaaa tctacacagg    300
cgagcaattc ggatctgatt tcgtcgccat taacccgaat agcaaaattc ggctatgat    360
ggaccatggt ctcgatccgc cgctccgttt atttgagtct ggttctatgt tagtttatct    420
ggccgaaaag tttggcgcat tcctcccgac cgaaatccgc aaacgtacgg aaacctttaa    480
ctggctcatg tggcagatgg ttctgctcc ttttgtgggt ggtggctttg gccacttcta    540
tgcgtacgcc ccatttaaaa tcgaatatgc cattgatcgt tacgcgatgg aaaccaagcg    600
ccaactggac gttctggata aaatctggcc gatcgtgaa tttatgatcg gcgatgaaat    660
caccatcgca gattttgcga ttttcccttg gtacggctcg attatgcgtg gcggttacaa    720
cgcgcaagaa ttcttgagca ctcacgagta ccgtaacgtt gatcgctggg ttacgcagct    780
ttctgaacgt acgggcgtaa agcgtggtct ccttgtcaat ccgcgggtc gcccgggagg    840
tggcattgcg gaacgccata gcgggctga tttagacgcg tcgattaaag cggctgaaca    900
agaggccgcg aagaccgaag cttaacagaa agccgaaaat aacaaagtta g    951

```
<210> SEQ ID NO 97
<211> LENGTH: 58
<212> TYPE: DNA
<213> ORGANISM: Artificial Sequence
<220> FEATURE:
<223> OTHER INFORMATION: Primer pK18-ligE OvExt F

<400> SEQUENCE: 97
gtttctgcgg actggctttc tagatgttcc agtgctctac aaccagtcgt accacatg      58

<210> SEQ ID NO 98
<211> LENGTH: 56
<212> TYPE: DNA
<213> ORGANISM: Artificial Sequence
<220> FEATURE:
<223> OTHER INFORMATION: Primer pK18-ligE OvExt R

<400> SEQUENCE: 98
cgattcatta atgcagctgg cacgacagcg agttgaacga aacctcctcg ttcatg        56

<210> SEQ ID NO 99
<211> LENGTH: 29
<212> TYPE: DNA
<213> ORGANISM: Artificial Sequence
<220> FEATURE:
<223> OTHER INFORMATION: Primer Saro2405 ligE del F

<400> SEQUENCE: 99
gcatcaccga aggcatgaag aagtaaacg                                      29

<210> SEQ ID NO 100
<211> LENGTH: 29
<212> TYPE: DNA
<213> ORGANISM: Artificial Sequence
<220> FEATURE:
<223> OTHER INFORMATION: Primer Saro2405 ligE del R

<400> SEQUENCE: 100
gtgactcaat tgccgtcacc ctgaacttg                                      29

<210> SEQ ID NO 101
<211> LENGTH: 30
<212> TYPE: DNA
<213> ORGANISM: Artificial Sequence
<220> FEATURE:
<223> OTHER INFORMATION: Primer Saro_2872 ampl AseI F2

<400> SEQUENCE: 101
catcattaat tcgacctggc cataggactg                                     30

<210> SEQ ID NO 102
<211> LENGTH: 29
<212> TYPE: DNA
<213> ORGANISM: Artificial Sequence
<220> FEATURE:
<223> OTHER INFORMATION: Primer Saro_2872 ampl XbaI R

<400> SEQUENCE: 102
tagttctaga ccatcttttc cgctggagc                                      29

<210> SEQ ID NO 103
<211> LENGTH: 21
<212> TYPE: DNA
<213> ORGANISM: Artificial Sequence
<220> FEATURE:
<223> OTHER INFORMATION: Primer Saro_2872 del R
```

```
<400> SEQUENCE: 103
gcttgtcaag gcctggcttg c                                      21

<210> SEQ ID NO 104
<211> LENGTH: 27
<212> TYPE: DNA
<213> ORGANISM: Artificial Sequence
<220> FEATURE:
<223> OTHER INFORMATION: Primer Saro_2872 del F

<400> SEQUENCE: 104
ttatccctcg atctccgcca tgatgag                                27

<210> SEQ ID NO 105
<211> LENGTH: 57
<212> TYPE: DNA
<213> ORGANISM: Artificial Sequence
<220> FEATURE:
<223> OTHER INFORMATION: Primer Saro_2873-pk18 hifi ampl R

<400> SEQUENCE: 105
gtttctgcgg actggctttc tagatgttcc ctacaaggga gggcagtgaa atgaagc    57

<210> SEQ ID NO 106
<211> LENGTH: 33
<212> TYPE: DNA
<213> ORGANISM: Artificial Sequence
<220> FEATURE:
<223> OTHER INFORMATION: Primer Saro_2873 hifi del F

<400> SEQUENCE: 106
catccctcga tctcgtccat ccgctgccca tcc                         33

<210> SEQ ID NO 107
<211> LENGTH: 56
<212> TYPE: DNA
<213> ORGANISM: Artificial Sequence
<220> FEATURE:
<223> OTHER INFORMATION: Primer Saro_2873-pk18 hifi ampl F

<400> SEQUENCE: 107
cgattcatta atgcagctgg cacgacaggg acgaatgata gaccagccac ttcagg     56

<210> SEQ ID NO 108
<211> LENGTH: 37
<212> TYPE: DNA
<213> ORGANISM: Artificial Sequence
<220> FEATURE:
<223> OTHER INFORMATION: Primer Saro_2873 hifi del R

<400> SEQUENCE: 108
gatggacgag atcgagggat gagcgcgctt ctttacc                     37

<210> SEQ ID NO 109
<211> LENGTH: 35
<212> TYPE: DNA
<213> ORGANISM: Artificial Sequence
<220> FEATURE:
<223> OTHER INFORMATION: Primer Saro2872 Ctag BsaI F

<400> SEQUENCE: 109
ggcatctgcg agacctcccc aacggttgat ttcag                       35

<210> SEQ ID NO 110
<211> LENGTH: 28
```

<210> SEQ ID NO 110
<211> LENGTH: 28 [likely, truncated] 
<212> TYPE: DNA
<213> ORGANISM: Artificial Sequence
<220> FEATURE:
<223> OTHER INFORMATION: Primer Saro2872 Ctag BspHI R

<400> SEQUENCE: 110
cgagtcatga gcgcgcttct ttaccacg                              28

<210> SEQ ID NO 111
<211> LENGTH: 28
<212> TYPE: DNA
<213> ORGANISM: Artificial Sequence
<220> FEATURE:
<223> OTHER INFORMATION: Primer Ctag 2872-pVP add Stop R

<400> SEQUENCE: 111
cgagttatcc ccaacggttg atttcagg                              28

<210> SEQ ID NO 112
<211> LENGTH: 60
<212> TYPE: DNA
<213> ORGANISM: Artificial Sequence
<220> FEATURE:
<223> OTHER INFORMATION: Primer 2872-pVP C to Ntag F

<400> SEQUENCE: 112
caagcgaaaa tctgtatttt cagagcgcga tcgcaggaat gagcgcgctt ctttaccacg    60

<210> SEQ ID NO 113
<211> LENGTH: 58
<212> TYPE: DNA
<213> ORGANISM: Artificial Sequence
<220> FEATURE:
<223> OTHER INFORMATION: Primer Saro2872 gNtag R

<400> SEQUENCE: 113
caagcgaaaa tctgtatttt cagagcgcga tcgcaggaag cgcgcttctt taccacgg     58

<210> SEQ ID NO 114
<211> LENGTH: 58
<212> TYPE: DNA
<213> ORGANISM: Artificial Sequence
<220> FEATURE:
<223> OTHER INFORMATION: Primer Saro2872 gNtag F

<400> SEQUENCE: 114
ccaatgcatg gtgatggtga tgatggtgat gtatcatccc tcgatctccg ccatgatg     58

<210> SEQ ID NO 115
<211> LENGTH: 50
<212> TYPE: DNA
<213> ORGANISM: Artificial Sequence
<220> FEATURE:
<223> OTHER INFORMATION: Primer 2872-3_pVP_HiFi_F

<400> SEQUENCE: 115
ctaactttgt tatttcggc tttctgttat ccccaacggt tgatttcagg              50

<210> SEQ ID NO 116
<211> LENGTH: 54
<212> TYPE: DNA
<213> ORGANISM: Artificial Sequence
<220> FEATURE:
<223> OTHER INFORMATION: Primer Saro2872-3NOTAG_pVP_HiFi_R

<400> SEQUENCE: 116

-continued gaattcatta aagaggagaa attaaccatg gacgaggtaa gcctctatca ttgg    54

<210> SEQ ID NO 117
<211> LENGTH: 39
<212> TYPE: DNA
<213> ORGANISM: Artificial Sequence
<220> FEATURE:
<223> OTHER INFORMATION: Primer pVP302K-HiFi-noTag-R

<400> SEQUENCE: 117
ggttaatttc tcctctttaa tgaattctgt gtgaaattg    39

<210> SEQ ID NO 118
<211> LENGTH: 52
<212> TYPE: DNA
<213> ORGANISM: Artificial Sequence
<220> FEATURE:
<223> OTHER INFORMATION: Primer Saro2872-3Ntag_pVP_HiFi_R

<400> SEQUENCE: 118
gtattttcag agcgcgatcg caggaatgga cgaggtaagc tctatcatt gg    52

<210> SEQ ID NO 119
<211> LENGTH: 21
<212> TYPE: DNA
<213> ORGANISM: Artificial Sequence
<220> FEATURE:
<223> OTHER INFORMATION: Primer Saro2872-S14A_R

<400> SEQUENCE: 119
cgcggcgctc accgttcttg c    21

<210> SEQ ID NO 120
<211> LENGTH: 26
<212> TYPE: DNA
<213> ORGANISM: Artificial Sequence
<220> FEATURE:
<223> OTHER INFORMATION: Primer Saro2872-S14A_F

<400> SEQUENCE: 120
ccgttgggct cgccgtggta aagaag    26

<210> SEQ ID NO 121
<211> LENGTH: 23
<212> TYPE: DNA
<213> ORGANISM: Artificial Sequence
<220> FEATURE:
<223> OTHER INFORMATION: Primer Saro2873-S15A_R

<400> SEQUENCE: 121
gcaagccgat gctcgcgttg atg    23

<210> SEQ ID NO 122
<211> LENGTH: 31
<212> TYPE: DNA
<213> ORGANISM: Artificial Sequence
<220> FEATURE:
<223> OTHER INFORMATION: Primer Saro2873-S15A_F

<400> SEQUENCE: 122
cagcgttggc attgggttcc caatgataga g    31

<210> SEQ ID NO 123
<211> LENGTH: 31
<212> TYPE: DNA
<213> ORGANISM: Artificial Sequence

```
<220> FEATURE:
<223> OTHER INFORMATION: Primer Saro2873-N14A_F

<400> SEQUENCE: 123
cagaggcggc attgggttcc caatgataga g                           31

<210> SEQ ID NO 124
<211> LENGTH: 28
<212> TYPE: DNA
<213> ORGANISM: Artificial Sequence
<220> FEATURE:
<223> OTHER INFORMATION: Primer pEU-HiFi-ATW-R

<400> SEQUENCE: 124
gtgatgatga tgatgatgtc ccattaac                               28

<210> SEQ ID NO 125
<211> LENGTH: 24
<212> TYPE: DNA
<213> ORGANISM: Artificial Sequence
<220> FEATURE:
<223> OTHER INFORMATION: Primer pEU-HiFi-ATW-F

<400> SEQUENCE: 125
tagtttaaac gaattcgagc tcgg                                   24

<210> SEQ ID NO 126
<211> LENGTH: 51
<212> TYPE: DNA
<213> ORGANISM: Artificial Sequence
<220> FEATURE:
<223> OTHER INFORMATION: Primer Saro2872-pEU2394-HiFi-F

<400> SEQUENCE: 126
ggacatcatc atcatcatca cgcattggca agcgaaaatc tgtattttca g     51

<210> SEQ ID NO 127
<211> LENGTH: 52
<212> TYPE: DNA
<213> ORGANISM: Artificial Sequence
<220> FEATURE:
<223> OTHER INFORMATION: Primer Saro2872-pEU2394-HiFi-R

<400> SEQUENCE: 127
ccgagctcga attcgtttaa actacgagtt atccccaacg gttgatttca gg    52

<210> SEQ ID NO 128
<211> LENGTH: 54
<212> TYPE: DNA
<213> ORGANISM: Artificial Sequence
<220> FEATURE:
<223> OTHER INFORMATION: Primer pEU-2872-fix-R

<400> SEQUENCE: 128
cattaactaa ctagtgtagt tgtagaatgt aaaatgtaat gttgttgttg tttg  54

<210> SEQ ID NO 129
<211> LENGTH: 28
<212> TYPE: DNA
<213> ORGANISM: Artificial Sequence
<220> FEATURE:
<223> OTHER INFORMATION: Primer pEU-2872-fix-F

<400> SEQUENCE: 129
ggacatcatc atcatcatca cgcattgg                               28
```

```
<210> SEQ ID NO 130
<211> LENGTH: 46
<212> TYPE: DNA
<213> ORGANISM: Artificial Sequence
<220> FEATURE:
<223> OTHER INFORMATION: Primer Saro_2873-pEU_HiFi-F

<400> SEQUENCE: 130
caactacact agttagttaa tggacgaggt aagcctctat cattgg          46

<210> SEQ ID NO 131
<211> LENGTH: 46
<212> TYPE: DNA
<213> ORGANISM: Artificial Sequence
<220> FEATURE:
<223> OTHER INFORMATION: Primer Saro_2873-pEU_HiFi-R

<400> SEQUENCE: 131
cgagctcgaa ttcgtttaaa ctactcatcc ctcgatctcc gccatg          46

<210> SEQ ID NO 132
<211> LENGTH: 29
<212> TYPE: DNA
<213> ORGANISM: Artificial Sequence
<220> FEATURE:
<223> OTHER INFORMATION: Primer pEU2394 F

<400> SEQUENCE: 132
gtagtttaaa cgaattcgag ctcggtacc                             29
```